(12) United States Patent
Rogers et al.

(10) Patent No.: US 10,745,416 B2
(45) Date of Patent: Aug. 18, 2020

(54) MACROCYCLIC COMPOUNDS FOR TREATING DISEASE

(71) Applicant: Turning Point Therapeutics, Inc., San Diego, CA (US)

(72) Inventors: Evan W. Rogers, San Diego, CA (US); Jingrong J. Cui, San Diego, CA (US); Dayong Zhai, San Diego, CA (US); Han Zhang, San Diego, CA (US); Jane Ung, San Diego, CA (US); Wei Deng, San Diego, CA (US); Jeffrey Whitten, San Diego, CA (US)

(73) Assignee: Turning Point Therapeutics, Inc., San Diego, CA (US)

( * ) Notice: Subject to any disclaimer, the term of this patent is extended or adjusted under 35 U.S.C. 154(b) by 0 days.

(21) Appl. No.: 16/777,717

(22) Filed: Jan. 30, 2020

(65) Prior Publication Data

US 2020/0190110 A1    Jun. 18, 2020

Related U.S. Application Data

(63) Continuation of application No. PCT/US2018/066158, filed on Dec. 18, 2018.

(60) Provisional application No. 62/779,283, filed on Dec. 13, 2018, provisional application No. 62/727,124, filed on Sep. 5, 2018, provisional application No. 62/607,528, filed on Dec. 19, 2017.

(51) Int. Cl.
*C07D 498/22* (2006.01)
*A61P 35/00* (2006.01)

(52) U.S. Cl.
CPC ............ *C07D 498/22* (2013.01); *A61P 35/00* (2018.01)

(58) Field of Classification Search
CPC .................................................. C07D 498/18
See application file for complete search history.

(56) References Cited

U.S. PATENT DOCUMENTS

| | | |
|---|---|---|
| 5,639,778 A | 6/1997 | Andersson |
| 5,698,578 A | 12/1997 | Heath, Jr. |
| 8,497,270 B2 | 7/2013 | Thuring |
| 8,680,111 B2 | 3/2014 | Bailey |
| 8,815,872 B2 | 8/2014 | Yu |
| 8,933,084 B2 | 1/2015 | Andrews |
| 9,714,258 B2 | 7/2017 | Cui |
| 10,246,466 B2 | 4/2019 | Cui |
| 10,294,242 B2 | 5/2019 | Cui |
| 10,316,044 B2 | 6/2019 | Cui |
| 2011/0294801 A1 | 12/2011 | Yu |
| 2013/0143895 A1 | 6/2013 | McAllister |
| 2013/0203776 A1 | 8/2013 | Andrews |
| 2013/0245021 A1 | 9/2013 | Bi |
| 2013/0252961 A1 | 9/2013 | Bailey |
| 2014/0107099 A1 | 4/2014 | Blaney |
| 2014/0206605 A1 | 7/2014 | Beutner |
| 2016/0339027 A1 | 11/2016 | Carter |
| 2017/0002023 A1 | 1/2017 | Cui |
| 2017/0334929 A1 | 11/2017 | Cui |
| 2018/0186813 A1 | 7/2018 | Cui |
| 2018/0194777 A1 | 7/2018 | Cui |
| 2018/0325901 A1 | 11/2018 | Cui |

FOREIGN PATENT DOCUMENTS

| | | |
|---|---|---|
| CL | 2012003227 | 2/2013 |
| CN | 102143750 | 8/2011 |
| CN | 102971322 | 3/2013 |
| JP | 2012502043 | 1/2012 |
| WO | 2002046197 A | 6/2002 |
| WO | 2010028116 | 3/2010 |
| WO | 2010033941 | 3/2010 |
| WO | 2010048314 | 4/2010 |
| WO | 2010051549 | 5/2010 |
| WO | 2011146336 | 11/2011 |
| WO | 2012034091 | 3/2012 |
| WO | 2012136859 | 10/2012 |
| WO | 2013001310 | 1/2013 |
| WO | 2013028465 | 2/2013 |
| WO | 2013045653 | 4/2013 |
| WO | 2013132376 | 9/2013 |
| WO | 2013134219 | 9/2013 |
| WO | 2013134228 | 9/2013 |
| WO | 2013147711 | 10/2013 |
| WO | 2015112806 | 7/2015 |
| WO | 2017004342 | 1/2017 |
| WO | 2017007759 | 1/2017 |
| WO | 2017015367 | 1/2017 |
| WO | 2018022911 | 2/2018 |
| WO | 2018140554 | 8/2018 |
| WO | 2019023417 | 1/2019 |
| WO | 2019120267 | 6/2019 |
| WO | 2019201282 | 10/2019 |

OTHER PUBLICATIONS

Apicella et al., "Dual MET/EGFR therapy leads to complete response and resistance prevention in a MET-amplified gastroesophageal xenopatient cohort", Oncogene (2017) 36, 1200-1210. Published online Aug. 15, 2016.

Baldanzi et al., "Physiological Signaling and Structure of the HGF Receptor MET", Biomedicines 2015, 3, 1-31. First published Dec. 31, 2014.

Bender et al., "Recurrent MET fusion genes represent a drug target in pediatric glioblastoma", Nature Medicine 22, 1314-1320 (2016). Published online Oct. 17, 2016.

Bradley et al., "Targeting c-MET in gastrointestinal tumours: rationale, opportunities and challenges", Nat Rev Clin Oncol, Sep. 2017;14(9):562-576. Published online Apr. 4, 2017.

(Continued)

*Primary Examiner* — Noble E Jarrell
(74) *Attorney, Agent, or Firm* — Barnes & Thornburg LLP

(57) ABSTRACT

The present disclosure relates to certain macrocyclic derivatives, pharmaceutical compositions containing them, and methods of using them to treat disease, such as cancer.

29 Claims, 8 Drawing Sheets

(56) References Cited

OTHER PUBLICATIONS

Glodde et al., "Reactive Neutrophil Responses Dependent on the Receptor Tyrosine Kinase c-MET Limit Cancer Immunotherapy", Immunity 47, 789-802, Oct. 17, 2017.
Heynen et al., "Resistance to targeted cancer drugs through hepatocyte growth factor signaling", Cell Cycle, 2014, 13:24, 3808-3817. Accepted Nov. 11, 2014.
Hughes et al., "Have Clinical Trials Properly Assessed c-MET Inhibitors?", Trends in Cancer, Feb. 2018, vol. 4, No. 2, pp. 94-97. Published online Dec. 18, 2017.
Katayama, "Therapeutic strategies and mechanisms of drug resistance in Anaplastic Lymphoma Kinase (ALK)—rearranged lung cancer", Pharmacol Ther., Sep. 2017; 177:1-8. Published online Feb. 7, 2017.
Kato et al., "RET Aberrations in Diverse Cancers: Next-Generation Sequencing of 4,871 Patients", Clin Cancer Res., Apr. 15, 2017; 23(8): 1988-1997. Published online Sep. 28, 2016.
Ko et al., "MET/HGF pathway activation as a paradigm of resistance to targeted therapies", Ann Transl Med., Jan. 2017; 5(1):4.
Lin et al., "Targeting ALK: Precision Medicine Takes on Drug Resistance", Cancer Discov., Feb. 2017; 7(2): 137-155. Published online Jan. 25, 2017.
Pennacchietti et al., "Microenvironment-Derived HGF Overcomes Genetically Determined Sensitivity Anti-MET Drugs", Cancer Res. Nov. 15, 2014; 74(22): 6598-609. Published online Sep. 12, 2014.
Shaw et al., "Lorlatinib in non-small-cell lung cancer with ALK or ROS1 rearrangement: an international, multicentre, open-label, single-arm first-in-man phase 1 trial", Lancet Oncol 2017; 18: 1590-99. Published online Oct. 23, 2017.
Rosell et al., "TPX-0005 with an EGFR tyrosine kinase inhibitor (TKI) overcomes innate resistance in EGFR mutant NSCLC", Poster, IASLC 18th World Conference on Lung Cancer, Oct. 15, 2017.
Mikami et al., "Discovery of a novel series of pyrazolo[1,5-a]pyrimidine-based phosphodiesterase 2A inhibitors structurally different from N-((1S)-1-(3-Fluoro-4-(trifluoromethoxy)phenyl)-2-methoxyethyl)-7-methoxy-2-oxo-2,3-dihydropyrido[2,3b] pyrazine-4(1H)-carboxamide (TAK-915), for the treatment of cognitive disorders," Chemical & Pharmaceutical Bulletin (2017), 65(11), 1058-1077.
Lim et al., "Discovery of 5-Amino-N-(1H-pyrazol-4-yl)pyrazolo[1,5-a]pyrimidine-3-carboxamide Inhibitors of IRAK4," ACS Medicinal Chemistry Letters (2015), 6(6), 683-688.
Wang et al., "Discovery of novel pyrazolo[1,5-a]pyrimidines as potent pan-Pim inhibitors by structure- and property-based drug design," Bioorganic & Medicinal Chemistry Letters (2013), 23(11), 3149-3153.
Gavrin et al., "Synthesis of Pyrazolo[1,5-alpha]pyrimidinone Regioisomers," Journal of Organic Chemistry (2007), 72(3), 1043-1046.
Pubchem-CID-347915314, Create Date: Nov. 9, 2017 (Nov. 3, 2017), p. 3, Fig.
Zou et al., "PF-06463922 is a potent and selective next-generation ROS1/ALK inhibitor capable of blocking crizotinib-resistant ROS1 mutations", PNAS, Mar. 17, 2015, vol. 112, No. 11, 3493-3498.
Johnson et al., "Discovery of (10R)-7-Amino-12-fluoro-2,10,16-trimethyl-15-oxo-10,15,16,17-tetrahydro-2H-8,4-(methano)pyrazolo[4,3-h][2,5,11]-benzoxadiazacyclotetradecine-3-carbonitrile (PF-06463922), a Macrocyclic Inhibitor of Anaplastic Lymphoma Kinase (ALK) and c-ros Oncogene 1 (ROS1) with Preclinical Brain Exposure and Broad-Spectrum Potency against ALK-Resistant Mutations", J. Med. Chem., Jun. 12, 2014, 57, 4720-4744.
Jordan, "Tamoxifen: A Most Unlikely Pioneering Medicine", Nature Reviews, vol. 2, Mar. 2003, pp. 205-213.
Hackam et al., "Translation of Research evidence From Animals to Humans", JAMA, 2006; 296(14): 1731-1732.
Stanley et al., "Synergistic effects of various Her inhibitors in combination with IGF-1R, C-MET and Src targeting agents in breast cancer cell lines", Scientific Reports, Jun. 21, 2017, vol. 7, pp. 1-15; Abstract p. 1.
Toso, A. et al., Cell Reports 2014, 9, 75-89.
Shaw, A. T. et al., N Engl J Med. 2014, 371(21):1963-1971.
Buchert M, et al. Oncogene, 2016, 25, 939-951; published May 18, 2015.
Pierotti, M.A. et al., Cancer Lett. 2006, 232, 90-98.
Vaishnavi, A. et al al., Nat. Med. 2013, 19, 1469-1472.
Verma, A. etal., Mol. CancerTher. 2011, JO, 1763-1773.
Zhang, Z. et al., Nat. Genet. 2012, 44, 852-860.
Cui, J. J. et al., J. Med. Chem. 2011, 54, 6342-6363.
Katayama, R. et al., Sci. Transl. Med. 2012, 4, 120ra17.
Quintas-Cardama, A. et al., Nat. Rev. Drug Discov. 2011, 10(2), 127-40.
Pesu, M. et al., Immunol. Rev. 2008, 223, 132-142.
Murray, P.J., J. Immunol. 2007, 178(5), 2623-2329.
Muller, M. et al., Nature 1993, 366(6451), 129-135.
Neubauer, H. et al., Cell 1998 93(3), 397-409.
Nosaka, T. et al., Science 1995, 270(5237), 800-802.
Vainchenker, W. et al., Semin. Cell. Dev. Biol. 2008, 19(4), 385-393.
Levine, R.L. etal., Cancer Cell 2005, 7(4), 387-397.
Kralovics, R. et al., N. Engl. J. Med. 2005, 253(17), 1779-1790.
James, C. et al., Nature 2005, 434(7037), 1144-1148.
Baxter, E.J. et al. Lancet 2005, 365(9464), 1054-1061.
Sonbol, M.B. et al., Ther. Adv. Hematol. 2013, 4(1), 15-35.
LaFave, L.M. et al., Trends Pharmacol. Sci. 2012, 33(11), 574-582.
Verstovsek, S. et al., N. Engl. J. Med. 2012, 366(9), 799-807.
Quintas-Cardama, A. et al., Blood 2010, 115(15), 3109-3117.
Nefedova, Y. et al., Cancer Res 2005; 65(20): 9525-35.
Davies, K. D. et al., Clin Cancer Res 2013, 19 (15): 4040-4045.
Awad, M. M. et al., N Engl J Med. 2013, 368(25):2396-2401.
Charest A, et al Genes Chromosomes Cancer 2003, 37, 58.
Takeuchi K, et al Nat. Med. 2012, 18, 378.
Gu TL, et al PLoS One. 2011, 6, e15640.
Lacronique V, et al. Science 1997, 278, 5341, 1309-12.
Reiter A, et al. Cancer Res. 2005, 65, 7, 2662-7.
Zhang S, et al Trends Pharmacol Sci. 2012, 33, 122.
Bromann PA, Oncogene 2004, 23, 7957-7968.
Summy JM, et al. Cancer Metastasis Rev. 2003, 22, 337-358.
Scancier F. et al. PLoS One. 2011, 6(2): el 7237.
Ongusaha PP, et al. EMBO J. 2003, 22, 1289-1301.
Hammerman PS, et al. Cancer Discov. 2011, 1, 78-89.
Tomasson MH, et al. Blood 2008, 111:4797-4808.
Yu J. et al., Cancer Cell, 2010, 17, 5, 443-54.
Advani, A.S. et al. Leukemia Research, 2002, 26, 8, 713-720.
Gottesman, M.M., Annu. Rev. Med., 2002, 53, 615-627.
Anastassiadis T, et al Nat Biotechnol. 2011, 29, 1039.
Vetrie D. et al. Nature 1993, 361, 226-233.
Mohamed AJ et al, immunological Reviews, 2009, 228, 58-73.
Grande, E. et al., Mol. Cancer Ther. 2011, 10, 569-579.
Monti, E 2007. Molecular Determinants of Intrinsic Multidrug Resistance in Cancer Cells and Tumors in B. Teicher (Ed.), Cancer Drug Resistance (pp. 241-260).
McCarthy et al. "Tropomyosin receptor kinase inhibitors: a patent update 2009-2013," Expert Opinions 2014, pp. 731-744.
Sen, B., et al. Distinct interactions between SRC and MET in mediating resistance to SRC inhibition in head and neck cancer. Clin Cancer Res. 2010, 17, 1-11.
Yu, Helena A., et al. Analysis of tumor specimens at the time of acquired resistance to EGFR-TKI therapy in 155 patients with EGFR-mutant lung cancers. Clin. Cancer Res. 2013, 19, 2240-2247.
Rover et al., "Identification of 4-methyl-1,2,3,4, 10, 1 Oa-hexahydropyrazino[l,2-a]indoles as 5-HT2C receptor agonists," Bioorganic & Medicinal Chemistry Letters (2005), 15(15), 3604-3608.
Xie, Q., et al. Hepatocyte growth factor (HGF) autocrine activation predicts sensitivity to MET inhibition in alioblastoma. Proc. Natl. Acad. Sci. U.S. A. 2012, 109, 570-575.
PubChem-CID348351330,Create Date: Nov. 26, 2017 (Nov. 26, 2017).

(56) References Cited

OTHER PUBLICATIONS

PubChem-CID98009788, Create Date: Dec. 11, 2015 (Dec. 11, 2015).
Peterson et al., "Expanding the Scope of Crystal Form Evaluation in Parmaceutical Science" Journal of Pharmacy & Pharmaceutical Science 2006 9(3):317-326.
Miller et al., "Solvent Systems for Crystallization and Polymorph Selection" Chapter 3 in Solvent Systems and Their Selection in Pharmaceutics and Biopharmaceutics Series Biotechnology: Pharmaceutical Aspects vol. VI Augustijns, Patrick; Brewster, Marcus (Eds.) 2007.
International Search Report and Written Opinion prepared for PCT/US2015/012597, dated Aug. 28, 2015, 11 pages.
International Search Report and Written Opinion prepared for PCT/US2016/040329, dated Sep. 7, 2016, 13 pages.
International Search Report and Written Opinion prepared for PCT/US2016/040972, dated Sep. 13, 2016, 8 pages.
European Search Report issued in EP 16828471, completed Mar. 15, 2019.
European Search Report issued in EP 16818768, completed Jan. 22, 2019.
Wiesner T, et al Nature 2015, 526, 453-457.
Voena C, et al. Oncotarget, Apr. 23, 2016, 8955.
Uguen A, et al Future Oncol. Jun. 3, 2016, Epub ahead of print.
Gao SP, et al. Sci Signal. 206, 9 (421):ra33: published online Mar. 29, 2016.
Balko JM, et al. Sci Transl Med. 2016, 8 (334):ra53, published Apr. 13, 2016.
Liu W, et al. Oncotarget. 2015, 6: 35522-35541.
Serrels A, et al, Cells 2015, 163, 160-173.
Shi L, et al. Br J Cancer. 2014, 111(12): 2316-27.
Xu T, et al. Cancer Lett. 2016, 377(2): 140-8, published online Apr. 25, 2016.
Elias D., et al Pharmacological Research 2015, 100, 250-254.
Ambrogio C, et al, Nature Medicine, 2016, 22, 270-277, published Feb. 8, 2016.
Bender AT, et al. Clinical Immunology 2016, 164, 65-77, available online Jan. 25, 2016.
Morgillo F, Della Corte CM, Fasano M. et al. Mechanisms of resistance to EGFR-targeted drugs: lunch cancer. ESMO Open 2016;1: e000060, published online May 11, 2016.
Pubchem, Compound Summary for SID 252159180, available date; Aug. 10, 2015, retrieved Aug. 31, 2017, retrieved from: https://pubchem.ncbi.nlm.nih.gov/substance/252159180.
Rahal, "The development of Potent and Selective RET inhibitors", Presentation at Annual AACR Meeting, Apr. 18, 2016.
Jiang H, et al. Nat Med. Jul. 4, 2016 [Epub ahead of print].
International Search Report and Written Opinion prepared for PCT/US2016/043132, dated Sep. 28, 2016, 8 pages.
Politi K, Clin Cancer Res. 2014, 20, 5576.
Crystal AS, Science. 2014, 346, 1480.
Vaishnavi A, et al Cancer Discov. 2015, 5, 25.
Park, K-S, et al. J Clin Invest. 2014, 124(7):3003-3015.
Golubovskaya VM, Front Biosci (Landmark Ed). 2014; 19: 687-706.
Liu L, et al. Nature, 2012, 483, 608-612.
Stransky N, et al. Nature Communications 2014, 5, 4846.
Schwarz LJ, et al. J Clin Invest. 2014, 124, 5490-5502.
Zardan A., et al. Oncogenesis 2014, 3, e 115.
Rudd ML, et al. BMC Cancer 2014, 14, 884.
Furman RR, et al. New England Journal of Medicine, 2014, 370, 2352-2354.
Chiron D, et al. Cancer Discovery, 2014, 4, 1022-1035.
Woyach JA, el al. New England Journal of Medicine, 2014, 370, 2286-2294.
Gunderson AJ, et al. Cancer Discov. 2016, 6, 270-285, published online Dec. 29, 2015.
Berndt N. et al. Curr. Opin. Chem. Biol. 2017, 39:126-132.

Drilon et al., "A Phase 1B Study of RXDX-105, A VEGFR-Sparing Potent RET Inhibitor, in RET Inhibitor Naïve Patients with RET Fusion-Positive NSCLC", ESMO Congress Presentation, Madrid, Aug. 31, 2017.
Mulligan, LM. Nat Rev Cancer. 2014, 14(3):173-86.
Das TK and Cagan RL Cell Rep. 2017, 20(10):2368-2383.
Pilotto S, MET exon 14 juxtamembrane splicing mutations: clinical and therapeutical perspectives for cancer therapy. Ann Transl Med. 2017 5(1):2.
Fujita-Sato, S., et al. Enhanced MET Translation and Signaling Sustains K-Ras-Driven Proliferation under Anchorage-Independent Growth Conditions. Cancer Res. 2015, 75, 2851-2862.
Song N, et al. Cetuximab-induced MET activation acts as a novel resistance mechanism in colon cancer cells. Int J Mol Sci. 2014, 15, 5838-5851.
Song, N., et al. Dual inhibition of MET and SRC kinase activity as a combined targeting strategy for colon cancer. Exp Ther Med etm.2017.4692.
Yang L, et al. Tumor-associated macrophages: from basic research to clinical application. J Hematol Oncol. 2017, 10, 58.
Ries CH, et al. Targeting tumor-associated macrophages with anti-CSFIR antibody reveals a strategy for cancer therapy. Cancer Cell. 2014, 25, 846-859.
Arlauckas SP, et al. In vivo imaging reveals a tumor-associated macrophage-mediated resistance pathway in anti-PD-1 therapy. Sci Transl Med. 2017, 9(389). pii: eaal3604.
Gargalionis et al., "The molecular rationale of Src inhibition in colorectal carcinomas", Int. J. Cancer: 134, 2019-2029 (2014). Published online Jun. 21, 2013.
Okamoto et al "Identification of c-Src as a Potential Activation as a Cause of Resistance to c-Src Published online Apr. 20, 2010 Inhibition", Therapeutic Target for Gastric Cancer and of MET Mol Cancer Ther., May 2010; 9(5): 1188-97.
Vergani et al., "Identification of MET and SRC Activation in Melanoma Cell Lines Showing Primary Resistance to PLX4032", Neoplasia. Dec. 2011; 13(12): 1132-42.
Pachter et al., "The Chemistry of Hortiamine and 6-Methoxyrhetsinine," J. Am. Chem. Soc., 1961, 83, 635-642.
Kiselyov, Alexander S., "Solid support synthesis of 15-membered macrocycles containing a serotonin unit," Tetrahedron Letters 46 (2005) 3007-3010.
Halland et al. "Small Macrocycles as Highly Active Integrin 0131 Antagonists," ACS Medicinal Chemistry Letters, Jan. 10, 2014, 5, 193-198.
International Search Report and Written Opinion prepared for PCT/US2017/044214, dated Dec. 1, 2017, 11 pages.
Couronne L, et al. Blood 2013, 122, 811.
Di Paolo JA, et al. Nature Chemical Bioloav 2011, 7, 41-50.
Schiller J H et al., N Engl J Med, 346: 92-98, 2002.
Takahashi, M. et al. Cell. 1985, 42:581-588.
Pachnis, V., et al. Development 1993, 119, 1005-1017.
Schuchardt, A. et al. Nature 1994, 367:380-383.
Grieco, M. et al. Cell. 1990, 23; 60 (4):557-63.
Gainor JF, Shaw AT. Oncologist. 2013, 18(7):865-75.
Kentsis, A., et al. Autocrine activation of the MET receptor tyrosine kinase in acute myeloid leukemia. Nat. Medd. 2012, 18, 1118-1122.
Yano, S., et al. Hepatocyte growth factor induces gefitinib resistance of lung adenocarcinoma with epidermal growth factor receptor-activating mutations. Cancer Res. 2008, 68, 9479-9487.
Bardelli, A., et al. Amplification of the Mli'T Receptor Drives Resistance to Anti-EGFR Therapies in Colorectal Cancer. Cancer Discov. 2013, 3, 658-673.
Straussman, R., et al. Tumour micro-environment elicits innate resistance to RAF inhibitors through HGF secretion. Nature 2012, 487, 500-504.
Harbinski F. et al. Rescue screens with secreted proteins reveal compensatory potential of receptor tyrosine kinases in driving cancer growth. Cancer Discov. 2012, 2, 948-959.
Parsons, S. J., et al. Src family kinases, key regulators of signal transduction. Oncogene, 2004, 23, 7906-7909.
Wojcik, E. J., et al. A novel activating function of SRC and STAT3 on HGF transcription in mammary carcinoma cells. Oncogene. 2006, 25, 2773-84.

(56) References Cited

OTHER PUBLICATIONS

Dulak AM et al. HGF-independent potentiation of EGFR action by Mli'l'. Oncogene. 2011, 30, 3625-3635.

Stabile, L. P., et al. c-SRC activation mediates erlotinib resistance in head and neck cancer by stimulating MET. Clin Cancer Res. 2012, 19, 1-13.

Bertotti, A., et al. Inhibition of SRC impairs the growth of MET-addicted gastric tumors. Clin Cancer Res. 2010, 16,3933-3943.

Wrobel CN, et al. Autocrine CSFIR activation promotes SRC-dependent disruption of mammary epithelial architecture. J Cell Biol. 2004, 165, 263-273.

Ravi V, et al. Treatment of tenosynovial giant cell tumor and pigmented villonodular synovitis. Curr Opin Oncol. 2011, 23,361-366.

Gridelli, C. et al., Cancer Treat Rev. 2014, 40, 300-306.

Liu Z, et al. J. Clin. Endocrinol. Metab. 2004, 89, 3503-3509.

Cooper, C. S., et al Molecular cloning of a new transforming gene from a chemically transformed human cell line. Nature 1984, 311, 29-33.

Boccaccio, C.; Comoglio, P. M. Invasive growth: a MET-driven generic programme for cancer and stem cells. Nat. Rev. Cancer 2006, 6, 637-645.

Ma, PC et al. Expression and mutational analysis of MET in human solid cancers. Genes Chromosomes Cancer 2008, 47, 1025-1037.

Maulik, G., et al. Role of the hepatocyte growth factor receptor, MET, in oncogenesis and potential for therapeutic inhibition. Cytokine Growth Factor Rev. 2002, 13, 41-59.

Smolen, G. A., et al. Amplification of MET may identify a subset of cancers with extreme sensitivity to the selective tyrosine kinase inhibitor PHA-665752. Proc. Natl. Acad. Sci. U.S. A. 2006, 103, 2316-2321.

Ghiso, E.; Giordano, S. Targeting MET: why, where and how? Curr. Opin. Pharmacol. 2013, 13, 511-518.

Otsuka, T., et al. MET autocrine activation induces development of malignant melanoma and acquisition of the metastatic phenotype. Cancer Res. 1998, 58, 5157-5167.

Sawyers, C., Nature 2004, 432, 294-297.

Park, M. et al., Cell 1986, 45, 895-904.

Bottaro, D. P. etal., Science 1991, 251, 802-804.

Trusolino, L. et al., Nature Rev. Mol. Cell Biol. 2010, 11, 834-848.

Gherardi, E. et al., Nature Rev. Cancer 2012, 12, 89-103.

Engelman, J. A. et al., Science 2007, 316, 1039-1043.

Wilson, T.R. et al., Nature 2012, 487, 505-509.

Pulford, K. et al., Cell Mol. Life Sci. 2004, 61, 2939.

Manning, G. et al., Science 2002, 298, 1912-1934.

Morris, S.W. et al., Science 1994, 263, 1281.

Bischof, D. et al., Mol. Cell Biol., 1997, 17, 2312-2325.

Soda, M. et al., Nature 2007, 448, 561-566.

Mosse, Y. P. et al., Nature 2008, 455, 930-935.

Thiele, C. J. et al., Clin. Cancer Res. 2009, 15, 5962-5967.

MACROCYCLIC COMPOUNDS FOR TREATING DISEASE

CROSS-REFERENCE TO RELATED APPLICATIONS

This application is a continuation which claims priority under 35 U.S.C. § 120 to International Application No. PCT/US2018/066158 filed on Dec. 18, 2018, which claims priority under 35 U.S.C. § 119(e) to U.S. Provisional Application Ser. No. 62/607,528 filed on Dec. 19, 2017, U.S. Provisional Application Ser. No. 62/727,124 filed on Sep. 5, 2018, and U.S. Provisional Application Ser. No. 62/779,283 filed on Dec. 13, 2018, the entire disclosures of which are incorporated herein by reference.

TECHNICAL FIELD

The present disclosure relates to certain macrocyclic derivatives, pharmaceutical compositions containing them, and methods of using them to treat disease, such as cancer.

BACKGROUND

Protein kinases regulate various functions in the cell including cell growth, proliferation and survival. Dysregulation of protein kinases is often the cause of many solid malignancies (Manning G. et al. Science. 2002, 298, 1912-1934). The use of protein kinase inhibitors has led to substantial clinical benefit in patients harboring oncogenic aberrations. More than thirty protein kinase inhibitors have been approved for clinical treatment of cancer (Berndt N. et al. Curr. Opin. Chem. Biol. 2017, 39:126-132). RET is a receptor tyrosine kinase that was initially discovered in 1985 through transfection of NIH3T3 cells with human lymphoma DNA (Takahashi, M. et al. Cell. 1985, 42:581-588.). RET is expressed with its highest levels in early embryogenesis (during which it has diverse roles in different tissues) and decreases to relatively low levels in normal adult tissues Pachnis, V., et al. *Development* 1993, 119, 1005-1017). RET plays a critical role in the development of enteric nervous system and kidneys during embryogenesis (Schuchardt, A. et al. Nature 1994, 367:380-383). RET activation regulates the downstream signalling pathways (RAS/MAPK/ERK, PI3K/AKT, and JAK-STAT etc.), leading to cellular proliferation, migration, and differentiation (Mulligan, L M. Nat Rev Cancer. 2014, 14(3):173-86).

Gain-of-function mutations of RET with constitutive activation have been found in heritable and sporadic tumors including activating point mutations within the full-length RET protein or genomic rearrangements that produce chimeric RET oncoproteins in the cytosol. The heritable oncogenic RET mutations are found in multiple endocrine neoplasia type 2 (MEN2) including medullary thyroid cancer (MTC) and familial MTC with more than 80 pathogenic variants spanning RET exons 5-16 reported (Mulligan, L M. Nat Rev Cancer. 2014, 14(3):173-86). Among them, RET M918T and RET A883F are found in 40-65% of sporadic MTC. The somatic mutation, chimeric RET fusion oncoproteins have been identified in sporadic tumors. The RET rearrangements are originally reported in papillary thyroid cancers (PTCs) (Grieco, M. et al. Cell. 1990, 23; 60 (4): 557-63.). The resulting fusion transcripts composed of the 3' end of RET kinase domain and the 5' end of separate partner genes (CCDC6, NCOA4, TRIM24, TRIM33, PRKAR1A, GOLGA5, KTN1, ERC1, MBD1, and TRIM27 etc.). RET fusions are identified in approximately 20%-40% of PTCs, and CCDC6-RET and NCOA4-RET are the most commonly identified RET fusions in PTCs (Drilon A, et al. Nat Rev Clin Oncol. 2017 Nov. 14. doi: 10.1038/nrclinonc.2017.175). RET gene fusions are also found in approximately 1%-2% of non-small cell lung cancer (NSCLC) (Gainor J F, Shaw A T. Oncologist. 2013, 18(7): 865-75), and over 50% of RET fusions in NSCLC is KIF5B-RET, representing the most frequent RET fusion form. However, the RET inhibitors have relatively low response rates and short treatment duration in the treatment of NSCLC patients with KIF5B-RET fusion gene in multiple clinical trials (Drilon, A. Nat Rev Clin Oncol. 2017 Nov. 14. doi: 10.1038/nrclinonc. 2017.175). It was reported that the kinesin and kinase domains of KIF5B-RET act together to establish an emergent microtubule and RAB-vesicle-dependent RET-SRC-EGFR-FGFR signaling hub (Das T K and Cagan R L Cell Rep. 2017, 20(10):2368-2383). The inhibition of SRC kinase will have the potential to stop the recruitment of multiple RTKs via the N terminus of the KIF5B-RET fusion protein and the oncogenic signaling to increase the therapeutic efficiency of RET inhibitors. In addition, Src family tyrosine kinases regulate MTC cellular proliferation in vitro and mediate growth signals by increasing DNA synthesis and decreasing apoptosis (Liu Z, et al. J. Clin. Endocrinol. Metab. 2004, 89, 3503-3509). Therefore, a dual inhibitor of RET and SRC represents a highly desired therapeutic intervention to maximally target abnormal RET signaling in cancers.

SUMMARY

In one aspect, the disclosure relates to a compound of the formula I

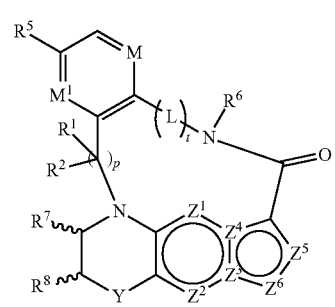

wherein

L is independently —C(R$^1$)(R$^2$)— or X;

X is —O—, —S—, —S(O)— or —S(O)$_2$—;

each R$^1$ and R$^2$ is independently H, deuterium, halogen, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl, —OR$^a$, —OC(O)R$^a$, —OC(O)R$^a$, —OC(O)NR$^a$R$^b$, —OS(O)R$^a$, —OS(O)$_2$R$^a$, —SR$^a$, —S(O)R$^a$, —S(O)$_2$R$^a$, —S(O)NR$^a$R$^b$, —S(O)$_2$NR$^a$R$^b$, —OS(O)NR$^a$R$^b$, —OS(O)$_2$NR$^a$R$^b$, —NR$^a$R$^b$, —NR$^a$C(O)R$^b$, —NR$^a$C(O)OR$^b$, —NR$^a$C(O)NR$^a$R$^b$, —NR$^a$S(O)R$^b$, —NR$^a$S(O)$_2$R$^b$, —NR$^a$S(O)NR$^a$R$^b$, —NR$^a$S(O)$_2$NR$^a$R$^b$, —C(O)R$^a$, —C(O)OR$^a$, —C(O)NR$^a$R$^b$, —PR$^a$R$^b$, —P(O)R$^a$R$^b$, —P(O)$_2$R$^a$R$^b$, —P(O)NR$^a$R$^b$, —P(O)$_2$NR$^a$R$^b$, —P(O)OR$^a$, —P(O)$_2$OR$^a$, —CN, or —NO$_2$, or R$^1$ and R$^2$ taken together with the carbon or carbons to which they are attached form a C$_3$-C$_6$ cycloalkyl or a 4- to 6-membered heterocycloalkyl, wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, $C_6$-$C_{10}$ aryl, mono- or bicyclic heteroaryl, 4- to 6-membered heterocycloalkyl is independently optionally substituted by deuterium, halogen, $C_1$-$C_6$ alkyl, $C_1$-$C_6$ haloalkyl, —$OR^e$, —$OC(O)R^e$, —OC(O)$NR^eR^f$, —OC(=N)$NR^eR^f$, —$OS(O)R^e$, —$OS(O)_2R^e$, —$OS(O)NR^eR^f$, —$OS(O)_2NR^eR^f$, —$SR^e$, —$S(O)R^e$, —$S(O)_2R^e$, —$S(O)NR^eR^f$, —$S(O)_2NR^eR^f$, —$NR^eR^f$, —$NR^eC(O)R^f$, —$NR^eC(O)OR^f$, —$NR^eC(O)NR^eR^f$, —$NR^eS(O)R^f$, —$NR^eS(O)_2R^f$, —$NR^eS(O)NR^eR^f$, —$NR^eS(O)_2NR^eR^f$, —$C(O)R^e$, —$C(O)OR^e$, —$C(O)NR^eR^f$, —$PR^eR^f$, —$P(O)R^eR^f$, —$P(O)_2R^eR^f$, —$P(O)NR^eR^f$, —$P(O)_2NR^eR^f$, —$P(O)OR^e$, —$P(O)_2OR^e$, —CN, or —$NO_2$;

M is $CR^3$ or N;

$M^1$ is $CR^4$;

each $R^3$, $R^4$, and $R^5$ is independently hydrogen, deuterium, halogen, —$OR^c$, —$OC(O)R^c$, —$OC(O)NR^cR^d$, —OC(=N)$NR^cR^d$, —$OS(O)R^c$, —$OS(O)_2R^c$, —$OS(O)NR^cR^d$, —$OS(O)_2NR^cR^d$, —$SR^c$, —$S(O)R^c$, —$S(O)_2R^c$, —$S(O)NR^cR^d$, —$S(O)_2NR^cR^d$, —$NR^cR^d$, —$NR^cC(O)R^d$, —$NR^cC(O)OR^d$, —$NR^cC(O)NR^cR^d$, —$NR^cC(=N)NR^cR^d$, —$NR^cS(O)R^d$, —$NR^cS(O)_2R^d$, —$NR^cS(O)NR^cR^d$, —$NR^cS(O)_2NR^cR^d$, —$C(O)R^c$, —$C(O)OR^c$, —$C(O)NR^cR^d$, —C(=N)$NR^cR^d$, —$PR^cR^d$, —$P(O)R^cR^d$, —$P(O)_2R^cR^d$, —$P(O)NR^cR^d$, —$P(O)_2NR^cR^d$, —$P(O)OR^c$, —$P(O)_2OR^c$, —CN, —$NO_2$, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl, or $R^4$ and $R^5$ taken together with the ring to which they are attached form a $C_5$-$C_8$ cycloalkyl, or a 5- to 8-membered heterocycloalkyl, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, mono- or bicyclic heteroaryl, $C_5$-$C_8$ cycloalkyl, or 5- to 8-membered heterocycloalkyl is independently optionally substituted by deuterium, halogen, $C_1$-$C_6$ alkyl, $C_1$-$C_6$ haloalkyl, —$OR^e$, —$OC(O)R^e$, —OC(O)$NR^eR^f$, —OC(=N)$NR^eR^f$, —$OS(O)R^e$, —$OS(O)_2R^e$, —$OS(O)NR^eR^f$, —$OS(O)_2NR^eR^f$, —$SR^e$, —$S(O)R^e$, —$S(O)_2R^e$, —$S(O)NR^eR^f$, —$S(O)_2NR^eR^f$, —$NR^eR^f$, —$NR^eC(O)R^f$, —$NR^eC(O)OR^f$, —$NR^eC(O)NR^eR^f$, —$NR^eS(O)R^f$, —$NR^eS(O)_2R^f$, —$NR^eS(O)NR^eR^f$, —$NR^eS(O)_2NR^eR^f$, —$C(O)R^e$, —$C(O)OR^e$, —$C(O)NR^eR^f$, —$PR^eR^f$, —$P(O)R^eR^f$, —$P(O)_2R^eR^f$, —$P(O)NR^eR^f$, —$P(O)_2NR^eR^f$, —$P(O)OR^e$, —$P(O)_2OR^e$, —CN, or —$NO_2$;

$R^6$ is H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, —$OR^e$, —$OC(O)R^e$, —$OC(O)NR^eR^f$, —OC(=N)$NR^eR^f$, —$OS(O)R^e$, —$OS(O)_2R^e$, —$OS(O)NR^eR^f$, —$OS(O)_2NR^eR^f$, —$SR^e$, —$S(O)R^e$, —$S(O)_2R^e$, —$S(O)NR^eR^f$, —$S(O)_2NR^eR^f$, —$NR^eR^f$, —$NR^eC(O)R^f$, —$NR^eC(O)OR^f$, —$NR^eC(O)NR^eR^f$, —$NR^eS(O)R^f$, —$NR^eS(O)_2R^f$, —$NR^eS(O)NR^eR^f$, —$NR^eS(O)_2NR^eR^f$, —$C(O)R^e$, —$C(O)OR^e$, —$C(O)NR^eR^f$, —$PR^eR^f$, —$P(O)R^eR^f$, —$P(O)_2R^eR^f$, —$P(O)NR^eR^f$, —$P(O)_2NR^eR^f$, —$P(O)OR^e$, —$P(O)_2OR^e$, —CN, or —$NO_2$;

$R^7$ and $R^8$ combine to form a $C_3$-$C_7$ cycloalkyl, a 5- to 8-membered heterocycloalkyl, $C_6$-$C_{10}$ aryl, or 5- to 7-membered heteroaryl; wherein each hydrogen atom in $C_3$-$C_7$ cycloalkyl, a 5- to 8-membered heterocycloalkyl, $C_6$-$C_{10}$ aryl, or 5- to 7-membered heteroaryl is independently optionally substituted by deuterium, halogen, —$OR^e$, —OC(O)$R^e$, —OC(O)$NR^eR^f$, —OC(=N)$NR^eR^f$, —$OS(O)R^e$, —$OS(O)_2R^e$, —$OS(O)NR^eR^f$, —$OS(O)_2NR^eR^f$, —$SR^e$, —$S(O)R^e$, —$S(O)_2R^e$, —$S(O)NR^eR^f$, —$S(O)_2NR^eR^f$, —$NR^eR^f$, —$NR^eC(O)R^f$, —$NR^eC(O)OR^f$, —$NR^eC(O)NR^eR^f$, —$NR^eS(O)R^f$, —$NR^eS(O)_2R^f$, —$NR^eS(O)NR^eR^f$, —$NR^eS(O)_2NR^eR^f$, —$C(O)R^e$, —$C(O)OR^e$, —$C(O)NR^eR^f$, —$PR^eR^f$, —$P(O)R^eR^f$, —$P(O)_2R^eR^f$, —$P(O)NR^eR^f$, —$P(O)_2NR^eR^f$, —$P(O)OR^e$, —$P(O)_2OR^e$, —CN, or —$NO_2$;

Y is O, S, $NR^9$, or $CR^9R^{10}$;

$R^9$ and $R^{10}$ are each independently H, deuterium, halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is optionally substituted by a halogen, —$OR^e$, —$OC(O)R^e$, —$OC(O)NR^eR^f$, —OC(=N)$NR^eR^f$, —$OS(O)R^e$, —$OS(O)_2R^e$, —$OS(O)NR^eR^f$, —$OS(O)_2NR^eR^f$, —$SR^e$, —$S(O)R^e$, —$S(O)_2R^e$, —$S(O)NR^eR^f$, —$S(O)_2NR^eR^f$, —$NR^eR^f$, —$NR^eC(O)R^f$, —$NR^eC(O)OR^f$, —$NR^eC(O)NR^eR^f$, —$NR^eS(O)R^f$, —$NR^eS(O)_2R^f$, —$NR^eS(O)NR^eR^f$, —$NR^eS(O)_2NR^eR^f$, —$C(O)R^e$, —$C(O)OR^e$, —$C(O)NR^eR^f$, —$PR^eR^f$, —$P(O)R^eR^f$, —$P(O)_2R^eR^f$, —$P(O)NR^eR^f$, —$P(O)_2NR^eR^f$, —$P(O)OR^e$, or —$P(O)_2OR^e$;

each $R^a$, $R^b$, $R^c$, $R^d$, $R^e$, and $R^f$ is independently selected from the group consisting of H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl;

each of $Z^1$, $Z^2$, $Z^3$, $Z^4$, $Z^5$, and $Z^6$ is independently N, NH, C or CH;

p is 1, 2, 3, or 4; and t is 1, 2, 3, 4, or 5;

or a pharmaceutically acceptable salt thereof.

In another aspect, the disclosure relates to a compound of the formula I

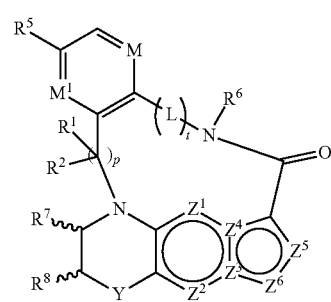

wherein

L is independently —$C(R^1)(R^2)$— or X;

X is O, S, S(O) or $S(O)_2$;

each $R^1$ and $R^2$ is independently H, deuterium, halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl, —$OR^a$, —$OC(O)R^a$, —OC(O)$R^a$, —OC(O)$NR^aR^b$, —$OS(O)R^a$, —$OS(O)_2R^a$, —$SR^a$, —$S(O)R^a$, —$S(O)_2R^a$, —$S(O)NR^aR^b$, —$S(O)_2NR^aR^b$, —$OS(O)NR^aR^b$, —$OS(O)_2NR^aR^b$, —$NR^aR^b$, —$NR^aC(O)R^b$, —$NR^aC(O)OR^b$, —$NR^aC(O)NR^aR^b$, —$NR^aS(O)R^b$, —$NR^aS(O)_2R^b$, —$NR^aS(O)NR^aR^b$, —$NR^aS(O)_2NR^aR^b$, —$C(O)R^a$, —$C(O)OR^a$, —$C(O)NR^aR^b$, —$PR^aR^b$, —$P(O)R^aR^b$, —$P(O)_2R^aR^b$, —$P(O)NR^aR^b$, —$P(O)_2NR^aR^b$, —$P(O)OR^a$, —$P(O)_2OR^a$, —CN, or —$NO_2$, or $R^1$ and $R^2$ taken together with the carbon or carbons to which they are attached form a $C_3$-$C_6$ cycloalkyl or a 4- to 6-membered heterocycloalkyl, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, mono- or bicyclic heteroaryl, 4- to 6-membered heterocycloalkyl is independently optionally substituted by deuterium, halogen, $C_1$-$C_6$ alkyl, $C_1$-$C_6$ haloalkyl, $C_3$-$C_6$ cycloalkyl, 3- to 7-membered heterocycloalkyl, —$OR^e$, —$OC(O)R^e$, —$OC(O)NR^eR^f$, —$OC(=N)NR^eR^f$, —$OS(O)R^e$, —$OS(O)_2R^e$, —$OS(O)NR^eR^f$, —$OS(O)_2NR^eR^f$, —$SR^e$, —$S(O)R^e$, —$S(O)_2R^e$, —$S(O)NR^eR^f$, —$S(O)_2NR^eR^f$, —$NR^eR^f$, —$NR^eC(O)R^f$, —$NR^eC(O)OR^f$, —$NR^eC(O)NR^eR^f$, —$NR^eS(O)R^f$, —$NR^eS(O)_2R^f$, —$NR^eS(O)NR^eR^f$, —$NR^eS(O)_2NR^eR^f$, —$C(O)R^e$, —$C(O)OR^e$, —$C(O)NR^eR^f$, —$PR^eR^f$, —$P(O)R^eR^f$, —$P(O)_2R^eR^f$, —$P(O)NR^eR^f$, —$P(O)_2NR^eR^f$, —$P(O)OR^e$, —$P(O)_2OR^e$, —CN, or —$NO_2$;

M is $CR^3$ or N;

$M^1$ is $CR^4$;

each $R^3$, $R^4$, and $R^5$ is independently hydrogen, deuterium, halogen, —$OR^c$, —$OC(O)R^c$, —$OC(O)NR^cR^d$, —$OC(=N)NR^cR^d$, —$OS(O)R^c$, —$OS(O)_2R^c$, —$OS(O)NR^cR^d$, —$OS(O)_2NR^cR^d$, —$SR^c$, —$S(O)R^c$, —$S(O)_2R^c$, —$S(O)NR^cR^d$, —$S(O)_2NR^cR^d$, —$NR^cR^d$, —$NR^cC(O)R^d$, —$NR^cC(O)OR^d$, —$NR^cC(O)NR^cR^d$, —$NR^cC(=N)NR^cR^d$, —$NR^cS(O)R^d$, —$NR^cS(O)_2R^d$, —$NR^cS(O)NR^cR^d$, —$NR^cS(O)_2NR^cR^d$, —$C(O)R^c$, —$C(O)OR^c$, —$C(O)NR^cR^d$, —$C(=N)NR^cR^d$, —$PR^cR^d$, —$P(O)R^cR^d$, —$P(O)_2R^cR^d$, —$P(O)NR^cR^d$, —$P(O)_2NR^cR^d$, —$P(O)OR^c$, —$P(O)_2OR^c$, —CN, —$NO_2$, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl, or $R^4$ and $R^5$ taken together with the ring to which they are attached form a $C_5$-$C_8$ cycloalkyl, or a 5- to 8-membered heterocycloalkyl, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, mono- or bicyclic heteroaryl, $C_5$-$C_8$ cycloalkyl, or 5- to 8-membered heterocycloalkyl is independently optionally substituted by deuterium, halogen, $C_1$-$C_6$ alkyl, $C_1$-$C_6$ haloalkyl, —$OR^e$, —$OC(O)R^e$, —$OC(O)NR^eR^f$, —$OC(=N)NR^eR^f$, —$OS(O)R^e$, —$OS(O)_2R^e$, —$OS(O)NR^eR^f$, —$OS(O)_2NR^eR^f$, —$SR^e$, —$S(O)R^e$, —$S(O)_2R^e$, —$S(O)NR^eR^f$, —$S(O)_2NR^eR^f$, —$NR^eR^f$, —$NR^eC(O)R^f$, —$NR^eC(O)OR^f$, —$NR^eC(O)NR^eR^f$, —$NR^eS(O)R^f$, —$NR^eS(O)_2R^f$, —$NR^eS(O)NR^eR^f$, —$NR^eS(O)_2NR^eR^f$, —$C(O)R^e$, —$C(O)OR^e$, —$C(O)NR^eR^f$, —$PR^eR^f$, —$P(O)R^eR^f$, —$P(O)_2R^eR^f$, —$P(O)NR^eR^f$, —$P(O)_2NR^eR^f$, —$P(O)OR^e$, —$P(O)_2OR^e$, —CN, or —$NO_2$;

$R^6$ is H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, $C_3$-$C_6$ cycloalkyl, or 5- to 7-membered heterocycloalkyl, —$OR^e$, —$OC(O)R^e$, —$OC(O)NR^eR^f$, —$OC(=N)NR^eR^f$, —$OS(O)R^e$, —$OS(O)_2R^e$, —$OS(O)NR^eR^f$, —$OS(O)_2NR^eR^f$, —$SR^e$, —$S(O)R^e$, —$S(O)_2R^e$, —$S(O)NR^eR^f$, —$S(O)_2NR^eR^f$, —$NR^eR^f$, —$NR^eC(O)R^f$, —$NR^eC(O)OR^f$, —$NR^eC(O)NR^eR^f$, —$NR^eS(O)R^f$, —$NR^eS(O)_2R^f$, —$NR^eS(O)NR^eR^f$, —$NR^eS(O)_2NR^eR^f$, —$C(O)R^e$, —$C(O)OR^e$, —$C(O)NR^eR^f$, —$PR^eR^f$, —$P(O)R^eR^f$, —$P(O)_2R^eR^f$, —$P(O)NR^eR^f$, —$P(O)_2NR^eR^f$, —$P(O)OR^e$, —$P(O)_2OR^e$, —CN, or —$NO_2$;

$R^7$ and $R^8$ combine to form a $C_3$-$C_7$ cycloalkyl, a 5- to 8-membered heterocycloalkyl, $C_6$-$C_{10}$ aryl, or 5- to 7-membered heteroaryl; wherein each hydrogen atom in $C_3$-$C_7$ cycloalkyl, a 5- to 8-membered heterocycloalkyl, $C_6$-$C_{10}$ aryl, or 5- to 7-membered heteroaryl is independently optionally substituted by deuterium, halogen, —$OR^e$, —$OC(O)R^e$, —$OC(O)NR^eR^f$, —$OC(=N)NR^eR^f$, —$OS(O)R^e$, —$OS(O)_2R^e$, —$OS(O)NR^eR^f$, —$OS(O)_2NR^eR^f$, —$SR^e$, —$S(O)R^e$, —$S(O)_2R^e$, —$S(O)NR^eR^f$, —$S(O)_2NR^eR^f$, —$NR^eR^f$, —$NR^eC(O)R^f$, —$NR^eC(O)OR^f$, —$NR^eC(O)NR^eR^f$, —$NR^eS(O)R^f$, —$NR^eS(O)_2R^f$, —$NR^eS(O)NR^eR^f$, —$NR^eS(O)_2NR^eR^f$, —$C(O)R^e$, —$C(O)OR^e$, —$C(O)NR^eR^f$, —$PR^eR^f$, —$P(O)R^eR^f$, —$P(O)_2R^eR^f$, —$P(O)NR^eR^f$, —$P(O)_2NR^eR^f$, —$P(O)OR^e$, —$P(O)_2OR^e$, —CN, or —$NO_2$;

Y is O, S, $NR^9$, or $CR^9R^{10}$;

$R^9$ and $R^{10}$ are each independently H, deuterium, halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is optionally substituted by a halogen, —$OR^e$, —$OC(O)R^e$, —$OC(O)NR^eR^f$, —$OC(=N)NR^eR^f$, —$OS(O)R^e$, —$OS(O)_2R^e$, —$OS(O)NR^eR^f$, —$OS(O)_2NR^eR^f$, —$SR^e$, —$S(O)R^e$, —$S(O)_2R^e$, —$S(O)NR^eR^f$, —$S(O)_2NR^eR^f$, —$NR^eR^f$, —$NR^eC(O)R^f$, —$NR^eC(O)OR^f$, —$NR^eC(O)NR^eR^f$, —$NR^eS(O)R^f$, —$NR^eS(O)_2R^f$, —$NR^eS(O)NR^eR^f$, —$NR^eS(O)_2NR^eR^f$, —$C(O)R^e$, —$C(O)OR^e$, —$C(O)NR^eR^f$, —$PR^eR^f$, —$P(O)R^eR^f$, —$P(O)_2R^eR^f$, —$P(O)NR^eR^f$, —$P(O)_2NR^eR^f$, —$P(O)OR^e$, or —$P(O)_2OR^e$;

each $R^a$, $R^b$, $R^c$, $R^d$, $R^e$, and $R^f$ is independently selected from the group consisting of H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl;

each of $Z^1$, $Z^2$, $Z^3$, $Z^4$, $Z^5$, and $Z^6$ is independently N, NH, C or CH;

p is 1, 2, 3, or 4; and t is 1, 2, 3, 4, or 5;

or a pharmaceutically acceptable salt thereof.

In another aspect, the disclosure relates to a compound or a pharmaceutically acceptable salt thereof, having the formula II

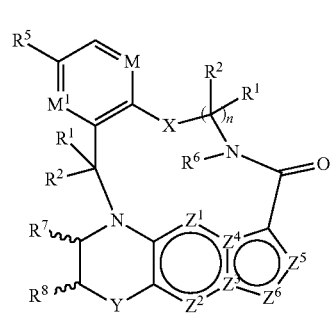

II wherein

M is $CR^3$ or N;

$M^1$ is $CR^4$;

X is O, S, S(O), or $S(O)_2$;

each $R^1$ and $R^2$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —$OR^a$, —$SR^a$, —$NR^aR^b$, —$C(O)OR^a$, —$C(O)NR^aR^b$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —$OC_1$-$C_6$ alkyl, —$NH_2$, —$OC(O)C_1$-$C_6$ alkyl, —$OC(O)N(C_1$-$C_6$ alkyl$)_2$, —$OC(O)NH(C_1$-$C_6$ alkyl), —OC(O)NH₂, —OC(=N)N(C₁-C₆ alkyl)₂, —OC(=N)NH(C₁-C₆ alkyl), —OC(=N)NH₂, —OS(O)C₁-C₆ alkyl, —OS(O)₂C₁-C₆ alkyl, —NH(C₁-C₆ alkyl), —N(C₁-C₆ alkyl)₂, —NHC(O)C₁-C₆ alkyl, —N(C₁-C₆ alkyl)C(O)C₁-C₆ alkyl, —NHC(O)NH₂, —NHC(O)NH(C₁-C₆ alkyl), —N(C₁-C₆ alkyl)C(O)NH₂, —N(C₁-C₆ alkyl)C(O)NH(C₁-C₆ alkyl), —NHC(O)N(C₁-C₆ alkyl)₂, —N(C₁-C₆ alkyl)C(O)N(C₁-C₆ alkyl)₂, —NHC(O)OC₁-C₆ alkyl, —N(C₁-C₆ alkyl)C(O)OC₁-C₆ alkyl, —NHC(O)OH, —N(C₁-C₆ alkyl)C(O)OH, —NHS(O)C₁-C₆ alkyl, —NHS(O)₂C₁-C₆ alkyl, —N(C₁-C₆ alkyl)S(O)C₁-C₆ alkyl, —N(C₁-C₆ alkyl)S(O)₂C₁-C₆ alkyl. —NHS(O)NH₂, —NHS(O)₂NH₂, —N(C₁-C₆ alkyl)S(O)NH₂, —N(C₁-C₆ alkyl)S(O)₂NH₂, —NHS(O)NH(C₁-C₆ alkyl), —NHS(O)₂NH(C₁-C₆ alkyl), —NHS(O)N(C₁-C₆ alkyl)₂, —NHS(O)₂N(C₁-C₆ alkyl)₂, —N(C₁-C₆ alkyl)S(O)NH(C₁-C₆ alkyl), —N(C₁-C₆ alkyl)S(O)₂NH(C₁-C₆ alkyl), —N(C₁-C₆ alkyl)S(O)N(C₁-C₆ alkyl)₂, —N(C₁-C₆ alkyl)S(O)₂N(C₁-C₆ alkyl)₂, —C(O)C₁-C₆ alkyl, —CO₂H, —C(O)OC₁-C₆ alkyl, —C(O)NH₂, —C(O)NH(C₁-C₆ alkyl), —C(O)N(C₁-C₆ alkyl)₂, —SC₁-C₆ alkyl, —S(O)C₁-C₆ alkyl, —S(O)₂C₁-C₆ alkyl, —S(O)NH(C₁-C₆ alkyl), —S(O)₂ NH(C₁-C₆ alkyl), —S(O)N(C₁-C₆ alkyl)₂, —S(O)₂N(C₁-C₆ alkyl)₂, —S(O)NH₂, —S(O)₂NH₂, —OS(O)N(C₁-C₆ alkyl)₂, —OS(O)₂N(C₁-C₆ alkyl)₂, —OS(O)NH(C₁-C₆ alkyl), —OS(O)₂NH(C₁-C₆ alkyl), —OS(O)NH₂, —OS(O)₂NH₂, —P(C₁-C₆ alkyl)₂, —P(O)(C₁-C₆ alkyl)₂, C₃-C₆ cycloalkyl, or 3- to 7-membered heterocycloalkyl;

R³, R⁴, and R⁵ are each independently H, fluoro, chloro, bromo, C₁-C₆ alkyl, —OH, —CN, —OC₁-C₆ alkyl, —NHC₁-C₆ alkyl, —N(C₁-C₆ alkyl)₂ or —CF₃;

R⁶ is H, C₁-C₆ alkyl or 3- to 7-membered heterocycloalkyl, wherein each hydrogen atom in C₁-C₆ alkyl or 3- to 7-membered heterocycloalkyl is independently optionally substituted by halogen, —OH, —CN, —OC₁-C₆ alkyl, —NH₂, —NH(C₁-C₆ alkyl), —N(C₁-C₆ alkyl)₂, —CO₂H, —C(O)OC₁-C₆ alkyl, —C(O)NH₂, —C(O)NH(C₁-C₆ alkyl), —C(O)N(C₁-C₆ alkyl)₂, C₃-C₆ cycloalkyl, or monocyclic 5- to 7-membered heterocycloalkyl;

R⁷ and R⁸ combine to form a C₃-C₇ cycloalkyl, a 5- to 8-membered heterocycloalkyl, C₆-C₁₀ aryl, or 5- to 7-membered heteroaryl; wherein each hydrogen atom in C₃-C₇ cycloalkyl, a 5- to 8-membered heterocycloalkyl, C₆-C₁₀ aryl, or 5- to 7-membered heteroaryl is independently optionally substituted by deuterium, halogen, —OH, —OC₁-C₆ alkyl, —OC(O)C₁-C₆ alkyl, —OC(O)NH₂, —OC(O)NH(C₁-C₆ alkyl), —OC(O)N(C₁-C₆ alkyl)₂, —OC(=N)NH₂, —OC(=N)NH(C₁-C₆ alkyl), —OC(=N)N(C₁-C₆ alkyl)₂, —OS(O)C₁-C₆ alkyl, —OS(O)₂C₁-C₆ alkyl, —OS(O)NH₂, —OS(O)NH(C₁-C₆ alkyl), —OS(O)N(C₁-C₆ alkyl)₂, —OS(O)₂NH₂, —OS(O)₂NH(C₁-C₆ alkyl), —OS(O)₂N(C₁-C₆ alkyl)₂, —SH, —SC₁-C₆ alkyl, —S(O)C₁-C₆ alkyl, —S(O)₂C₁-C₆ alkyl, —S(O)NH₂, —S(O)NH(C₁-C₆ alkyl), —S(O)(C₁-C₆ alkyl)₂, —S(O)₂NH₂, —S(O)₂NH(C₁-C₆ alkyl), —S(O)₂N(C₁-C₆ alkyl)₂, —NH₂, —NH(C₁-C₆ alkyl), —N(C₁-C₆ alkyl)₂, —NHC(O)C₁-C₆ alkyl, —N(C₁-C₆ alkyl)C(O)C₁-C₆ alkyl, —NHC(O)OH, —NHC(O)OC₁-C₆ alkyl, —N(C₁-C₆ alkyl)C(O)OH, —N(C₁-C₆ alkyl)C(O)OC₁-C₆ alkyl, —NHC(O)NH₂, —NHC(O)NH(C₁-C₆ alkyl), —NHC(O)N(C₁-C₆ alkyl)₂, —N(C₁-C₆ alkyl)C(O)NH₂, —N(C₁-C₆ alkyl)C(O)NH(C₁-C₆ alkyl), —N(C₁-C₆ alkyl)C(O)N(C₁-C₆ alkyl)₂, —NHS(O)C₁-C₆ alkyl, —N(C₁-C₆ alkyl)S(O)C₁-C₆ alkyl, —NHS(O)₂C₁-C₆ alkyl, —N(C₁-C₆ alkyl)S(O)₂C₁-C₆ alkyl, —N(C₁-C₆ alkyl)S(O)NH(C₁-C₆ alkyl), —N(C₁-C₆ alkyl)S(O)₂NH(C₁-C₆ alkyl), —N(C₁-C₆ alkyl)S(O)NH₂, —N(C₁-C₆ alkyl)S(O)₂NH₂, —NHS(O)NH(C₁-C₆ alkyl), —NHS(O)₂NH(C₁-C₆ alkyl), —N(C₁-C₆ alkyl)S(O)NH(C₁-C₆ alkyl), —N(C₁-C₆ alkyl)S(O)₂NH(C₁-C₆ alkyl), —N(C₁-C₆ alkyl)S(O)₂NH₂, —NHS(O)₂N(C₁-C₆ alkyl)₂, —NHS(O)₂NH(C₁-C₆ alkyl), —NHS(O)₂NH₂, —C(O)C₁-C₆ alkyl, —C(O)OC₁-C₆ alkyl, —C(O)N(C₁-C₆ alkyl)₂, —C(O)NH(C₁-C₆ alkyl), —C(O)NH₂, —P(C₁-C₆ alkyl)₂, —P(O)(C₁-C₆ alkyl)₂, —P(O)₂(C₁-C₆ alkyl)₂, —P(O)N(C₁-C₆ alkyl)₂, —P(O)₂N(C₁-C₆ alkyl)₂, —P(O)OC₁-C₆ alkyl, or —P(O)₂OC₁-C₆ alkyl;

each of Z¹, Z², Z³, Z⁴, Z⁵, and Z⁶ is independently N, NH, C or CH; and n is 2 or 3.

In another aspect, the disclosure relates to a compound selected from the group consisting of

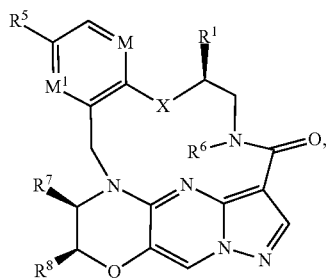

-continued

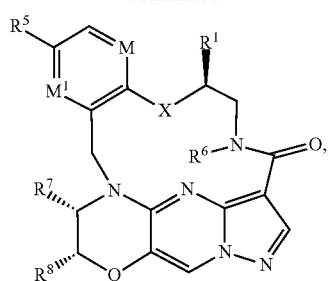

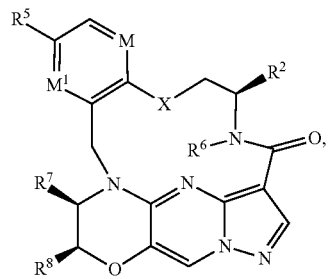

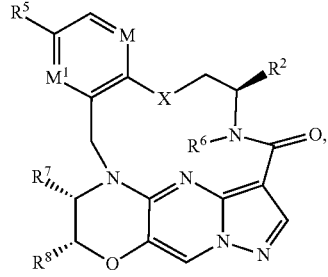

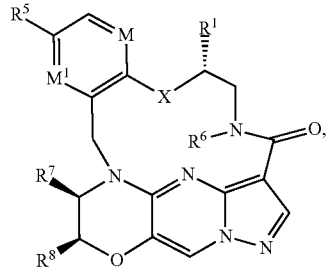

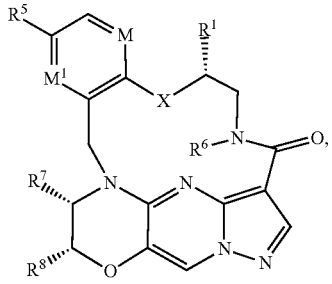

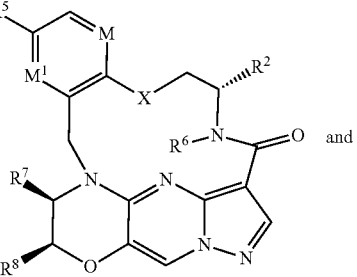 and

-continued

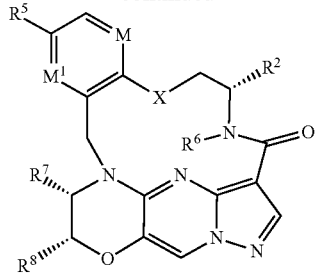

wherein

M is $CR^3$ or N;

$M^1$ is $CR^4$;

X is O, S, S(O), or $S(O)_2$;

$R^1$ and $R^2$ are each independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —$OR^a$, —$SR^a$, —$NR^aR^b$, —C(O)$OR^a$, —C(O)$NR^aR^b$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —$OC_1$-$C_6$ alkyl, —$OC_1$-$C_6$ alkyl($C_6$-$C_{10}$ aryl), —$NH_2$, —OC(O)$C_1$-$C_6$ alkyl, —OC(O)N($C_1$-$C_6$ alkyl)$_2$, —OC(O)NH($C_1$-$C_6$ alkyl), —OC(O)$NH_2$, —OC(=N)N($C_1$-$C_6$ alkyl)$_2$, —OC(=N)NH($C_1$-$C_6$ alkyl), —OC(=N)$NH_2$, —OS(O)$C_1$-$C_6$ alkyl, —$OS(O)_2C_1$-$C_6$ alkyl, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)$NH_2$, —NHC(O)NH($C_1$-$C_6$ alkyl), —N($C_1$-$C_6$ alkyl)C(O)$NH_2$, —N($C_1$-$C_6$ alkyl)C(O)NH($C_1$-$C_6$ alkyl), —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHC(O)OH, —N($C_1$-$C_6$ alkyl)C(O)OH, —NHS(O)$C_1$-$C_6$ alkyl, —$NHS(O)_2C_1$-$C_6$ alkyl, —N($C_1$-$C_6$ alkyl)S(O)$C_1$-$C_6$ alkyl, —N($C_1$-$C_6$ alkyl)$S(O)_2C_1$-$C_6$ alkyl. —NHS(O)$NH_2$, —$NHS(O)_2NH_2$, —N($C_1$-$C_6$ alkyl)S(O)$NH_2$, —N($C_1$-$C_6$ alkyl)$S(O)_2NH_2$, —NHS(O)NH($C_1$-$C_6$ alkyl), —$NHS(O)_2$NH($C_1$-$C_6$ alkyl), —NHS(O)N($C_1$-$C_6$ alkyl)$_2$, —$NHS(O)_2$N($C_1$-$C_6$ alkyl)$_2$, —N($C_1$-$C_6$ alkyl)S(O)NH($C_1$-$C_6$ alkyl), —N($C_1$-$C_6$ alkyl)$S(O)_2$NH($C_1$-$C_6$ alkyl), —N($C_1$-$C_6$ alkyl)S(O)N($C_1$-$C_6$ alkyl)$_2$, —N($C_1$-$C_6$ alkyl)$S(O)_2$N($C_1$-$C_6$ alkyl)$_2$, —C(O)$C_1$-$C_6$ alkyl, —$CO_2$H, —C(O)O$C_1$-$C_6$ alkyl, —C(O)$NH_2$, —C(O)NH($C_1$-$C_6$ alkyl), —C(O)N($C_1$-$C_6$ alkyl)$_2$, —$SC_1$-$C_6$ alkyl, —S(O)$C_1$-$C_6$ alkyl, —$S(O)_2C_1$-$C_6$ alkyl, —S(O)NH($C_1$-$C_6$ alkyl), —$S(O)_2$NH($C_1$-$C_6$ alkyl), —S(O)N($C_1$-$C_6$ alkyl)$_2$, —$S(O)_2$N($C_1$-$C_6$ alkyl)$_2$, —S(O)$NH_2$, —$S(O)_2NH_2$, —OS(O)N($C_1$-$C_6$ alkyl)$_2$, —$OS(O)_2$N($C_1$-$C_6$ alkyl)$_2$, —OS(O)NH($C_1$-$C_6$ alkyl), —$OS(O)_2$NH($C_1$-$C_6$ alkyl), —OS(O)$NH_2$, —$OS(O)_2NH_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

$R^3$, $R^4$, and $R^5$ are each independently H, fluoro, chloro, bromo, $C_1$-$C_6$ alkyl, —OH, —CN, —$OC_1$-$C_6$ alkyl, —$NHC_1$-$C_6$ alkyl, —N($C_1$-$C_6$ alkyl)$_2$ or —$CF_3$;

$R^6$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —$OC_1$-$C_6$ alkyl, —$NH_2$, —NH($C_1$-$C_6$ alkyl), —N($C_1$-$C_6$ alkyl)$_2$, —$CO_2$H, —C(O)O$C_1$-$C_6$ alkyl, —C(O)$NH_2$, —C(O)NH($C_1$-$C_6$ alkyl), —C(O)N($C_1$-$C_6$ alkyl)$_2$, $C_3$-$C_6$ cycloalkyl, or monocyclic 5- to 7-membered heterocycloalkyl;

$R^7$ and $R^8$ combine to form a $C_3$-$C_7$ cycloalkyl, a 5- to 8-membered heterocycloalkyl, $C_6$-$C_{10}$ aryl, or 5- to 7-membered heteroaryl; wherein each hydrogen atom in $C_3$-$C_7$ cycloalkyl, a 5- to 8-membered heterocycloalkyl, $C_6$-$C_{10}$ aryl, or 5- to 7-membered heteroaryl is independently optionally substituted by deuterium, halogen, —OH, —$OC_1$-$C_6$ alkyl, —OC(O)$C_1$-$C_6$ alkyl, —OC(O)NH$_2$, —OC(O)NH($C_1$-$C_6$ alkyl), —OC(O)N($C_1$-$C_6$ alkyl)$_2$, —OC(=N)NH$_2$, —OC(=N)NH($C_1$-$C_6$ alkyl), —OC(=N)N($C_1$-$C_6$ alkyl)$_2$, —OS(O)$C_1$-$C_6$ alkyl, —OS(O)$_2C_1$-$C_6$ alkyl, —OS(O)NH$_2$, —OS(O)NH($C_1$-$C_6$ alkyl), —OS(O)N($C_1$-$C_6$ alkyl)$_2$, —OS(O)$_2$NH$_2$, —OS(O)$_2$NH($C_1$-$C_6$ alkyl), —OS(O)$_2$N($C_1$-$C_6$ alkyl)$_2$, —SH, —S$C_1$-$C_6$ alkyl, —S(O)$C_1$-$C_6$ alkyl, —S(O)$_2C_1$-$C_6$ alkyl, —S(O)NH$_2$, —S(O)NH($C_1$-$C_6$ alkyl), —S(O)($C_1$-$C_6$ alkyl)$_2$, —S(O)$_2$NH$_2$, —S(O)$_2$NH($C_1$-$C_6$ alkyl), —S(O)$_2$N($C_1$-$C_6$ alkyl)$_2$, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)OH, —NHC(O)O$C_1$-$C_6$ alkyl, —N($C_1$-$C_6$ alkyl)C(O)OH, —N($C_1$-$C_6$ alkyl)C(O)O$C_1$-$C_6$ alkyl, —NHC(O)NH$_2$, —NHC(O)NH($C_1$-$C_6$ alkyl), —NHC(O)N($C_1$-$C_6$ alkyl)$_2$, —N($C_1$-$C_6$ alkyl)C(O)NH$_2$, —N($C_1$-$C_6$ alkyl)C(O)NH($C_1$-$C_6$ alkyl), —N($C_1$-$C_6$ alkyl)C(O)N($C_1$-$C_6$ alkyl)$_2$, —NHS(O)$C_1$-$C_6$ alkyl, —N($C_1$-$C_6$ alkyl)S(O)$C_1$-$C_6$ alkyl, —NHS(O)$_2C_1$-$C_6$ alkyl, —N($C_1$-$C_6$ alkyl)S(O)$_2C_1$-$C_6$ alkyl, —NHS(O)NH$_2$, —NHS(O)NH($C_1$-$C_6$ alkyl), —NHS(O)N($C_1$-$C_6$ alkyl)$_2$, —N($C_1$-$C_6$ alkyl)S(O)NH$_2$, —N($C_1$-$C_6$ alkyl)S(O)NH($C_1$-$C_6$ alkyl), —N($C_1$-$C_6$ alkyl)S(O)N($C_1$-$C_6$ alkyl)$_2$, —NHS(O)$_2$NH$_2$, —NHS(O)$_2$NH($C_1$-$C_6$ alkyl), —NHS(O)$_2$N($C_1$-$C_6$ alkyl)$_2$, —N($C_1$-$C_6$ alkyl)S(O)$_2$NH$_2$, —N($C_1$-$C_6$ alkyl)S(O)$_2$NH($C_1$-$C_6$ alkyl), —N($C_1$-$C_6$ alkyl)S(O)$_2$N($C_1$-$C_6$ alkyl)$_2$, —C(O)$C_1$-$C_6$ alkyl, —C(O)O$C_1$-$C_6$ alkyl, —C(O)NH$_2$, —C(O)NH($C_1$-$C_6$ alkyl), —C(O)N($C_1$-$C_6$ alkyl)$_2$, —P($C_1$-$C_6$ alkyl)$_2$, —P(O)($C_1$-$C_6$ alkyl)$_2$, —P(O)$_2$($C_1$-$C_6$ alkyl)$_2$, —P(O)NH$_2$, —P(O)NH($C_1$-$C_6$ alkyl), —P(O)N($C_1$-$C_6$ alkyl)$_2$, —P(O)$_2$NH$_2$, —P(O)$_2$NH($C_1$-$C_6$ alkyl), —P(O)$_2$N($C_1$-$C_6$ alkyl)$_2$, —P(O)OH, —P(O)O$C_1$-$C_6$ alkyl, —P(O)$_2$OH, —P(O)$_2$O$C_1$-$C_6$ alkyl, —CN, or —NO$_2$;

Y is O, S, NR$^9$, or CR$^9$R$^{10}$; and

R$^9$ and R$^{10}$ are each independently H, deuterium, halogen, or $C_1$-$C_6$ alkyl, wherein each hydrogen atom in $C_1$-$C_6$ alkyl is optionally substituted by a halogen, —OH, —O$C_1$-$C_6$ alkyl, —OC(O)$C_1$-$C_6$ alkyl, —OC(O)N($C_1$-$C_6$ alkyl)$_2$, —OC(O)NH($C_1$-$C_6$ alkyl), —OC(O)NH$_2$, —OC(=N)N($C_1$-$C_6$ alkyl)$_2$, —OC(=N)NH($C_1$-$C_6$ alkyl), —OC(=N)NH$_2$, —OS(O)$C_1$-$C_6$ alkyl, —OS(O)$_2C_1$-$C_6$ alkyl, —OS(O)N($C_1$-$C_6$ alkyl)$_2$, —OS(O)NH($C_1$-$C_6$ alkyl), —OS(O)NH$_2$, —OS(O)$_2$N($C_1$-$C_6$ alkyl)$_2$, —OS(O)$_2$NH($C_1$-$C_6$ alkyl), —OS(O)$_2$NH$_2$, —SH, —S$C_1$-$C_6$ alkyl, —S(O)$C_1$-$C_6$ alkyl, —S(O)$_2C_1$-$C_6$ alkyl, —S(O)N($C_1$-$C_6$ alkyl)$_2$, —S(O)NH($C_1$-$C_6$ alkyl), —S(O)NH$_2$, —S(O)$_2$N($C_1$-$C_6$ alkyl)$_2$, —S(O)$_2$NH($C_1$-$C_6$ alkyl), —S(O)$_2$NH$_2$, —N($C_1$-$C_6$ alkyl)$_2$, —NH($C_1$-$C_6$ alkyl), —NH$_2$, —N($C_1$-$C_6$ alkyl)C(O)$C_1$-$C_6$ alkyl, —NHC(O)$C_1$-$C_6$ alkyl, —N($C_1$-$C_6$ alkyl)C(O)O$C_1$-$C_6$ alkyl, —N($C_1$-$C_6$ alkyl)C(O)OH, —NHC(O)O$C_1$-$C_6$ alkyl, —NHC(O)OH, —N($C_1$-$C_6$ alkyl)C(O)N($C_1$-$C_6$ alkyl)$_2$, —N($C_1$-$C_6$ alkyl)C(O)NH($C_1$-$C_6$ alkyl), —N($C_1$-$C_6$ alkyl)C(O)NH$_2$, —NHC(O)N($C_1$C_6$ alkyl)$_2$, —NHC(O)NH($C_1$C_6$ alkyl), —NHC(O)NH$_2$, —N($C_1$-$C_6$ alkyl)S(O)$C_1$-$C_6$ alkyl, —NHS(O)$C_1$-$C_6$ alkyl, —N($C_1$-$C_6$ alkyl)S(O)$_2C_1$-$C_6$ alkyl, —NHS(O)$_2C_1$-$C_6$ alkyl, —N($C_1$-$C_6$ alkyl)S(O)N($C_1$-$C_6$ alkyl)$_2$, —N($C_1$-$C_6$ alkyl)S(O)NH($C_1$-$C_6$ alkyl), —N($C_1$-$C_6$ alkyl)S(O)NH$_2$, —NHS(O)N($C_1$-$C_6$ alkyl)$_2$, —NHS(O)NH($C_1$-$C_6$ alkyl), —NHS(O)NH$_2$, —N($C_1$-$C_6$ alkyl)S(O)$_2$N($C_1$-$C_6$ alkyl)$_2$, —N($C_1$-$C_6$ alkyl)S(O)$_2$NH($C_1$-$C_6$ alkyl), —N($C_1$-$C_6$ alkyl)S(O)$_2$NH$_2$, —NHS(O)$_2$N($C_1$-$C_6$ alkyl)$_2$, —NHS(O)$_2$NH($C_1$-$C_6$ alkyl), —NHS(O)$_2$NH$_2$, —C(O)$C_1$-$C_6$ alkyl, —C(O)O$C_1$-$C_6$ alkyl, —C(O)N($C_1$-$C_6$ alkyl)$_2$, —C(O)NH($C_1$-$C_6$ alkyl), —C(O)NH$_2$, —P($C_1$-$C_6$ alkyl)$_2$, —P(O)($C_1$-$C_6$ alkyl)$_2$, —P(O)$_2$($C_1$-$C_6$ alkyl)$_2$, —P(O)N($C_1$-$C_6$ alkyl)$_2$, —P(O)$_2$N($C_1$-$C_6$ alkyl)$_2$, —P(O)O$C_1$-$C_6$ alkyl, or —P(O)$_2$O$C_1$-$C_6$ alkyl.

Additional embodiments, features, and advantages of the disclosure will be apparent from the following detailed description and through practice of the disclosure. The compounds of the present disclosure can be described as embodiments in any of the following enumerated clauses. It will be understood that any of the embodiments described herein can be used in connection with any other embodiments described herein to the extent that the embodiments do not contradict one another.

1. A compound of the formula I

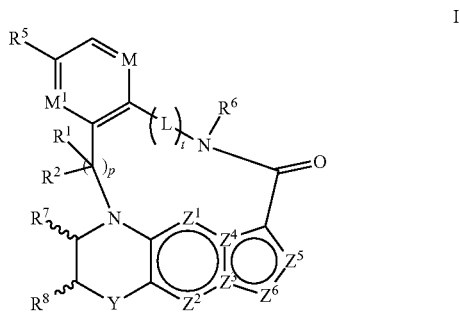

I wherein

L is independently —C(R$^1$)(R$^2$)— or X;

X is —O—, —S—, —S(O)— or —S(O)$_2$—;

each R$^1$ and R$^2$ is independently H, deuterium, halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl, —OR$^a$, —OC(O)R$^a$, —OC(O)R$^a$, —OC(O)NR$^a$R$^b$, —OS(O)R$^a$, —OS(O)$_2$R$^a$, —SR$^a$, —S(O)R$^a$, —S(O)$_2$R$^a$, —S(O)NR$^a$R$^b$, —S(O)$_2$NR$^a$R$^b$, —OS(O)NR$^a$R$^b$, —OS(O)$_2$NR$^a$R$^b$, —NR$^a$R$^b$, —NR$^a$C(O)R$^b$, —NR$^a$C(O)OR$^b$, —NR$^a$C(O)NR$^a$R$^b$, —NR$^a$S(O)R$^b$, —NR$^a$S(O)$_2$R$^b$, —NR$^a$S(O)NR$^a$R$^b$, —NR$^a$S(O)$_2$NR$^a$R$^b$, —C(O)R$^a$, —C(O)OR$^a$, —C(O)NR$^a$R$^b$, —PR$^a$R$^b$, —P(O)R$^a$R$^b$, —P(O)$_2$R$^a$R$^b$, —P(O)NR$^a$R$^b$, —P(O)$_2$NR$^a$R$^b$, —P(O)OR$^a$, —P(O)$_2$OR$^a$, —CN, or —NO$_2$, or R$^1$ and R$^2$ taken together with the carbon or carbons to which they are attached form a $C_3$-$C_6$ cycloalkyl or a 4- to 6-membered heterocycloalkyl, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, mono- or bicyclic heteroaryl, 4- to 6-membered heterocycloalkyl is independently optionally substituted by deuterium, halogen, $C_1$-$C_6$ alkyl, $C_1$-$C_6$ haloalkyl, —OR$^e$, —OC(O)R$^e$, —OC(O)NR$^e$R$^f$, —OC(=N)NR$^e$R$^f$, —OS(O)R$^e$, —OS(O)$_2$R$^e$, —OS(O)NR$^e$R$^f$, —OS(O)$_2$NR$^e$R$^f$, —SR$^e$, —S(O)R$^e$, —S(O)$_2$R$^e$, —S(O)NR$^e$R$^f$, —S(O)$_2$NR$^e$R$^f$, —NR$^e$R$^f$, —NR$^e$C(O)R$^f$, —NR$^e$C(O)OR$^f$, —NR$^e$C(O)NR$^e$R$^f$, —NR$^e$S(O)R$^f$, —NR$^e$S(O)$_2$R$^f$, —NR$^e$S(O)NR$^e$R$^f$, —NR$^e$S(O)$_2$NR$^e$R$^f$, —C(O)R$^e$, —C(O)OR$^e$, —C(O)NR$^e$R$^f$, —PR$^e$R$^f$, —P(O)R$^e$R$^f$, —P(O)$_2$R$^e$R$^f$, —P(O)NR$^e$R$^f$, —P(O)$_2$NR$^e$R$^f$, —P(O)OR$^e$, —P(O)$_2$OR$^e$, —CN, or —NO$_2$;

M is CR$^3$ or N;

M$^1$ is CR$^4$;

each R$^3$, R$^4$, and R$^5$ is independently hydrogen, deuterium, halogen, —OR$^c$, —OC(O)R$^c$, —OC(O)NR$^c$R$^d$, —OC(=N)NR$^c$R$^d$, —OS(O)R$^c$, —OS(O)$_2$R$^c$, —OS(O)NR$^c$R$^d$, —OS(O)$_2$NR$^c$R$^d$, —SR$^c$, —S(O)R$^c$, —S(O)$_2$R$^c$, —S(O)NR$^c$R$^d$, —S(O)$_2$NR$^c$R$^d$, —NR$^c$R$^d$, —NR$^c$C(O)R$^d$, —NR$^c$C (O)OR$^d$, —NR$^c$C(O)NR$^c$R$^d$, —NR$^c$C(=N)NR$^c$R$^d$, —NR$^c$S(O)R$^d$, —NR$^c$S(O)$_2$R$^d$, —NR$^c$S(O)NR$^c$R$^d$, —NR$^c$S(O)$_2$NR$^c$R$^d$, —C(O)R$^c$, —C(O)OR$^c$, —C(O)NR$^c$R$^d$, —C(=N)NR$^c$R$^d$, —PR$^c$R$^d$, —P(O)R$^c$R$^d$, —P(O)$_2$R$^c$R$^d$, —P(O)NR$^c$R$^d$, —P(O)$_2$NR$^c$R$^d$, —P(O)OR$^c$, —P(O)$_2$OR$^c$, —CN, —NO$_2$, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl, or R$^4$ and R$^5$ taken together with the ring to which they are attached form a C$_5$-C$_8$ cycloalkyl, or a 5- to 8-membered heterocycloalkyl, wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, mono- or bicyclic heteroaryl, C$_5$-C$_8$ cycloalkyl, or 5- to 8-membered heterocycloalkyl is independently optionally substituted by deuterium, halogen, C$_1$-C$_6$ alkyl, C$_1$-C$_6$ haloalkyl, —OR$^e$, —OC(O)R$^e$, —OC(O)NR$^e$R$^f$, —OC(=N)NR$^e$R$^f$, —OS(O)R$^e$, —OS(O)$_2$R$^e$, —OS(O)NR$^e$R$^f$, —OS(O)$_2$NR$^e$R$^f$, —SR$^e$, —S(O)R$^e$, —S(O)$_2$R$^e$, —S(O)NR$^e$R$^f$, —S(O)$_2$NR$^e$R$^f$, —NR$^e$R$^f$, —NR$^e$C(O)R$^f$, —NR$^e$C(O)OR$^f$, —NR$^e$C(O)NR$^e$CR$^f$, —NR$^e$S(O)R$^f$, —NR$^e$S(O)$_2$R$^f$, —NR$^e$S(O)NR$^e$R$^f$, —NR$^e$S(O)$_2$NR$^e$CR$^f$, —C(O)R$^e$, —C(O)OR$^e$, —C(O)NR$^e$R$^f$, —PR$^e$R$^f$, —P(O)R$^e$R$^f$, —P(O)$_2$R$^e$R$^f$, —P(O)NR$^e$R$^f$, —P(O)$_2$ NR$^e$R$^f$, —P(O)OR$^e$, —P(O)$_2$OR$^e$, —CN, or —NO$_2$;

R$^6$ is H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl, wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl is independently optionally substituted by deuterium, halogen, —OR$^e$, —OC(O)R$^e$, —OC(O)NR$^e$R$^f$, —OC(=N)NR$^e$R$^f$, —OS(O)R$^e$, —OS(O)$_2$R$^e$, —OS(O)NR$^e$R$^f$, —OS(O)$_2$NR$^e$R$^f$, —SR$^e$, —S(O)R$^e$, —S(O)$_2$R$^e$, —S(O)NR$^e$R$^f$, —S(O)$_2$NR$^e$R$^f$, —NR$^e$R$^f$, —NR$^e$C(O)R$^f$, —NR$^e$C(O)OR$^f$, —NR$^e$C(O)NR$^e$R$^f$, —NR$^e$S(O)R$^f$, —NR$^e$S(O)$_2$R$^f$, —NR$^e$S(O)NR$^e$R$^f$, —NR$^e$S(O)$_2$NR$^e$R$^f$, —C(O)R$^e$, —C(O)OR$^e$, —C(O)NR$^e$R$^f$, —PR$^e$R$^f$, —P(O)R$^e$R$^f$, —P(O)$_2$R$^e$R$^f$, —P(O)NR$^e$R$^f$, —P(O)$_2$ NR$^e$R$^f$, —P(O)OR$^e$, —P(O)$_2$OR$^e$, —CN, or —NO$_2$;

R$^7$ and R$^8$ combine to form a C$_3$-C$_7$ cycloalkyl, a 5- to 8-membered heterocycloalkyl, C$_6$-C$_{10}$ aryl, or 5- to 7-membered heteroaryl; wherein each hydrogen atom in C$_3$-C$_7$ cycloalkyl, a 5- to 8-membered heterocycloalkyl, C$_6$-C$_{10}$ aryl, or 5- to 7-membered heteroaryl is independently optionally substituted by deuterium, halogen, —OR$^e$, —OC(O)R$^e$, —OC(O)NR$^e$R$^f$, —OC(=N)NR$^e$R$^f$, —OS(O)R$^e$, —OS(O)$_2$R$^e$, —OS(O)NR$^e$R$^f$, —OS(O)$_2$NR$^e$R$^f$, —SR$^e$, —S(O)R$^e$, —S(O)$_2$R$^e$, —S(O)NR$^e$CR$^f$, —S(O)$_2$NR$^e$R$^f$, —NR$^e$R$^f$, —NR$^e$C(O)R$^f$, —NR$^e$C(O)OR$^f$, —NR$^e$C(O)NR$^e$R$^f$, —NR$^e$S(O)R$^f$, —NR$^e$S(O)$_2$R$^f$, —NR$^e$S(O)NR$^e$R$^f$, —NR$^a$S(O)$_2$NR$^e$R$^f$, —C(O)R$^e$, —C(O)OR$^e$, —C(O)NR$^e$R$^f$, —PR$^e$R$^f$, —P(O)R$^e$R$^f$, —P(O)$_2$R$^e$R$^f$, —P(O)NR$^e$R$^f$, —P(O)$_2$ NR$^e$R$^f$, —P(O)OR$^e$, —P(O)$_2$OR$^e$, —CN, or —NO$_2$;

Y is O, S, NR$^9$, or CR$^9$R$^{10}$;

R$^9$ and R$^{10}$ are each independently H, deuterium, halogen, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl, wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl is optionally substituted by a halogen, —OR$^e$, —OC(O)R$^e$, —OC(O)NR$^e$R$^f$, —OC(=N)NR$^e$R$^f$, —OS(O)R$^e$, —OS(O)$_2$R$^e$, —OS(O)NR$^e$R$^f$, —OS(O)$_2$NR$^e$R$^f$, —SR$^e$, —S(O)R$^e$, —S(O)$_2$R$^e$, —S(O)NR$^e$R$^f$, —S(O)$_2$NR$^e$R$^f$, —NR$^e$R$^f$, —NR$^e$C(O)R$^f$, —NR$^e$C(O)OR$^f$, —NR$^e$C(O)NR$^e$R$^f$, —NR$^e$S(O)R$^f$, —NR$^e$S(O)$_2$R$^f$, —NR$^e$S(O)NR$^e$R$^f$, —NR$^e$S(O)$_2$NR$^e$R$^f$, —C(O)R$^e$, —C(O)OR$^e$, —C(O)NR$^e$R$^f$, —PR$^e$R$^f$, —P(O)R$^e$R$^f$, —P(O)$_2$R$^e$R$^f$, —P(O)NR$^e$R$^f$, —P(O)$_2$ R$^e$R$^f$, —P(O)NR$^e$R$^f$, —P(O)$_2$NR$^e$R$^f$, —P(O)OR$^e$, or —P(O)$_2$ OR$^e$;

each R$^a$, R$^b$, R$^c$, R$^d$, R$^e$, and R$^f$ is independently selected from the group consisting of H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl;

each of Z$^1$, Z$^2$, Z$^3$, Z$^4$, Z$^5$, and Z$^6$ is independently N, NH, C or CH;

p is 1, 2, 3, or 4; and t is 1, 2, 3, 4, or 5;

or a pharmaceutically acceptable salt thereof.

1a. A compound of the formula I

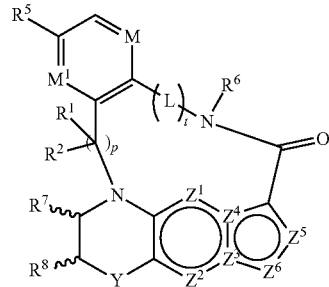

wherein

L is independently —C(R$^1$)(R$^2$)— or X;

X is O, S, S(O) or S(O)$_2$;

each R$^1$ and R$^2$ is independently H, deuterium, halogen, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl, —OR$^a$, —OC(O)R$^a$, —OC(O)R$^a$, —OC(O)NR$^a$R$^b$, —OS(O)R$^a$, —OS(O)$_2$R$^a$, —SR$^a$, —S(O)R$^a$, —S(O)$_2$R$^a$, —S(O)NR$^a$R$^b$, —S(O)$_2$NR$^a$R$^b$, —OS(O)NR$^a$R$^b$, —OS(O)$_2$NR$^a$R$^b$, —NR$^a$R$^b$, —NR$^a$C(O)R$^b$, —NR$^a$C(O)OR$^b$, —NR$^a$C(O)NR$^a$R$^b$, —NR$^a$S(O)R$^b$, —NR$^a$S(O)$_2$R$^b$, —NR$^a$S(O)NR$^a$R$^b$, —NR$^a$S(O)$_2$NR$^a$R$^b$, —C(O)R$^a$, —C(O)OR$^a$, —C(O)NR$^a$R$^b$, —PR$^a$R$^b$, —P(O)R$^a$R$^b$, —P(O)$_2$R$^a$R$^b$, —P(O)NR$^a$R$^b$, —P(O)$_2$NR$^a$R$^b$, —P(O)OR$^a$, —P(O)$_2$OR$^a$, —CN, or —NO$_2$, or R$^1$ and R$^2$ taken together with the carbon or carbons to which they are attached form a C$_3$-C$_6$ cycloalkyl or a 4- to 6-membered heterocycloalkyl, wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, mono- or bicyclic heteroaryl, 4- to 6-membered heterocycloalkyl is independently optionally substituted by deuterium, halogen, C$_1$-C$_6$ alkyl, C$_1$-C$_6$ haloalkyl, C$_3$-C$_6$ cycloalkyl, 3- to 7-membered heterocycloalkyl, —OR$^e$, —OC(O)R$^e$, —OC(O)NR$^e$R$^f$, —OC(=N)NR$^e$R$^f$, —OS(O)R$^e$, —OS(O)$_2$R$^e$, —OS(O)NR$^e$R$^f$, —OS(O)$_2$NR$^e$R$^f$, —SR$^e$, —S(O)R$^e$, —S(O)$_2$R$^e$, —S(O)NR$^e$R$^f$, —S(O)$_2$NR$^e$R$^f$, —NR$^e$R$^f$, —NR$^e$C(O)R$^f$, —NR$^e$C(O)OR$^f$, —NR$^e$C(O)NR$^e$R$^f$, —NR$^e$S(O)R$^f$, —NR$^e$S(O)$_2$R$^f$, —NR$^e$S(O)NR$^e$R$^f$, —NR$^e$S(O)$_2$NR$^e$R$^f$, —C(O)R$^e$, —C(O)OR$^e$, —C(O)NR$^e$R$^f$, —PR$^e$R$^f$, —P(O)R$^e$R$^f$, —P(O)$_2$R$^e$R$^f$, —P(O)NR$^e$R$^f$, —P(O)$_2$ NR$^e$R$^f$, —P(O)OR$^e$, —P(O)$_2$OR$^e$, —CN, or —NO$_2$;

M is CR$^3$ or N;

M$^1$ is CR$^4$;

each R$^3$, R$^4$, and R$^5$ is independently hydrogen, deuterium, halogen, —OR$^c$, —OC(O)R$^c$, —OC(O)NR$^c$R$^d$, —OC (=N)NR$^c$R$^d$, —OS(O)R$^c$, —OS(O)$_2$R$^c$, —OS(O)NR$^c$R$^d$, —OS(O)$_2$NR$^c$R$^d$, —SR$^c$, —S(O)R$^c$, —S(O)$_2$R$^c$, —S(O)NR$^c$R$^d$, —S(O)$_2$NR$^c$R$^d$, —NR$^c$R$^d$, —NR$^c$C(O)R$^d$, —NR$^c$C(O)R$^d$, —NR$^c$C(O)NR$^c$R$^d$, —NR$^c$C(=N)NR$^c$R$^d$, —NR$^c$S(O)R$^d$, —NR$^c$S(O)$_2$R$^d$, —NR$^c$S(O)NR$^c$R$^d$, —NR$^c$S(O)$_2$NR$^c$R$^d$, —C(O)R$^c$, —C(O)OR$^c$, —C(O)NR$^c$R$^d$, —C(=N)NR$^c$R$^d$, —PR$^c$R$^d$, —P(O)R$^c$R$^d$, —P(O)$_2$R$^c$R$^d$, —P(O)NR$^c$R$^d$, —P(O)$_2$NR$^c$R$^d$, —P(O)OR$^c$, —P(O)$_2$OR$^c$, —CN, —NO$_2$, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl, or R$^4$ and R$^5$ taken together with the ring to which they are attached form a C$_5$-C$_8$ cycloalkyl, or a 5- to 8-membered heterocycloalkyl, wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, mono- or bicyclic heteroaryl, C$_5$-C$_8$ cycloalkyl, or 5- to 8-membered heterocycloalkyl is independently optionally substituted by deuterium, halogen, C$_1$-C$_6$ alkyl, C$_1$-C$_6$ haloalkyl, —OR$^e$, —OC(O)R$^e$, —OC(O)NR$^e$R$^f$, —OC(=N)NR$^e$R$^f$, —OS(O)R$^e$, —OS(O)$_2$R$^e$, —OS(O)NR$^e$R$^f$, —OS(O)$_2$NR$^e$R$^f$, —SR$^e$, —S(O)R$^e$, —S(O)$_2$R$^e$, —S(O)NR$^e$R$^f$, —S(O)$_2$NR$^e$R$^f$, —NR$^e$R$^f$, —NR$^e$C(O)R$^f$, —NR$^e$C(O)OR$^f$, —NR$^e$C(O)NR$^e$R$^f$, —NR$^e$S(O)R$^f$, —NR$^e$S(O)$_2$R$^f$, —NR$^e$S(O)NR$^e$R$^f$, —NR$^e$S(O)$_2$NR$^e$R$^f$, —C(O)R$^e$, —C(O)OR$^e$, —C(O)NR$^e$R$^f$, —PR$^e$R$^f$, —P(O)R$^e$R$^f$, —P(O)$_2$R$^e$R$^f$, —P(O)NR$^e$R$^f$, —P(O)$_2$ NR$^e$R$^f$, —P(O)OR$^e$, —P(O)$_2$OR$^e$, —CN, or —NO$_2$;

R$^6$ is H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl, wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl is independently optionally substituted by deuterium, halogen, C$_3$-C$_6$ cycloalkyl, or 5- to 7-membered heterocycloalkyl, —OR$^e$, —OC(O)R$^e$, —OC(O)NR$^e$R$^f$, —OC(=N)NR$^e$R$^f$, —OS(O)R$^e$, —OS(O)$_2$R$^e$, —OS(O)NR$^e$R$^f$, —OS(O)$_2$NR$^e$R$^f$, —SR$^e$, —S(O)R$^e$, —S(O)$_2$R$^e$, —S(O)NR$^e$R$^f$, —S(O)$_2$NR$^e$R$^f$, —NR$^e$R$^f$, —NR$^e$C(O)R$^f$, —NR$^e$C(O)OR$^f$, —NR$^e$C(O)NR$^e$R$^f$, —NR$^e$S(O)R$^f$, —NR$^e$S(O)$_2$R$^f$, —NR$^e$S(O)NR$^e$R$^f$, —NR$^e$S(O)$_2$NR$^e$R$^f$, —C(O)R$^e$, —C(O)OR$^e$, —C(O)NR$^e$R$^f$, —PR$^e$R$^f$, —P(O)R$^e$R$^f$, —P(O)$_2$R$^e$R$^f$, —P(O)NR$^e$R$^f$, —P(O)$_2$NR$^e$R$^f$, —P(O)OR$^e$, —P(O)$_2$OR$^e$, —CN, or —NO$_2$;

R$^7$ and R$^8$ combine to form a C$_3$-C$_7$ cycloalkyl, a 5- to 8-membered heterocycloalkyl, C$_6$-C$_{10}$ aryl, or 5- to 7-membered heteroaryl; wherein each hydrogen atom in C$_3$-C$_7$ cycloalkyl, a 5- to 8-membered heterocycloalkyl, C$_6$-C$_{10}$ aryl, or 5- to 7-membered heteroaryl is independently optionally substituted by deuterium, halogen, —OR$^e$, —OC(O)R$^e$, —OC(O)NR$^e$R$^f$, —OC(=N)NR$^e$R$^f$, —OS(O)R$^e$, —OS(O)$_2$R$^e$, —OS(O)NR$^e$R$^f$, —OS(O)$_2$NR$^e$R$^f$, —SR$^e$, —S(O)R$^e$, —S(O)$_2$R$^e$, —S(O)NR$^e$R$^f$, —S(O)$_2$NR$^e$R$^f$, —NR$^e$R$^f$, —NR$^e$C(O)R$^f$, —NR$^e$C(O)OR$^f$, —NR$^e$C(O)NR$^e$R$^f$, —NR$^e$S(O)R$^f$, —NR$^e$S(O)$_2$R$^f$, —NR$^e$S(O)NR$^e$R$^f$, —NR$^e$S(O)$_2$NR$^e$R$^f$, —C(O)R$^e$, —C(O)OR$^e$, —C(O)NR$^e$R$^f$, —PR$^e$R$^f$, —P(O)R$^e$R$^f$, —P(O)$_2$R$^e$R$^f$, —P(O)NR$^e$R$^f$, —P(O)$_2$ NR$^e$R$^f$, —P(O)OR$^e$, —P(O)$_2$OR$^e$, —CN, or —NO$_2$;

Y is O, S, NR$^9$, or CR$^9$R$^{10}$;

R$^9$ and R$^{10}$ are each independently H, deuterium, halogen, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl, wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl is optionally substituted by a halogen, —OR$^e$, —OC(O)R$^e$, —OC(O)NR$^e$R$^f$, —OC(=N)NR$^e$R$^f$, —OS(O)R$^e$, —OS(O)$_2$R$^e$, —OS(O)NR$^e$R$^f$, —OS(O)$_2$NR$^e$R$^f$, —SR$^e$, —S(O)R$^e$, —S(O)$_2$R$^e$, —S(O)NR$^e$R$^f$, —S(O)$_2$NR$^e$R$^f$, —NR$^e$R$^f$, —NR$^e$C(O)R$^f$, —NR$^e$C(O)OR$^f$, —NR$^e$C(O)NR$^e$R$^f$, —NR$^e$S(O)R$^f$, —NR$^e$S(O)$_2$R$^f$, —NR$^e$S(O)NR$^e$R$^f$, —NR$^e$S(O)$_2$NR$^e$R$^f$, —C(O)R$^e$, —C(O)OR$^e$, —C(O)NR$^e$R$^f$, —PR$^e$R$^f$, —P(O)R$^e$R$^f$, —P(O)$_2$R$^e$R$^f$, —P(O)NR$^e$R$^f$, —P(O)$_2$NR$^e$R$^f$, —P(O)OR$^e$, or —P(O)$_2$OR$^e$;

each R$^a$, R$^b$, R$^c$, R$^d$, R$^e$, and R$^f$ is independently selected from the group consisting of H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl;

each of Z$^1$, Z$^2$, Z$^3$, Z$^4$, Z$^5$, and Z$^6$ is independently N, NH, C or CH;

p is 1, 2, 3, or 4; and t is 1, 2, 3, 4, or 5;

or a pharmaceutically acceptable salt thereof.

2. The compound of clause 1, or a pharmaceutically acceptable salt thereof, wherein p is 1.

3. The compound of clause 1 or 2, or a pharmaceutically acceptable salt thereof, wherein t is 3.

3a. The compound of clause 1 or 2, or a pharmaceutically acceptable salt thereof, wherein t is 3 or 4.

4. The compound of clause 1, or a pharmaceutically acceptable salt thereof, having the formula II

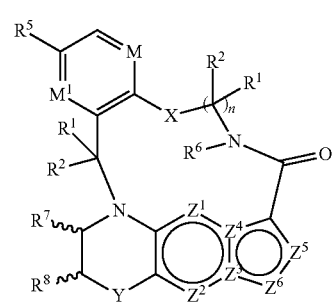

wherein

M is CR$^3$ or N;

M$^1$ is CR$^4$;

X is O, S, S(O), or S(O)$_2$;

each R$^1$ and R$^2$ is independently H, deuterium, C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —OR$^a$, —SR$^a$, —NR$^a$R$^b$, —C(O)OR$^a$, —C(O)NR$^a$R$^b$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —OC(O)C$_1$-C$_6$ alkyl, —OC(O)N(C$_1$-C$_6$ alkyl)$_2$, —OC(O)NH(C$_1$-C$_6$ alkyl), —OC(O)NH$_2$, —OC(=N)N(C$_1$-C$_6$ alkyl)$_2$, —OC(=N)NH(C$_1$-C$_6$ alkyl), —OC(=N)NH$_2$, —OS(O)C$_1$-C$_6$ alkyl, —OS(O)$_2$C$_1$-C$_6$ alkyl, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NH(C$_1$-C$_6$ alkyl), —N(C$_1$-C$_6$ alkyl)C(O)NH$_2$, —N(C$_1$-C$_6$ alkyl)C(O)NH(C$_1$-C$_6$ alkyl), —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHC(O)OH, —N(C$_1$-C$_6$ alkyl)C(O)OH, —NHS(O)C$_1$-C$_6$ alkyl, —NHS(O)$_2$C$_1$-C$_6$ alkyl, —N(C$_1$-C$_6$ alkyl)S(O)C$_1$-C$_6$ alkyl, —N(C$_1$-C$_6$ alkyl)S(O)$_2$C$_1$-C$_6$ alkyl. —NHS(O)NH$_2$, —NHS(O)$_2$NH$_2$, —N(C$_1$-C$_6$ alkyl)S(O)

$NH_2$, $-N(C_1-C_6 \text{ alkyl})S(O)_2NH_2$, $-NHS(O)NH(C_1-C_6 \text{ alkyl})$, $-NHS(O)_2NH(C_1-C_6 \text{ alkyl})$, $-NHS(O)N(C_1-C_6 \text{ alkyl})_2$, $-NHS(O)_2N(C_1-C_6 \text{ alkyl})_2$, $-N(C_1-C_6 \text{ alkyl})S(O)NH(C_1-C_6 \text{ alkyl})$, $-N(C_1-C_6 \text{ alkyl})S(O)_2NH(C_1-C_6 \text{ alkyl})$, $-N(C_1-C_6 \text{ alkyl})S(O)N(C_1-C_6 \text{ alkyl})_2$, $-N(C_1-C_6 \text{ alkyl})S(O)_2N(C_1-C_6 \text{ alkyl})_2$, $-C(O)C_1-C_6 \text{ alkyl}$, $-CO_2H$, $-C(O)OC_1-C_6 \text{ alkyl}$, $-C(O)NH_2$, $-C(O)NH(C_1-C_6 \text{ alkyl})$, $-C(O)N(C_1-C_6 \text{ alkyl})_2$, $-SC_1-C_6 \text{ alkyl}$, $-S(O)C_1-C_6 \text{ alkyl}$, $-S(O)_2C_1-C_6 \text{ alkyl}$, $-S(O)NH(C_1-C_6 \text{ alkyl})$, $-S(O)_2NH(C_1-C_6 \text{ alkyl})$, $-S(O)N(C_1-C_6 \text{ alkyl})_2$, $-S(O)_2N(C_1-C_6 \text{ alkyl})_2$, $-S(O)NH_2$, $-S(O)_2NH_2$, $-OS(O)N(C_1-C_6 \text{ alkyl})_2$, $-OS(O)_2N(C_1-C_6 \text{ alkyl})_2$, $-OS(O)NH(C_1-C_6 \text{ alkyl})$, $-OS(O)_2NH(C_1-C_6 \text{ alkyl})$, $-OS(O)NH_2$, $-OS(O)_2NH_2$, $-P(C_1-C_6 \text{ alkyl})_2$, $-P(O)(C_1-C_6 \text{ alkyl})_2$, $C_3-C_6$ cycloalkyl, or 3- to 7-membered heterocycloalkyl;

$R^3$, $R^4$, and $R^5$ are each independently H, fluoro, chloro, bromo, $C_1-C_6$ alkyl, $-OH$, $-CN$, $-OC_1-C_6$ alkyl, $-NHC_1-C_6$ alkyl, $-N(C_1-C_6 \text{ alkyl})_2$ or $-CF_3$;

$R^6$ is H, $C_1-C_6$ alkyl or 3- to 7-membered heterocycloalkyl, wherein each hydrogen atom in $C_1-C_6$ alkyl or 3- to 7-membered heterocycloalkyl is independently optionally substituted by halogen, $-OH$, $-CN$, $-OC_1-C_6$ alkyl, $-NH_2$, $-NH(C_1-C_6 \text{ alkyl})$, $-N(C_1-C_6 \text{ alkyl})_2$, $-CO_2H$, $-C(O)OC_1-C_6$ alkyl, $-C(O)NH_2$, $-C(O)NH(C_1-C_6 \text{ alkyl})$, $-C(O)N(C_1-C_6 \text{ alkyl})_2$, $C_3-C_6$ cycloalkyl, or monocyclic 5- to 7-membered heterocycloalkyl;

$R^7$ and $R^8$ combine to form a $C_3-C_7$ cycloalkyl, a 5- to 8-membered heterocycloalkyl, $C_6-C_{10}$ aryl, or 5- to 7-membered heteroaryl; wherein each hydrogen atom in $C_3-C_7$ cycloalkyl, a 5- to 8-membered heterocycloalkyl, $C_6-C_{10}$ aryl, or 5- to 7-membered heteroaryl is independently optionally substituted by deuterium, halogen, $-OH$, $-OC_1-C_6$ alkyl, $-OC(O)C_1-C_6$ alkyl, $-OC(O)NH_2$, $-OC(O)NH(C_1-C_6 \text{ alkyl})$, $-OC(O)N(C_1-C_6 \text{ alkyl})_2$, $-OC(=N)NH_2$, $-OC(=N)NH(C_1-C_6 \text{ alkyl})$, $-OC(=N)N(C_1-C_6 \text{ alkyl})_2$, $-OS(O)C_1-C_6$ alkyl, $-OS(O)_2C_1-C_6$ alkyl, $-OS(O)NH_2$, $-OS(O)NH(C_1-C_6 \text{ alkyl})$, $-OS(O)N(C_1-C_6 \text{ alkyl})_2$, $-OS(O)_2NH_2$, $-OS(O)_2NH(C_1-C_6 \text{ alkyl})$, $-OS(O)_2N(C_1-C_6 \text{ alkyl})_2$, $-SH$, $-SC_1-C_6$ alkyl, $-S(O)C_1-C_6$ alkyl, $-S(O)_2C_1-C_6$ alkyl, $-S(O)NH_2$, $-S(O)NH(C_1-C_6 \text{ alkyl})$, $-S(O)(C_1-C_6 \text{ alkyl})_2$, $-S(O)_2NH_2$, $-S(O)_2NH(C_1-C_6 \text{ alkyl})$, $-S(O)_2N(C_1-C_6 \text{ alkyl})_2$, $-NH_2$, $-NH(C_1-C_6 \text{ alkyl})$, $-N(C_1-C_6 \text{ alkyl})_2$, $-NHC(O)C_1-C_6$ alkyl, $-N(C_1-C_6 \text{ alkyl})C(O)C_1-C_6$ alkyl, $-NHC(O)OH$, $-NHC(O)OC_1-C_6$ alkyl, $-N(C_1-C_6 \text{ alkyl})C(O)OH$, $-N(C_1-C_6 \text{ alkyl})C(O)OC_1-C_6$ alkyl, $-NHC(O)NH_2$, $-NHC(O)NH(C_1-C_6 \text{ alkyl})$, $-NHC(O)N(C_1-C_6 \text{ alkyl})_2$, $-N(C_1-C_6 \text{ alkyl})C(O)NH_2$, $-N(C_1-C_6 \text{ alkyl})C(O)NH(C_1-C_6 \text{ alkyl})$, $-N(C_1-C_6 \text{ alkyl})C(O)N(C_1-C_6 \text{ alkyl})_2$, $-NHS(O)C_1-C_6$ alkyl, $-N(C_1-C_6 \text{ alkyl})S(O)C_1-C_6$ alkyl, $-NHS(O)_2C_1-C_6$ alkyl, $-N(C_1-C_6 \text{ alkyl})S(O)_2C_1-C_6$ alkyl, $-NHS(O)NH_2$, $-NHS(O)NH(C_1-C_6 \text{ alkyl})$, $-NHS(O)N(C_1-C_6 \text{ alkyl})_2$, $-N(C_1-C_6 \text{ alkyl})S(O)NH_2$, $-N(C_1-C_6 \text{ alkyl})S(O)NH(C_1-C_6 \text{ alkyl})$, $-N(C_1-C_6 \text{ alkyl})S(O)N(C_1-C_6 \text{ alkyl})_2$, $-NHS(O)_2NH_2$, $-NHS(O)_2NH(C_1-C_6 \text{ alkyl})$, $-NHS(O)_2N(C_1-C_6 \text{ alkyl})_2$, $-N(C_1-C_6 \text{ alkyl})S(O)_2NH_2$, $-N(C_1-C_6 \text{ alkyl})S(O)_2NH(C_1-C_6 \text{ alkyl})$, $-N(C_1-C_6 \text{ alkyl})S(O)_2N(C_1-C_6 \text{ alkyl})_2$, $-C(O)C_1-C_6$ alkyl, $-C(O)OC_1-C_6$ alkyl, $-C(O)NH_2$, $-C(O)NH(C_1-C_6 \text{ alkyl})$, $-C(O)N(C_1-C_6 \text{ alkyl})_2$, $-P(C_1-C_6 \text{ alkyl})_2$, $-P(O)(C_1-C_6 \text{ alkyl})_2$, $-P(O)_2(C_1-C_6 \text{ alkyl})_2$, $-P(O)N(C_1-C_6 \text{ alkyl})_2$, $-P(O)_2N(C_1-C_6 \text{ alkyl})_2$, $-P(O)OH$, $-P(O)OC_1-C_6$ alkyl, $-P(O)_2OH$, $-P(O)_2OC_1-C_6$ alkyl, $-CN$, or $-NO_2$;

Y is O, S, $NR^9$, or $CR^9R^{10}$;

$R^9$ and $R^{10}$ are each independently H, deuterium, halogen, or $C_1-C_6$ alkyl, wherein each hydrogen atom in $C_1-C_6$ alkyl is optionally substituted by a halogen, $-OH$, $-OC_1-C_6$ alkyl, $-OC(O)C_1-C_6$ alkyl, $-OC(O)N(C_1-C_6 \text{ alkyl})_2$, $-OC(O)NH(C_1-C_6 \text{ alkyl})$, $-OC(O)NH_2$, $-OC(=N)N(C_1-C_6 \text{ alkyl})_2$, $-OC(=N)NH(C_1-C_6 \text{ alkyl})$, $-OC(=N)NH_2$, $-OS(O)C_1-C_6$ alkyl, $-OS(O)_2C_1-C_6$ alkyl, $-OS(O)N(C_1-C_6 \text{ alkyl})_2$, $-OS(O)NH(C_1-C_6 \text{ alkyl})$, $-OS(O)NH_2$, $-OS(O)_2N(C_1-C_6 \text{ alkyl})_2$, $-OS(O)_2NH(C_1-C_6 \text{ alkyl})$, $-OS(O)_2NH_2$, $-SH$, $-SC_1-C_6$ alkyl, $-S(O)C_1-C_6$ alkyl, $-S(O)_2C_1-C_6$ alkyl, $-S(O)N(C_1-C_6 \text{ alkyl})_2$, $-S(O)NH(C_1-C_6 \text{ alkyl})$, $-S(O)NH_2$, $-S(O)_2N(C_1-C_6 \text{ alkyl})_2$, $-S(O)_2NH(C_1-C_6 \text{ alkyl})$, $-S(O)_2NH_2$, $-N(C_1-C_6 \text{ alkyl})_2$, $-NH(C_1-C_6 \text{ alkyl})$, $-NH_2$, $-N(C_1-C_6 \text{ alkyl})C(O)C_1-C_6$ alkyl, $-NHC(O)C_1-C_6$ alkyl, $-N(C_1-C_6 \text{ alkyl})C(O)OC_1-C_6$ alkyl, $-N(C_1-C_6 \text{ alkyl})C(O)OH$, $-NHC(O)OC_1-C_6$ alkyl, $-NHC(O)OH$, $-N(C_1-C_6 \text{ alkyl})C(O)N(C_1-C_6 \text{ alkyl})_2$, $-N(C_1-C_6 \text{ alkyl})C(O)NH(C_1-C_6 \text{ alkyl})$, $-N(C_1-C_6 \text{ alkyl})C(O)NH_2$, $-NHC(O)N(C_1-C_6 \text{ alkyl})_2$, $-NHC(O)NH(C_1-C_6 \text{ alkyl})$, $-NHC(O)NH_2$, $-N(C_1-C_6 \text{ alkyl})S(O)C_1-C_6$ alkyl, $-NHS(O)C_1-C_6$ alkyl, $-N(C_1-C_6 \text{ alkyl})S(O)_2C_1-C_6$ alkyl, $-NHS(O)_2C_1-C_6$ alkyl, $-N(C_1-C_6 \text{ alkyl})S(O)N(C_1-C_6 \text{ alkyl})_2$, $-N(C_1-C_6 \text{ alkyl})S(O)NH(C_1-C_6 \text{ alkyl})$, $-N(C_1-C_6 \text{ alkyl})S(O)NH_2$, $-NHS(O)N(C_1-C_6 \text{ alkyl})_2$, $-NHS(O)NH(C_1-C_6 \text{ alkyl})$, $-NHS(O)NH_2$, $-N(C_1-C_6 \text{ alkyl})S(O)_2N(C_1-C_6 \text{ alkyl})_2$, $-N(C_1-C_6 \text{ alkyl})S(O)_2NH(C_1-C_6 \text{ alkyl})$, $-N(C_1-C_6 \text{ alkyl})S(O)_2NH_2$, $-NHS(O)_2N(C_1-C_6 \text{ alkyl})_2$, $-NHS(O)_2NH(C_1-C_6 \text{ alkyl})$, $-NHS(O)_2NH_2$, $-C(O)C_1-C_6$ alkyl, $-C(O)OC_1-C_6$ alkyl, $-C(O)N(C_1-C_6 \text{ alkyl})_2$, $-C(O)NH(C_1-C_6 \text{ alkyl})$, $-C(O)NH_2$, $-P(C_1-C_6 \text{ alkyl})_2$, $-P(O)(C_1-C_6 \text{ alkyl})_2$, $-P(O)_2(C_1-C_6 \text{ alkyl})_2$, $-P(O)N(C_1-C_6 \text{ alkyl})_2$, $-P(O)_2N(C_1-C_6 \text{ alkyl})_2$, $-P(O)OC_1-C_6$ alkyl, or $-P(O)_2OC_1-C_6$ alkyl;

each of $Z^1$, $Z^2$, $Z^3$, $Z^4$, $Z^5$, and $Z^6$ is independently N, NH, C or CH; and n is 2 or 3.

5. The compound of any of the preceding clause, having the formula III

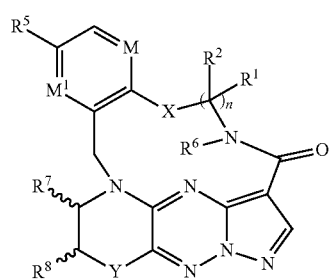

or a pharmaceutically acceptable salt thereof.

6. The compound of clause 4 or 5, or a pharmaceutically acceptable salt thereof, wherein n is 2.

6a. The compound of clause 4 or 5, or a pharmaceutically acceptable salt thereof, wherein n is 2 or 3.

7. The compound of any one of the preceding clauses, having the formula IV

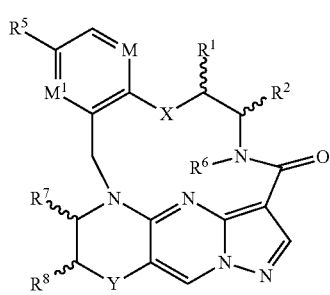

or a pharmaceutically acceptable salt thereof.

7a. The compound of any one of the preceding clauses, having the formula IV or V

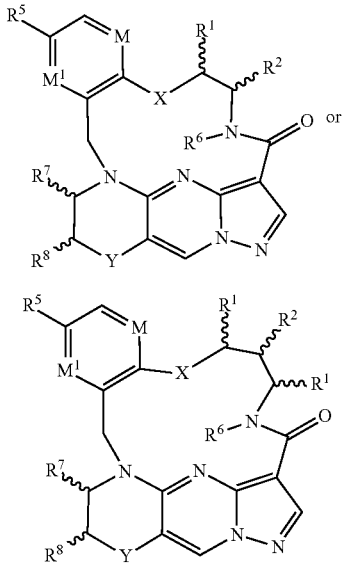

or a pharmaceutically acceptable salt thereof.

8. The compound of any one of the preceding clauses, or a pharmaceutically acceptable salt thereof, wherein Y is O.

9. The compound of any one of the preceding clauses, or a pharmaceutically acceptable salt thereof, wherein M is $CR^3$.

10. The compound of any one of the preceding clauses, or a pharmaceutically acceptable salt thereof, wherein $R^3$ is H, deuterium, $C_1$-$C_6$ alkyl or halogen.

11. The compound of any one of the preceding clauses, or a pharmaceutically acceptable salt thereof, wherein $R^3$ is H or F.

12. The compound of any one of clauses 1 to 8, or a pharmaceutically acceptable salt thereof, wherein M is N.

13. The compound of any one of the preceding clauses, or a pharmaceutically acceptable salt thereof, wherein $M^1$ is $CR^4$.

14. The compound of any one of the preceding clauses, or a pharmaceutically acceptable salt thereof, wherein $R^4$ is H, deuterium, $C_1$-$C_6$ alkyl or halogen.

15. The compound of any one of the preceding clauses, or a pharmaceutically acceptable salt thereof, wherein $R^4$ is H or Cl.

16. The compound of any one of the preceding clauses, or a pharmaceutically acceptable salt thereof, wherein $R^5$ is F.

17. The compound of any one of the preceding clauses, or a pharmaceutically acceptable salt thereof, wherein $R^2$ is H.

17a. The compound of any one of the preceding clauses, or a pharmaceutically acceptable salt thereof, wherein at least one of $R^2$ is H.

18. The compound of any one of the preceding clauses, or a pharmaceutically acceptable salt thereof, wherein $R^1$ is H.

18a. The compound of any one of the preceding clauses, or a pharmaceutically acceptable salt thereof, wherein at least one of $R^1$ is H.

19. The compound of any one of clauses 1 to 17, or a pharmaceutically acceptable salt thereof, wherein $R^1$ is $C_1$-$C_6$ alkyl.

19a. The compound of any one of clauses 1 to 17, or a pharmaceutically acceptable salt thereof, wherein at least one of $R^1$ is $C_1$-$C_6$ alkyl.

20. The compound of any one of clauses 1 to 17, or a pharmaceutically acceptable salt thereof, wherein $R^1$ is H, and $R^2$ is $C_1$-$C_6$ alkyl.

20a. The compound of any one of clauses 1 to 16, or a pharmaceutically acceptable salt thereof, wherein $R^1$ is H, and $R^2$ is $C_1$-$C_6$ alkyl; or $R^1$ is $C_1$-$C_6$ alkyl, and $R^2$ is H; or $R^1$ is H or $C_1$-$C_6$ alkyl, and $R^2$ is H; or $R^1$ is H, and $R^2$ is $C_3$-$C_7$ cycloalkyl; or $R^1$ is $C_3$-$C_7$ cycloalkyl, and $R^2$ is H; or wherein one of $R^1$ is $C_1$-$C_6$ alkyl, any other $R^1$, when present, is H, and any $R^2$, when present, is H.

21. The compound of any one of the preceding clauses, or a pharmaceutically acceptable salt thereof, wherein $R^7$ and $R^8$ combine to form a 5- or 6-membered cycloalkyl, wherein each hydrogen atom in the 5- or 6-membered cycloalkyl is independently optionally substituted by deuterium, halogen, —OH, —CN, —O$C_1$-$C_6$ alkyl, —O$C_1$-$C_6$ alkyl($C_6$-$C_{10}$ aryl), —NH$_2$, —OC(O)$C_1$-$C_6$ alkyl, —OC(O)N($C_1$-$C_6$ alkyl)$_2$, —OC(O)NH($C_1$-$C_6$ alkyl), —OC(O)NH$_2$, —OC(=N)N($C_1$-$C_6$ alkyl)$_2$, —OC(=N)NH($C_1$-$C_6$ alkyl), —OC(=N)NH$_2$, —OS(O)$C_1$-$C_6$ alkyl, —OS(O)$_2$$C_1$-$C_6$ alkyl, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH($C_1$-$C_6$ alkyl), —N($C_1$-$C_6$ alkyl)C(O)NH$_2$, —N($C_1$-$C_6$ alkyl)C(O)NH($C_1$-$C_6$ alkyl), —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHC(O)OH, —N($C_1$-$C_6$ alkyl)C(O)OH, —NHS(O)$C_1$-$C_6$ alkyl, —NHS(O)$_2$$C_1$-$C_6$ alkyl, —N($C_1$-$C_6$ alkyl)S(O)$C_1$-$C_6$ alkyl, —N($C_1$-$C_6$ alkyl)S(O)$_2$$C_1$-$C_6$ alkyl. —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —C(O)$C_1$-$C_6$ alkyl, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —S(O)NH$_2$, —S(O)$_2$NH$_2$, —OS(O)N($C_1$-$C_6$ alkyl)$_2$, —OS(O)$_2$N($C_1$-$C_6$ alkyl)$_2$, —OS(O)NH($C_1$-$C_6$ alkyl), —OS(O)$_2$NH($C_1$-$C_6$ alkyl), —OS(O)NH$_2$, —OS(O)$_2$NH$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl.

21a. The compound of any one of the preceding clauses, or a pharmaceutically acceptable salt thereof, wherein $R^7$ and $R^8$ combine to form a 4-, 5- or 6-membered cycloalkyl, wherein each hydrogen atom in the 5- or 6-membered cycloalkyl is independently optionally substituted by deuterium, halogen, —OH, —CN, —O$C_1$-$C_6$ alkyl, —O$C_1$-$C_6$ alkyl($C_6$-$C_{10}$ aryl), —NH$_2$, —OC(O)$C_1$-$C_6$ alkyl, —OC(O)N($C_1$-$C_6$ alkyl)$_2$, —OC(O)NH($C_1$-$C_6$ alkyl), —OC(O)NH$_2$, —OC(=N)N($C_1$-$C_6$ alkyl)$_2$, —OC(=N)NH($C_1$-$C_6$ alkyl), —OC(=N)NH$_2$, —OS(O)$C_1$-$C_6$ alkyl, —OS(O)$_2$$C_1$-$C_6$ alkyl, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH($C_1$-$C_6$ alkyl), —N($C_1$-$C_6$ alkyl)C(O)NH$_2$, —N($C_1$-$C_6$ alkyl)C(O)NH($C_1$-$C_6$ alkyl), —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHC(O)OH, —N($C_1$-$C_6$ alkyl)C(O)OH, —NHS(O)$C_1$-$C_6$ alkyl, —NHS(O)$_2$$C_1$-$C_6$ alkyl, —N($C_1$-$C_6$ alkyl)S(O)$C_1$-$C_6$ alkyl, —N($C_1$-$C_6$ alkyl)S(O)$_2$$C_1$-$C_6$ alkyl.

—NHS(O)NH$_2$, —NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —C(O)C$_1$-C$_6$ alkyl, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —S(O)NH$_2$, —S(O)$_2$NH$_2$, —OS(O)N(C$_1$-C$_6$ alkyl)$_2$, —OS(O)$_2$N(C$_1$-C$_6$ alkyl)$_2$, —OS(O)NH(C$_1$-C$_6$ alkyl), —OS(O)$_2$NH(C$_1$-C$_6$ alkyl), —OS(O)NH$_2$, —OS(O)$_2$NH$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl.

22. The compound of any one of clauses 1 to 20, or a pharmaceutically acceptable salt thereof, wherein R$^7$ and R$^8$ combine to form a 3-, 4-, 5- or 6-membered heterocycloalkyl, wherein each hydrogen atom in the 3-, 4-, 5- or 6-membered heterocycloalkyl is independently optionally substituted by deuterium, halogen, —OH, —CN, —OC$_1$-C$_6$ alkyl, —OC$_1$-C$_6$ alkyl(C$_6$-C$_{10}$ aryl), —NH$_2$, —OC(O)C$_1$-C$_6$ alkyl, —OC(O)N(C$_1$-C$_6$ alkyl)$_2$, —OC(O)NH(C$_1$-C$_6$ alkyl), —OC(O)NH$_2$, —OC(=N)N(C$_1$-C$_6$ alkyl)$_2$, —OC(=N)NH(C$_1$-C$_6$ alkyl), —OC(=N)NH$_2$, —OS(O)C$_1$-C$_6$ alkyl, —OS(O)$_2$C$_1$-C$_6$ alkyl, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NH(C$_1$-C$_6$ alkyl), —N(C$_1$-C$_6$ alkyl)C(O)NH$_2$, —N(C$_1$-C$_6$ alkyl)C(O)NH(C$_1$-C$_6$ alkyl), —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHC(O)OH, —N(C$_1$-C$_6$ alkyl)C(O)OH, —NHS(O)C$_1$-C$_6$ alkyl, —NHS(O)$_2$C$_1$-C$_6$ alkyl, —N(C$_1$-C$_6$ alkyl)S(O)C$_1$-C$_6$ alkyl, —N(C$_1$-C$_6$ alkyl)S(O)$_2$C$_1$-C$_6$ alkyl. —NHS(O)NH$_2$, —NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —C(O)C$_1$-C$_6$ alkyl, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —S(O)NH$_2$, —S(O)$_2$NH$_2$, —OS(O)N(C$_1$-C$_6$ alkyl)$_2$, —OS(O)$_2$N(C$_1$-C$_6$ alkyl)$_2$, —OS(O)NH(C$_1$-C$_6$ alkyl), —OS(O)$_2$NH(C$_1$-C$_6$ alkyl), —OS(O)NH$_2$, —OS(O)$_2$NH$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl.

23. The compound of clause 22, or a pharmaceutically acceptable salt thereof, wherein R$^7$ and R$^8$ combine to form a tetrahydrofuran ring.

24. The compound of clause 21, or a pharmaceutically acceptable salt thereof, wherein R$^7$ and R$^8$ combine to form a cyclopentane ring.

24a. The compound of clause 21 or 21a, or a pharmaceutically acceptable salt thereof, wherein R$^7$ and R$^8$ combine to form a cyclobutane ring, cyclopentane ring, or cyclohexane ring.

25. The compound of clause 1, or a pharmaceutically acceptable salt thereof, selected form the group consisting of

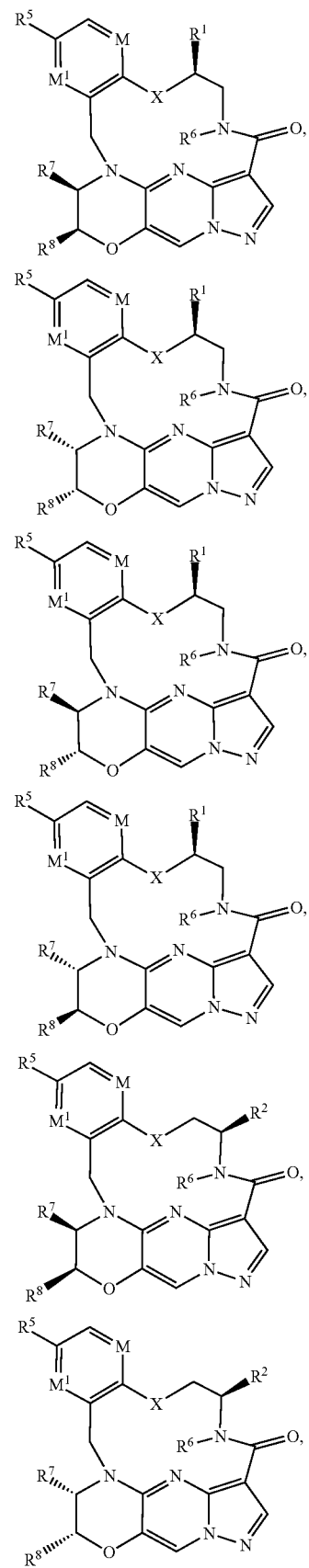

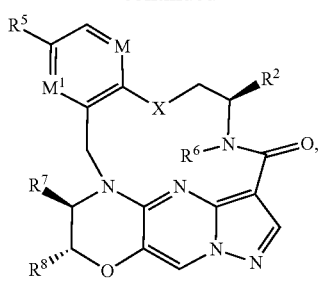
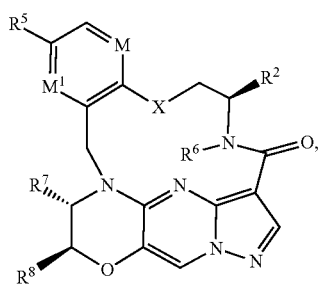
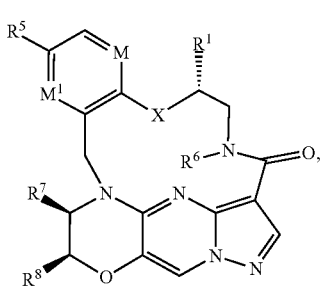
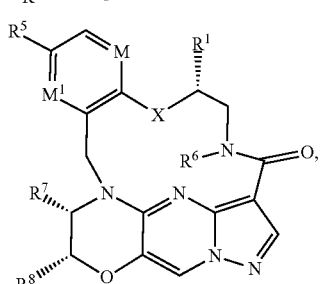
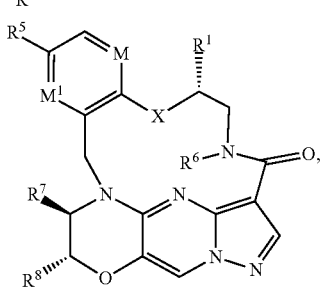
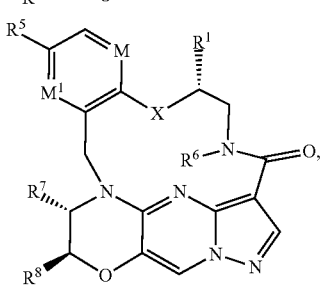
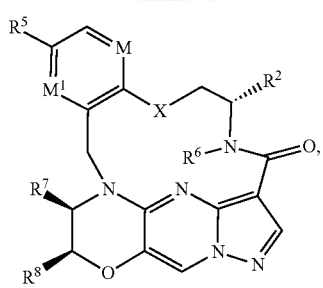
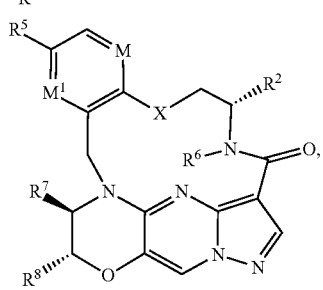
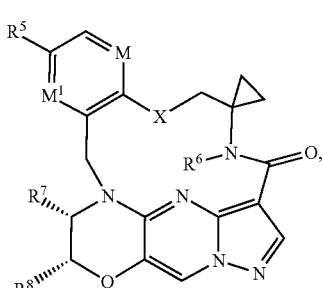

-continued

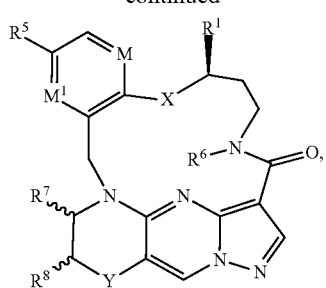

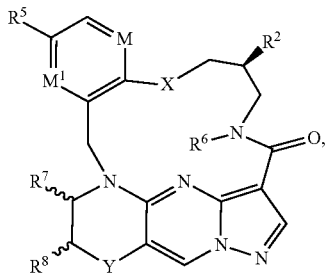

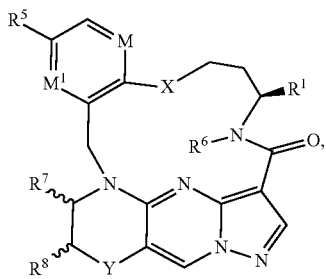

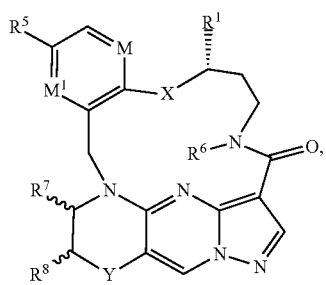

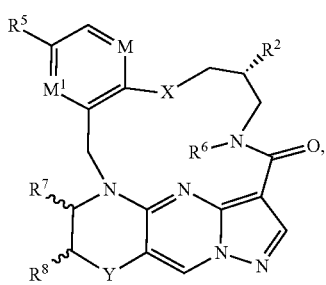

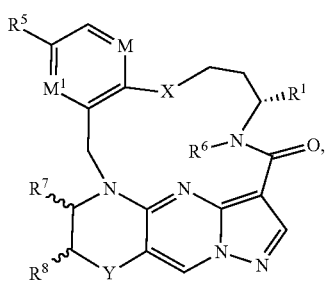

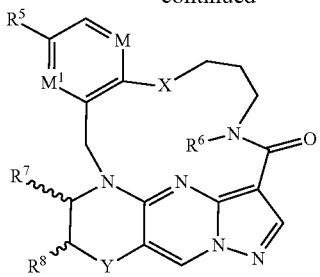

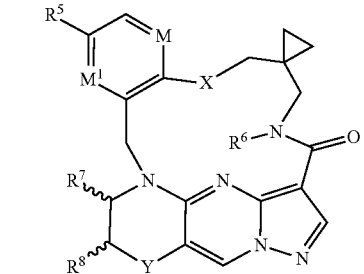

wherein

M is $CR^3$ or N;

$M^1$ is $CR^4$;

X is O, S, S(O), or $S(O)_2$;

$R^1$ and $R^2$ are each independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —$OR^a$, —$SR^a$, —$NR^aR^b$, —C(O)$OR^a$, —C(O)$NR^aR^b$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —$OC_1$-$C_6$ alkyl, —$OC_1$-$C_6$ alkyl($C_6$-$C_{10}$ aryl), —$NH_2$, —OC(O)$C_1$-$C_6$ alkyl, —OC(O)N($C_1$-$C_6$ alkyl)$_2$, —OC(O)NH($C_1$-$C_6$ alkyl), —OC(O)$NH_2$, —OC(=N)N($C_1$-$C_6$ alkyl)$_2$, —OC(=N)NH($C_1$-$C_6$ alkyl), —OC(=N)$NH_2$, —OS(O)$C_1$-$C_6$ alkyl, —OS(O)$_2C_1$-$C_6$ alkyl, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)$NH_2$, —NHC(O)NH($C_1$-$C_6$ alkyl), —N($C_1$-$C_6$ alkyl)C(O)$NH_2$, —N($C_1$-$C_6$ alkyl)C(O)NH($C_1$-$C_6$ alkyl), —NHC(O)N($C_1$-$C_6$ alkyl)$_2$, —N($C_1$-$C_6$ alkyl)C(O)N($C_1$-$C_6$ alkyl)$_2$, —NHC(O)$OC_1$-$C_6$ alkyl, —N($C_1$-$C_6$ alkyl)C(O)$OC_1$-$C_6$ alkyl, —NHC(O)OH, —N($C_1$-$C_6$ alkyl)C(O)OH, —NHS(O)$C_1$-$C_6$ alkyl, —NHS(O)$_2C_1$-$C_6$ alkyl, —N($C_1$-$C_6$ alkyl)S(O)$C_1$-$C_6$ alkyl, —N($C_1$-$C_6$ alkyl)S(O)$_2C_1$-$C_6$ alkyl. —NHS(O)$NH_2$, —NHS(O)$_2NH_2$, —N($C_1$-$C_6$ alkyl)S(O)$NH_2$, —N($C_1$-$C_6$ alkyl)S(O)$_2NH_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —C(O)$C_1$-$C_6$ alkyl, —$CO_2H$, —C(O)$OC_1$-$C_6$ alkyl, —C(O)$NH_2$, —C(O)NH($C_1$-$C_6$ alkyl), —C(O)N($C_1$-$C_6$ alkyl)$_2$, —$SC_1$-$C_6$ alkyl, —S(O)$C_1$-$C_6$ alkyl, —S(O)$_2C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —S(O)$NH_2$, —S(O)$_2NH_2$, —OS(O)N($C_1$-$C_6$ alkyl)$_2$, —OS(O)$_2$N($C_1$-$C_6$ alkyl)$_2$, —OS(O)NH($C_1$-$C_6$ alkyl), —OS(O)$_2$NH($C_1$-$C_6$ alkyl), —OS(O)$NH_2$, —OS(O)$_2NH_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

$R^3$, $R^4$, and $R^5$ are each independently H, fluoro, chloro, bromo, $C_1$-$C_6$ alkyl, —OH, —CN, —$OC_1$-$C_6$ alkyl, —$NHC_1$-$C_6$ alkyl, —N($C_1$-$C_6$ alkyl)$_2$ or —$CF_3$;

$R^6$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —O$C_1$-$C_6$ alkyl, —NH$_2$, —NH($C_1$-$C_6$ alkyl), —N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, $C_3$-$C_6$ cycloalkyl, or monocyclic 5- to 7-membered heterocycloalkyl;

$R^7$ and $R^8$ combine to form a $C_3$-$C_7$ cycloalkyl, a 5- to 8-membered heterocycloalkyl, $C_6$-$C_{10}$ aryl, or 5- to 7-membered heteroaryl; wherein each hydrogen atom in $C_3$-$C_7$ cycloalkyl, a 5- to 8-membered heterocycloalkyl, $C_6$-$C_{10}$ aryl, or 5- to 7-membered heteroaryl is independently optionally substituted by deuterium, halogen, —OH, —O$C_1$-$C_6$ alkyl, —OC(O)$C_1$-$C_6$ alkyl, —OC(O)NH$_2$, —OC(O)NH($C_1$-$C_6$ alkyl), —OC(O)N($C_1$-$C_6$ alkyl)$_2$, —OC(=N)NH$_2$, —OC(=N)NH($C_1$-$C_6$ alkyl), —OC(=N)N($C_1$-$C_6$ alkyl)$_2$, —OS(O)$C_1$-$C_6$ alkyl, —OS(O)$_2$$C_1$-$C_6$ alkyl, —OS(O)NH$_2$, —OS(O)NH($C_1$-$C_6$ alkyl), —OS(O)N($C_1$-$C_6$ alkyl)$_2$, —OS(O)$_2$NH$_2$, —OS(O)$_2$NH($C_1$-$C_6$ alkyl), —OS(O)$_2$N($C_1$-$C_6$ alkyl)$_2$, —SH, —S$C_1$-$C_6$ alkyl, —S(O)$C_1$-$C_6$ alkyl, —S(O)$_2$$C_1$-$C_6$ alkyl, —S(O)NH$_2$, —S(O)NH($C_1$-$C_6$ alkyl), —S(O)($C_1$-$C_6$ alkyl)$_2$, —S(O)$_2$NH$_2$, —S(O)$_2$NH($C_1$-$C_6$ alkyl), —S(O)$_2$N($C_1$-$C_6$ alkyl)$_2$, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)OH, —NHC(O)O$C_1$-$C_6$ alkyl, —N($C_1$-$C_6$ alkyl)C(O)OH, —N($C_1$-$C_6$ alkyl)C(O)O$C_1$-$C_6$ alkyl, —NHC(O)NH$_2$, —NHC(O)NH($C_1$-$C_6$ alkyl), —NHC(O)N($C_1$-$C_6$ alkyl)$_2$, —N($C_1$-$C_6$ alkyl)C(O)NH$_2$, —N($C_1$-$C_6$ alkyl)C(O)NH($C_1$-$C_6$ alkyl), —N($C_1$-$C_6$ alkyl)C(O)N($C_1$-$C_6$ alkyl)$_2$, —NHS(O)$C_1$-$C_6$ alkyl, —N($C_1$-$C_6$ alkyl)S(O)$C_1$-$C_6$ alkyl, —NHS(O)$_2$$C_1$-$C_6$ alkyl, —N($C_1$-$C_6$ alkyl)S(O)$_2$$C_1$-$C_6$ alkyl, —NHS(O)NH$_2$, —NHS(O)NH($C_1$-$C_6$ alkyl), —NHS(O)N($C_1$-$C_6$ alkyl)$_2$, —N($C_1$-$C_6$ alkyl)S(O)NH$_2$, —N($C_1$-$C_6$ alkyl)S(O)NH($C_1$-$C_6$ alkyl), —N($C_1$-$C_6$ alkyl)S(O)N($C_1$-$C_6$ alkyl)$_2$, —NHS(O)$_2$NH$_2$, —NHS(O)$_2$NH($C_1$-$C_6$ alkyl), —NHS(O)$_2$N($C_1$-$C_6$ alkyl)$_2$, —N($C_1$-$C_6$ alkyl)S(O)$_2$NH$_2$, —N($C_1$-$C_6$ alkyl)S(O)$_2$NH($C_1$-$C_6$ alkyl), —N($C_1$-$C_6$ alkyl)S(O)$_2$N($C_1$-$C_6$ alkyl)$_2$, —C(O)$C_1$-$C_6$ alkyl, —C(O)O$C_1$-$C_6$ alkyl, —C(O)NH$_2$, —C(O)NH($C_1$-$C_6$ alkyl), —C(O)N($C_1$-$C_6$ alkyl)$_2$, —P($C_1$-$C_6$ alkyl)$_2$, —P(O)($C_1$-$C_6$ alkyl)$_2$, —P(O)$_2$($C_1$-$C_6$ alkyl)$_2$, —P(O)NH$_2$, —P(O)NH($C_1$-$C_6$ alkyl), —P(O)N($C_1$-$C_6$ alkyl)$_2$, —P(O)$_2$NH$_2$, —P(O)$_2$NH($C_1$-$C_6$ alkyl), —P(O)$_2$N($C_1$-$C_6$ alkyl)$_2$, —P(O)OH, —P(O)O$C_1$-$C_6$ alkyl, —P(O)$_2$OH, —P(O)$_2$O$C_1$-$C_6$ alkyl, —CN, or —NO$_2$;

Y is O, S, N$R^9$, or C$R^9$$R^{10}$; and $R^9$ and $R^{10}$ are each independently H, deuterium, halogen, or $C_1$-$C_6$ alkyl, wherein each hydrogen atom in $C_1$-$C_6$ alkyl is optionally substituted by a halogen, —OH, —O$C_1$-$C_6$ alkyl, —OC(O)$C_1$-$C_6$ alkyl, —OC(O)N($C_1$-$C_6$ alkyl)$_2$, —OC(O)NH($C_1$-$C_6$ alkyl), —OC(O)NH$_2$, —OC(=N)N($C_1$-$C_6$ alkyl)$_2$, —OC(=N)NH($C_1$-$C_6$ alkyl), —OC(=N)NH$_2$, —OS(O)$C_1$-$C_6$ alkyl, —OS(O)$_2$$C_1$-$C_6$ alkyl, —OS(O)N($C_1$-$C_6$ alkyl)$_2$, —OS(O)NH($C_1$-$C_6$ alkyl), —OS(O)NH$_2$, —OS(O)$_2$N($C_1$-$C_6$ alkyl)$_2$, —OS(O)$_2$NH($C_1$-$C_6$ alkyl), —OS(O)$_2$NH$_2$, —SH, —S$C_1$-$C_6$ alkyl, —S(O)$C_1$-$C_6$ alkyl, —S(O)$_2$$C_1$-$C_6$ alkyl, —S(O)N($C_1$-$C_6$ alkyl)$_2$, —S(O)NH($C_1$-$C_6$ alkyl), —S(O)NH$_2$, —S(O)$_2$N($C_1$-$C_6$ alkyl)$_2$, —S(O)$_2$NH($C_1$-$C_6$ alkyl), —S(O)$_2$NH$_2$, —N($C_1$-$C_6$ alkyl)$_2$, —NH($C_1$-$C_6$ alkyl), —NH$_2$, —N($C_1$-$C_6$ alkyl)C(O)$C_1$-$C_6$ alkyl, —NHC(O)$C_1$-$C_6$ alkyl, —N($C_1$-$C_6$ alkyl)C(O)O$C_1$-$C_6$ alkyl, —N($C_1$-$C_6$ alkyl)C(O)OH, —NHC(O)O$C_1$-$C_6$ alkyl, —NHC(O)OH, —N($C_1$-$C_6$ alkyl)C(O)N($C_1$-$C_6$ alkyl)$_2$, —N($C_1$-$C_6$ alkyl)C(O)NH($C_1$-$C_6$ alkyl), —N($C_1$-$C_6$ alkyl)C(O)NH$_2$, —NHC(O)N($C_1$-$C_6$ alkyl)$_2$, —NHC(O)NH($C_1$-$C_6$ alkyl), —NHC(O)NH$_2$, —N($C_1$-$C_6$ alkyl)S(O)$C_1$-$C_6$ alkyl, —NHS(O)$C_1$-$C_6$ alkyl, —N($C_1$-$C_6$ alkyl)S(O)$_2$$C_1$-$C_6$ alkyl, —NHS(O)$_2$$C_1$-$C_6$ alkyl, —N($C_1$-$C_6$ alkyl)S(O)N($C_1$-$C_6$ alkyl)$_2$, —N($C_1$-$C_6$ alkyl)S(O)NH($C_1$-$C_6$ alkyl), —N($C_1$-$C_6$ alkyl)S(O)NH$_2$, —NHS(O)N($C_1$-$C_6$ alkyl)$_2$, —NHS(O)NH($C_1$-$C_6$ alkyl), —NHS(O)NH$_2$, —N($C_1$-$C_6$ alkyl)S(O)$_2$N($C_1$-$C_6$ alkyl)$_2$, —N($C_1$-$C_6$ alkyl)S(O)$_2$NH($C_1$-$C_6$ alkyl), —N($C_1$-$C_6$ alkyl)S(O)$_2$NH$_2$, —NHS(O)$_2$N($C_1$-$C_6$ alkyl)$_2$, —NHS(O)$_2$NH($C_1$-$C_6$ alkyl), —NHS(O)$_2$NH$_2$, —C(O)$C_1$-$C_6$ alkyl, —C(O)O$C_1$-$C_6$ alkyl, —C(O)N($C_1$-$C_6$ alkyl)$_2$, —C(O)NH($C_1$-$C_6$ alkyl), —C(O)NH$_2$, —P($C_1$-$C_6$ alkyl)$_2$, —P(O)($C_1$-$C_6$ alkyl)$_2$, —P(O)$_2$($C_1$-$C_6$ alkyl)$_2$, —P(O)N($C_1$-$C_6$ alkyl)$_2$, —P(O)$_2$N($C_1$-$C_6$ alkyl)$_2$, —P(O)O$C_1$-$C_6$ alkyl, or —P(O)$_2$O$C_1$-$C_6$ alkyl.

26. The compound of clause 25, or a pharmaceutically acceptable salt thereof, wherein M is C$R^3$.

27. The compound of clause 25 or 26, or a pharmaceutically acceptable salt thereof, wherein $R^3$ is H, deuterium, $C_1$-$C_6$ alkyl or halogen.

28. The compound of any one of clauses 25 to 27, or a pharmaceutically acceptable salt thereof, wherein $R^3$ is H or F.

29. The compound of clause 25, or a pharmaceutically acceptable salt thereof, wherein M is N.

30. The compound of any one of clauses 25 to 29, or a pharmaceutically acceptable salt thereof, wherein $M^1$ is C$R^4$.

31. The compound of any one of clauses 25 to 30, or a pharmaceutically acceptable salt thereof, wherein $R^4$ is H, deuterium, $C_1$-$C_6$ alkyl or halogen.

32. The compound of any one of clauses 25 to 31, or a pharmaceutically acceptable salt thereof, wherein $R^4$ is H or Cl.

33. The compound of any one of clauses 25 to 32, or a pharmaceutically acceptable salt thereof, wherein $R^5$ is F.

34. The compound of any one of clauses 25 to 33, or a pharmaceutically acceptable salt thereof, wherein $R^2$ is H.

35. The compound of any one of clauses 25 to 34, or a pharmaceutically acceptable salt thereof, wherein $R^1$ is $C_1$-$C_6$ alkyl.

36. The compound of any one of clauses 25 to 33, or a pharmaceutically acceptable salt thereof, wherein $R^2$ is $C_1$-$C_6$ alkyl.

36a. The compound of any one of clauses 25 to 33, or a pharmaceutically acceptable salt thereof, wherein $R^2$ is $C_1$-$C_6$ alkyl; or $C_3$-$C_7$ cycloalkyl.

37. The compound of any one of clauses 25 to 36, or a pharmaceutically acceptable salt thereof, wherein $R^7$ and $R^8$ combine to form a 5- or 6-membered cycloalkyl, wherein each hydrogen atom in the 5- or 6-membered cycloalkyl is independently optionally substituted by deuterium, halogen, —OH, —CN, —O$C_1$-$C_6$ alkyl, —O$C_1$-$C_6$ alkyl($C_6$-$C_{10}$ aryl), —NH$_2$, —OC(O)$C_1$-$C_6$ alkyl, —OC(O)N($C_1$-$C_6$ alkyl)$_2$, —OC(O)NH($C_1$-$C_6$ alkyl), —OC(O)NH$_2$, —OC(=N)N($C_1$-$C_6$ alkyl)$_2$, —OC(=N)NH($C_1$-$C_6$ alkyl), —OC(=N)NH$_2$, —OS(O)$C_1$-$C_6$ alkyl, —OS(O)$_2$$C_1$-$C_6$ alkyl, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH($C_1$-$C_6$ alkyl), —N($C_1$-$C_6$ alkyl)C(O)NH$_2$, —N($C_1$-$C_6$ alkyl)C(O)NH($C_1$-$C_6$ alkyl), —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHC(O)OH, —N($C_1$-$C_6$ alkyl)C(O)OH, —NHS(O)$C_1$-$C_6$ alkyl, —NHS(O)$_2$$C_1$-$C_6$ alkyl, —N($C_1$-$C_6$ alkyl)S(O)$C_1$-$C_6$ alkyl, —N($C_1$-$C_6$ alkyl)S(O)$_2$$C_1$-$C_6$ alkyl. —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS (O)₂N(C₁-C₆ alkyl)₂, —N(C₁-C₆ alkyl)S(O)NH(C₁-C₆ alkyl), —N(C₁-C₆ alkyl)S(O)₂NH(C₁-C₆ alkyl), —N(C₁-C₆ alkyl)S(O)N(C₁-C₆ alkyl)₂, —N(C₁-C₆ alkyl)S(O)₂N(C₁-C₆ alkyl)₂, —C(O)C₁-C₆ alkyl, —CO₂H, —C(O)OC₁-C₆ alkyl, —C(O)NH₂, —C(O)NH(C₁-C₆ alkyl), —C(O)N(C₁-C₆ alkyl)₂, —SC₁-C₆ alkyl, —S(O)C₁-C₆ alkyl, —S(O)₂C₁-C₆ alkyl, —S(O)NH(C₁-C₆ alkyl), —S(O)₂NH(C₁-C₆ alkyl), —S(O)N(C₁-C₆ alkyl)₂, —S(O)₂N(C₁-C₆ alkyl)₂, —S(O)NH₂, —S(O)₂NH₂, —OS(O)N(C₁-C₆ alkyl)₂, —OS(O)₂N(C₁-C₆ alkyl)₂, —OS(O)NH(C₁-C₆ alkyl), —OS(O)₂NH(C₁-C₆ alkyl), —OS(O)NH₂, —OS(O)₂NH₂, —P(C₁-C₆ alkyl)₂, —P(O)(C₁-C₆ alkyl)₂, C₃-C₆ cycloalkyl, or 3- to 7-membered heterocycloalkyl.

37a. The compound of any one of clauses 25 to 36, or a pharmaceutically acceptable salt thereof, wherein $R^7$ and $R^8$ combine to form a 4-, 5- or 6-membered cycloalkyl, wherein each hydrogen atom in the 5- or 6-membered cycloalkyl is independently optionally substituted by deuterium, halogen, —OH, —CN, —OC₁-C₆ alkyl, —OC₁-C₆ alkyl(C₆-C₁₀ aryl), —NH₂, —OC(O)C₁-C₆ alkyl, —OC(O)N(C₁-C₆ alkyl)₂, —OC(O)NH(C₁-C₆ alkyl), —OC(O)NH₂, —OC(=N)N(C₁-C₆ alkyl)₂, —OC(=N)NH(C₁-C₆ alkyl), —OC(=N)NH₂, —OS(O)C₁-C₆ alkyl, —OS(O)₂C₁-C₆ alkyl, —NH(C₁-C₆ alkyl), —N(C₁-C₆ alkyl)₂, —NHC(O)C₁-C₆ alkyl, —N(C₁-C₆ alkyl)C(O)C₁-C₆ alkyl, —NHC(O)NH₂, —NHC(O)NH(C₁-C₆ alkyl), —N(C₁-C₆ alkyl)C(O)NH₂, —N(C₁-C₆ alkyl)C(O)NH(C₁-C₆ alkyl), —NHC(O)N(C₁-C₆ alkyl)₂, —N(C₁-C₆ alkyl)C(O)N(C₁-C₆ alkyl)₂, —NHC(O)OC₁-C₆ alkyl, —N(C₁-C₆ alkyl)C(O)OC₁-C₆ alkyl, —NHC(O)OH, —N(C₁-C₆ alkyl)C(O)OH, —NHS(O)C₁-C₆ alkyl, —NHS(O)₂C₁-C₆ alkyl, —N(C₁-C₆ alkyl)S(O)C₁-C₆ alkyl, —N(C₁-C₆ alkyl)S(O)₂C₁-C₆ alkyl. —NHS(O)NH₂, —NHS(O)₂NH₂, —N(C₁-C₆ alkyl)S(O)NH₂, —N(C₁-C₆ alkyl)S(O)₂NH₂, —NHS(O)NH(C₁-C₆ alkyl), —NHS(O)₂NH(C₁-C₆ alkyl), —NHS(O)N(C₁-C₆ alkyl)₂, —NHS(O)₂N(C₁-C₆ alkyl)₂, —N(C₁-C₆ alkyl)S(O)NH(C₁-C₆ alkyl), —N(C₁-C₆ alkyl)S(O)₂NH(C₁-C₆ alkyl), —N(C₁-C₆ alkyl)S(O)N(C₁-C₆ alkyl)₂, —N(C₁-C₆ alkyl)S(O)₂N(C₁-C₆ alkyl)₂, —C(O)C₁-C₆ alkyl, —CO₂H, —C(O)OC₁-C₆ alkyl, —C(O)NH₂, —C(O)NH(C₁-C₆ alkyl), —C(O)N(C₁-C₆ alkyl)₂, —SC₁-C₆ alkyl, —S(O)C₁-C₆ alkyl, —S(O)₂C₁-C₆ alkyl, —S(O)NH(C₁-C₆ alkyl), —S(O)₂NH(C₁-C₆ alkyl), —S(O)N(C₁-C₆ alkyl)₂, —S(O)₂N(C₁-C₆ alkyl)₂, —S(O)NH₂, —S(O)₂NH₂, —OS(O)N(C₁-C₆ alkyl)₂, —OS(O)₂N(C₁-C₆ alkyl)₂, —OS(O)NH(C₁-C₆ alkyl), —OS(O)₂NH(C₁-C₆ alkyl), —OS(O)NH₂, —OS(O)₂NH₂, —P(C₁-C₆ alkyl)₂, —P(O)(C₁-C₆ alkyl)₂, C₃-C₆ cycloalkyl, or 3- to 7-membered heterocycloalkyl.

38. The compound of any one of clauses 25 to 36, or a pharmaceutically acceptable salt thereof, wherein $R^7$ and $R^8$ combine to form a 3-, 4-, 5- or 6-membered heterocycloalkyl, wherein each hydrogen atom in the 3-, 4-, 5- or 6-membered heterocycloalkyl is independently optionally substituted by deuterium, halogen, —OH, —CN, —OC₁-C₆ alkyl, —OC₁-C₆ alkyl(C₆-C₁₀ aryl), —NH₂, —OC(O)C₁-C₆ alkyl, —OC(O)N(C₁-C₆ alkyl)₂, —OC(O)NH(C₁-C₆ alkyl), —OC(O)NH₂, —OC(=N)N(C₁-C₆ alkyl)₂, —OC(=N)NH(C₁-C₆ alkyl), —OC(=N)NH₂, —OS(O)C₁-C₆ alkyl, —OS(O)₂C₁-C₆ alkyl, —NH(C₁-C₆ alkyl), —N(C₁-C₆ alkyl)₂, —NHC(O)C₁-C₆ alkyl, —N(C₁-C₆ alkyl)C(O)C₁-C₆ alkyl, —NHC(O)NH₂, —NHC(O)NH(C₁-C₆ alkyl), —N(C₁-C₆ alkyl)C(O)NH₂, —N(C₁-C₆ alkyl)C(O)NH(C₁-C₆ alkyl), —NHC(O)N(C₁-C₆ alkyl)₂, —N(C₁-C₆ alkyl)C(O)N(C₁-C₆ alkyl)₂, —NHC(O)OC₁-C₆ alkyl, —N(C₁-C₆ alkyl)C(O)OC₁-C₆ alkyl, —NHC(O)OH, —N(C₁-C₆ alkyl)C(O)OH, —NHS(O)C₁-C₆ alkyl, —NHS(O)₂C₁-C₆ alkyl, —N(C₁-C₆ alkyl)S(O)C₁-C₆ alkyl, —N(C₁-C₆ alkyl)S(O)₂C₁-C₆ alkyl. —NHS(O)NH₂, —NHS(O)₂NH₂, —N(C₁-C₆ alkyl)S(O)NH₂, —N(C₁-C₆ alkyl)S(O)₂NH₂, —NHS(O)NH(C₁-C₆ alkyl), —NHS(O)₂NH(C₁-C₆ alkyl), —NHS(O)N(C₁-C₆ alkyl)₂, —NHS(O)₂N(C₁-C₆ alkyl)₂, —N(C₁-C₆ alkyl)S(O)NH(C₁-C₆ alkyl), —N(C₁-C₆ alkyl)S(O)₂NH(C₁-C₆ alkyl), —N(C₁-C₆ alkyl)S(O)N(C₁-C₆ alkyl)₂, —N(C₁-C₆ alkyl)S(O)₂N(C₁-C₆ alkyl)₂, —C(O)C₁-C₆ alkyl, —CO₂H, —C(O)OC₁-C₆ alkyl, —C(O)NH₂, —C(O)NH(C₁-C₆ alkyl), —C(O)N(C₁-C₆ alkyl)₂, —SC₁-C₆ alkyl, —S(O)C₁-C₆ alkyl, —S(O)₂C₁-C₆ alkyl, —S(O)NH(C₁-C₆ alkyl), —S(O)₂ NH(C₁-C₆ alkyl), —S(O)N(C₁-C₆ alkyl)₂, —S(O)₂N(C₁-C₆ alkyl)₂, —S(O)NH₂, —S(O)₂NH₂, —OS(O)N(C₁-C₆ alkyl)₂, —OS(O)₂N(C₁-C₆ alkyl)₂, —OS(O)NH(C₁-C₆ alkyl), —OS(O)₂NH(C₁-C₆ alkyl), —OS(O)NH₂, —OS(O)₂NH₂, —P(C₁-C₆ alkyl)₂, —P(O)(C₁-C₆ alkyl)₂, C₃-C₆ cycloalkyl, or 3- to 7-membered heterocycloalkyl.

39. The compound of clause 38, or a pharmaceutically acceptable salt thereof, wherein $R^7$ and $R^8$ combine to form a tetrahydrofuran ring.

40. The compound of clause 37, or a pharmaceutically acceptable salt thereof, wherein $R^7$ and $R^8$ combine to form a cyclopentane ring.

40a. The compound of clause 37 or 37a, or a pharmaceutically acceptable salt thereof, wherein $R^7$ and $R^8$ combine to form a cyclobutane ring, cyclopentane ring, or cyclohexane ring.

41. The compound of any of the preceding clauses, or a pharmaceutically acceptable salt thereof, wherein X is O.

42. The compound of clause 1, selected from the group consisting of

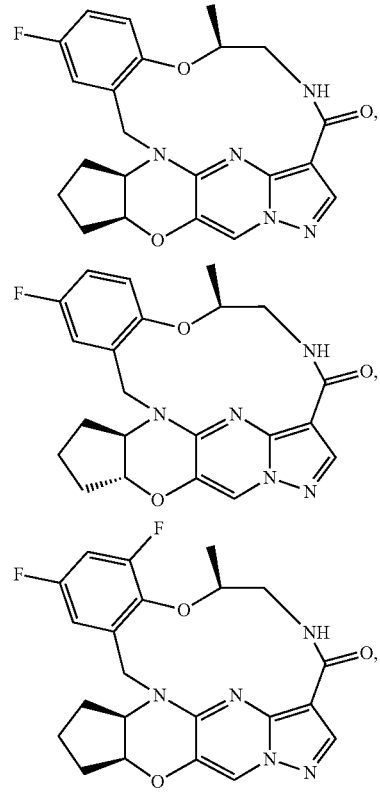

31
-continued
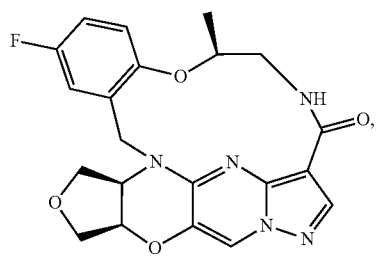
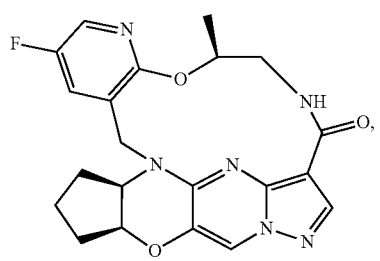
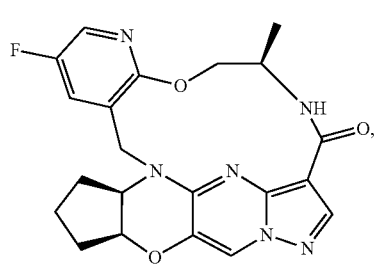
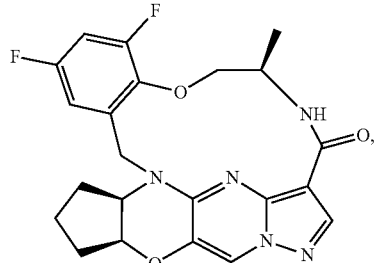
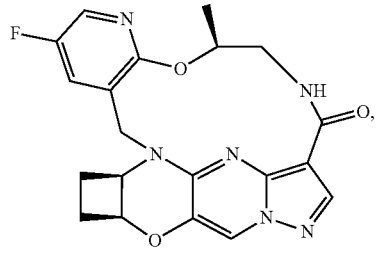
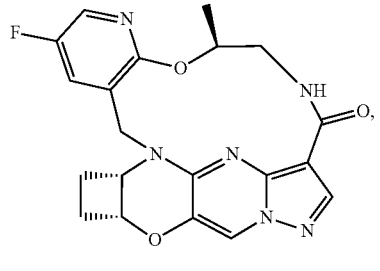
32
-continued
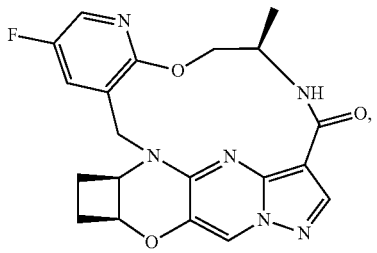
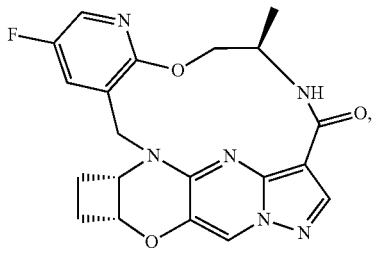
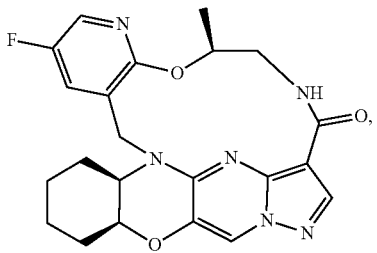
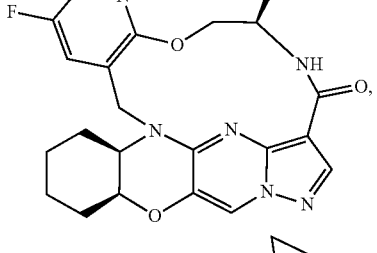
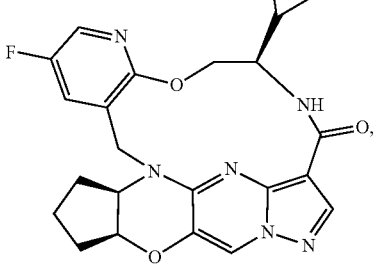
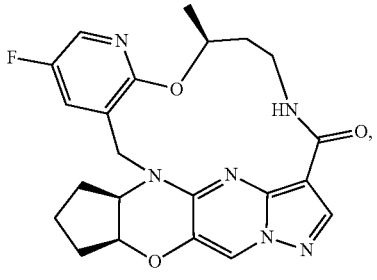

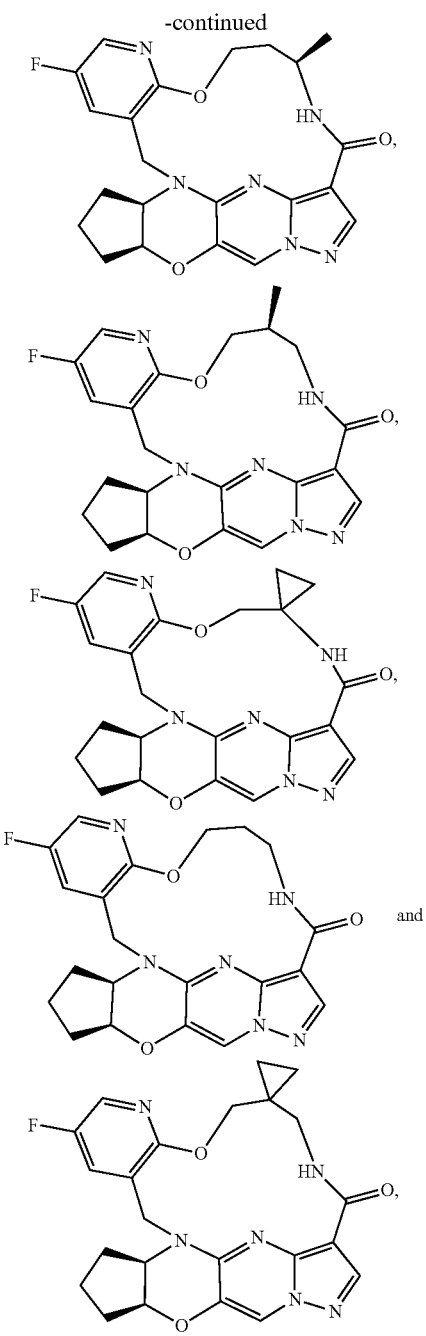

or a pharmaceutically acceptable salt thereof.

43. A pharmaceutical composition comprising a compound of any one of the preceding clauses, or a pharmaceutically acceptable salt thereof, and optionally at least one diluent, carrier or excipient.

44. A method of treating cancer comprising administering to a subject in need of such treatment an effective amount of at least one compound of any one of clauses 1 to 42, or a pharmaceutically acceptable salt thereof.

45. Use of a compound of any one of clauses 1 to 42, or a pharmaceutically acceptable salt thereof, in the preparation of a medicament for the treatment of cancer.

46. Use of a compound of any one of clauses 1 to 42, or a pharmaceutically acceptable salt thereof, for treating cancer.

47. A method of inhibiting RET or SRC, comprising contacting a cell comprising one or more of such kinases with an effective amount of at least one compound of any one of clauses 1 to 42, or a pharmaceutically acceptable salt thereof, and/or with at least one pharmaceutical composition of the disclosure, wherein the contacting is in vitro, ex vivo, or in vivo.

48. A compound of any one of clauses 1 to 42, for use in treating cancer in a patient.

DETAILED DESCRIPTION

Figure 1:
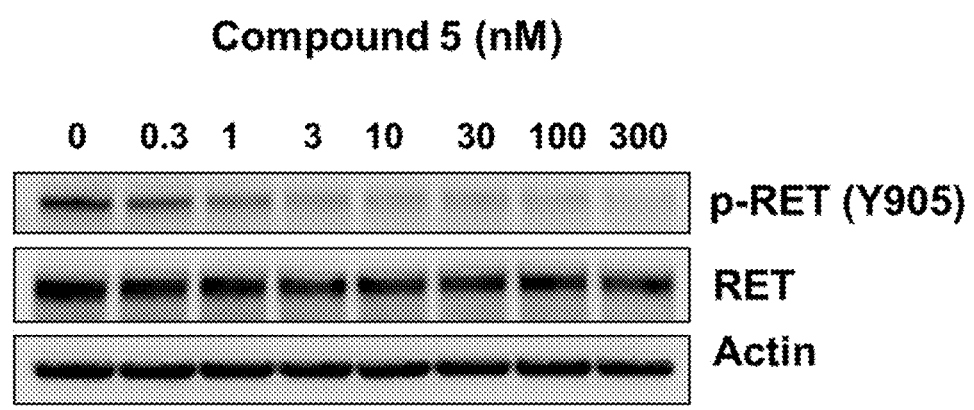
FIG. 1 shows the pharmacodynamic inhibiting activity of Compound 5 on RET in RET-driven cells, specifically that Compound 5 caused the suppression of RET autophosphorylation at IC50s of around 0.3 nM in TI.

Before the present disclosure is further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as is commonly understood by one of ordinary skill in the art to which this disclosure belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

As used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the terms "including," "containing," and "comprising" are used in their open, non-limiting sense.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

Chemical nomenclature for compounds described herein has generally been derived using the commercially-available ACD/Name 2014 (ACD/Labs) or ChemBioDraw Ultra 13.0 (Perkin Elmer).

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination. All combinations of the embodiments pertaining to the chemical groups represented by the variables are specifically embraced by the present disclosure and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present disclosure and are disclosed herein just as if each and every such sub-combination of chemical groups was individually and explicitly disclosed herein.

DEFINITIONS

As used herein, the term "alkyl" includes a chain of carbon atoms, which is optionally branched and contains from 1 to 20 carbon atoms. It is to be further understood that in certain embodiments, alkyl may be advantageously of limited length, including $C_1$-$C_{12}$, $C_1$-$C_{10}$, $C_1$-$C_9$, $C_1$-$C_8$, $C_1$-$C_7$, $C_1$-$C_6$, and $C_1$-$C_4$. Illustratively, such particularly limited length alkyl groups, including $C_1$-$C_8$, $C_1$-$C_7$, $C_1$-$C_6$, and $C_1$-$C_4$, and the like may be referred to as "lower alkyl." Illustrative alkyl groups include, but are not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like. Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halo, carbonyl, oxo, (=O), thiocarbonyl, O-carbamyl, N-carbamyl, O-thiocarbamyl, N-thiocarbamyl, C-amido, N-amido, C-carboxy, O-carboxy, nitro, and amino, or as described in the various embodiments provided herein. It will be understood that "alkyl" may be combined with other groups, such as those provided above, to form a functionalized alkyl. By way of example, the combination of an "alkyl" group, as described herein, with a "carboxy" group may be referred to as a "carboxyalkyl" group. Other non-limiting examples include hydroxyalkyl, aminoalkyl, and the like.

As used herein, the term "alkenyl" includes a chain of carbon atoms, which is optionally branched, and contains from 2 to 20 carbon atoms, and also includes at least one carbon-carbon double bond (i.e. C=C). It will be understood that in certain embodiments, alkenyl may be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkenyl groups, including $C_2$-$C_8$, $C_2$-$C_7$, $C_2$-$C_6$, and $C_2$-$C_4$ may be referred to as lower alkenyl. Alkenyl may be unsubstituted, or substituted as described for alkyl or as described in the various embodiments provided herein. Illustrative alkenyl groups include, but are not limited to, ethenyl, 1-propenyl, 2-propenyl, 1-, 2-, or 3-butenyl, and the like.

As used herein, the term "alkynyl" includes a chain of carbon atoms, which is optionally branched, and contains from 2 to 20 carbon atoms, and also includes at least one carbon-carbon triple bond (i.e. C≡C). It will be understood that in certain embodiments, alkynyl may each be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkynyl groups, including $C_2$-$C_8$, $C_2$-$C_7$, $C_2$-$C_6$, and $C_2$-$C_4$ may be referred to as lower alkynyl. Alkenyl may be unsubstituted, or substituted as described for alkyl or as described in the various embodiments provided herein. Illustrative alkenyl groups include, but are not limited to, ethynyl, 1-propynyl, 2-propynyl, 1-, 2-, or 3-butynyl, and the like.

As used herein, the term "aryl" refers to an all-carbon monocyclic or fused-ring polycyclic groups of 6 to 12 carbon atoms having a completely conjugated pi-electron system. It will be understood that in certain embodiments, aryl may be advantageously of limited size such as $C_6$-$C_{10}$ aryl. Illustrative aryl groups include, but are not limited to, phenyl, naphthylenyl and anthracenyl. The aryl group may be unsubstituted, or substituted as described for alkyl or as described in the various embodiments provided herein.

As used herein, the term "cycloalkyl" refers to a 3 to 15 member all-carbon monocyclic ring, including an all-carbon 5-member/6-member or 6-member/6-member fused bicyclic ring, or a multicyclic fused ring (a "fused" ring system means that each ring in the system shares an adjacent pair of carbon atoms with each other ring in the system) group, or a carbocyclic ring that is fused to another group such as a heterocyclic, such as ring 5- or 6-membered cycloalkyl fused to a 5- to 7-membered heterocyclic ring, where one or more of the rings may contain one or more double bonds but the cycloalkyl does not contain a completely conjugated pi-electron system. It will be understood that in certain embodiments, cycloalkyl may be advantageously of limited size such as $C_3$-$C_{13}$, $C_3$-$C_9$, $C_3$-$C_6$ and $C_4$-$C_6$. Cycloalkyl may be unsubstituted, or substituted as described for alkyl or as described in the various embodiments provided herein. Illustrative cycloalkyl groups include, but are not limited to, cyclopropyl, cyclobutyl, cyclopentyl, cyclopentenyl, cyclopentadienyl, cyclohexyl, cyclohexenyl, cycloheptyl, adamantyl, norbornyl, norbornenyl, 9H-fluoren-9-yl, and the like. Illustrative examples of cycloalkyl groups shown in graphical representations include the following entities, in the form of properly bonded moieties:

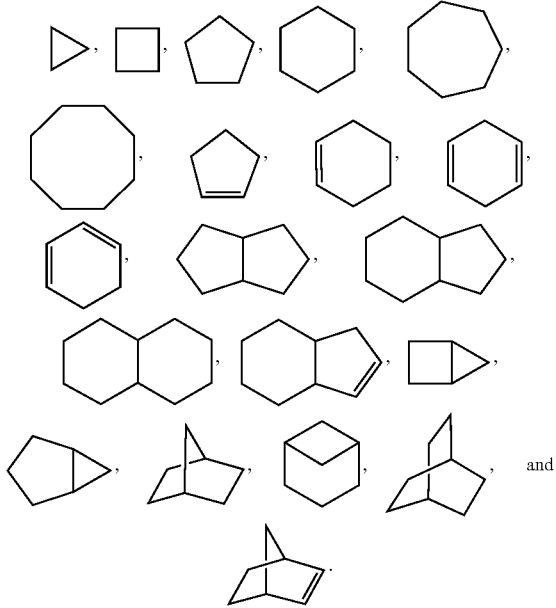

As used herein, the term "heterocycloalkyl" refers to a monocyclic or fused ring group having in the ring(s) from 3 to 12 ring atoms, in which at least one ring atom is a heteroatom, such as nitrogen, oxygen or sulfur, the remaining ring atoms being carbon atoms. Heterocycloalkyl may optionally contain 1, 2, 3 or 4 heteroatoms. A heterocycloalkyl group may be fused to another group such as another heterocycloalkyl, or a heteroaryl group. Heterocycloalkyl may also have one or more double bonds, including double bonds to nitrogen (e.g. C=N or N=N) but does not contain a completely conjugated pi-electron system. It will be understood that in certain embodiments, heterocycloalkyl may be advantageously of limited size such as 3- to 7-membered heterocycloalkyl, 5- to 7-membered heterocycloalkyl, 3-, 4-, 5- or 6-membered heterocycloalkyl, and the like. Heterocycloalkyl may be unsubstituted, or substituted as described for alkyl or as described in the various embodiments provided herein. Illustrative heterocycloalkyl groups include, but are not limited to, oxiranyl, thianaryl, azetidinyl, oxetanyl, tetrahydrofuranyl, pyrrolidinyl, tetrahydropyranyl, piperidinyl, 1,4-dioxanyl, morpholinyl, 1,4-dithianyl, piperazinyl, oxepanyl, 3,4-dihydro-2H-pyranyl, 5,6-dihydro-2H-pyranyl, 2H-pyranyl, 1, 2, 3, 4-tetrahydropyridinyl, and the like. Illustrative examples of heterocycloalkyl groups shown in graphical representations include the following entities, in the form of properly bonded moieties:

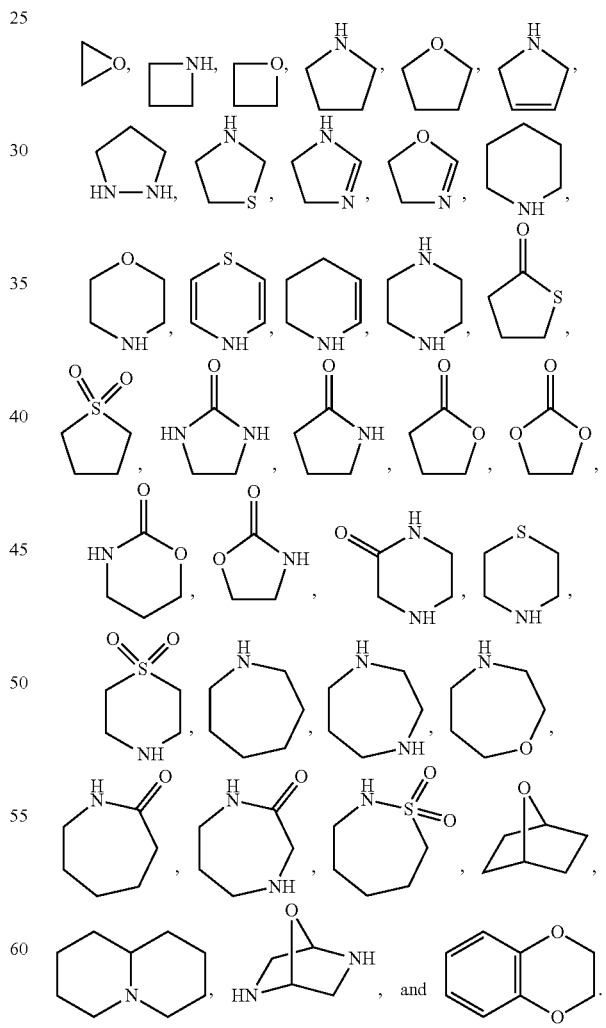

As used herein, the term "heteroaryl" refers to a monocyclic or fused ring group of 5 to 12 ring atoms containing one, two, three or four ring heteroatoms selected from nitrogen, oxygen and sulfur, the remaining ring atoms being carbon atoms, and also having a completely conjugated pi-electron system. It will be understood that in certain embodiments, heteroaryl may be advantageously of limited size such as 3- to 7-membered heteroaryl, 5- to 7-membered heteroaryl, and the like. Heteroaryl may be unsubstituted, or substituted as described for alkyl or as described in the various embodiments provided herein. Illustrative heteroaryl groups include, but are not limited to, pyrrolyl, furanyl, thiophenyl, imidazolyl, oxazolyl, thiazolyl, pyrazolyl, pyridinyl, pyrimidinyl, quinolinyl, isoquinolinyl, purinyl, tetrazolyl, triazinyl, pyrazinyl, tetrazinyl, quinazolinyl, quinoxalinyl, thienyl, isoxazolyl, isothiazolyl, oxadiazolyl, thiadiazolyl, triazolyl, benzimidazolyl, benzoxazolyl, benzthiazolyl, benzisoxazolyl, benzisothiazolyl and carbazolyl, and the like. Illustrative examples of heteroaryl groups shown in graphical representations, include the following entities, in the form of properly bonded moieties:

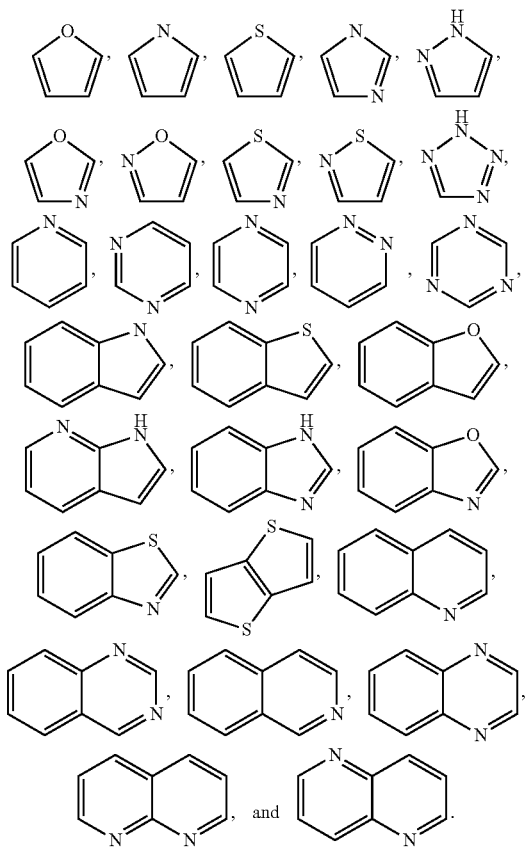

As used herein, "hydroxy" or "hydroxyl" refers to an —OH group.

As used herein, "alkoxy" refers to both an —O-(alkyl) or an —O-(unsubstituted cycloalkyl) group. Representative examples include, but are not limited to, methoxy, ethoxy, propoxy, butoxy, cyclopropyloxy, cyclobutyloxy, cyclopentyloxy, cyclohexyloxy, and the like.

As used herein, "aryloxy" refers to an —O-aryl or an —O-heteroaryl group. Representative examples include, but are not limited to, phenoxy, pyridinyloxy, furanyloxy, thienyloxy, pyrimidinyloxy, pyrazinyloxy, and the like, and the like.

As used herein, "mercapto" refers to an —SH group.

As used herein, "alkylthio" refers to an —S-(alkyl) or an —S-(unsubstituted cycloalkyl) group. Representative examples include, but are not limited to, methylthio, ethylthio, propylthio, butylthio, cyclopropylthio, cyclobutylthio, cyclopentylthio, cyclohexylthio, and the like.

As used herein, "arylthio" refers to an —S-aryl or an —S-heteroaryl group. Representative examples include, but are not limited to, phenylthio, pyridinylthio, furanylthio, thienylthio, pyrimidinylthio, and the like.

As used herein, "halo" or "halogen" refers to fluorine, chlorine, bromine or iodine.

As used herein, "cyano" refers to a —CN group.

The term "oxo" represents a carbonyl oxygen. For example, a cyclopentyl substituted with oxo is cyclopentanone.

As used herein, "bond" refers to a covalent bond.

The term "substituted" means that the specified group or moiety bears one or more substituents. The term "unsubstituted" means that the specified group bears no substituents. Where the term "substituted" is used to describe a structural system, the substitution is meant to occur at any valency-allowed position on the system. In some embodiments, "substituted" means that the specified group or moiety bears one, two, or three substituents. In other embodiments, "substituted" means that the specified group or moiety bears one or two substituents. In still other embodiments, "substituted" means the specified group or moiety bears one substituent.

As used herein, "optional" or "optionally" means that the subsequently described event or circumstance may but need not occur, and that the description includes instances where the event or circumstance occurs and instances in which it does not. For example, "wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by $C_1$-$C_6$ alkyl" means that an alkyl may be but need not be present on any of the $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl by replacement of a hydrogen atom for each alkyl group, and the description includes situations where the $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is substituted with an alkyl group and situations where the $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is not substituted with the alkyl group.

As used herein, "independently" means that the subsequently described event or circumstance is to be read on its own relative to other similar events or circumstances. For example, in a circumstance where several equivalent hydrogen groups are optionally substituted by another group described in the circumstance, the use of "independently optionally" means that each instance of a hydrogen atom on the group may be substituted by another group, where the groups replacing each of the hydrogen atoms may be the same or different. Or for example, where multiple groups exist all of which can be selected from a set of possibilities, the use of "independently" means that each of the groups can be selected from the set of possibilities separate from any other group, and the groups selected in the circumstance may be the same or different.

As used herein, the phrase "taken together with the carbon to which they are attached" or "taken together with the carbon atom to which they are attached" means that two substituents (e.g. $R^1$ and $R^2$) attached to the same carbon atom form the groups that are defined by the claim, such as $C_3$-$C_6$ cycloalkyl or a 4- to 6-membered heterocycloalkyl. In particular, the phrase "taken together with the carbon to which they are attached" means that when, for example, $R^1$ and $R^2$, and the carbon atom to which they are attached form a $C_3$-$C_6$ cycloalkyl, then the formed ring will be attached at the same carbon atom. For example, the phrase "$R^1$ and $R^2$ taken together with the carbon to which they are attached form a $C_3$-$C_6$ cycloalkyl" used in connection with the embodiments described herein includes fragments represented as follows:

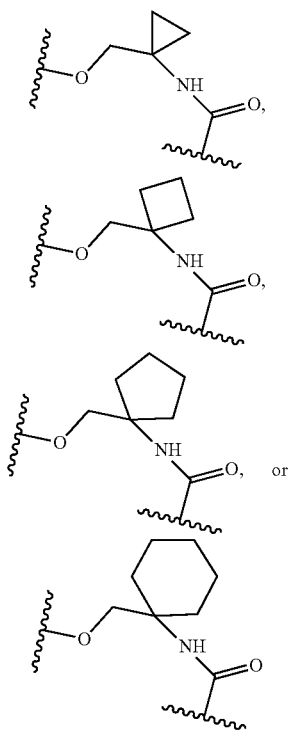

where the above spirocyclic rings can be optionally substituted as defined in a given embodiment.

As used herein, the phrase "taken together with the carbons to which they are attached" or "taken together with the carbon atoms to which they are attached" means that two substituents (e.g. $R^1$ and $R^2$) attached to different carbon atoms form the groups that are defined by the claim, such as $C_3$-$C_6$ cycloalkyl or a 4- to 6-membered heterocycloalkyl. In particular, the phrase "taken together with the carbons to which they are attached form a" means that when, for example, $R^1$ and $R^2$, and the carbon atoms, which are not the same carbon atom, to which they are attached form a $C_3$-$C_6$ cycloalkyl, then the formed ring will be attached at different carbon atoms. For example, the phrase "$R^1$ and $R^2$ taken together with the carbons to which they are attached form a $C_3$-$C_6$ cycloalkyl" used in connection with the embodiments described herein includes fragments represented as follows:

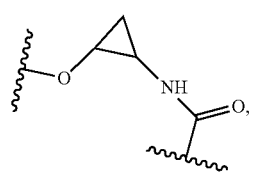

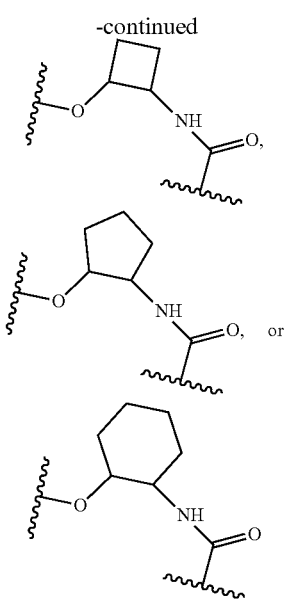

where the above fused rings can be optionally substituted as defined in a given embodiment. Likewise, the phrase "$R^7$ and $R^8$ combine to form a $C_3$-$C_7$ cycloalkyl, a 5- to 8-membered heterocycloalkyl, $C_6$-$C_{10}$ aryl, or 5- to 7-membered heteroaryl" also means that $R^7$ and $R^8$ are taken together with the carbon atoms to which they are attached to form a $C_3$-$C_7$ cycloalkyl, a 5- to 8-membered heterocycloalkyl, $C_6$-$C_{10}$ aryl, or 5- to 7-membered heteroaryl. In particular, "$R^7$ and $R^8$ combine to form a $C_3$-$C_7$ cycloalkyl" used in connection with the embodiments described herein includes fragments represented by the following:

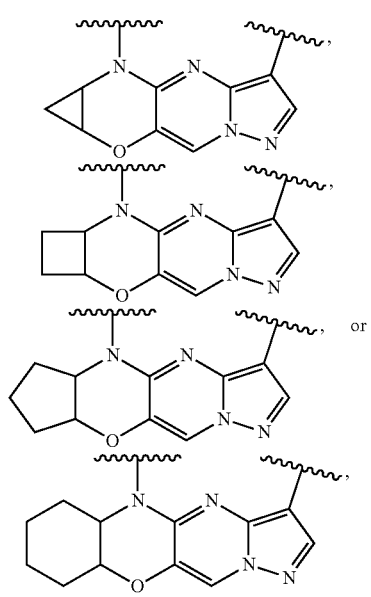

where the above fused rings can be optionally substituted as defined in a given embodiment. One of skill in the art will appreciate that all stereochemical arrangements are included within the structures provided above, such as with respect to the five-carbon ring formed by $R^7$ and $R^8$ as provided in the following fragments:

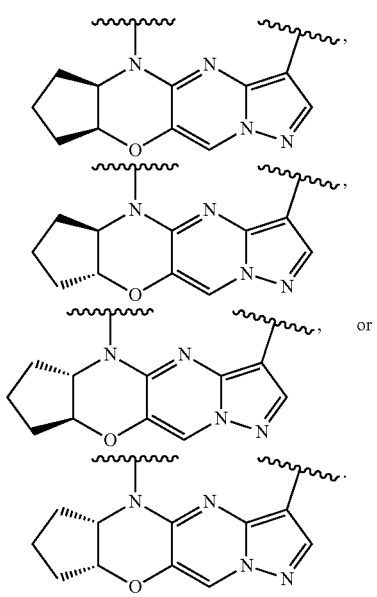

As used herein, the term "pharmaceutically acceptable salt" refers to those salts which counter ions which may be used in pharmaceuticals. See, generally, S. M. Berge, et al., "Pharmaceutical Salts," J. Pharm. Sci., 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt. Such salts include:

(1) acid addition salts, which can be obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methane sulfonic acid, ethanesulfonic acid, p-toluenesulfonic acid, salicylic acid, tartaric acid, citric acid, succinic acid or malonic acid and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, trimethamine, N-methylglucamine, and the like.

Pharmaceutically acceptable salts are well known to those skilled in the art, and any such pharmaceutically acceptable salt may be contemplated in connection with the embodiments described herein. Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington's Pharmaceutical Sciences, 17th Edition, Mack Publishing Company, Easton, Pa., 1985.

For a compound of Formula I, II, III, IV or V that contains a basic nitrogen, a pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, or ethanesulfonic acid, or any compatible mixture of acids such as those given as examples herein, and any other acid and mixture thereof that are regarded as equivalents or acceptable substitutes in light of the ordinary level of skill in this technology.

The disclosure also relates to pharmaceutically acceptable prodrugs of the compounds of Formula I, II, III, IV or V, and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula I, II, III, IV or V). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

The present disclosure also relates to pharmaceutically active metabolites of compounds of Formula I, II, III, IV or V, and uses of such metabolites in the methods of the disclosure. A "pharmaceutically active metabolite" means a pharmacologically active product of metabolism in the body of a compound of Formula I, II, III, IV or V, or salt thereof. Prodrugs and active metabolites of a compound may be determined using routine techniques known or available in the art. See, e.g., Bertolini et al., J. Med. Chem. 1997, 40, 2011-2016; Shan et al., J. Pharm. Sci. 1997, 86 (7), 765-767; Bagshawe, Drug Dev. Res. 1995, 34, 220-230; Bodor, Adv. Drug Res. 1984, 13, 255-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

Any formula depicted herein is intended to represent a compound of that structural formula as well as certain variations or forms. For example, a formula given herein is intended to include a racemic form, or one or more enantiomeric, diastereomeric, or geometric isomers, or a mixture thereof. Additionally, any formula given herein is intended to refer also to a hydrate, solvate, or polymorph of such a compound, or a mixture thereof. For example, it will be appreciated that compounds depicted by a structural formula containing the symbol "∿" include both stereoisomers for the carbon atom to which the symbol "∿" is attached, specifically both the bonds "━" and "┅" are encompassed by the meaning of "∿". For example, in some exemplary embodiments, certain compounds provided herein can be described by the formula

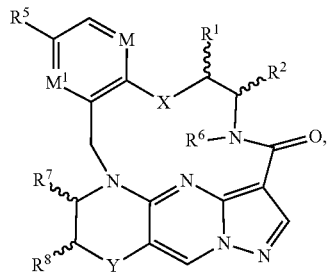

which formula will be understood to encompass compounds having both stereochemical configurations at the relevant carbon atom, specifically in this example

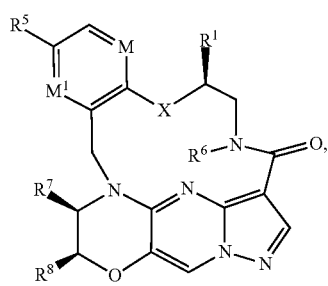

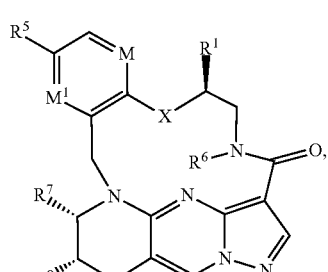

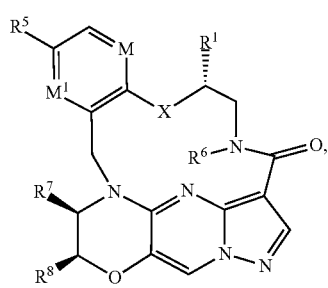

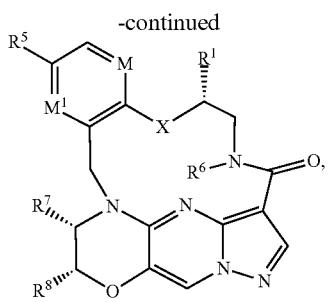

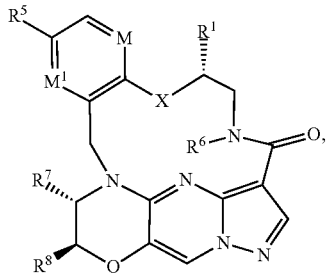

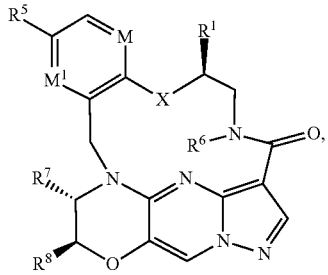

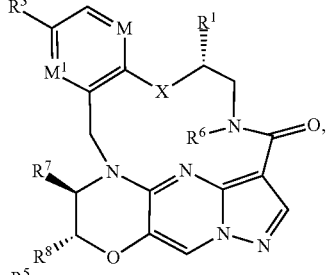

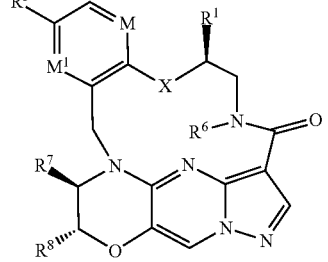

and other stereochemical combinations.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine, chlorine, and iodine, such as $^{2}$H, $^{3}$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, and $^{125}$I, respectively. Such isotopically labelled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent.

Any disubstituent referred to herein is meant to encompass the various attachment possibilities when more than one of such possibilities are allowed. For example, reference to disubstituent -A-B—, where A≠B, refers herein to such disubstituent with A attached to a first substituted member and B attached to a second substituted member, and it also refers to such disubstituent with A attached to the second substituted member and B attached to the first substituted member.

Representative Embodiments

In some embodiments, compounds described herein comprise a moiety of the formula

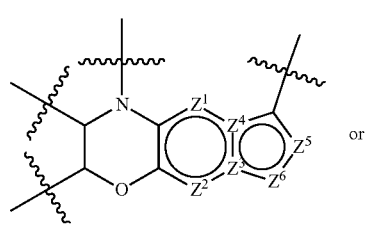

wherein $Z^1$-$Z^6$ and Y are defined as described herein, and the substituents on the non-aromatic ring marked by a bond and ~ correspond to $R^7$ and $R^8$ as described herein. In other embodiments, compounds described herein comprise a moiety of the formula

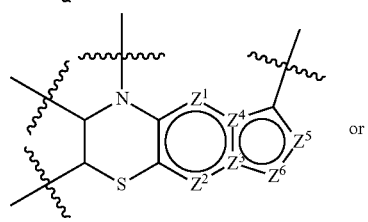

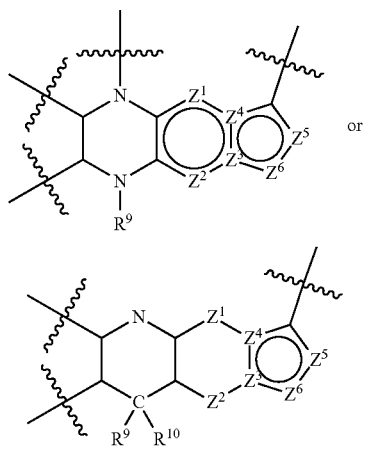

wherein $Z^1$-$Z^6$, $R^9$, and $R^{10}$ are otherwise defined as described herein, and the substituents on the non-aromatic ring marked by a bond and ~ correspond to $R^7$ and $R^8$ as described herein. In still other embodiments, compounds described herein comprise a moiety of the formula

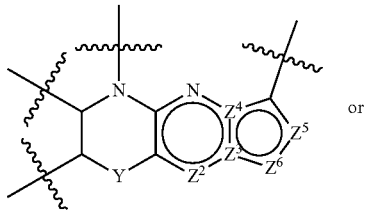

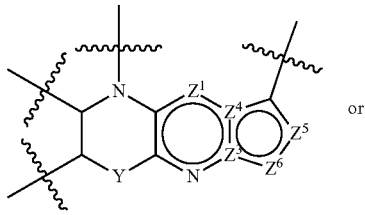

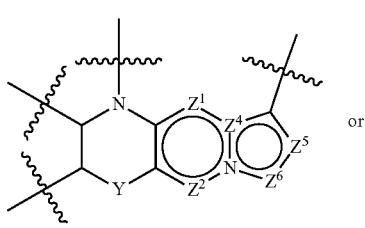

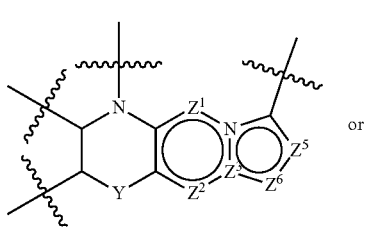

-continued

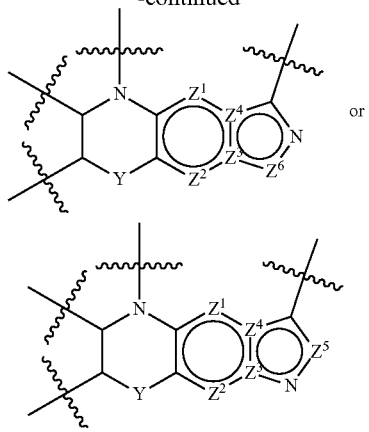

or

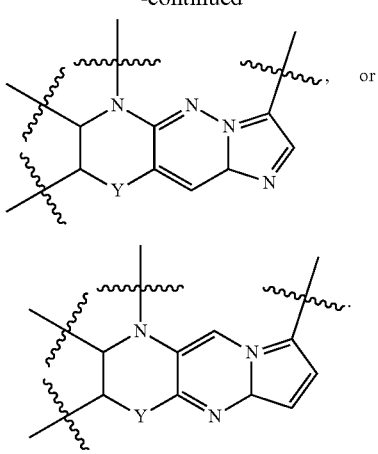

or

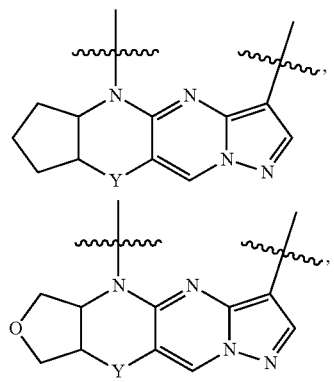

wherein $Z^1$-$Z^6$ and Y are otherwise defined as described herein, and the substituents on the non-aromatic ring marked by a bond and ~ correspond to $R^7$ and $R^8$ as described herein. In some embodiments, each of $Z^1$, $Z^2$, $Z^3$, $Z^4$, $Z^5$, and $Z^6$ is independently N, NH, C or CH. In some embodiments, $Z^1$, $Z^3$ and $Z^6$ are N, $Z^2$ and $Z^5$ are CH, and $Z^4$ is C. In some embodiments, $Z^1$, $Z^3$ and $Z^6$ are N, $Z^2$ and $Z^5$ are CH, $Z^4$ is C, and Y is O. In some embodiments, $Z^1$, $Z^2$ and $Z^6$ are N, $Z^5$ is CH, and $Z^3$ and $Z^4$ are C. In some embodiments, $Z^1$, $Z^2$ and $Z^6$ are N, $Z^5$ is CH, $Z^3$ and $Z^4$ are C, and Y is O. In some embodiments, $Z^2$, $Z^4$ and $Z^5$ are N, $Z^1$ and $Z^6$ are CH, and $Z^3$ is C. In some embodiments, $Z^2$, $Z^4$ and $Z^5$ are N, $Z^1$ and $Z^6$ are CH, $Z^3$ is C and Y is O. In some embodiments, $Z^1$, $Z^4$ and $Z^6$ are N, $Z^2$ and $Z^5$ are CH, and $Z^3$ is C. In some embodiments, $Z^1$, $Z^4$ and $Z^6$ are N, $Z^2$ and $Z^5$ are CH, $Z^3$ is C, and Y is O. In some embodiments, $Z^2$ and $Z^4$ are N, $Z^1$, $Z^5$ and $Z^6$ are CH, and $Z^3$ is C. In some embodiments, $Z^2$ and $Z^4$ are N, $Z^1$, $Z^5$ and $Z^6$ are CH, $Z^3$ is C, and Y is O.

In still other embodiments, compounds described herein comprise a moiety of the formula

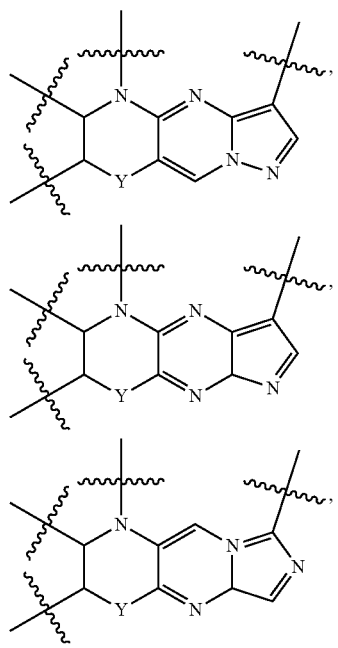

wherein Y is otherwise defined as described herein, and the substituents on the non-aromatic ring marked by a bond and ~ correspond to $R^7$ and $R^8$ as described herein. In still other embodiments, compounds described herein comprise a moiety of the formula

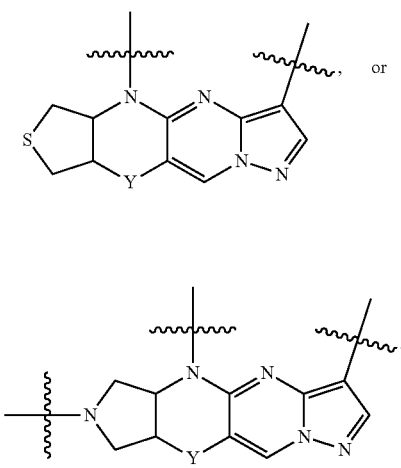

wherein Y is otherwise defined as described herein. In still other embodiments, compounds described herein comprise a moiety of the formula

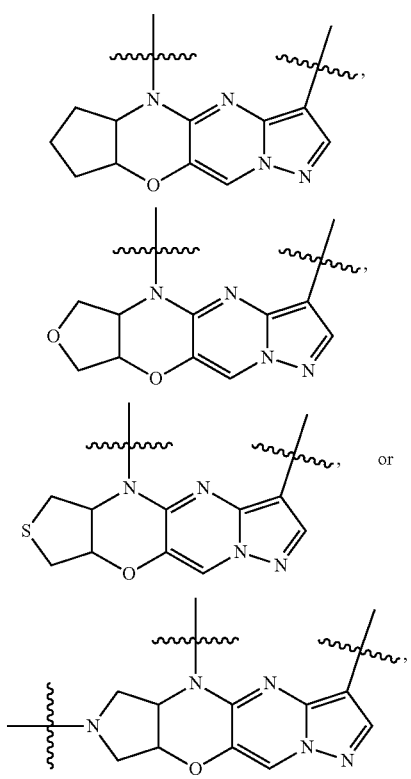
In still other embodiments, compounds described herein comprise a moiety of the formula
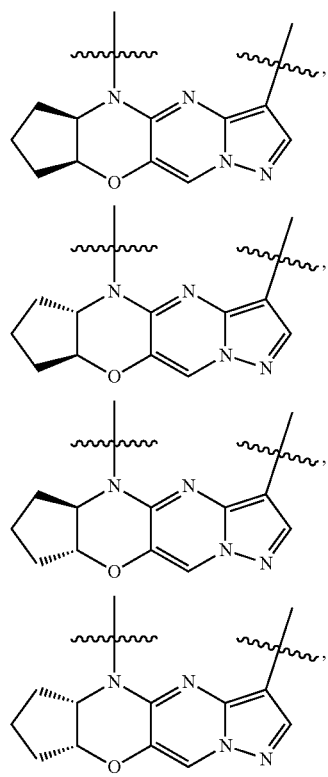
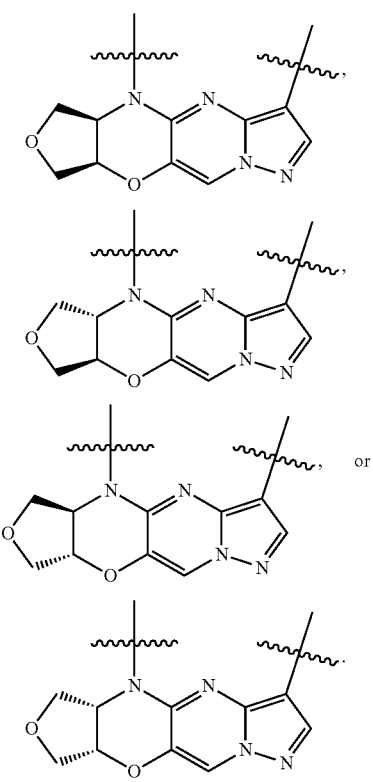
In still other embodiments, compounds described herein comprise a moiety of the formula
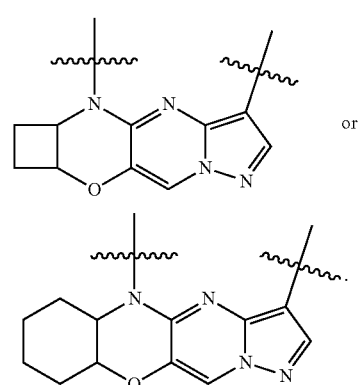
In still other embodiments, compounds described herein comprise a moiety of the formula
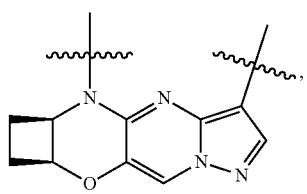

-continued

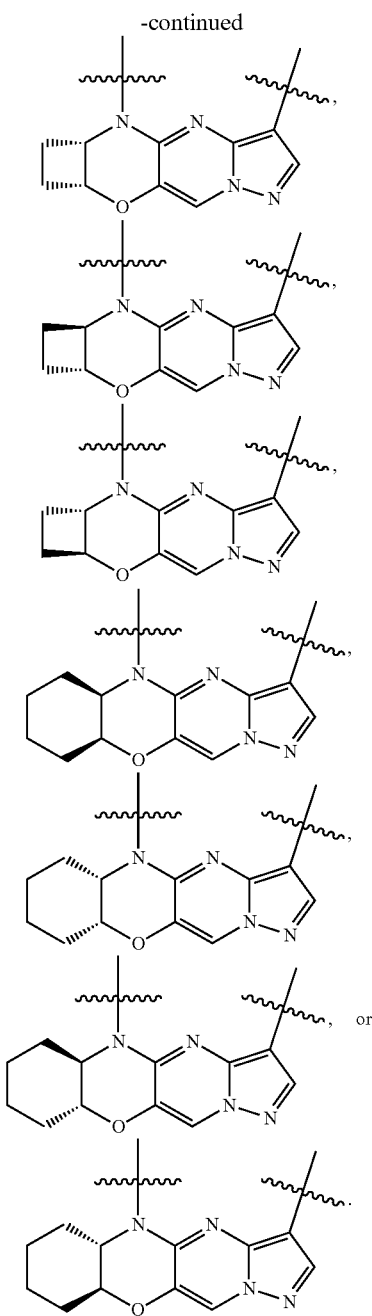

In some embodiments, L is —C(R$^1$)(R$^2$)—. In some embodiments, L is X. In some embodiments, when t is 1, L is —C(R$^1$)(R$^2$)—.

In some embodiments, X is —O—. In some embodiments, X is —S—. In some embodiments, X is —S(O)—. In some embodiments, X is —S(O)$_2$. In some embodiments, when t is 1, L is not X. In some embodiments, when t is 2, 2, or 4, the L attached directly to the amide nitrogen in the macrocycle is not X.

In some embodiments, each R$^1$ and R$^2$ is independently H, deuterium, halogen, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl, —OR$^a$, —OC(O)R$^a$, —OC(O)NR$^a$R$^b$, —OS(O)R$^a$, —OS(O)$_2$R$^a$, —SR$^a$, —S(O)R$^a$, —S(O)$_2$R$^a$, —S(O)NR$^a$R$^b$, —S(O)$_2$NR$^a$R$^b$, —OS(O)NR$^a$R$^b$, —OS(O)$_2$NR$^a$R$^b$, —NR$^a$R$^b$, —NR$^a$C(O)R$^b$, —NR$^a$C(O)OR$^b$, —NR$^a$C(O)NR$^a$R$^b$, —NR$^a$S(O)R$^b$, —NR$^a$S(O)$_2$R$^b$, —NR$^a$S(O)NR$^a$R$^b$, —NR$^a$S(O)$_2$NR$^a$R$^b$, —C(O)R$^a$, —C(O)OR$^a$, —C(O)NR$^a$R$^b$, —PR$^a$R$^b$, —P(O)R$^a$R$^b$, —P(O)$_2$R$^a$R$^b$, —P(O)NR$^a$R$^b$, —P(O)$_2$NR$^a$R$^b$, —P(O)OR$^a$, —P(O)$_2$OR$^a$, —CN, or —NO$_2$, or R$^1$ and R$^2$ taken together with the carbon or carbons to which they are attached form a C$_3$-C$_6$ cycloalkyl or a 4- to 6-membered heterocycloalkyl, wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, mono- or bicyclic heteroaryl, 4- to 6-membered heterocycloalkyl is independently optionally substituted by deuterium, halogen, C$_1$-C$_6$ alkyl, C$_1$-C$_6$ haloalkyl, —OR$^e$, —OC(O)R$^e$, —OC(O)NR$^e$R$^f$, —OC(=N)NR$^e$R$^f$, —OS(O)R$^e$, —OS(O)$_2$R$^e$, —OS(O)NR$^e$R$^f$, —OS(O)$_2$NR$^e$R$^f$, —SR$^e$, —S(O)R$^e$, —S(O)$_2$R$^e$, —S(O)NR$^e$R$^f$, —S(O)$_2$NR$^e$R$^f$, —NR$^e$R$^f$, —NR$^e$C(O)R$^f$, —NR$^e$C(O)OR$^f$, —NR$^e$C(O)NR$^e$R$^f$, —NR$^e$S(O)R$^f$, —NR$^e$S(O)$_2$R$^f$, —NR$^e$S(O)NR$^e$R$^f$, —NR$^e$S(O)$_2$NR$^e$R$^f$, —C(O)R$^e$, —C(O)OR$^e$, —C(O)NR$^e$R$^f$, —PR$^e$R$^f$, —P(O)R$^e$R$^f$, —P(O)$_2$R$^e$R$^f$, —P(O)NR$^e$R$^f$, —P(O)$_2$NR$^e$R$^f$, —P(O)OR$^e$, —P(O)$_2$OR$^e$, —CN, or —NO$_2$.

In some embodiments, R$^1$ and R$^2$ are each independently H, deuterium, C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —OR$^a$, —SR$^a$, —NR$^a$R$^b$, —C(O)OR$^a$, —C(O)NR$^a$R$^b$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —OC$_1$-C$_6$ alkyl(C$_6$-C$_{10}$ aryl), —NH$_2$, —OC(O)C$_1$-C$_6$ alkyl, —OC(O)N(C$_1$-C$_6$ alkyl)$_2$, —OC(O)NH(C$_1$-C$_6$ alkyl), —OC(O)NH$_2$, —OC(=N)N(C$_1$-C$_6$ alkyl)$_2$, —OC(=N)NH(C$_1$-C$_6$ alkyl), —OC(=N)NH$_2$, —OS(O)C$_1$-C$_6$ alkyl, —OS(O)$_2$C$_1$-C$_6$ alkyl, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NH(C$_1$-C$_6$ alkyl), —N(C$_1$-C$_6$ alkyl)C(O)NH$_2$, —N(C$_1$-C$_6$ alkyl)C(O)NH(C$_1$-C$_6$ alkyl), —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHC(O)OH, —N(C$_1$-C$_6$ alkyl)C(O)OH, —NHS(O)C$_1$-C$_6$ alkyl, —NHS(O)$_2$C$_1$-C$_6$ alkyl, —N(C$_1$-C$_6$ alkyl)S(O)C$_1$-C$_6$ alkyl, —N(C$_1$-C$_6$ alkyl)S(O)$_2$C$_1$-C$_6$ alkyl, —NHS(O)NH$_2$, —NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —C(O)C$_1$-C$_6$ alkyl, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —S(O)NH$_2$, —S(O)$_2$NH$_2$, —OS(O)N(C$_1$-C$_6$ alkyl)$_2$, —OS(O)$_2$N(C$_1$-C$_6$ alkyl)$_2$, —OS(O)NH(C$_1$-C$_6$ alkyl), —OS(O)$_2$NH(C$_1$-C$_6$ alkyl), —OS(O)NH$_2$, —OS(O)$_2$NH$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl.

In some embodiments, R$^1$ is H. In some embodiments, R$^2$ is H. In some embodiments, R$^1$ is C$_1$-C$_6$ alkyl. In some embodiments, R$^1$ is methyl. In some embodiments, R$^1$ is C$_3$-C$_6$ cycloalkyl. In some embodiments, R$^1$ is cyclopropyl. In some embodiments, R$^2$ is C$_1$-C$_6$ alkyl. In some embodiments, R$^2$ is methyl. In some embodiments, R$^2$ is C$_3$-C$_6$ cycloalkyl. In some embodiments, R$^2$ is cyclopropyl. In some embodiments, R$^1$ is H and R$^2$ is C$_1$-C$_6$ alkyl. In some embodiments, R$^1$ and R$^2$ taken together with the carbon or carbons to which they are attached form a C$_3$-C$_6$ cycloalkyl.

In some embodiments, $R^1$ and $R^2$ taken together with the carbon or carbons to which they are attached form a cyclopropane ring.

In some embodiments, M is $CR^3$. In some embodiments, M is N. In some embodiments, $M^1$ is $CR^4$.

In some embodiments, each $R^3$, $R^4$, and $R^5$ is independently hydrogen, deuterium, halogen, —$OR^c$, —$OC(O)R^c$, —$OC(O)NR^cR^d$, —$OC(=N)NR^cR^d$, —$OS(O)R^c$, —$OS(O)_2R^c$, —$OS(O)NR^cR^d$, —$OS(O)_2NR^cR^d$, —$SR^c$, —$S(O)R^c$, —$S(O)_2R^c$, —$S(O)NR^cR^d$, —$S(O)_2NR^cR^d$, —$NR^cR^d$, —$NR^cC(O)R^d$, —$NR^cC(O)OR^d$, —$NR^cC(O)NR^cR^d$, —$NR^cC(=N)NR^cR^d$, —$NR^cS(O)R^d$, —$NR^cS(O)_2R^d$, —$NR^cS(O)NR^cR^d$, —$NR^cS(O)_2NR^cR^d$, —$C(O)R^c$, —$C(O)OR^c$, —$C(O)NR^cR^d$, —$C(=N)NR^cR^d$, —$PR^cR^d$, —$P(O)R^cR^d$, —$P(O)_2R^cR^d$, —$P(O)NR^cR^d$, —$P(O)_2NR^cR^d$, —$P(O)OR^c$, —$P(O)_2OR^c$, —CN, —$NO_2$, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl, or $R^4$ and $R^5$ taken together with the ring to which they are attached form a $C_5$-$C_8$ cycloalkyl, or a 5- to 8-membered heterocycloalkyl, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, mono- or bicyclic heteroaryl, $C_5$-$C_8$ cycloalkyl, or 5- to 8-membered heterocycloalkyl is independently optionally substituted by deuterium, halogen, $C_1$-$C_6$ alkyl, $C_1$-$C_6$ haloalkyl, —$OR^e$, —$OC(O)R^e$, —$OC(O)NR^eR^f$, —$OC(=N)NR^eR^f$, —$OS(O)R^e$, —$OS(O)_2R^e$, —$OS(O)NR^eR^f$, —$OS(O)_2NR^eR^f$, —$SR^e$, —$S(O)R^e$, —$S(O)_2R^e$, —$S(O)NR^eR^f$, —$S(O)_2NR^eR^f$, —$NR^eR^f$, —$NR^eC(O)R^f$, —$NR^eC(O)OR^f$, —$NR^eC(O)NR^eR^f$, —$NR^eS(O)R^f$, —$NR^eS(O)_2R^f$, —$NR^eS(O)NR^eR^f$, —$NR^eS(O)_2NR^eR^f$, —$C(O)R^e$, —$C(O)OR^e$, —$C(O)NR^eR^f$, —$PR^eR^f$, —$P(O)R^eR^f$, —$P(O)_2R^eR^f$, —$P(O)NR^eR^f$, —$P(O)_2NR^eR^f$, —$P(O)OR^e$, —$P(O)_2OR^e$, —CN, or —$NO_2$. In some embodiments, each $R^3$, $R^4$, and $R^5$ are each independently H, fluoro, chloro, bromo, $C_1$-$C_6$ alkyl, —OH, —CN, —$OC_1$-$C_6$ alkyl, —$NHC_1$-$C_6$ alkyl, —$N(C_1$-$C_6$ alkyl$)_2$ or —$CF_3$. In some embodiments, $R^3$ is H, deuterium, $C_1$-$C_6$ alkyl or halogen. In some embodiments, $R^3$ is H or F. In some embodiments, $R^4$ is H, deuterium, $C_1$-$C_6$ alkyl or halogen. In some embodiments, $R^4$ is H or Cl. In some embodiments, $R^5$ is F.

In some embodiments, $R^6$ is H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, —$OR^e$, —$OC(O)R^e$, —$OC(O)NR^eR^f$, —$OC(=N)NR^eR^f$, —$OS(O)R^e$, —$OS(O)_2R^e$, —$OS(O)NR^eR^f$, —$OS(O)_2NR^eR^f$, —$SR^e$, —$S(O)R^e$, —$S(O)_2R^e$, —$S(O)NR^eR^f$, —$S(O)_2NR^eR^f$, —$NR^eR^f$, —$NR^eC(O)R^f$, —$NR^eC(O)OR^f$, —$NR^eC(O)NR^eR^f$, —$NR^eS(O)R^f$, —$NR^eS(O)_2R^f$, —$NR^eS(O)NR^eR^f$, —$NR^eS(O)_2NR^eR^f$, —$C(O)R^e$, —$C(O)OR^e$, —$C(O)NR^eR^f$, —$PR^eR^f$, —$P(O)R^eR^f$, —$P(O)_2R^eR^f$, —$P(O)NR^eR^f$, —$P(O)_2NR^eR^f$, —$P(O)OR^e$, —$P(O)_2OR^e$, —CN, or —$NO_2$. In some embodiments, $R^6$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —$OC_1$-$C_6$ alkyl, —$NH_2$, —$NH(C_1$-$C_6$ alkyl), —$N(C_1$-$C_6$ alkyl$)_2$, —$CO_2H$, —$C(O)OC_1$-$C_6$ alkyl, —$C(O)NH_2$, —$C(O)NH(C_1$-$C_6$ alkyl), —$C(O)N(C_1$-$C_6$ alkyl$)_2$, $C_3$-$C_6$ cycloalkyl, or monocyclic 5- to 7-membered heterocycloalkyl.

In some embodiments, $R^7$ and $R^8$ combine to form a $C_3$-$C_7$ cycloalkyl, a 5- to 8-membered heterocycloalkyl, $C_6$-$C_{10}$ aryl, or 5- to 7-membered heteroaryl; wherein each hydrogen atom in $C_3$-$C_7$ cycloalkyl, a 5- to 8-membered heterocycloalkyl, $C_6$-$C_{10}$ aryl, or 5- to 7-membered heteroaryl is independently optionally substituted by deuterium, halogen, —$OR^e$, —$OC(O)R^e$, —$OC(O)NR^eR^f$, —$OC(=N)NR^eR^f$, —$OS(O)R^e$, —$OS(O)_2R^e$, —$OS(O)NR^eR^f$, —$OS(O)_2NR^eR^f$, —$SR^e$, —$S(O)R^e$, —$S(O)_2R^e$, —$S(O)NR^eR^f$, —$S(O)_2NR^eR^f$, —$NR^eR^f$, —$NR^eC(O)R^f$, —$NR^eC(O)OR^f$, —$NR^eC(O)NR^eCR^f$, —$NR^eS(O)R^f$, —$NR^eS(O)_2R^f$, —$NR^eS(O)NR^eCR^f$, —$NR^eS(O)_2NR^eR^f$, —$C(O)R^e$, —$C(O)OR^e$, —$C(O)NR^eR^f$, —$PR^eR^f$, —$P(O)R^eR^f$, —$P(O)_2R^eR^f$, —$P(O)NR^eR^f$, —$P(O)_2NR^eR^f$, —$P(O)OR^e$, —$P(O)_2OR^e$, —CN, or —$NO_2$.

In some embodiments, $R^7$ and $R^8$ combine to form a $C_3$-$C_7$ cycloalkyl, a 5- to 8-membered heterocycloalkyl, $C_6$-$C_{10}$ aryl, or 5- to 7-membered heteroaryl; wherein each hydrogen atom in $C_3$-$C_7$ cycloalkyl, a 5- to 8-membered heterocycloalkyl, $C_6$-$C_{10}$ aryl, or 5- to 7-membered heteroaryl is independently optionally substituted by deuterium, halogen, —OH, —$OC_1$-$C_6$ alkyl, —$OC(O)C_1$-$C_6$ alkyl, —$OC(O)NH_2$, —$OC(O)NH(C_1$-$C_6$ alkyl), —$OC(O)N(C_1$-$C_6$ alkyl$)_2$, —$OC(=N)NH_2$, —$OC(=N)NH(C_1$-$C_6$ alkyl), —$OC(=N)N(C_1$-$C_6$ alkyl$)_2$, —$OS(O)C_1$-$C_6$ alkyl, —$OS(O)NH_2$, —$OS(O)NH(C_1$-$C_6$ alkyl), —$OS(O)N(C_1$-$C_6$ alkyl$)_2$, —$OS(O)_2NH_2$, —$OS(O)_2NH(C_1$-$C_6$ alkyl), —$OS(O)_2N(C_1$-$C_6$ alkyl$)_2$, —SH, —$SC_1$-$C_6$ alkyl, —$S(O)C_1$-$C_6$ alkyl, —$S(O)_2C_1$-$C_6$ alkyl, —$S(O)NH_2$, —$S(O)NH(C_1$-$C_6$ alkyl), —$S(O)(C_1$-$C_6$ alkyl$)_2$, —$S(O)_2NH_2$, —$S(O)_2NH(C_1$-$C_6$ alkyl), —$S(O)_2N(C_1$-$C_6$ alkyl$)_2$, —$NH_2$, —$NH(C_1$-$C_6$ alkyl), —$N(C_1$-$C_6$ alkyl$)_2$, —$NHC(O)C_1$-$C_6$ alkyl, —$N(C_1$-$C_6$ alkyl)$C(O)C_1$-$C_6$ alkyl, —$NHC(O)OH$, —$NHC(O)OC_1$-$C_6$ alkyl, —$N(C_1$-$C_6$ alkyl)$C(O)OH$, —$N(C_1$-$C_6$ alkyl)$C(O)OC_1$-$C_6$ alkyl, —$NHC(O)NH_2$, —$NHC(O)NH(C_1$-$C_6$ alkyl), —$NHC(O)N(C_1$-$C_6$ alkyl$)_2$, —$N(C_1$-$C_6$ alkyl)$C(O)NH_2$, —$N(C_1$-$C_6$ alkyl)$C(O)NH(C_1$-$C_6$ alkyl), —$N(C_1$-$C_6$ alkyl)$C(O)N(C_1$-$C_6$ alkyl$)_2$, —$NHS(O)C_1$-$C_6$ alkyl, —$N(C_1$-$C_6$ alkyl)$S(O)C_1$-$C_6$ alkyl, —$NHS(O)_2C_1$-$C_6$ alkyl, —$N(C_1$-$C_6$ alkyl)$S(O)_2C_1$-$C_6$ alkyl, —$NHS(O)NH_2$, —$NHS(O)NH(C_1$-$C_6$ alkyl), —$NHS(O)N(C_1$-$C_6$ alkyl$)_2$, —$N(C_1$-$C_6$ alkyl)$S(O)NH_2$, —$N(C_1$-$C_6$ alkyl)$S(O)NH(C_1$-$C_6$ alkyl), —$N(C_1$-$C_6$ alkyl)$S(O)N(C_1$-$C_6$ alkyl$)_2$, —$NHS(O)_2NH_2$, —$NHS(O)_2NH(C_1$-$C_6$ alkyl), —$NHS(O)_2N(C_1$-$C_6$ alkyl$)_2$, —$N(C_1$-$C_6$ alkyl)$S(O)_2NH_2$, —$N(C_1$-$C_6$ alkyl)$S(O)_2NH(C_1$-$C_6$ alkyl), —$N(C_1$-$C_6$ alkyl)$S(O)_2N(C_1$-$C_6$ alkyl$)_2$, —$C(O)C_1$-$C_6$ alkyl, —$C(O)OC_1$-$C_6$ alkyl, —$C(O)NH_2$, —$C(O)NH(C_1$-$C_6$ alkyl), —$C(O)N(C_1$-$C_6$ alkyl$)_2$, —$P(C_1$-$C_6$ alkyl$)_2$, —$P(O)(C_1$-$C_6$ alkyl$)_2$, —$P(O)_2(C_1$-$C_6$ alkyl$)_2$, —$P(O)NH_2$, —$P(O)NH(C_1$-$C_6$ alkyl), —$P(O)N(C_1$-$C_6$ alkyl$)_2$, —$P(O)_2NH_2$, —$P(O)_2NH(C_1$-$C_6$ alkyl), —$P(O)_2N(C_1$-$C_6$ alkyl$)_2$, —$P(O)OH$, —$P(O)OC_1$-$C_6$ alkyl, —$P(O)_2OH$, —$P(O)_2OC_1$-$C_6$ alkyl, —CN, or —$NO_2$.

In some embodiments, $R^7$ and $R^8$ combine to form a 5- or 6-membered cycloalkyl, wherein each hydrogen atom in the 4-, 5- or 6-membered cycloalkyl is independently optionally substituted by deuterium, halogen, —OH, —CN, —$OC_1$-$C_6$ alkyl, —$OC_1$-$C_6$ alkyl($C_6$-$C_{10}$ aryl), —$NH_2$, —$OC(O)C_1$-$C_6$ alkyl, —$OC(O)N(C_1$-$C_6$ alkyl$)_2$, —$OC(O)NH(C_1$-$C_6$ alkyl), —$OC(O)NH_2$, —$OC(=N)N(C_1$-$C_6$ alkyl$)_2$, —$OC(=N)NH(C_1$-$C_6$ alkyl), —$OC(=N)NH_2$, —$OS(O)C_1$-$C_6$ alkyl, —$OS(O)_2C_1$-$C_6$ alkyl, —$NH(C_1$-$C_6$ alkyl), —$N(C_1$-$C_6$ alkyl$)_2$, —$NHC(O)C_1$-$C_6$ alkyl, —$N(C_1$-$C_6$ alkyl)$C(O)C_1$-$C_6$ alkyl, —$NHC(O)NH_2$, —$NHC(O)NH(C_1$-$C_6$ alkyl), —$N(C_1$-$C_6$ alkyl)$C(O)NH_2$, —$N(C_1$-$C_6$ alkyl)$C(O)NH(C_1$-$C_6$ alkyl), —$NHC(O)N(C_1$-$C_6$ alkyl$)_2$, —$N(C_1$-$C_6$ alkyl)$C(O)N(C_1$-$C_6$ alkyl)$_2$, —NHC(O)OC$_1$-C$_6$ alkyl, —N(C$_1$-C$_6$ alkyl)C(O)OC$_1$-C$_6$ alkyl, —NHC(O)OH, —N(C$_1$-C$_6$ alkyl)C(O)OH, —NHS(O)C$_1$-C$_6$ alkyl, —NHS(O)$_2$C$_1$-C$_6$ alkyl, —N(C$_1$-C$_6$ alkyl)S(O)C$_1$-C$_6$ alkyl, —N(C$_1$-C$_6$ alkyl)S(O)$_2$C$_1$-C$_6$ alkyl. —NHS(O)NH$_2$, —NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —C(O)C$_1$-C$_6$ alkyl, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —S(O)NH$_2$, —S(O)$_2$NH$_2$, —OS(O)N(C$_1$-C$_6$ alkyl)$_2$, —OS(O)$_2$N(C$_1$-C$_6$ alkyl)$_2$, —OS(O)NH(C$_1$-C$_6$ alkyl), —OS(O)$_2$NH(C$_1$-C$_6$ alkyl), —OS(O)NH$_2$, —OS(O)$_2$NH$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl.

In some embodiments, R$^7$ and R$^8$ combine to form a 3-, 4-, 5- or 6-membered heterocycloalkyl, wherein each hydrogen atom in the 3-, 4-, 5- or 6-membered heterocycloalkyl is independently optionally substituted by deuterium, halogen, —OH, —CN, —OC$_1$-C$_6$ alkyl, —OC$_1$-C$_6$ alkyl(C$_6$-C$_{10}$ aryl), —NH$_2$, —OC(O)C$_1$-C$_6$ alkyl, —OC(O)N(C$_1$-C$_6$ alkyl)$_2$, —OC(O)NH(C$_1$-C$_6$ alkyl), —OC(O)NH$_2$, —OC(=N)N(C$_1$-C$_6$ alkyl)$_2$, —OC(=N)NH(C$_1$-C$_6$ alkyl), —OC(=N)NH$_2$, —OS(O)C$_1$-C$_6$ alkyl, —OS(O)$_2$C$_1$-C$_6$ alkyl, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NH(C$_1$-C$_6$ alkyl), —N(C$_1$-C$_6$ alkyl)C(O)NH$_2$, —N(C$_1$-C$_6$ alkyl)C(O)NH(C$_1$-C$_6$ alkyl), —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHC(O)OH, —N(C$_1$-C$_6$ alkyl)C(O)OH, —NHS(O)C$_1$-C$_6$ alkyl, —NHS(O)$_2$C$_1$-C$_6$ alkyl, —N(C$_1$-C$_6$ alkyl)S(O)C$_1$-C$_6$ alkyl, —N(C$_1$-C$_6$ alkyl)S(O)$_2$C$_1$-C$_6$ alkyl. —NHS(O)NH$_2$, —NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —C(O)C$_1$-C$_6$ alkyl, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —S(O)NH$_2$, —S(O)$_2$NH$_2$, —OS(O)N(C$_1$-C$_6$ alkyl)$_2$, —OS(O)$_2$N(C$_1$-C$_6$ alkyl)$_2$, —OS(O)NH(C$_1$-C$_6$ alkyl), —OS(O)$_2$NH(C$_1$-C$_6$ alkyl), —OS(O)NH$_2$, —OS(O)$_2$NH$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl. In some embodiments, R$^7$ and R$^8$ combine to form a tetrahydrofuran ring. In some embodiments, R$^7$ and R$^8$ combine to form a cyclopentane ring.

In some embodiments, Y is —O—, —S—, —NR$^9$, or —CR$^9$R$^{10}$—. In some embodiments, Y is —O—.

In some embodiments, R$^9$ and R$^{10}$ are each independently H, deuterium, halogen, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl, wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl is optionally substituted by a halogen, —OR$^e$, —OC(O)R$^e$, —OC(O)NR$^e$R$^f$, —OC(=N)NR$^e$R$^f$, —OS(O)R$^e$, —OS(O)$_2$R$^e$, —OS(O)NR$^e$R$^f$, —OS(O)$_2$NR$^e$R$^f$, —SR$^e$, —S(O)R$^e$, —S(O)$_2$R$^e$, —S(O)NR$^e$R$^f$, —S(O)$_2$NR$^e$R$^f$, —NR$^e$R$^f$, —NR$^e$C(O)R$^f$, —NR$^e$C(O)OR$^f$, —NR$^e$C(O)NR$^e$R$^f$, —NR$^e$S(O)R$^f$, —NR$^e$S(O)$_2$R$^f$, —NR$^e$S(O)NR$^e$CR$^f$, —NR$^e$S(O)$_2$NR$^e$CR$^f$, —C(O)R$^e$, —C(O)OR$^e$, —C(O)NR$^e$R$^f$, —PR$^e$R$^f$, —P(O)R$^e$R$^f$, —P(O)$_2$R$^e$R$^f$, —P(O)NR$^e$R$^f$, —P(O)$_2$NR$^e$R$^f$, —P(O)OR$^e$, or —P(O)$_2$OR$^e$.

In some embodiments, R$^9$ and R$^{1'}$ are each independently H, deuterium, halogen, or C$_1$-C$_6$ alkyl, wherein each hydrogen atom in C$_1$-C$_6$ alkyl is optionally substituted by a halogen, —OH, —OC$_1$-C$_6$ alkyl, —OC(O)C$_1$-C$_6$ alkyl, —OC(O)N(C$_1$-C$_6$ alkyl)$_2$, —OC(O)NH(C$_1$-C$_6$ alkyl), —OC(O)NH$_2$, —OC(=N)N(C$_1$-C$_6$ alkyl)$_2$, —OC(=N)NH(C$_1$-C$_6$ alkyl), —OC(=N)NH$_2$, —OS(O)C$_1$-C$_6$ alkyl, —OS(O)$_2$C$_1$-C$_6$ alkyl, —OS(O)N(C$_1$-C$_6$ alkyl)$_2$, —OS(O)NH(C$_1$-C$_6$ alkyl), —OS(O)NH$_2$, —OS(O)$_2$N(C$_1$-C$_6$ alkyl)$_2$, —OS(O)$_2$NH(C$_1$-C$_6$ alkyl), —OS(O)$_2$NH$_2$, —SH, —SC$_1$-C$_6$ alkyl, —S(O)C$_1$-C$_6$ alkyl, —S(O)$_2$C$_1$-C$_6$ alkyl, —S(O)N(C$_1$-C$_6$ alkyl)$_2$, —S(O)NH(C$_1$-C$_6$ alkyl), —S(O)NH$_2$, —S(O)$_2$N(C$_1$-C$_6$ alkyl)$_2$, —S(O)$_2$NH(C$_1$-C$_6$ alkyl), —S(O)$_2$NH$_2$, —N(C$_1$-C$_6$ alkyl)$_2$, —NH(C$_1$-C$_6$ alkyl), —NH$_2$, —N(C$_1$-C$_6$ alkyl)C(O)C$_1$-C$_6$ alkyl, —NHC(O)C$_1$-C$_6$ alkyl, —N(C$_1$-C$_6$ alkyl)C(O)OC$_1$-C$_6$ alkyl, —N(C$_1$-C$_6$ alkyl)C(O)OH, —NHC(O)OC$_1$-C$_6$ alkyl, —NHC(O)OH, —N(C$_1$-C$_6$ alkyl)C(O)N(C$_1$-C$_6$ alkyl)$_2$, —N(C$_1$-C$_6$ alkyl)C(O)NH(C$_1$-C$_6$ alkyl), —N(C$_1$-C$_6$ alkyl)C(O)NH$_2$, —NHC(O)N(C$_1$C$_6$ alkyl)$_2$, —NHC(O)NH(C$_1$C$_6$ alkyl), —NHC(O)NH$_2$, —N(C$_1$-C$_6$ alkyl)S(O)C$_1$-C$_6$ alkyl, —NHS(O)C$_1$-C$_6$ alkyl, —N(C$_1$-C$_6$ alkyl)S(O)$_2$C$_1$-C$_6$ alkyl, —NHS(O)$_2$C$_1$-C$_6$ alkyl, —N(C$_1$-C$_6$ alkyl)S(O)N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)NH$_2$, —NHS(O)N(C$_1$-C$_6$ alkyl)$_2$, —NHS(O)NH(C$_1$-C$_6$ alkyl), —NHS(O)NH$_2$, —N(C$_1$-C$_6$ alkyl)S(O)$_2$N(C$_1$-C$_6$ alkyl)$_2$, —N(C$_1$-C$_6$ alkyl)S(O)$_2$NH(C$_1$-C$_6$ alkyl), —N(C$_1$-C$_6$ alkyl)S(O)$_2$NH$_2$, —NHS(O)$_2$N(C$_1$-C$_6$ alkyl)$_2$, —NHS(O)$_2$NH(C$_1$-C$_6$ alkyl), —NHS(O)$_2$NH$_2$, —C(O)C$_1$-C$_6$ alkyl, —C(O)OC$_1$-C$_6$ alkyl, —C(O)N(C$_1$-C$_6$ alkyl)$_2$, —C(O)NH(C$_1$-C$_6$ alkyl), —C(O)NH$_2$, —P(C$_1$-C$_6$ alkyl)$_2$, —P(O)(C$_1$-C$_6$ alkyl)$_2$, —P(O)$_2$(C$_1$-C$_6$ alkyl)$_2$, —P(O)N(C$_1$-C$_6$ alkyl)$_2$, —P(O)$_2$N(C$_1$-C$_6$ alkyl)$_2$, —P(O)OC$_1$-C$_6$ alkyl, or —P(O)$_2$OC$_1$-C$_6$ alkyl.

In some embodiments, each R$^a$, R$^b$, R$^c$, R$^d$, R$^e$, and R$^f$ is independently selected from the group consisting of H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl.

In some embodiments, p is 1, 2, 3, or 4. In some embodiments, p is 1.

In some embodiments, t is 1, 2, 3, 4, or 5. In some embodiments, t is 3. In some embodiments, t is 4. In some embodiments, t is 3 or 4.

In some embodiments, n, if present, is 1, 2, or 3. In some embodiments, n is 2. In some embodiments, n is 3. In some embodiments, n is 2 or 3.

The following represent illustrative embodiments of compounds of the formula I, II, III, and IV:

| Compound | Structure | Name |
|---|---|---|
| 1 | 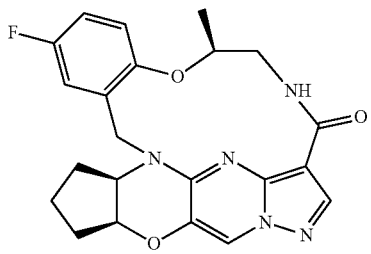 [SMILES: C[C@H]1CNC(=O)c2cnn3cc4c(nc23)N(Cc2cc(F)ccc2O1)[C@@H]1COC[C@@H]1O4] | (3aR,11S,20aS)-7-fluoro-11-methyl-2,3,3a,12,13,20a-hexahydro-1H,5H-17-19-(metheno)cyclopenta[5,6][1,4]oxazino[3,4-i]pyrazolo[4,3-f][1,4,8,10]benzoxatriacyclotridecin-14(11H)-one |
| 2 | 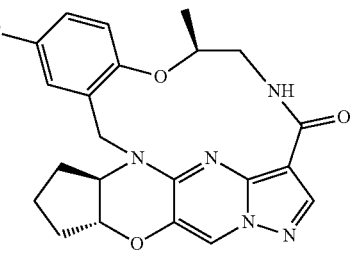 | (7S)-3-amino-11-fluoro-7-methyl-4-oxo-14-(propan-2-yl)-4,5,6,7,13,14-hexahydro-1,15-ethenopyrazolo[4,3-f][1,4,8,10]benzoxatriacyclotridecine-12-carbonitrile |
| 3 | 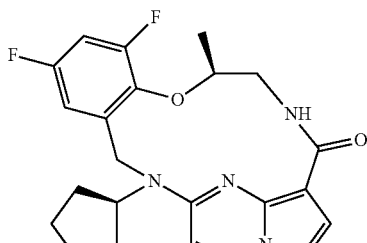 | (3aR,11S,20aS)-7,9-difluoro-11-methyl-2,3,3a,12,13,20a-hexahydro-1H,5H-17-19-(metheno)cyclopenta[5,6][1,4]oxazino[3,4-i]pyrazolo[4,3-f][1,4,8,10]benzoxatriacyclotridecin-14(11H)-one |
| 4 | 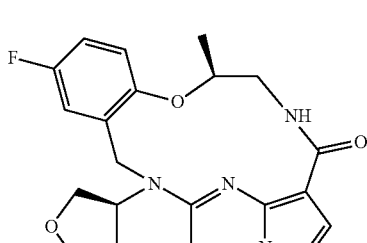 | (3aR,11S,20aS)-7-fluoro-11-methyl-1,3,3a,12,13,20a-hexahydro-5H-17-19-(metheno)furo[3',4':5,6][1,4]oxazino[3,4-i]pyrazolo[4,3-f][1,4,8,10]benzoxatriacyclotridecin-14(11H)-one |
| 5 | 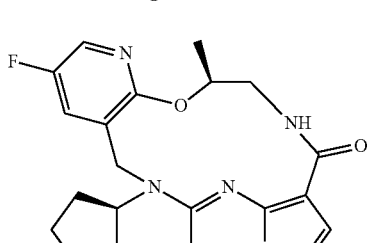 | (3aR,11S,20aS)-7-fluoro-11-methyl-2,3,3a,12,13,20a-hexahydro-1H,5H-17-19-(metheno)cyclopenta[5,6][1,4]oxazino[3,4-i]pyrazolo[4,3-f]pyrido[3,2-l][1,4,8,10]oxatriazacyclotridecin-14(11H)-one |
| 6 | 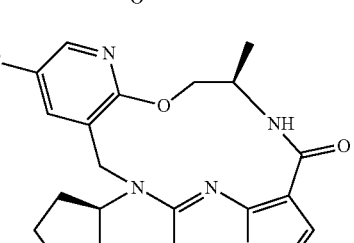 | (3aR,12R,20aS)-7-fluoro-12-methyl-2,3,3a,12,13,20a-hexahydro-1H,5H-17-19-(metheno)cyclopenta[5,6][1,4]oxazino[3,4-i]pyrazolo[4,3-f]pyrido[3,2-l][1,4,8,10]oxatriazacyclotridecin-14(11H)-one |

-continued

| Compound | Structure | Name |
|---|---|---|
| 7 | 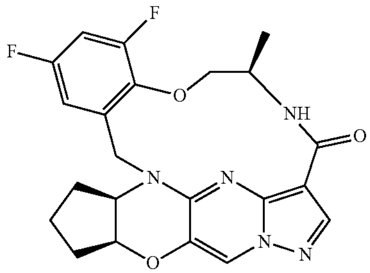 [SMILES: C[C@@H]1COc2c(F)cc(F)cc2CN2c3nc4c(cnn4cc3O[C@H]3CCC[C@H]32)C(=O)N1] | (3aR,12R,20aS)-7,9-difluoro-12-methyl-2,3,3a,12,13,20a-hexahydro-1H,5H-17-19-(metheno)cyclopenta[5,6][1,4]oxazino[3,4-i]pyrazolo[4,3-f][1,4,8,10]benzoxatriazacyclotridecin-14(11H)-one |
| 8 | 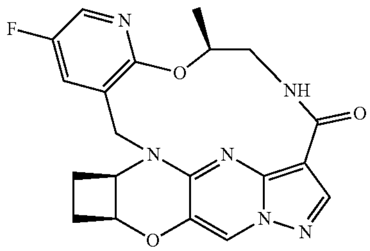 [SMILES: C[C@H]1CNC(=O)c2cnn3cc4c(nc23)N(Cc2cc(F)cnc2O1)[C@@H]1CC[C@@H]1O4] | (2aR,10S,19aS)-6-fluoro-10-methyl-1,2,2a,11,12,19a-hexahydro-4H-16,18-(metheno)cyclobuta[5,6][1,4]oxazino[3,4-i]pyrazolo[4,3-f]pyrido[3,2-l][1,4,8,10]oxatriazacyclotridecin-13(10H)-one |
| 9 | 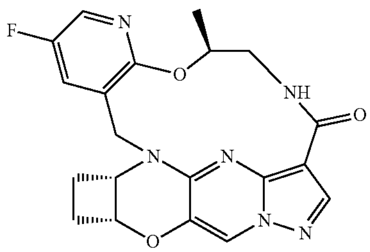 [SMILES: C[C@H]1CNC(=O)c2cnn3cc4c(nc23)N(Cc2cc(F)cnc2O1)[C@H]1CC[C@H]1O4] | (2aS,10S,19aR)-6-fluoro-10-methyl-1,2,2a,11,12,19a-hexahydro-4H-16,18-(metheno)cyclobuta[5,6][1,4]oxazino[3,4-i]pyrazolo[4,3-f]pyrido[3,2-l][1,4,8,10]oxatriazacyclotridecin-13(10H)-one |
| 10 | 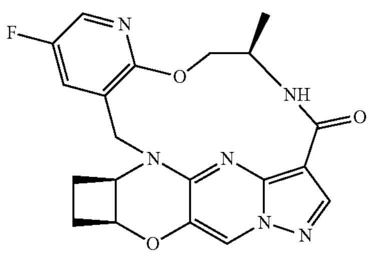 [SMILES: C[C@@H]1COc2ncc(F)cc2CN2c3nc4c(cnn4cc3O[C@H]3CC[C@H]32)C(=O)N1] | (2aR,11R,19aS)-6-fluoro-11-methyl-1,2,2a,11,12,19a-hexahydro-4H-16,18-(metheno)cyclobuta[5,6][1,4]oxazino[3,4-i]pyrazolo[4,3-f]pyrido[3,2-l][1,4,8,10]oxatriazacyclotridecin-13(10H)-one |
| 11 | 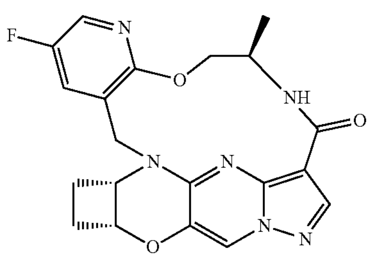 [SMILES: C[C@@H]1COc2ncc(F)cc2CN2c3nc4c(cnn4cc3O[C@@H]3CC[C@@H]32)C(=O)N1] | (2aS,11R,19aR)-6-fluoro-11-methyl-1,2,2a,11,12,19a-hexahydro-4H-16,18-(metheno)cyclobuta[5,6][1,4]oxazino[3,4-i]pyrazolo[4,3-f]pyrido[3,2-l][1,4,8,10]oxatriazacyclotridecin-13(10H)-one |
| 12 | 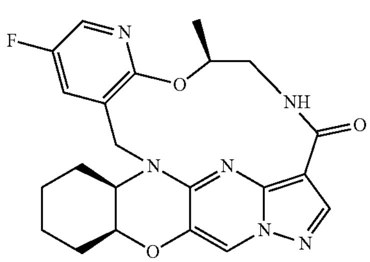 [SMILES: C[C@H]1CNC(=O)c2cnn3cc4c(nc23)N(Cc2cc(F)cnc2O1)[C@@H]1CCCC[C@@H]1O4] | (4aR,12S,21aS)-8-fluoro-12-methyl-1,2,3,4,4a,13,14,21a-octahydro-6H-18,20-(metheno)pyrazolo[4',3':6,7]pyrido[3',2':12,13][1,4,8,10]oxatriazacyclotridecino[9,10-c][1,4]benzoxazin-15(12H)-one |

| Compound | Structure | Name |
|---|---|---|
| 13 | 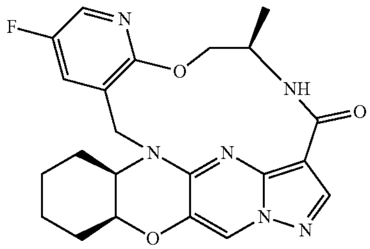 [SMILES: C[C@@H]1COc2ncc(F)cc2CN2c3nc4c(cnn4cc3O[C@H]3CCCC[C@H]32)C(=O)N1] | (4aR,13S,21aS)-8-fluoro-13-methyl-1,2,3,4,4a,13,14,21a-octahydro-6H-18,20-(metheno)pyrazolo[4',3':6,7]pyrido[3',2':12,13][1,4,8,10]oxatriazacyclotridecino[9,10-c][1,4]benzoxazin-15(12H)-one |
| 14 | 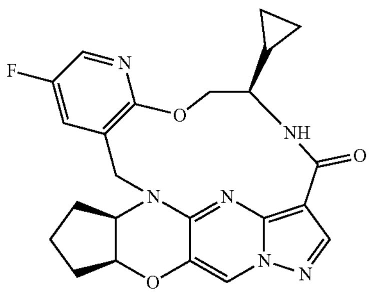 [SMILES: O=C1N[C@H](C2CC2)COc2ncc(F)cc2CN2c3nc4c1cnn4cc3O[C@H]1CCC[C@H]12] | (3aR,12R,20aS)-12-cyclopropyl-7-fluoro-2,3,3a,12,13,20a-hexahydro-1H,5H-17-19-(metheno)cyclopenta[5,6][1,4]oxazino[4,3-i]pyrazolo[4,3-f]pyrido[3,2-l][1,4,8,10]oxatriazacyclotridecin-14(11H)-one |
| 15 | 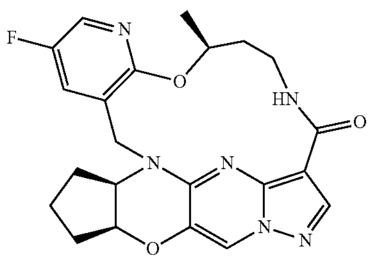 [SMILES: C[C@H]1CCNC(=O)c2cnn3cc4c(nc23)N(Cc2cc(F)cnc2O1)[C@@H]1CCC[C@@H]1O4] | (3aR,11S,21aS)-7-fluoro-11-methyl-2,3,3a,12,13,14,21a-octahydro-1H,5H,15H-18,20-(metheno)cyclopenta[5,6][1,4]oxazino[4,3-e]pyrazolo[3,4-h]pyrido[2,3-b][1,5,7,11]oxatriazacyclotetradecin-15-one |
| 16 | 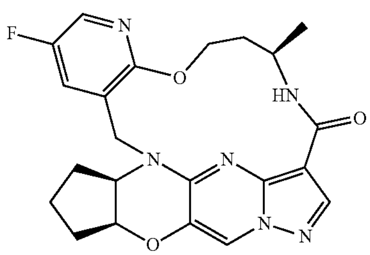 [SMILES: C[C@@H]1CCOc2ncc(F)cc2CN2c3nc4c(cnn4cc3O[C@H]3CCC[C@H]32)C(=O)N1] | (3aR,13R,21aS)-7-fluoro-13-methyl-2,3,3a,11,12,13,14,21a-octahydro-1H,5H,15H-18,20-(metheno)cyclopenta[5,6][1,4]oxazino[4,3-e]pyrazolo[3,4-h]pyrido[2,3-b][1,5,7,11]oxatriazacyclotetradecin-15-one |
| 17 | 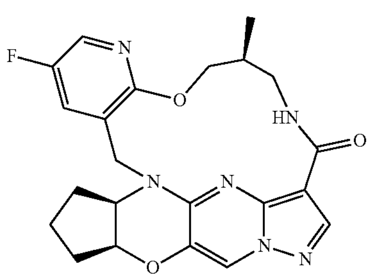 [SMILES: C[C@H]1CNC(=O)c2cnn3cc4c(nc23)N(Cc2cc(F)cnc2OC1)[C@@H]1CCC[C@@H]1O4] | (3aR,12S,21aS)-7-fluoro-12-methyl-2,3,3a,11,12,13,14,21a-octahydro-1H,5H,15H-18,20-(metheno)cyclopenta[5,6][1,4]oxazino[4,3-e]pyrazolo[3,4-h]pyrido[2,3-b][1,5,7,11]oxatriazacyclotetradecin-15-one |
| 18 | 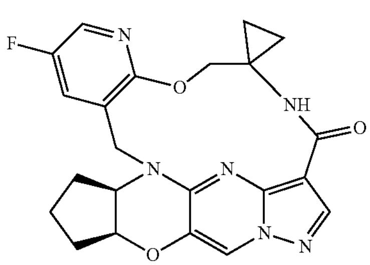 [SMILES: O=C1NC2(CC2)COc2ncc(F)cc2CN2c3nc4c1cnn4cc3O[C@H]1CCC[C@H]12] | (3a'R,20a'S)-7'-fluoro-1'H,2'H,3'H,3a'H,5'H,11'H,13'H,14'H,20a'H-spiro[cyclopropane-1,12'-[10,20]dioxa[4,9,13,16,17,18][hexaaza[17,19](metheno)cyclopenta[5,6][1,4]oxazino[3,4-i]pyrazolo[4,3-f]pyrido[3,2-l][1,4,8,10]oxatriazacyclotridecin]-14'-one |

| Compound | Structure | Name |
|---|---|---|
| 19 | 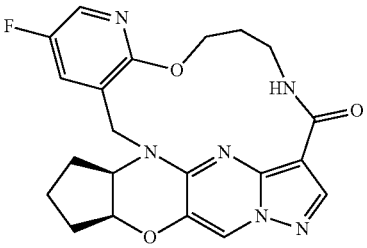 [SMILES: O=C1NCCCOc2ncc(F)cc2CN2c3nc4c1cnn4cc3O[C@H]1CCC[C@H]12] | (3aR,21aS)-7-fluoro-2,3,3a,11,12,13,14,21a-octahydro-1H,5H,15H-18,20-(metheno)cyclopenta[5,6][1,4]oxazino[4,3-e]pyrazolo[3,4-h]pyrido[2,3-b][1,5,7,11]oxatriazacyclotetradecin-15-one |
| 20 | 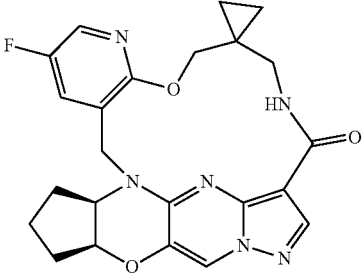 [SMILES: O=C1NCC2(CC2)COc2ncc(F)cc2CN2c3nc4c1cnn4cc3O[C@H]1CCC[C@H]12] | (3a'R,21a'S)-7'-fluoro-1'H,2'H,3'H,3a'H,5'H,11'H,13'H,14'H,15'H,21a'H-spiro[cyclopropane-1,12'-[10,21]dioxa[4,9,14,17,18,19][hexaaza[18,20](metheno)cyclopenta[5,6][1,4]oxazino[4,3-e]pyrazolo[3,4-h]pyrido[3,2-b][1,5,7,11]oxatriazacyclotetradecin]-15'-one |
| 21 | 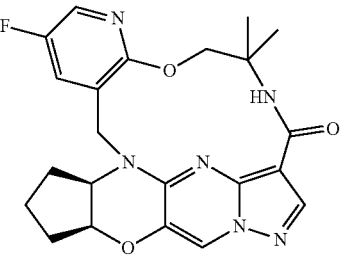 [SMILES: CC1(C)COc2ncc(F)cc2CN2c3nc4c(cnn4cc3O[C@H]3CCC[C@H]32)C(=O)N1] | (3aR,20aS)-7-fluoro-12,12-dimethyl-2,3,3a,12,13,20a-hexahydro-1H,5H-17,19-(metheno)cyclopenta[5,6][1,4]oxazino[3,4-i]pyrazolo[4,3-f]pyrido[3,2-l][1,4,8,10]oxatriazacyclotridecin-14(11H)-one |
| 22 | 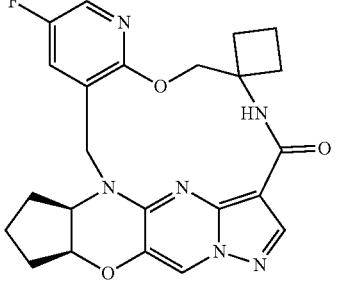 | (3a'R,20a'S)-7'-fluoro-1'H,2'H,3'H,3a'H,5'H,11'H,13'H,14'H,20a'H-spiro[cyclobutane-1,12'-[10,20]dioxa[4,9,13,16,17,18][hexaaza[17,19](metheno)cyclopenta[5,6][1,4]oxazino[3,4-i]pyrazolo[4,3-f]pyrido[3,2-l][1,4,8,10]oxatriazacyclotridecin]-14'-one |
| 23 | 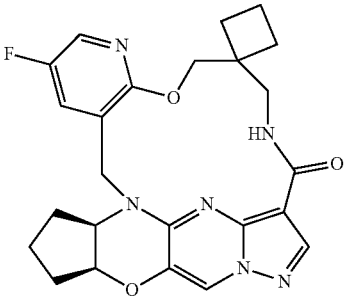 [SMILES: O=C1NCC2(CCC2)COc2ncc(F)cc2CN2c3nc4c1cnn4cc3O[C@H]1CCC[C@H]12] | (3a'R,21a'S)-7'-fluoro-1'H,2'H,3'H,3a'H,5'H,11'H,13'H,14'H,15'H,21a'H-spiro[cyclobutane-1,12'-[10,21]dioxa[4,9,14,17,18,19][hexaaza[18,20](metheno)cyclopenta[5,6][1,4]oxazino[4,3-e]pyrazolo[3,4-h]pyrido[2,3-b][1,5,7,11]oxatriazacyclotetradecin]-15'-one |

-continued

| Compound | Structure | Name |
|---|---|---|
| 24 | 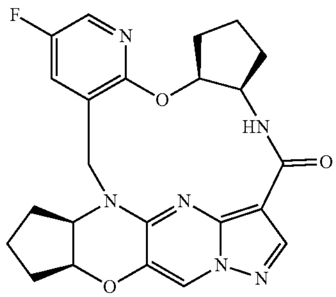 [SMILES: O=C1N[C@@H]2CCC[C@@H]2Oc2ncc(F)cc2CN2c3nc4c1cnn4cc3O[C@H]1CCC[C@H]12] | (3aS,11aR,14aS,21aR)-18-fluoro-2,3,3a,11,11a,12,13,14,14a,21a-decahydro-1H,10H,20H-7,5-(metheno)cyclopenta[b]cyclopenta[5,6][1,4]oxazino[3,4-i]pyrazolo[4,3-f]pyrido[3,2-l][1,4,8,10]oxatriazacyclotridecin-10-one |
| 25 | 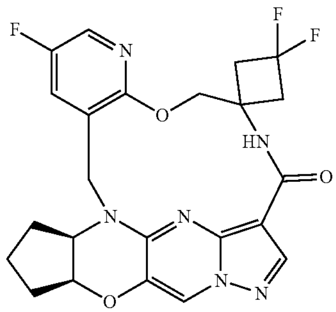 [SMILES: O=C1NC2(COc3ncc(F)cc3CN3c4nc5c1cnn5cc4O[C@H]1CCC[C@H]13)CC(F)(F)C2] | (3a'R,20a'S)-3,3,7'-trifluoro-1'H,2'H,3'H,3a'H,5'H,11'H,13'H,14'H,20a'H-spiro[cyclobutane-1,12'-[10,20]dioxa[4,9,13,16,17,18][hexaaza[17,19](metheno)cyclopenta[5,6][1,4]oxazino[3,4-i]pyrazolo[4,3-f]pyrido[3,2-l][1,4,8,10]oxatriazacyclotridecin]-14'-one |
| 26 | 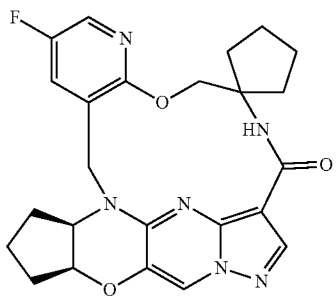 [SMILES: O=C1NC2(CCCC2)COc2ncc(F)cc2CN2c3nc4c1cnn4cc3O[C@H]1CCC[C@H]12] | (3a'R,20a'S)-7'-fluoro-1'H,2'H,3'H,3a'H,5'H,11'H,13'H,14'H,20a'H-spiro[cyclopentane-1,12'-[10,20]dioxa[4,9,13,16,17,18][hexaaza[17,19](metheno)cyclopenta[5,6][1,4]oxazino[3,4-i]pyrazolo[4,3-f]pyrido[3,2-l][1,4,8,10]oxatriazacyclotridecin]-14'-one |
| 27 | 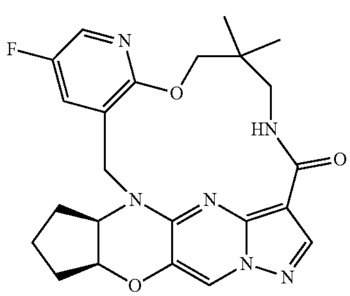 [SMILES: CC1(C)CNC(=O)c2cnn3cc4c(nc23)N(Cc2cc(F)cnc2OC1)[C@@H]1CCC[C@@H]1O4] | (3aR,21aS)-7-fluoro-12,12-dimethyl-2,3,3a,11,12,13,14,21a-octahydro-1H,5H,15H-18,20-(metheno)cyclopenta[5,6][1,4]oxazino[4,3-e]pyrazolo[3,4-h]pyrido[2,3-b][1,5,7,11]oxatriazacyclotetradecin-15-one |
| 28 | 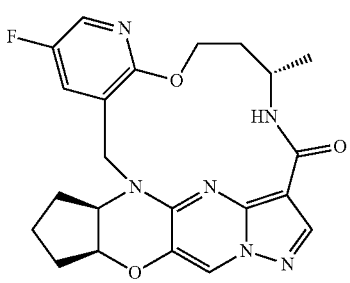 [SMILES: C[C@H]1CCOc2ncc(F)cc2CN2c3nc4c(cnn4cc3O[C@H]3CCC[C@H]32)C(=O)N1] | (3aR,13S,21aS)-7-fluoro-13-methyl-2,3,3a,11,12,13,14,21a-octahydro-1H,5H,15H-18,20-(metheno)cyclopenta[5,6][1,4]oxazino[4,3-e]pyrazolo[3,4-h]pyrido[2,3-b][1,5,7,11]oxatriazacyclotetradecin-15-one |

-continued

| Compound | Structure | Name |
|---|---|---|
| 29 | 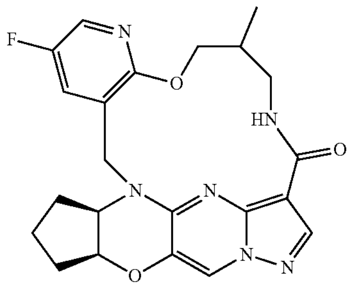 [SMILES: CC1CNC(=O)c2cnn3cc4c(nc23)N(Cc2cc(F)cnc2OC1)[C@@H]1CCC[C@@H]1O4] | (3aR,21aS)-7-fluoro-12-methyl-2,3,3a,11,12,13,14,21a-octahydro-1H,5H,15H-18,20-(metheno)cyclopenta[5,6][1,4]oxazino[4,3-e]pyrazolo[3,4-h]pyrido[2,3-b][1,5,7,11]oxatriazacyclotetradecin-15-one |
| 30 | 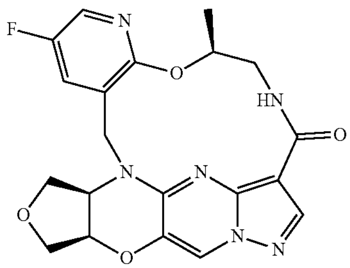 [SMILES: C[C@H]1CNC(=O)c2cnn3cc4c(nc23)N(Cc2cc(F)cnc2O1)[C@@H]1COC[C@@H]1O4] | (3aR,11S,20aR)-7-fluoro-11-methyl-1,3,3a,12,13,20a-hexahydro-5H-17,19-(metheno)furo[3',4':5,6][1,4]oxazino[3,4-i]pyrazolo[4,3-f]pyrido[3,2-l][1,4,8,10]oxatriazacyclotridecin-14(11H)-one |
| 31 | 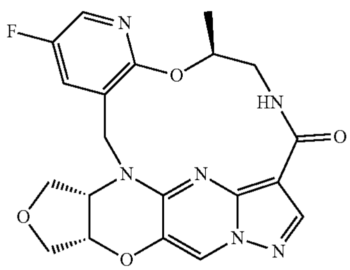 [SMILES: C[C@H]1CNC(=O)c2cnn3cc4c(nc23)N(Cc2cc(F)cnc2O1)[C@H]1COC[C@H]1O4] | (3aS,11S,20aS)-7-fluoro-11-methyl-1,3,3a,12,13,20a-hexahydro-5H-17,19-(metheno)furo[3',4':5,6][1,4]oxazino[3,4-i]pyrazolo[4,3-f]pyrido[3,2-l][1,4,8,10]oxatriazacyclotridecin-14(11H)-one |
| 32 | 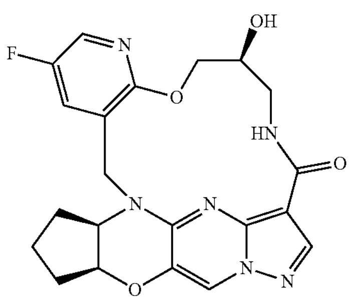 [SMILES: O=C1NC[C@H](O)COc2ncc(F)cc2CN2c3nc4c1cnn4cc3O[C@H]1CCC[C@H]12] | (3aR,12S,21aS)-7-fluoro-12-hydroxy-2,3,3a,11,12,13,14,21a-octahydro-1H,5H,15H-18,20-(metheno)cyclopenta[5,6][1,4]oxazino[4,3-e]pyrazolo[3,4-h]pyrido[2,3-b][1,5,7,11]oxatriazacyclotetradecin-15-one |
| 33 | 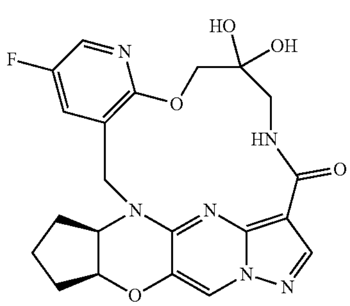 [SMILES: O=C1NCC(O)(O)COc2ncc(F)cc2CN2c3nc4c1cnn4cc3O[C@H]1CCC[C@H]12] | (3aR,21aS)-7-fluoro-12,12-dihydroxy-2,3,3a,11,12,13,14,21a-octahydro-1H,5H,15H-18,20-(metheno)cyclopenta[5,6][1,4]oxazino[4,3-e]pyrazolo[3,4-h]pyrido[2,3-b][1,5,7,11]oxatriazacyclotetradecin-15-one |

-continued

| Compound | Structure | Name |
|---|---|---|
| 34 | 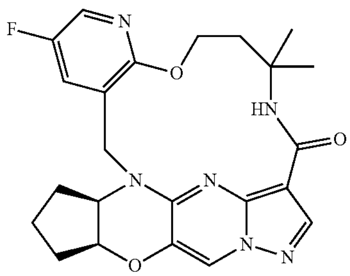 [SMILES: CC1(C)CCOc2ncc(F)cc2CN2c3nc4c(cnn4cc3O[C@H]3CCC[C@H]32)C(=O)N1] | (3aR,21aS)-7-fluoro-13,13-dimethyl-2,3,3a,11,12,13,14,21a-octahydro-1H,5H,15H-18,20-(metheno)cyclopenta[5,6][1,4]oxazino[4,3-e]pyrazolo[3,4-h]pyrido[2,3-b][1,5,7,11]oxatriazacyclotetradecin-15-one |
| 35 | 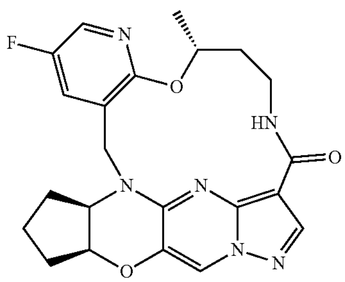 [SMILES: C[C@@H]1CCNC(=O)c2cnn3cc4c(nc23)N(Cc2cc(F)cnc2O1)[C@@H]1CCC[C@@H]1O4] | (3aR,11R,21aS)-7-fluoro-11-methyl-2,3,3a,11,12,13,14,21a-octahydro-1H,5H,15H-18,20-(metheno)cyclopenta[5,6][1,4]oxazino[4,3-e]pyrazolo[3,4-h]pyrido[2,3-b][1,5,7,11]oxatriazacyclotetradecin-15-one |
| 36 | 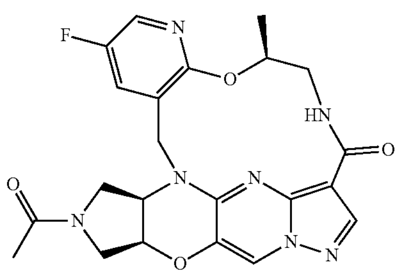 [SMILES: CC(=O)N1C[C@@H]2Oc3cn4ncc5c4nc3N(Cc3cc(F)cnc3O[C@@H](C)CNC5=O)[C@@H]2C1] | (3aR,11S,20aS)-2-acetyl-7-fluoro-11-methyl-2,3,3a,12,13,20a-hexahydro-1H,5H-17,19-(metheno)pyrazolo[4,3-f]pyrido[3,2-l]pyrrolo[3',4':5,6][1,4]oxazino[3,4-i][1,4,8,10]oxatriazacyclotridecin-14(11H)-one |
| 37 | 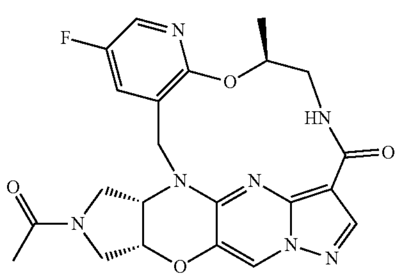 [SMILES: CC(=O)N1C[C@H]2Oc3cn4ncc5c4nc3N(Cc3cc(F)cnc3O[C@@H](C)CNC5=O)[C@H]2C1] | (3aS,11S,20aR)-2-acetyl-7-fluoro-11-methyl-2,3,3a,12,13,20a-hexahydro-1H,5H-17,19-(metheno)pyrazolo[4,3-f]pyrido[3,2-l]pyrrolo[3',4':5,6][1,4]oxazino[3,4-i][1,4,8,10]oxatriazacyclotridecin-14(11H)-one |
| 38 | 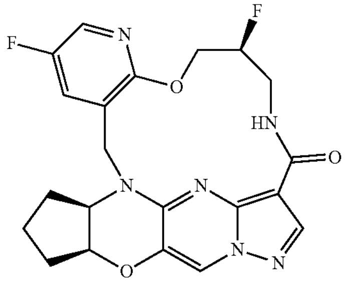 [SMILES: O=C1NC[C@H](F)COc2ncc(F)cc2CN2c3nc4c1cnn4cc3O[C@H]1CCC[C@H]12] | (3aR,12S,21aS)-7,12-difluoro-2,3,3a,11,12,13,21a-octahydro-1H,5H,15H-18,20-(metheno)cyclopenta[5,6][1,4]oxazino[4,3-e]pyrazolo[3,4-h]pyrido[2,3-b][1,5,7,11]oxatriazacyclotetradecin-15-one |

-continued

| Compound | Structure | Name |
|---|---|---|
| 39 | 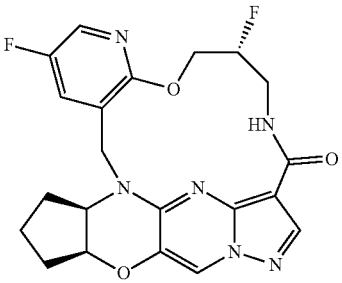 [SMILES: O=C1NC[C@@H](F)COc2ncc(F)cc2CN2c3nc4c1cnn4cc3O[C@H]1CCC[C@H]12] | 3aR,12R,21aS)-7,12-difluoro-2,3,3a,11,12,13,21a-octahydro-1H,5H,15H-18,20-(metheno)cyclopenta[5,6][1,4]oxazino[4,3-e]pyrazolo[3,4-h]pyrido[2,3-b][1,5,7,11]oxatriazacyclotetradecin-15-one |
| 40 | 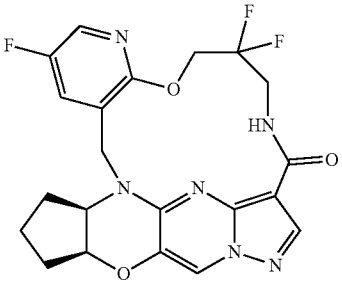 [SMILES: O=C1NCC(F)(F)COc2ncc(F)cc2CN2c3nc4c1cnn4cc3O[C@H]1CCC[C@H]12] | (3aR,21aS)-7,12,12-trifluoro-2,3,3a,11,12,13,14,21a-octahydro-1H,5H,15H-18,20-(metheno)cyclopenta[5,6][1,4]oxazino[4,3-e]pyrazolo[3,4-h]pyrido[2,3-b][1,5,7,11]oxatriazacyclotetradecin-15-one |
| 41 | 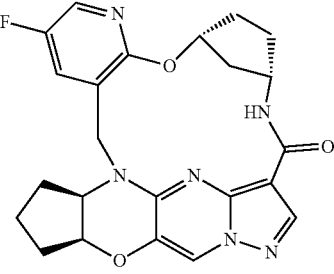 [SMILES: O=C1N[C@H]2CC[C@H](C2)Oc2ncc(F)cc2CN2c3nc4c1cnn4cc3O[C@H]1CCC[C@H]12] | (3aR,11R,14S,22aS)-7-fluoro-2,3,3a,12,13,14,15,22a-octahydro-1H,5H-11,14-metheno-19,21-(metheno)cyclopenta[5,6][1,4]oxazino[4,3-e]pyrazolo[3,4-h]pyrido[2,3-b][1,5,7,11]oxatriazacyclopentadecin-16(11H)-one |
| 42 | 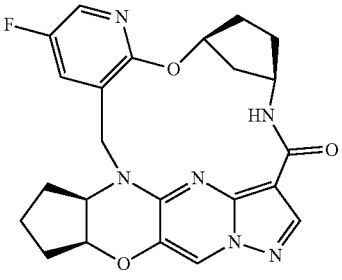 [SMILES: O=C1N[C@@H]2CC[C@@H](C2)Oc2ncc(F)cc2CN2c3nc4c1cnn4cc3O[C@H]1CCC[C@H]12] | (3aR,11S,14R,22aS)-7-fluoro-2,3,3a,12,13,14,15,22a-octahydro-1H,5H-11,14-metheno-19,21-(metheno)cyclopenta[5,6][1,4]oxazino[4,3-e]pyrazolo[3,4-h]pyrido[2,3-b][1,5,7,11]oxatriazacyclopentadecin-16(11H)-one |
| 43 | 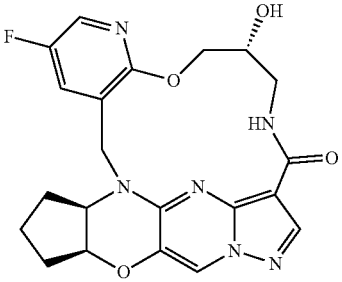 [SMILES: O=C1NC[C@@H](O)COc2ncc(F)cc2CN2c3nc4c1cnn4cc3O[C@H]1CCC[C@H]12] | (3aR,12R,21aS)-7-fluoro-12-hydroxy-2,3,3a,11,12,13,14,21a-octahydro-1H,5H,15H-18,20-(metheno)cyclopenta[5,6][1,4]oxazino[4,3-e]pyrazolo[3,4-h]pyrido[2,3-b][1,5,7,11]oxatriazacyclotetradecin-15-one |

-continued

| Compound | Structure | Name |
|---|---|---|
| 44 | 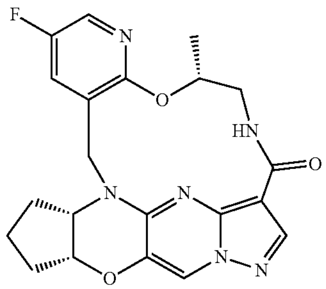 [SMILES: C[C@@H]1CNC(=O)c2cnn3cc4c(nc23)N(Cc2cc(F)cnc2O1)[C@H]1CCC[C@H]1O4] | (3aS,11R,20aR)-7-fluoro-11-methyl-2,3 3a,12,13,20a-hexahydro-1H,5H-17,19-(metheno)cyclopenta[5,6][1,4]oxazino[3,4-i]pyrazolo[4,3-f]pyrido[3,2-l][1,4,8,10]oxatriazacyclotridecin-14(11H)-one |
| 45 | 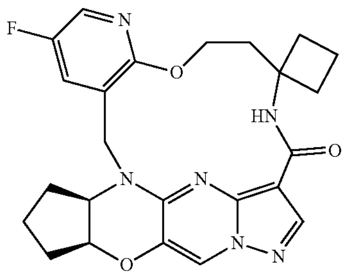 [SMILES: O=C1NC2(CCC2)CCOc2ncc(F)cc2CN2c3nc4c1cnn4cc3O[C@H]1CCC[C@H]12] | (3a'R,21a'S)-7'-fluoro-1'H,2'H,3'H,3a'H,5'H,11'H,12'H,14'H,15'H,21a'H-spiro[cyclopentane-1,13'-[10,21]dioxa[4,9,14,17,18,19][hexaaza[18,19](metheno)cyclopenta[5,6][1,4]oxazino[4,3-e]pyrazolo[3,4-h]pyrido[2,3-b][1,5,7,11]oxatriazacyclotetradecin]-15'-one |
| 46 | 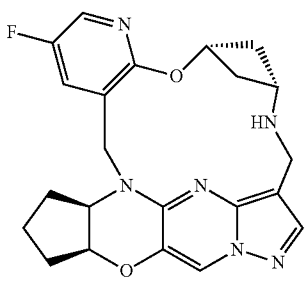 [SMILES: Fc1cnc2c(c1)CN1c3nc4c(cnn4cc3O[C@H]3CCC[C@H]31)CN[C@H]1C[C@H](C1)O2] | (3aR,11s,13S,21aS)-7-fluoro-2,3,3a,12,13,14,15,21a-octahydro-1H,5H,11H-11,13-methano-18,20-(metheno)cyclopenta[5,6][1,4]oxazino[4,3-e]pyrazolo[3,4-h]pyrido[2,3-b][1,5,7,11]oxatriazacyclotetradecine |
| 47 | 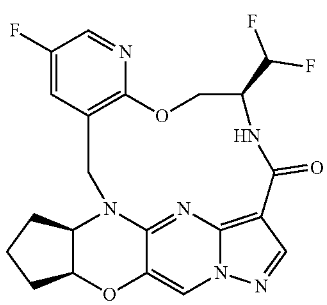 [SMILES: O=C1N[C@H](C(F)F)COc2ncc(F)cc2CN2c3nc4c1cnn4cc3O[C@H]1CCC[C@H]12] | (3aR,12S,20aS)-12-(difluoromethyl)-7-fluoro-2,3,3a,12,13,20a-hexahydro-1H,5H-17,19-(metheno)cyclopenta[5,6][1,4]oxazino[3,4-i]pyrazolo[4,3-f]pyrido[3,2-l][1,4,8,10]oxatriazacyclotridecin-14(11H)-one |
| 48 | 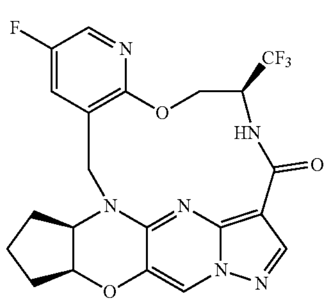 [SMILES: O=C1N[C@H](C(F)(F)F)COc2ncc(F)cc2CN2c3nc4c1cnn4cc3O[C@H]1CCC[C@H]12] | (3aR,12S,20aS)-7-fluoro-12-(trifluoromethyl)-2,3,3a,12,13,20a-hexahydro-1H,5H-17,19-(metheno)cyclopenta[5,6][1,4]oxazino[3,4-i]pyrazolo[4,3-f]pyrido[3,2-l][1,4,8,10]oxatriazacyclotridecin-14(11H)-one |

| Compound | Structure | Name |
|---|---|---|
| 49 | 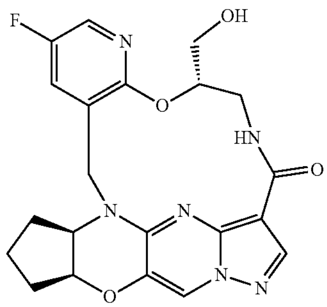 [SMILES: O=C1NC[C@@H](CO)Oc2ncc(F)cc2CN2c3nc4c1cnn4cc3O[C@H]1CCC[C@H]12] | (3aR,11S,20aS)-7-fluoro-11-(hydroxymethyl)-2,3,3a,12,13,20a-hexahydro-1H,5H-17,19-(metheno)cyclopenta[5,6][1,4]oxazino[3,4-i]pyrazolo[4,3-f]pyrido[3,2-l][1,4,8,10]oxatriazacyclotridecin-14(11H)-one |

Those skilled in the art will recognize that the species listed or illustrated herein are not exhaustive, and that additional species within the scope of these defined terms may also be selected.

Pharmaceutical Compositions

For treatment purposes, pharmaceutical compositions comprising the compounds described herein may further comprise one or more pharmaceutically-acceptable excipients. A pharmaceutically-acceptable excipient is a substance that is non-toxic and otherwise biologically suitable for administration to a subject. Such excipients facilitate administration of the compounds described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the invention are sterile compositions. Pharmaceutical compositions may be prepared using compounding techniques known or that become available to those skilled in the art.

Sterile compositions are also contemplated by the invention, including compositions that are in accord with national and local regulations governing such compositions.

The pharmaceutical compositions and compounds described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the invention may be administered by a suitable route of delivery, such as oral, parenteral, rectal, nasal, topical, or ocular routes, or by inhalation. Preferably, the compositions are formulated for intravenous or oral administration.

For oral administration, the compounds the invention may be provided in a solid form, such as a tablet or capsule, or as a solution, emulsion, or suspension. To prepare the oral compositions, the compounds of the invention may be formulated to yield a dosage of, e.g., from about 0.1 mg to 1 g daily, or about 1 mg to 50 mg daily, or about 50 to 250 mg daily, or about 250 mg to 1 g daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil, such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

For parenteral use, including intravenous, intramuscular, intraperitoneal, intranasal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For nasal, inhaled, or oral administration, the inventive pharmaceutical compositions may be administered using, for example, a spray formulation also containing a suitable carrier. The inventive compositions may be formulated for rectal administration as a suppository.

For topical applications, the compounds of the present invention are preferably formulated as creams or ointments or a similar vehicle suitable for topical administration. For topical administration, the inventive compounds may be mixed with a pharmaceutical carrier at a concentration of about 0.1% to about 10% of drug to vehicle. Another mode of administering the agents of the invention may utilize a patch formulation to effect transdermal delivery.

As used herein, the terms "treat" or "treatment" encompass both "preventative" and "curative" treatment. "Preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition. Thus, treatment includes ameliorating or preventing the worsening of existing disease symptoms, preventing additional symptoms from occurring, ameliorating or preventing the underlying systemic causes of symptoms, inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

The term "subject" refers to a mammalian patient in need of such treatment, such as a human.

Exemplary diseases include cancer, pain, neurological diseases, autoimmune diseases, and inflammation. Cancer includes, for example, lung cancer, colon cancer, breast cancer, prostate cancer, hepatocellular carcinoma, renal cell carcinoma, gastric and esophago-gastric cancers, glioblastoma, head and neck cancers, inflammatory myofibroblastic tumors, and anaplastic large cell lymphoma. Pain includes, for example, pain from any source or etiology, including cancer pain, pain from chemotherapeutic treatment, nerve pain, pain from injury, or other sources. Autoimmune diseases include, for example, rheumatoid arthritis, Sjogren syndrome, Type I diabetes, and lupus. Exemplary neurological diseases include Alzheimer's Disease, Parkinson's Disease, Amyotrophic lateral sclerosis, and Huntington's disease. Exemplary inflammatory diseases include atherosclerosis, allergy, and inflammation from infection or injury.

In one aspect, the compounds and pharmaceutical compositions of the invention specifically target receptor tyrosine kinases, in particular RET. In another aspect, the compounds and pharmaceutical compositions of the invention specifically target non-receptor tyrosine kinases, in particular SRC. In yet another aspect, the compounds and pharmaceutical compositions of the invention specifically target receptor tyrosine kinases and non-receptor tyrosine kinases, such as RET and SRC, respectively. Thus, these compounds and pharmaceutical compositions can be used to prevent, reverse, slow, or inhibit the activity of one or more of these kinases. In preferred embodiments, methods of treatment target cancer. In other embodiments, methods are for treating lung cancer or non-small cell lung cancer.

In the inhibitory methods of the invention, an "effective amount" means an amount sufficient to inhibit the target protein. Measuring such target modulation may be performed by routine analytical methods such as those described below. Such modulation is useful in a variety of settings, including in vitro assays. In such methods, the cell is preferably a cancer cell with abnormal signaling due to upregulation of RET and/or SRC.

In treatment methods according to the invention, an "effective amount" means an amount or dose sufficient to generally bring about the desired therapeutic benefit in subjects needing such treatment. Effective amounts or doses of the compounds of the invention may be ascertained by routine methods, such as modeling, dose escalation, or clinical trials, taking into account routine factors, e.g., the mode or route of administration or drug delivery, the pharmacokinetics of the agent, the severity and course of the infection, the subject's health status, condition, and weight, and the judgment of the treating physician. An exemplary dose is in the range of about from about 0.1 mg to 1 g daily, or about 1 mg to 50 mg daily, or about 50 to 250 mg daily, or about 250 mg to 1 g daily. The total dosage may be given in single or divided dosage units (e.g., BID, TID, QID).

Once improvement of the patient's disease has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms. Patients may also require chronic treatment on a long-term basis.

Drug Combinations

The inventive compounds described herein may be used in pharmaceutical compositions or methods in combination with one or more additional active ingredients in the treatment of the diseases and disorders described herein. Further additional active ingredients include other therapeutics or agents that mitigate adverse effects of therapies for the intended disease targets. Such combinations may serve to increase efficacy, ameliorate other disease symptoms, decrease one or more side effects, or decrease the required dose of an inventive compound. The additional active ingredients may be administered in a separate pharmaceutical composition from a compound of the present invention or may be included with a compound of the present invention in a single pharmaceutical composition. The additional active ingredients may be administered simultaneously with, prior to, or after administration of a compound of the present invention.

Combination agents include additional active ingredients are those that are known or discovered to be effective in treating the diseases and disorders described herein, including those active against another target associated with the disease. For example, compositions and formulations of the invention, as well as methods of treatment, can further comprise other drugs or pharmaceuticals, e.g., other active agents useful for treating or palliative for the target diseases or related symptoms or conditions. For cancer indications, additional such agents include, but are not limited to, kinase inhibitors, such as EGFR inhibitors (e.g., erlotinib, gefitinib), Raf inhibitors (e.g., vemurafenib), VEGFR inhibitors (e.g., sunitinib), ALK inhibitors (e.g., crizotinib) standard chemotherapy agents such as alkylating agents, antimetabolites, anti-tumor antibiotics, topoisomerase inhibitors, platinum drugs, mitotic inhibitors, antibodies, hormone therapies, or corticosteroids. For pain indications, suitable combination agents include anti-inflammatories such as NSAIDs. The pharmaceutical compositions of the invention may additionally comprise one or more of such active agents, and methods of treatment may additionally comprise administering an effective amount of one or more of such active agents.

Chemical Synthesis

Exemplary chemical entities useful in methods of the description will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups.

Abbreviations: The examples described herein use materials, including but not limited to, those described by the following abbreviations known to those skilled in the art:

| | |
|---|---|
| g | grams |
| eq | equivalents |
| mmol | millimoles |
| mL | milliliters |
| EtOAc | ethyl acetate |
| MHz | megahertz |
| ppm | parts per million |
| δ | chemical shift |
| s | singlet |
| d | doublet |
| t | triplet |
| q | quartet |
| quin | quintet |
| br | broad |
| m | multiplet |
| Hz | hertz |
| THF | tetrahydrofuran |
| °C. | degrees Celsius |
| PE | petroleum ether |
| EA | ethyl acetate |
| $R_f$ | retardation factor |
| N | normal |
| J | coupling constant |
| DMSO-$d_6$ | deuterated dimethyl sulfoxide |
| n-BuOH | n-butanol |
| DIEA | n,n-diisopropylethylamine |
| TMSCl | trimethylsilyl chloride |
| min | minutes |
| hr | hours |
| Me | methyl |
| Et | ethyl |
| i-Pr | isopropyl |
| TLC | thin layer chromatography |
| M | molar |
| Compd# | compound number |
| MS | mass spectrum |
| m/z | mass-to-charge ratio |
| Ms | methanesulfonyl |
| FDPP | pentafluorophenyl diphenylphosphinate |
| Boc | tert-butyloxycarbonyl |
| TFA | trifluoroacetic acid |
| Tos | toluenesulfonyl |
| DMAP | 4-(dimethylamino)pyridine |
| μm | micromolar |
| ATP | adenosine triphosphate |
| $IC_{50}$ | half maximal inhibitory concentration |
| U/mL | units of activity per milliliter |
| KHMDS | potassium bis(trimethylsilyl)amide |

-continued

| | |
|---|---|
| DIAD | diisopropyl azodicarboxylate |
| MeTHF | 2-methyltetrahydrofuran |
| MOM | methoxymethyl |
| DCM | dichloromethane |
| DMF | N,N-dimethylformamide |
| DPPA | diphenyl phosphoryl azide |
| DBU | 1,8-diazabicyclo[5.4.0]undec-7-ene |
| DIPEA | N,N-diisopropylethylamine |
| TBAF | Tetrabutylammonium Fluoride |
| TEA | Triethylamine |
| TBS | Tert-butyldimethylsilyl |

General Method A.

Preparation of tert-butyl {(2S)-2-[4-fluoro-2-({[(1R, 2S)-2-hydroxycyclopentyl]amino}methyl)phenoxy]propyl}carbamate (A-1)

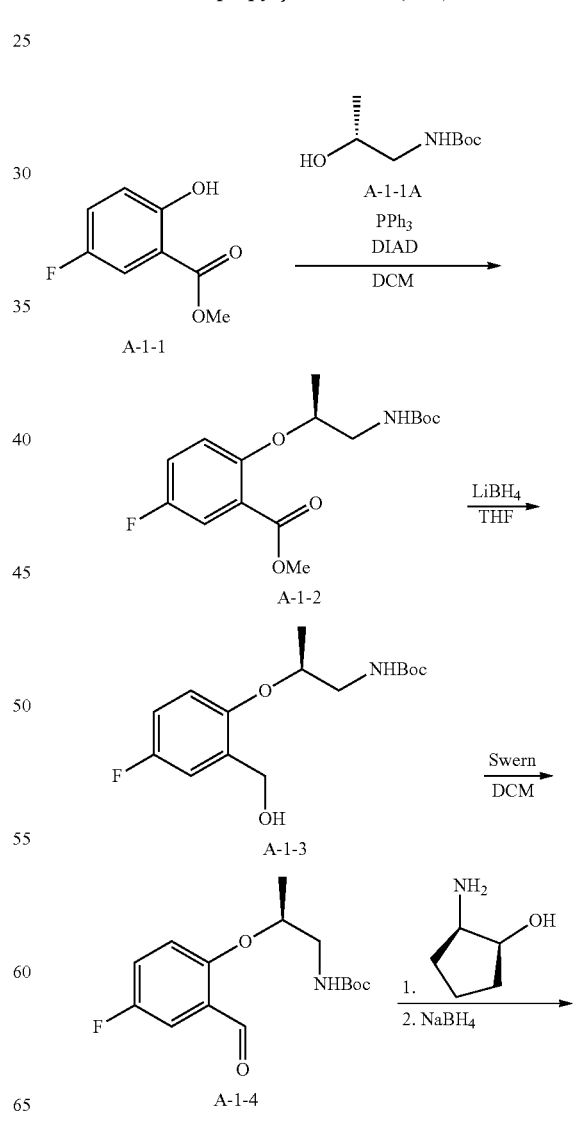

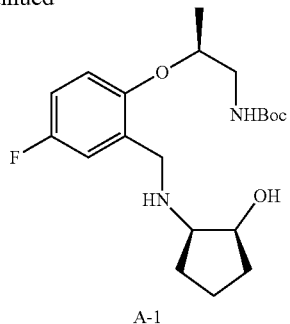

A-1

Step 1. To an azeotrope dried mixture of A-1-1 (0.9615 g, 5.65 mmol) and A-1-1A (1.19 g, 6.78 mmol) in DCM (3.62 mL) was added PPh$_3$ (2.22 g, 8.48 mmol) The mixture was stirred until everything dissolved. DIAD (1.83 g, 9.04 mmol, 1.78 mL) was added very slowly with mixing at 0° C. The reaction was warmed to 25° C. and stirred for 16 hr. DCM (5 mL) and 2M NaOH solution (20 mL) were added and stirred vigorously for 4 hours. The mixture was extracted with DCM (3×15 mL), dried with Na$_2$SO$_4$ and concentrated under reduced pressure. Flash chromatography (ISCO system, silica 12 g, 0-30% ethyl acetate in hexane) provided A-1-2 (1.35 g, 73%).

Step 2. To a solution of A-1-2 (1.35 g, 4.13 mmol) in THF (8.27 mL) at 0° C. was added lithium borohydride (720.51 mg, 33.08 mmol) in small batches and the mixture was stirred for 1 hr and was removed from the cold bath. The mixture stirred at ambient temperature for 20 hr, then diluted with water (5 mL) and extracted with ethyl acetate (3×5 mL). The combined organic phase was washed with brine and dried over sodium sulfate. Flash column chromatography (ISCO, silica, 24 g, ethyl acetate in hexanes) afforded A-1-3 (1.08 g, 3.60 mmol, 87.09% yield).

Step 3. DMSO (422.82 mg, 5.41 mmol, 384.38 uL) in DCM (6 mL) was added dropwise at –78° C. to oxalyl chloride (686.85 mg, 5.41 mmol, 464.09 uL) in DCM (6 mL). The mixture was stirred for 20 minutes and A-1-3 (1.08 g, 3.61 mmol) in DCM (6 mL) was added dropwise at –78° C. and stirred for 20 minutes followed by addition of TEA (1.83 g, 18.04 mmol, 2.51 mL). The mixture was stirred as temperature increased to ambient temperature over 18 h. The reaction was quenched with water (10 mL) and the layers were separated. The aqueous layer was extracted twice more with DCM (2×10 mL). The combined organic layer was washed with brine and dried over sodium sulfate. Flash chromatography (ISCO, 24 g Silica Gold, 0-30% ethyl acetate in hexanes) afforded A-1-4 (460.2 mg, 1.55 mmol, 42.90% yield).

Step 4. A solution of (1S,2R)-2-aminocyclopentanol HCl salt (69 mg, 504 μmol), Hunig's Base (196 mg, 0.26 mL, 1.5 mmol) and A-1-4 (150.00 mg, 504 μmol) in dry MeOH (2.50 mL) was heated to 65° C. for 1 hr. The reaction was cooled to room temperature and NaBH$_4$ (38 mg, 1.0 mmol) was added. The mixture was stirred for 2 hr then quenched with water (3 mL) and stirred for 5 min. The mixture was extracted with DCM (3×5 mL), dried with Na$_2$SO$_4$ and concentrated under reduced pressure. Flash chromatography (ISCO system, silica (12 g), 25-50% ethyl acetate in hexane) provided A-1 (125.3 mg, 327 μmol, 64.9% yield).

Compound A-2 was prepared according to General Method A using (1R,2R)-2-aminocyclopentanol in step 4.

General Method B.

Preparation of tert-butyl {(2S)-2-[2,4-difluoro-6-({[(1R,2S)-2-hydroxycyclopentyl]amino}methyl)phenoxy]propyl}carbamate (A-3)

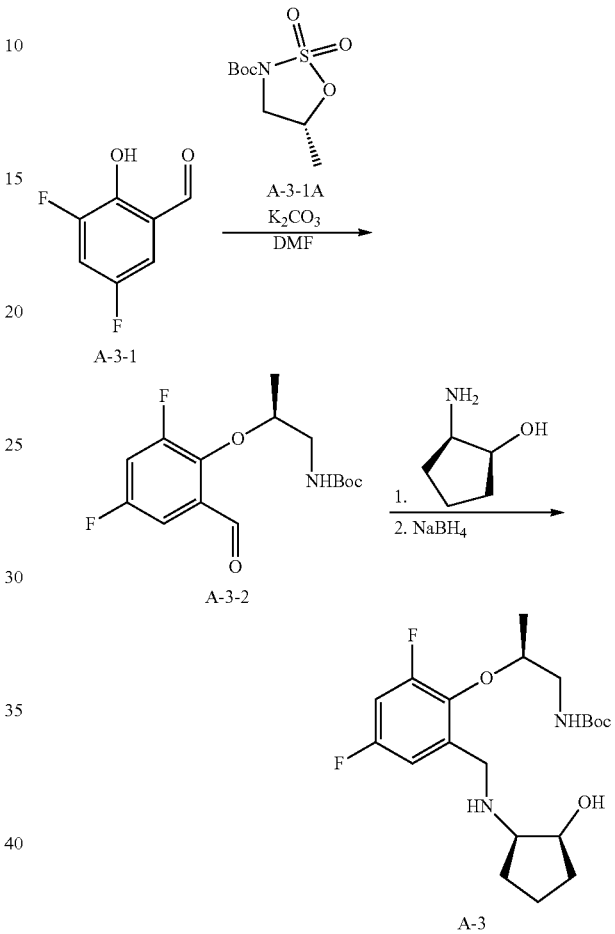

Step 1. Added K$_2$CO$_3$ (330.00 mg, 2.39 mmol) to A-3-1 (151 mg, 955.08 μmol) and A-3-1A (283.27 mg, 1.19 mmol) in DMF (4.78 mL) and heated to 50° C. with stirring for 1 hr. The mixture was cooled and diluted with DCM (3 mL), filtered through a syringe filter and concentrated under reduced pressure. Flash chromatography (ISCO system, silica (12 g), 0-30% ethyl acetate in hexane) provide A-3-2 (301 mg, 954 μmol, 99% yield).

Step 4. A solution of (1S,2R)-2-aminocyclopentanol HCl salt (104 mg, 0.76 μmol) and A-3-2 (200 mg, 634 μmol) in dry MeOH (3.17 mL) was heated to 65° C. for 1 hour. The reaction was cooled to room temperature and NaBH$_4$ (72 mg, 1.9 mmol) was added. The mixture was stirred for 2 hours then quenched with water (5 mL) and stirred for 5 min. The mixture was extracted with DCM (3×15 mL), dried with Na$_2$SO$_4$ and concentrated under reduced pressure. Flash chromatography (ISCO system, silica (12 g), 0-20% methanol in dichloromethane) provided A-3 (108 mg, 270 μmol, 42% yield).

Compound A-4 was prepared according to General Method A using (3R,4R)-4-aminotetrahydrofuran-3-ol in step 4.

Compound A-5 was prepared according to General Method A using 5-Fluoro-2-methoxynicotinaldehyde in step 4.

Compound A-6 was prepared according to General Method A using rac cis-tert-butyl-3-amino-4-hydroxypyrrolidine-1-carboxylate and 5-Fluoro-2-methoxynicotinaldehyde.

| Compd# | Structure | MS [M + H] m/z |
|---|---|---|
| A-1 | 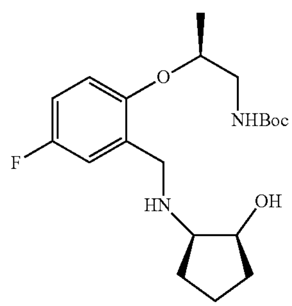 [SMILES: C[C@@H](CNC(=O)OC(C)(C)C)Oc1ccc(F)cc1CN[C@@H]1CCC[C@@H]1O] | 383.2 |
| A-2 | 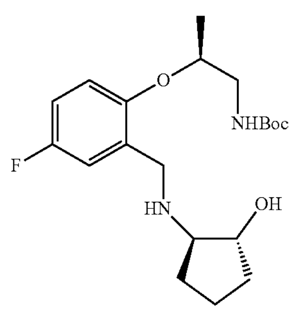 [SMILES: C[C@@H](CNC(=O)OC(C)(C)C)Oc1ccc(F)cc1CN[C@@H]1CCC[C@H]1O] | 383.2 |
| A-3 | 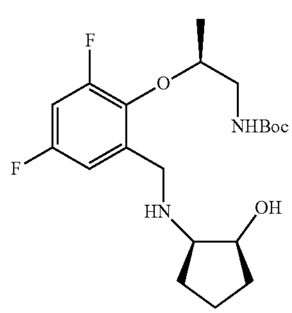 [SMILES: C[C@@H](CNC(=O)OC(C)(C)C)Oc1c(F)cc(F)cc1CN[C@@H]1CCC[C@@H]1O] | 401.2 |
| A-4 | 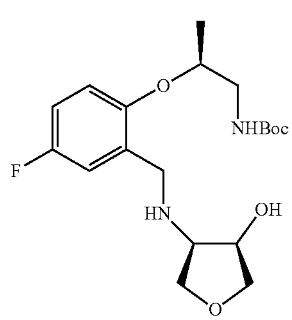 [SMILES: C[C@@H](CNC(=O)OC(C)(C)C)Oc1ccc(F)cc1CN[C@@H]1COC[C@@H]1O] | 385.2 |
| A-5 | | 241.1 |
| A-6 | | 342.1 |

General Method C.

Preparation of ethyl 6-bromo-5-chloropyrazolo[1,5-a]pyrimidine-3-carboxylate (B-1)

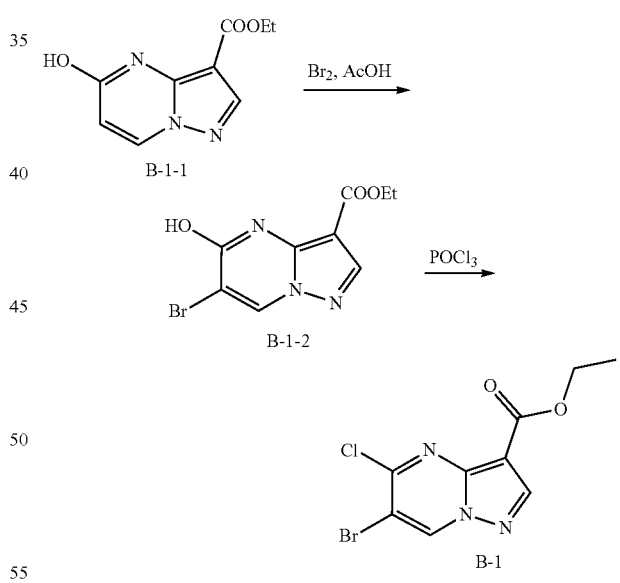

Step 1. To a solution of B-1-1 (10.00 g, 47.80 mmol, 1.00 eq.) in acetic acid (100.00 mL) was added bromine (7.64 g, 47.80 mmol, 2.46 mL, 1.00 eq.). The mixture was stirred at 180° C. for 6 hr. TLC (petroleum ether/ethyl acetate=1/1) showed the starting material was consumed completely and one new spot was found. The mixture was quenched by water (30 mL). The mixture was filtered and the cake was concentrated to give B-1-2 (10.00 g, 34.71 mmol, 72.62% yield) as a white solid: $^1$H NMR (400 MHz, DMSO-d6) δ:12.34 (br. s., 1H), 9.25 (s, 1H), 8.15 (s, 1H), 4.28 (q, J=7.2 Hz, 2H), 1.29 (t, J=7.2 Hz, 3H).

Step 2. To a solution of B-1-2 (6.00 g, 20.97 mmol, 1.00 eq.) in phosphorus oxychloride (60 mL). The mixture was stirred at 120° C. for 16 hr. TLC (petroleum ether/ethyl acetate=3/1) indicated the starting material was consumed completely and one new spot was found. The reaction mixture was filtered and concentrated under reduced pressure to give a residue. The residue was purified by column chromatography (SiO$_2$, petroleum ether/ethyl acetate=10/1 to 1/1) to give B-1 (2.50 g, 8.21 mmol, 39.15% yield) as a white solid; $^1$H NMR (400 MHz, CDCl$_3$) δ: 8.94 (s, 1H), 8.54 (s, 1H), 4.43 (q, J=7.2 Hz, 2H), 1.42 (t, J=7.2 Hz, 3H).

General Method D.

Preparation of (3aR,11S,20aS)-7-fluoro-11-methyl-2,3,3a,12,13,20a-hexahydro-1H,5H-17,19-(metheno)cyclopenta[5,6][1,4]oxazino[3,4-i]pyrazolo[4,3-][1,4,8,10]benzoxatriazacyclotridecin-14(11H)-one (1)

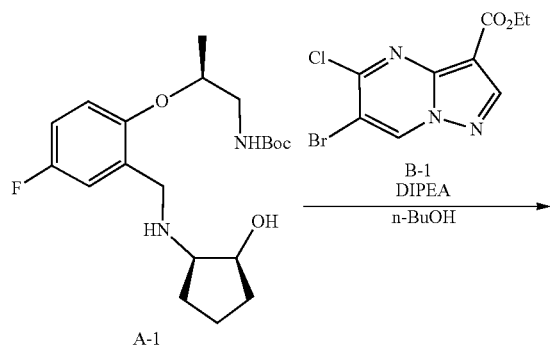

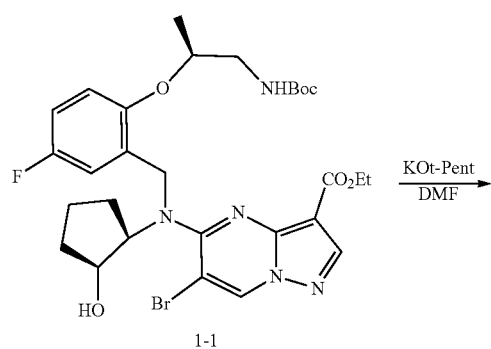

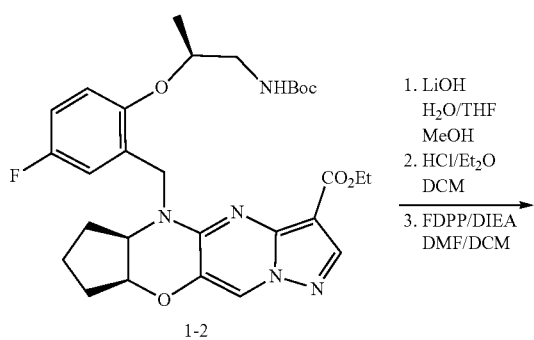

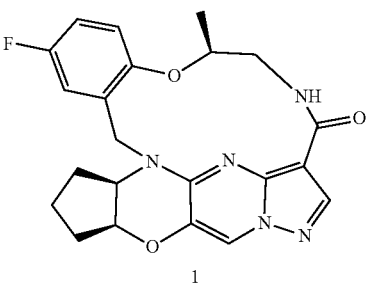

Step 1. To a solution of B-1 (325 mg, 1.07 mmol) and A-1 (408 mg, 1.07 mmol) in n-BuOH (5.3 mL) was added Hunig's base (689 mg, 5.3 mmol, 929 μL). The mixture was heated to 90° C. for 15 hr. The reaction was cooled and concentrated under reduced pressure. Flash chromatography (ISCO system, silica (12 g), 10-50% ethyl acetate in hexane) provided 1-1 (197.7 mg, 303 μmol, 28% yield).

Step 2. To a solution of 1-1 (36.6 mg, 48.5 μmol) in DMF (3 mL) was added KOt-Pent (1.7 M, 86 μL) in toluene. The reaction stirred at room temperature for 1.5 hours. The reaction was cooled to −20° C. and quenched with saturated NH$_4$Cl sol. (5 mL) then extracted with DCM (3×10 mL). Combined extracts were dried with Na$_2$SO$_4$ and concentrated under reduced pressure. Flash chromatography (ISCO system, silica (12 g), 10-35% ethyl acetate in hexane) provided 1-2 (12.8 mg, 22 μmol, 46% yield).

Step 3. To a solution of 1-2 (12.8 mg, 22 μmol) in MeOH (3 mL) and THF (1 mL) at ambient temperature was added aqueous LiOH solution (2.0 M, 1.0 mL). The mixture was heated at 60° C. for 17 hr, cooled to −20° C. then quenched with aqueous HCl solution (2.0 M) to acidic. The mixture was extracted with DCM (3×5 mL), dried with Na$_2$SO$_4$. concentrated under reduced pressure, and dried under high vacuum. The crude material was dissolved in DCM (4 mL) followed by addition of HCl in 1,4-dioxane (4 M, 3 mL). The mixture was stirred at ambient temperature for 1.5 hr, concentrated under reduced pressure, and dried under high vacuum. The crude material was dissolved in DMF (2.0 mL) and DCM (4.0 mL) and Hünig's base (185 mg, 1.4 mmol, 250 μL) then FDPP (34.5 mg, 89 μmol) was added in one portion. The reaction was stirred for 1.5 hours then quenched with 2 M Na$_2$CO$_3$ solution (5 mL). The mixture was stirred for 5 min then extracted with DCM (4×10 mL). Combined extracts were dried with Na$_2$SO$_4$ and concentrated under reduced pressure. Flash chromatography (ISCO system, silica (12 g), 0-5% methanol in dichloromethane) provided 1 (8.13 mg, 19 μmol, 85% yield).

Compounds 2 through 4 were prepared according to General Method D using A-2 through A-4 in step 1 respectively.

General Method E.

Preparation of (3aR,11S,20aS)-7-fluoro-11-methyl-2,3,3a,12,13,20a-hexahydro-1H,5H-17,19-(metheno)cyclopenta[5,6][1,4]oxazino[3,4-i]pyrazolo[4,3-f]pyrido[3,2-l][1,4,8,10]oxatriazacyclotridecin-14(11H)-one (5)

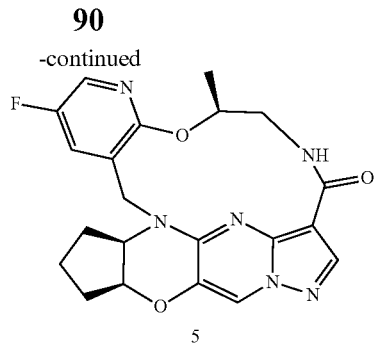

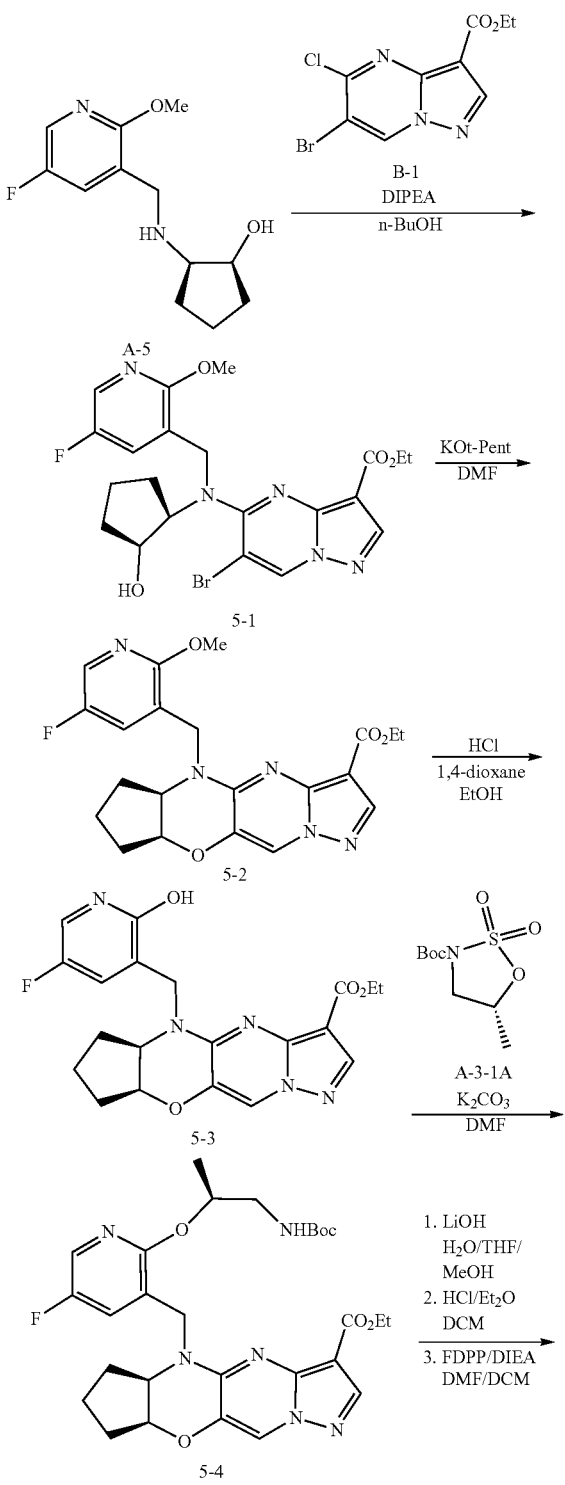

Step 1. To a solution of B-1 (454 mg, 1.49 mmol) and A-5 (358 mg, 1.49 mmol) in t-BuOH (5.0 mL) was added Hunig's base (963 mg, 7.45 mmol, 1.30 mL). The mixture was heated to 105° C. for 17 hr. The reaction was cooled and concentrated under reduced pressure. Flash chromatography (ISCO system, silica (12 g), 10-40% ethyl acetate in hexane) provided 5-1 (292 mg, 38% yield).

Step 2. To a solution of 5-1 (18.8 mg, 37 μmol) in DMF (3 mL) was added KOt-Pent (1.7 M, 65 μL) in toluene. The reaction stirred at room temperature for 20 hours. The reaction was cooled to −20° C. and quenched with saturated NH$_4$Cl sol. (5 mL) then extracted with DCM (3×10 mL). Combined extracts were dried with Na$_2$SO$_4$ and concentrated under reduced pressure. Flash chromatography (ISCO system, silica (12 g), 0-5% methanol in dichloromethane) provided 5-2 (6.2 mg, 39% yield).

Step 3. To a solution of 5-2 (6.2 mg, 14.5 μmol) in EtOH (4 mL) was added aqueous HCl solution (4.0 M, 3.0 mL) in 1,4-dioxane. The mixture was heated at 70° C. for 6 hours. The mixture was cooled, concentrated under reduced pressure, and dried under high vacuum to provide crude 5-3. Compound was used as is.

Step 4. Added K$_2$CO$_3$ (14.0 mg, 101 μmol) to 5-3 (6.2 mg, 14.5 μmol) and A-3-1A (17 mg, 73 μmol) in DMF (250 μL) and stirred for 2 hours. The mixture was cooled and quenched with water (5 mL) then extracted with DCM (3×10 mL). Combined extracts were dried with Na$_2$SO$_4$ and concentrated under reduced pressure. Flash chromatography (ISCO system, silica (12 g), 20-100% ethyl acetate in hexane) provide 5-4 (6.1 mg, 73% yield).

Step 5. To a solution of 5-4 (6.1 mg, 10.7 μmol) in MeOH (3 mL) and THF (1 mL) at ambient temperature was added aqueous LiOH solution (2.0 M, 1.0 mL). The mixture was heated at 60° C. for 16 hr, cooled to −20° C. then quenched with aqueous HCl solution (2.0 M) to acidic. The mixture was extracted with DCM (3×5 mL), dried with Na$_2$SO$_4$, concentrated under reduced pressure, and dried under high vacuum. The crude material was dissolved in DCM (4 mL) followed by addition of HCl in 1,4-dioxane (4 M, 3 mL). The mixture was stirred at ambient temperature for 2 hours, concentrated under reduced pressure, and dried under high vacuum. The crude material was dissolved in DMF (2.0 mL) and DCM (4.0 mL) and Hünig's base (185 mg, 1.4 mmol, 250 μL) then FDPP (34.5 mg, 89 μmol) was added in one portion. The reaction was stirred for 1 hour then quenched with 2 M Na$_2$CO$_3$ solution (5 mL). The mixture was stirred for 5 min then extracted with DCM (4×10 mL). Combined extracts were dried with Na$_2$SO$_4$ and concentrated under reduced pressure. Flash chromatography (ISCO system, silica (12 g), 0-5% methanol in dichloromethane) provided 5 (3.21 mg, 71% yield).

Compound 6 was prepared according to General Method E using (R)-3-Boc-4-methyl-2,2-dioxo-[1,2,3]oxathiazolidine in step 4.

General Method F.

Preparation of ethyl (5aR,8aS)-5,5a,6,7,8,8a-hexahydrocyclopenta[b]pyrazolo [1',5': 1,2]pyrimido[4,5-e][1,4]oxazine-3-carboxylate (C-1)

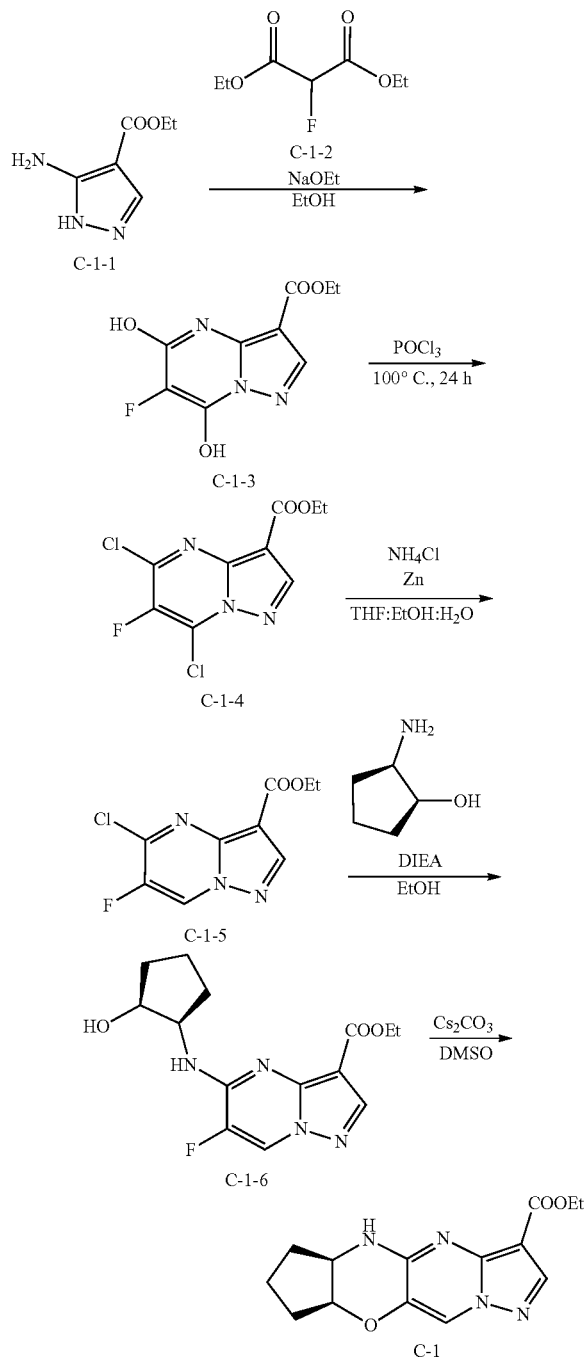

Step 1. To a solution of C-1-1 (5.0 g, 28.1 mmol, 1 eq.) and C-1-2 (6.1 g, 39.3 mmol, 1.4 eq.) in EtOH (56 mL) at 90° C. was added NaOEt (2.68 M, 26.2 mL, 2.5 eq.) and was stirred for 6 hours. The reaction mixture cooled and diluted with Toluene (60 mL) and concentrated to dryness under reduced pressure. The material was resuspended in Toluene (60 mL) and again concentrated to dryness and placed on a high vac overnight to provide crude C-1-3. Crude material was used as is in next step.

Step 2. The crude C-1-3 from step 1 was suspended in POCl₃ (99 g, 60 mL, 646 mmol, 23.00 eq.) and heated to 100° C. for 24 hours. The reaction was cooled to room temperature and concentrated to dryness under reduced pressure. The crude material was suspended in DCM (100 mL) and water (100 mL) was added. The mixture was stirred for 30 min then extracted with DCM (3×100 mL). The combined organic extracts were washed by brine (100 mL), dried over anhydrous sodium sulfate, filtered and concentrated under reduced pressure. Purification through a Silica plug (60 g Si), eluted with DCM (~1.5 L) gave C-1-4 (5.68 g, 72% yield, purity=86% by LC/MS) as a yellow solid.

Step 3. To a solution of C-1-4 (5.68 g, 20.4 mmol) and NH₄Cl (5.46 g, 102 mmol) in THF (68 mL), EtOH (204 mL) and water (136 mL) at 0° C. was added Zn powder (5.34 g, 81.7 mmol). The mixture was stirred at 0° C. for 3 hours. The reaction mixture was filtered through a celite pad and the celite pad was rinsed with DCM (100 mL). The filtrate was concentrated to dryness under reduced pressure then resuspended in DCM (500 mL) dried with Na₂SO₄ and concentrated under reduced pressure. Purification using a silica plug (50 g Si) and elution with DCM provided C-1-5 (3.17 g, 63.8% yield) as a white solid.

Step 4. To a solution of C-1-5 (1.74 g, 7.1 mmol) and the HCl salt of (1S,2R)-2-aminocyclopentanol (1.08 g, 7.8 mmol) in EtOH (14 mL) was added DIEA (4.6 g, 6.2 mL 35.6 mmol). The mixture was heated to 80° C. for 1 hour. The reaction cooled and concentrated under reduced pressure. Flash chromatography (ISCO system, silica (40 g), 20-80% ethyl acetate in hexane) provided C-1-6 (2.13 g, 97% yield) as a white solid.

Step 5. To a solution of C-1-6 (1.0 g, 3.24 mmol) in DMSO (162 mL) was added Cs₂CO₃ (9.51 g, 29 mmol). The mixture was heated to 100° C. and stirred for 91 hours. The reaction mixture was cooled and quenched with 30% brine solution (700 mL) then extracted with ethyl acetate (4×200 mL). Combined extracts were washed with 15% brine solution (2×250 mL). Brine solutions were back extracted with ethyl acetate (1×250 mL). Organic extracts were combined and dried with brine (250 mL), Na₂SO₄ and concentrated under reduced pressure to provide C-1 (803 mg, 86% yield, 97% purity by LC/MS) as a light-yellow solid.

Compounds C-2, C-3, and C-4 were prepared according to General Method F using rac cis-2-aminocyclobutanol, (1S,2R)-2-aminocyclohexanol, and rac cis-4-aminooxolan-3-ol, respectively in step 4.

| Compd# | Structure | MS [M + H] m/z |
|---|---|---|
| C-1 | ![structure] | 289.0 |
| C-2 | ![structure] | 275.0 |

| Compd# | Structure | MS [M + H] m/z |
|---|---|---|
| C-3 | (cyclohexane-fused pyrazolo-pyrimidine oxazine with COOEt) | 303.0 |
| C-4 | (tetrahydrofuran-fused pyrazolo-pyrimidine oxazine with COOEt) | 291.1 |

General Method G.

Preparation of tert-butyl {(2R)-1-[2-(chloromethyl)-4,6-difluorophenoxy]propan-2-yl}carbamate (D-1)

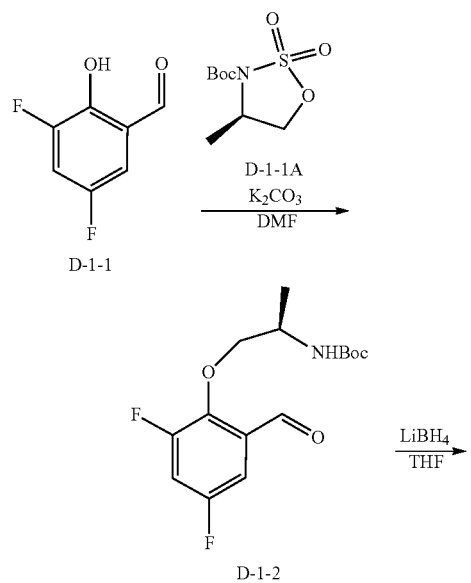

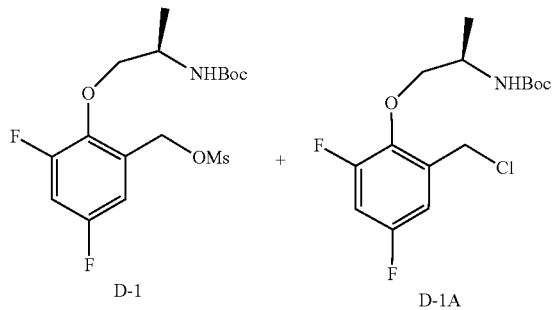

Step 1. To a solution of D-1-1 (200 mg, 1.27 mmol) and D-1-1A (315 mg, 1.33 mmol) in DMF (6.3 mL) was added $K_2CO_3$ (437 mg, 3.2 mmol) The reaction was stirred for 2 hours then quenched with citric acid solution (1 M in $H_2O$, 6 mL) was added and the mixture was vigorously stirred for 30 minutes. The mixture was extracted with DCM (3×10 mL) and combined organic extracts were collected and dried over $Na_2SO_4$, filtered and concentrated under reduced pressure and high vacuum to afforded desired product D-1-2 (theoretical yield 399 mg). Compound was used as is.

Step 2. To a solution of D-1-2 (399 mg (theoretical), 1.27 mmol) in dry THF (15 mL) was added $LiBH_4$ (193 mg, 8.86 mmol). The mixture was stirred for 20 hours then quenched with water (25 mL) and stirred for 5 min. The mixture was extracted with DCM (3×15 mL), dried with $Na_2SO_4$ and concentrated under reduced pressure. Flash chromatography (ISCO system, silica (24 g), 0-50% ethyl acetate in hexane) provided D-1-3 (33.2 mg, 8% yield).

Step 3. To a solution of D-1-3 (33.2 mg, 105 µmol) and DIPEA (67.6 mg, 91 µL, 523 µmol) in DCM (525 µL) at 0° C. was added MsCl (15 mg, 10 µL 131 µmol) dropwise. The mixture stirred at 0° C. for 1 hour. The reaction was quenched with water (3 mL) and 2M HCl (100 µL) then extracted with DCM (3×5 mL). The organic phases were combined, dried over $Na_2SO_4$, and concentrated under reduced pressure. Flash chromatography (ISCO system, silica (12 g), 0-50% ethyl acetate in hexane) provided a mixture of D-1 and D-1A (40.2 mg, 91% yield).

General Method H.

Preparation of (S)-(2-((1-((tert-butoxycarbonyl)amino)propan-2-yl)oxy)-5-fluoropyridin-3-yl)methyl Methanesulfonate (D-2)

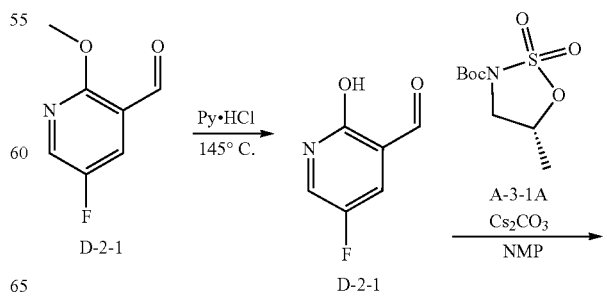

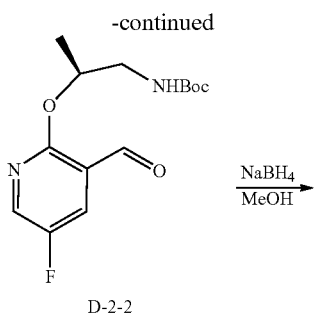

D-2-2

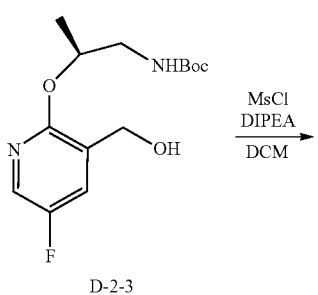

D-2-3

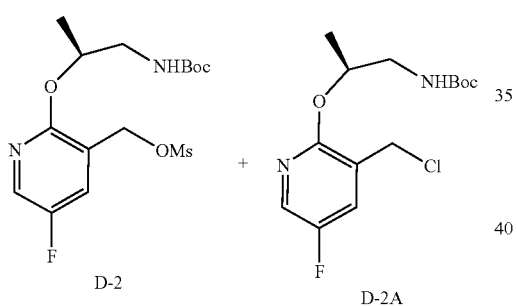

D-2  D-2A

Step 1. D-2-1 (7 g, 45.12 mmol) and pyridine hydrochloride (20.86 g, 180.5 mmol) were mixed in a round bottom flask and heated up to 145° C. and the molten mixture was stirred at 145° C. for 30 min then cooled down. The mixture was diluted with H$_2$O (200 mL) and ethyl acetate (200 mL), partitioned and the aqueous layer was extracted with EA (5×100 mL), organic phases were combined and dried over Na$_2$SO$_4$, the solution was then concentrated under reduced pressure to afford desired product D-2-1 (5.19 g, 36.78 mmol, 81.51% yield) as yellow solid.

Step 2. To an ice-bathed mixture of compound D-2-1 (2.37 mg, 16.79 mmol) and Cs$_2$CO$_3$ (21.88 g, 67.15 mmol in NMP (33.57 mL) was added compound A-3-1A (4 g, 16.79 mmol), the reaction was stirred at 0° C. for 2 hours. The reaction was diluted with dichloromethane (200 mL) and H$_2$O (100 mL). Citric acid solution (1 M in H$_2$O, 100 mL) was added and the mixture was vigorously stirred for 10 minutes, layers were separated, organic layer was collected and dried over Na$_2$SO$_4$, filtered and concentrated under reduced pressure. Purification by flash chromatography (ISCO system, silica (80 g), 0-30% ethyl acetate in hexanes) afforded desired product D-2-2 (4.2 g, 14.06 mmol, 83.79% yield) as white solid.

Step 3. To an ice-bathed solution of compound D-2-2 (4.2 g, 14.06 mmol) in MeOH (46.88 mL) was added NaBH$_4$ (798.17 mg, 21.10 mmol). The reaction was stirred under 0° C. for 1 hour. The reaction was quenched with H$_2$O (100 mL) and was extracted with dichloromethane (3×100 mL). The organic phases were combined and dried over Na$_2$SO$_4$, filtered and concentrated under reduced pressure. Purification by flash chromatography (ISCO system, silica (80 g), 0-50% ethyl acetate in hexanes) afforded desired product D-2-3 (3.46 g, 11.53 mmol, 81.96% yield) as colorless oil.

Step 4. To a solution of D-2-3 (2.41 g, 8.02 mmol) and the DIPEA (4.15 g, 5.6 mL, 32.1 mmol) in DCM (14 mL) at 0° C. was added MsCl (1.10 g, 0.74 mL 9.62 mmol) dropwise. The mixture stirred at 0° C. for 2 hours. The was quenched with 1% HCl solution (100 mL) and extracted with DCM (3×100 mL). The organic phases were combined, dried over Na$_2$SO$_4$, and concentrated under reduced pressure. Flash chromatography (ISCO system, silica (80 g), 0-40% ethyl acetate in hexane) provided D-2 (2.0 g, 66% yield) as a white solid and D-2A (627 mg, 24% yield) as an oil.

Compound D-3 was prepared according to General Method H using (R)-3-boc-4-methyl-2,2-dioxo-[1,2,3]oxathiazolidine in step 2.

| Compd# | Structure | MS [M + Na] m/z |
|---|---|---|
| D-1 | 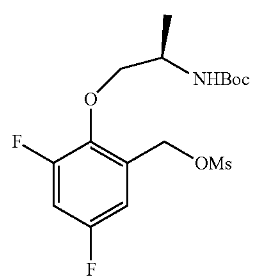 [SMILES: C[C@H](COc1c(F)cc(F)cc1COS(C)(=O)=O)NC(=O)OC(C)(C)C] | 418.1 |
| D-2 | 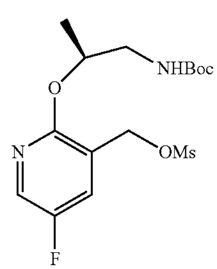 [SMILES: C[C@@H](CNC(=O)OC(C)(C)C)Oc1ncc(F)cc1COS(C)(=O)=O] | 401.1 |
| D-3 | 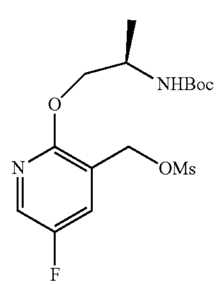 [SMILES: C[C@H](COc1ncc(F)cc1COS(C)(=O)=O)NC(=O)OC(C)(C)C] | 401.1 |

General Method I.

Preparation of (3aR,12R,20aS)-7,9-difluoro-12-methyl-2,3,3a,12,13,20a-hexahydro-1H,5H-17,19-(metheno)cyclopenta[5,6][1,4]oxazino[3,4-i]pyrazolo[4,3-f][1,4,8,10]benzoxatriazacyclotridecin-14(11H)-one (7)

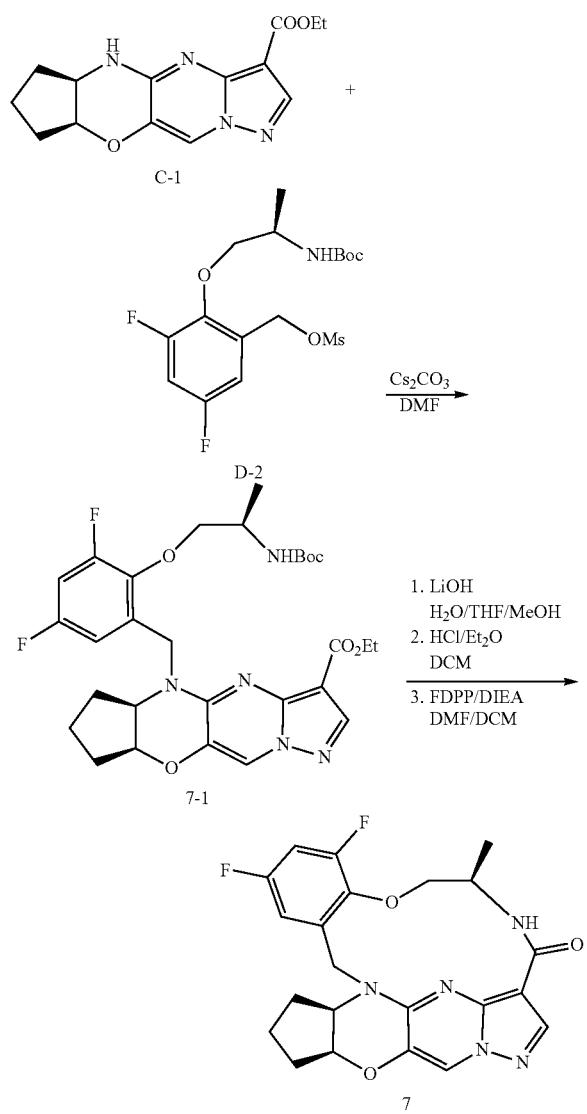

Compounds 10 and 11 were prepared according to General Method I using starting materials C-2 and D-3 in step 1 and separating the stereoisomers after the last step.

Compound 12 was prepared according to General Method I using starting materials C-3 and D-2 in step 1.

Compound 13 was prepared according to General Method I using starting materials C-3 and D-3 in step 1.

General Method J.

Preparation of (3aR,12R,20aS)-12-cyclopropyl-7-fluoro-2,3,3a,12,13,20a-hexahydro-1H,5H-17,19-(metheno)cyclopenta[5,6][1,4]oxazino[3,4-i]pyrazolo[4,3-f]pyrido[3,2-1][1,4,8,10]oxatriazacyclotridecin-14(11H)-one (14)

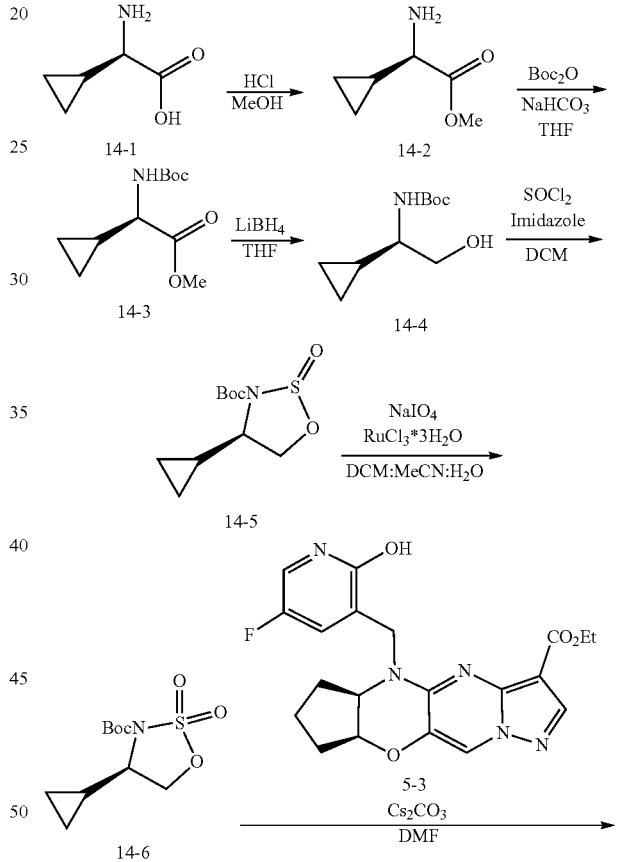

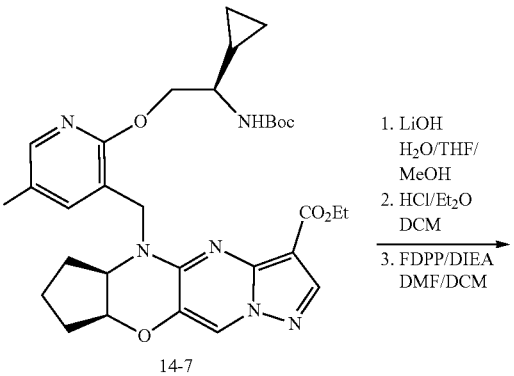

Step 1. To a solution of C-1 (30 mg, 104 μmol) and D-1 (41 mg, 104 μmol) in DMF (1 mL) was added Cs₂CO₃ (102 mg, 312 μmol). The reaction was stirred at room temperature for 4 hours. The reaction was cooled, diluted with DCM (3 mL), filtered through a syringe filter and concentrated under reduced pressure. Flash chromatography (ISCO system, silica (12 g), 0-50% ethyl acetate in hexane) provided 7-1 (61 mg, 100% yield).

Step 2. Compound 7-1 was converted to 7 following the procedure used in General Method E.

Compounds 8 and 9 were prepared according to General Method I using starting materials C-2 and D-2 in step 1 and separating the stereoisomers after the last step.

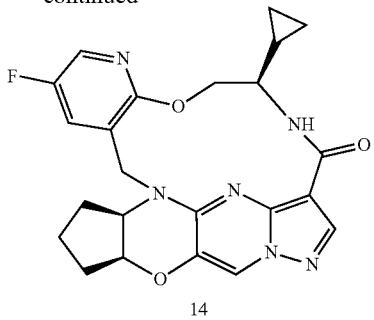

14

Step 1. To a solution of 14-1 (1.0 g, 8.69 mmol) in dry MeOH (87 mL) was added HCl (4.0 M, 4.3 mL, 2.0 eq.) in dioxane. The mixture was heated to 70° C. and stirred for 40 hours. The reaction mixture cooled and concentrated to dryness under reduced pressure to provide crude 14-2. The material was used as is in next step.

Step 2. To a solution of crude 14-2 from step 1 in THF (60 mL) was added Boc$_2$O (2.08 g, 9.54 mmol) and NaHCO$_3$ solution (1 M, 34.69 mL). The reaction was stirred for 4 hours then diluted with water (50 mL) and then extracted with ethyl acetate (3×50 mL). The combined organic extracts were washed by brine (50 mL), dried over anhydrous sodium sulfate, filtered and concentrated under reduced pressure. Flash chromatography (ISCO system, silica (40 g), 0-50% ethyl acetate in hexane) provided 14-3 (1.66 g, 83% yield).

Step 3. To a solution of 14-3 (1.66 g, 7.24 mmol) in THF (36 mL) at 0° C. was added LiBH$_4$ (789 mg, 36 mmol). The mixture was slowly warmed to room temperature and stirred for 20 hours. The reaction mixture was quenched by addition of water (20 mL) and aqueous saturated NH$_4$Cl (25 mL) then extracted with ethyl acetate (3×50 mL). Combined extracts were dried with brine (50 mL), Na$_2$SO$_4$ and concentrated under reduced pressure. Flash chromatography (ISCO system, silica (40 g), 10-40% ethyl acetate in hexane) provide 14-4 (1.23 g, 84% yield).

Step 4. To a solution of Imidazole (1.0 g, 14.9 mmol) in DCM (16 mL) at −5° C. was added SOCl$_2$ (532 mg, 4.47 mmol, 324 μL) in DCM (5 mL) dropwise. The mixture was stirred at −5° C. for 1 hour. The mixture was cooled to −10° C. and 14-4 (0.5 g, 2.48 mmol) in DCM (4 mL) was added dropwise. The mixture was slowly warmed to 10° C. and stirred at this temperature for 2 hr. The reaction was quenched with water (10 mL) and stirred at 10° C. for 10 min. The organic layer was removed and washed with 10% citric acid solution (10 mL) then dried with brine (5 mL) and Na$_2$SO$_4$ and concentrated under reduced pressure. Flash chromatography (ISCO system, silica (24 g), 0-20% ethyl acetate in hexane) provide 14-5 (294 mg, 48% yield).

Step 5. To a solution of 14-5 (294 mg, 1.19 mmol) in DCM (5.66 mL) and NaIO4 (610.25 mg, 2.85 mmol) in H2O (5.66 mL) at 0° C. was added RuCl$_3$*3H$_2$O (6.2 mg, 24 μmol). The mixture was warmed to room temperature and stirred for 1 hour. The reaction was quenched with water (15 mL) then extracted with DCM (3×15 mL). Combined extracts were dried with brine (5 mL), Na$_2$SO$_4$ and concentrated under reduced pressure. Flash chromatography (ISCO system, silica (12 g), 0-30% ethyl acetate in hexane) provide 14-6 (308 mg, 98% yield).

Step 6. To a solution of 5-3 (40 mg, 97 μmol) and 14-6 (32 mg, 121 μmol) in DMF (484 μL) was added CS2CO3 (95 mg, 290 μmol). The reaction mixture was stirred for 1 hour then diluted with DCM (5 mL) and filtered through syringe filter then stirred with 20% citric acid solution (10 mL) for 30 min. The mixture was extracted with DCM (3×15 mL) and combined extracts dried with Na$_2$SO$_4$ and concentrated under reduced pressure. Flash chromatography (ISCO system, silica (12 g), 10-50% ethyl acetate in hexane) provide 14-7 (45.6 mg, 79% yield).

Step 7. Compound 14-7 was converted to 14 following the procedure used in General Method E.

General Method K.

Preparation of (3aR,11S,21aS)-7-fluoro-11-methyl-2,3,3a,11,12,13,14,21a-octahydro-1H,5H,15H-18,20-(metheno)cyclopenta[5,6][1,4]oxazino[4,3-e]pyrazolo[3,4-h]pyrido[2,3-b][1,5,7,11]oxatriazacyclotetradecin-15-one (15)

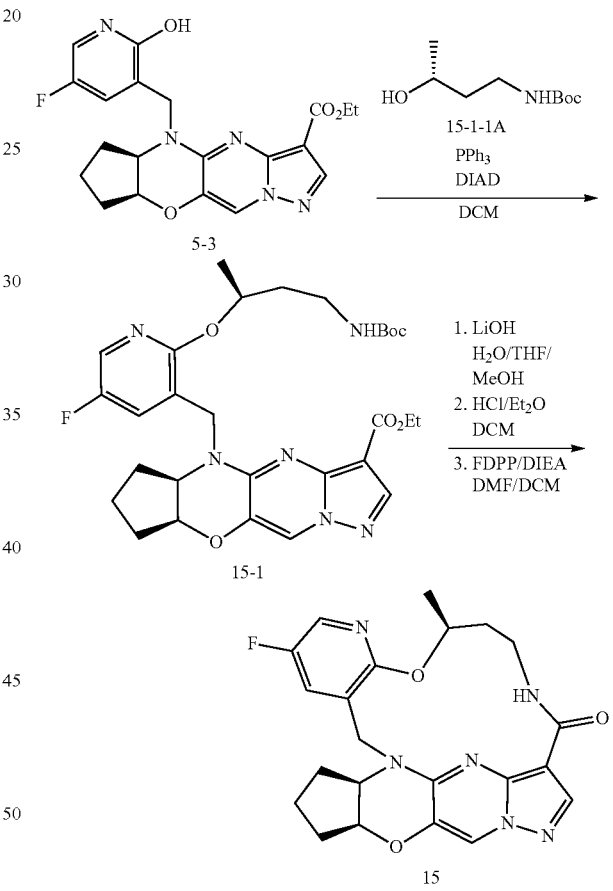

Step 1. To a solution of 5-3 (50 mg, 121 μmol), 15-1-1A (27.5 mg, 145 μmol) and PPh$_3$ (41 mg, 157 μmol) in DCM (194 μL) at 0° C. was added DIAD (41 mg, 157 μmol). The mixture was warmed to room temperature and stirred for 16 hours. The reaction cooled and diluted with DCM. The solution was filtered and the filtrate was concentrated under reduced pressure. Flash column chromatography (ISCO, silica, a 12 g, ethyl acetate in hexanes) to afford 15-1 (58.8 mg, 83% yield)

Step 2. Compound 15-1 was converted to 15 following the procedure used in General Method E.

Compounds 16 and 17 were prepared according to General Method K.

Compound 18 was prepared according to General Method J.

General Method L.

Preparation of (3aR,21aS)-7-fluoro-2,3,3a,11,12,13,14,21a-octahydro-1H,5H,15H-18,20-(metheno)cyclopenta[5,6][1,4]oxazino[4,3-e]pyrazolo[3,4-h]pyrido[2,3-b][1,5,7,11]oxatriazacyclotetradecin-15-one (19)

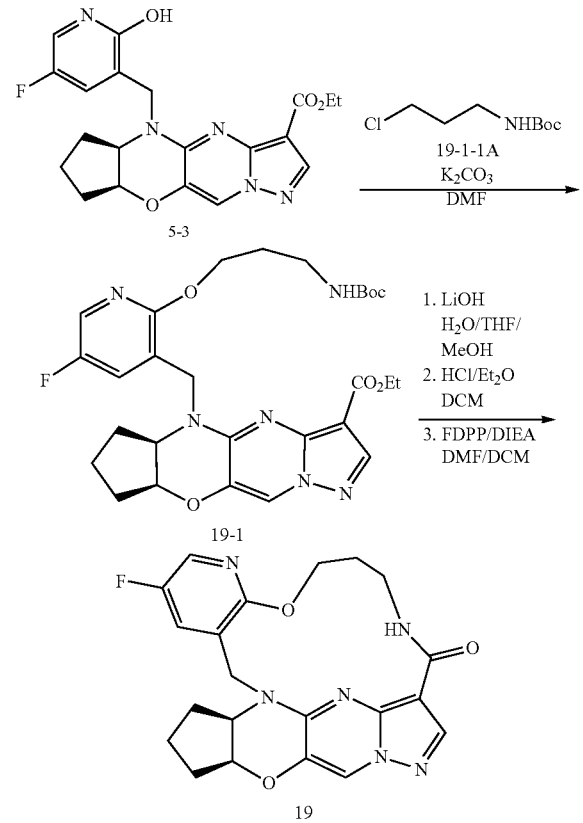

Step 1. To a solution of 5-3 (40 mg, 97 μmol) and 19-1-1A (23 mg, 116 μmol) in DMF (300 uL) was added K₂CO₃ (27 mg, 194 μmol). The mixture was mixture was stirred at room temperature for 16 hr. The reaction cooled and diluted with DCM (5 mL). The solution was filtered and the filtrate was concentrated under reduced pressure. The crude was purified by flash column chromatography (ISCO, silica, 12 g, ethyl acetate in hexanes) to afford 15 (18.9 mg, 34% yield).

Step 2. Compound 19-1 was converted to 19 following the procedure used in General Method E.

Compound 20 was prepared according to General Method K.

Compound 21 and 22 were prepared according to General Method J.

Compound 23 and 24 were prepared according to General Method K.

Compound 25 and 26 were prepared according to General Method J.

Compound 27, 28, and 29 were prepared according to General Method K.

Compound 30 and 31 were prepared according to General Method I using starting materials D-2A and C-4 in step 1 and separating the stereoisomers after the last step by flash column chromatography (ISCO, reverse phase C-18, 50 g, acetonitrile in water with 0.035% TFA).

General Method M.

Preparation of (3aR,12S,21aS)-7-fluoro-12-hydroxy-2,3,3a,11,12,13,14,21a-octahydro-1H,5H,15H-18,20-(metheno)cyclopenta[5,6][1,4]oxazino[4,3-e]pyrazolo[3,4-h]pyrido[2,3-b][1,5,7,11]oxatriazacyclotetradecin-15-one (32)

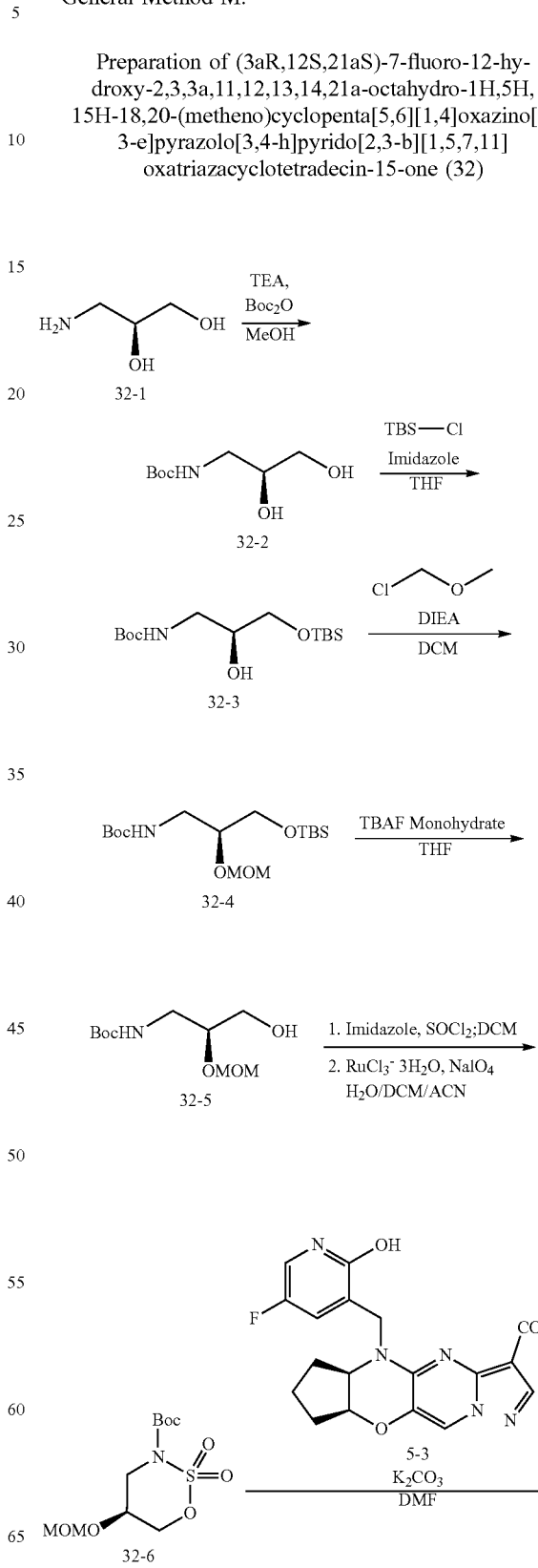

-continued

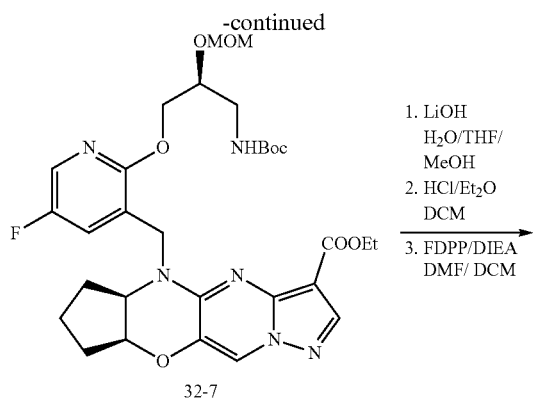

32-7

1. LiOH H₂O/THF/ MeOH
2. HCl/Et₂O DCM
3. FDPP/DIEA DMF/DCM

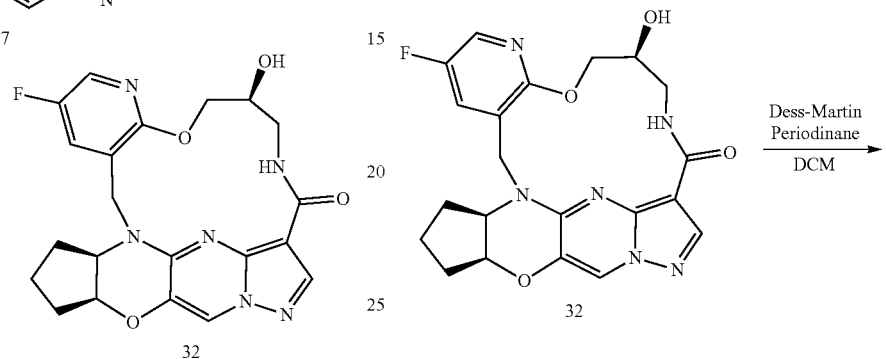

32

Compound 32 was prepared following General Method J from 32-5 in step 4 and 5-3 in step 6.

General Procedure N.

Preparation of (3aR,21aS)-7-fluoro-12,12-dihydroxy-2,3,3a,11,12,13,14,21a-octahydro-1H,5H, 15H-18,20-(metheno)cyclopenta[5,6][1,4]oxazino[4, 3-e]pyrazolo[3,4-h]pyrido[2,3-b][1,5,7,11] oxatriazacyclotetradecin-15-one (33)

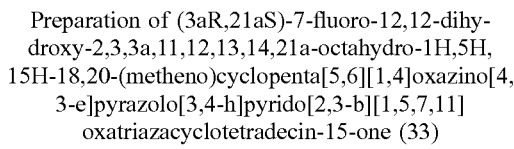

Dess-Martin Periodinane DCM

Step 1. To a solution of 32-1 (3.1 g, 34.03 mmol) and Boc anhydride (7.43 g, 34.03 mmol) in MeOH (68.05 mL) was added TEA (6.89 g, 68.05 mmol, 9.48 mL). The mixture was stirred at room temperature for 16 hr. The reaction was concentrated under reduced pressure and purified by flash column chromatography (ISCO, silica, 40 g, methanol in dichloromethane) to afford 32-2 (6.36 g, 33.26 mmol, 97.75% yield).

Step 2. 32-2 (6.36 g, 33.26 mmol) and imidazole (4.53 g, 66.52 mmol) were dissolved in THF (110.86 mL) and TBS chloride (6.02 g, 39.91 mmol) was added. The mixture was stirred for 2 hr then diluted with water (200 mL) and extracted with DCM (3×200 mL). The combined organic phase was washed with brine (200 mL) and dried over Na₂SO₄. The solution was filtered and the filtrate was concentrated under reduced pressure. The crude was purified by flash chromatography (ISCO system, silica, 80 g, 0-40% ethyl acetate in hexanes) to afford 32-3 (8.75 g, 28.64 mmol, 86.12% yield).

Step 3. To a solution of 32-3 (8.75 g, 28.64 mmol) and DIEA (11.11 g, 85.93 mmol, 14.97 mL) in DCM (95.48 mL) at 0° C. was added MOM chloride (3.46 g, 42.96 mmol, 3.26 mL) slowly. The mixture was stirred for 16 hr. warming to ambient temperature. The reaction was quenched with water (100 mL) and extracted with DCM (3×100 mL). The combined extracts were dried over Na₂SO₄. The crude was purified by flash column chromatography (ISCO, silica, 80 g, 0-30% ethyl acetate in hexanes) to afford 32-4 (7.44 g, 21.29 mmol, 74.31% yield).

Step 4. To a solution of 32-4 (7.44 g, 21.29 mmol) in THF (106.43 mL) was added TBAF Monohydrate (11.90 g, 42.57 mmol). The mixture was stirred for 1 hr. then quenched with saturated aqueous NH₄Cl solution (10 mL) and diluted with DCM (100 mL). The mixture was dried over Na₂SO₄ and filtered. The filtrate was concentrated under reduced pressure and the crude was purified by flash column chromatography (ISCO, silica, 80 g, ethyl acetate in hexanes) to afford 32-5 (4.67 g, 19.85 mmol, 93.25% yield).

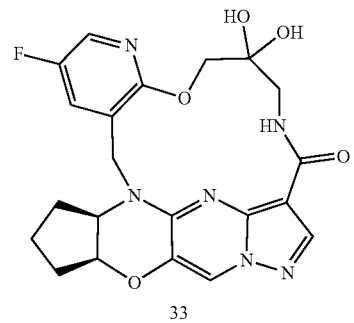

33

To a solution of 32 (13.8 mg, 31.33 umol) in DCM (626.66 uL) was added Dess-Martin Periodinane (26.58 mg, 62.67 umol). The mixture was stirred at room temperature for 2 hr and quenched with saturated NaHCO₃ solution (5 mL). The mixture was extracted with DCM (3×5 mL) and the organic layers dried over Na₂SO₄. The salts were filtered and the filtrate concentrated under reduced pressure. The crude was purified by flash column chromatography (ISCO, silica, 12 g, methanol in dichloromethane) and result mixture of products was stirred in acetonitrile (1 mL) with drops of 2M HCl (2 drops), diluted with 2M sodium carbonate and extracted with dichloromethane (3×5 mL) to provide compound 33 (9.1 mg, 19.94 μmol, 64% yield).

Compound 34 and 35 were prepared according to General Method K.

General Method O.

Preparation of (3aR,13R,21aS)-7-fluoro-13-methyl-2,3,3a,11,12,13,14,21a-octahydro-1H,5H,15H-18,20-(metheno)cyclopenta[5,6][1,4]oxazino[4,3-e]pyrazolo[3,4-h]pyrido[2,3-b][1,5,7,11]oxatriazacyclotetradecin-15-one (36) and (3aS,11S,20aR)-2-acetyl-7-fluoro-11-methyl-2,3,3a, 12,13,20a-hexahydro-1H,5H-17,19-(metheno)pyrazolo[4,3-f]pyrido[3,2-l]pyrrolo[3',4':5,6][1,4]oxazino[3,4-i][1,4,8,10]oxatriazacyclotridecin-14(11H)-one (37)

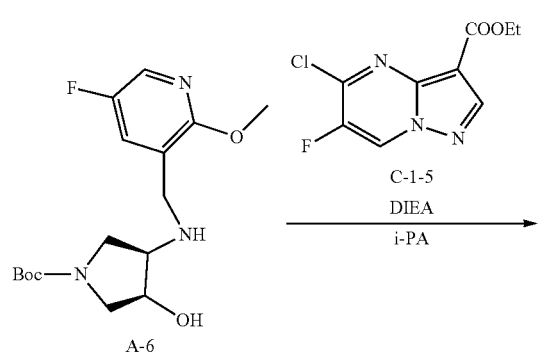

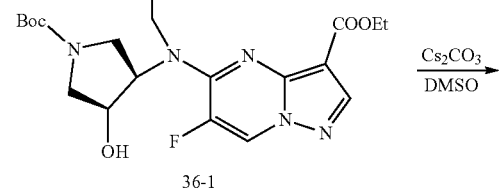

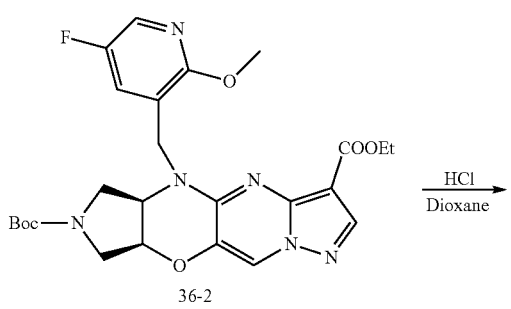

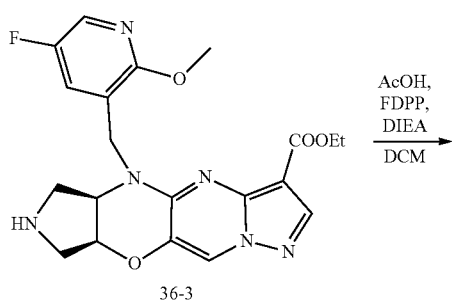

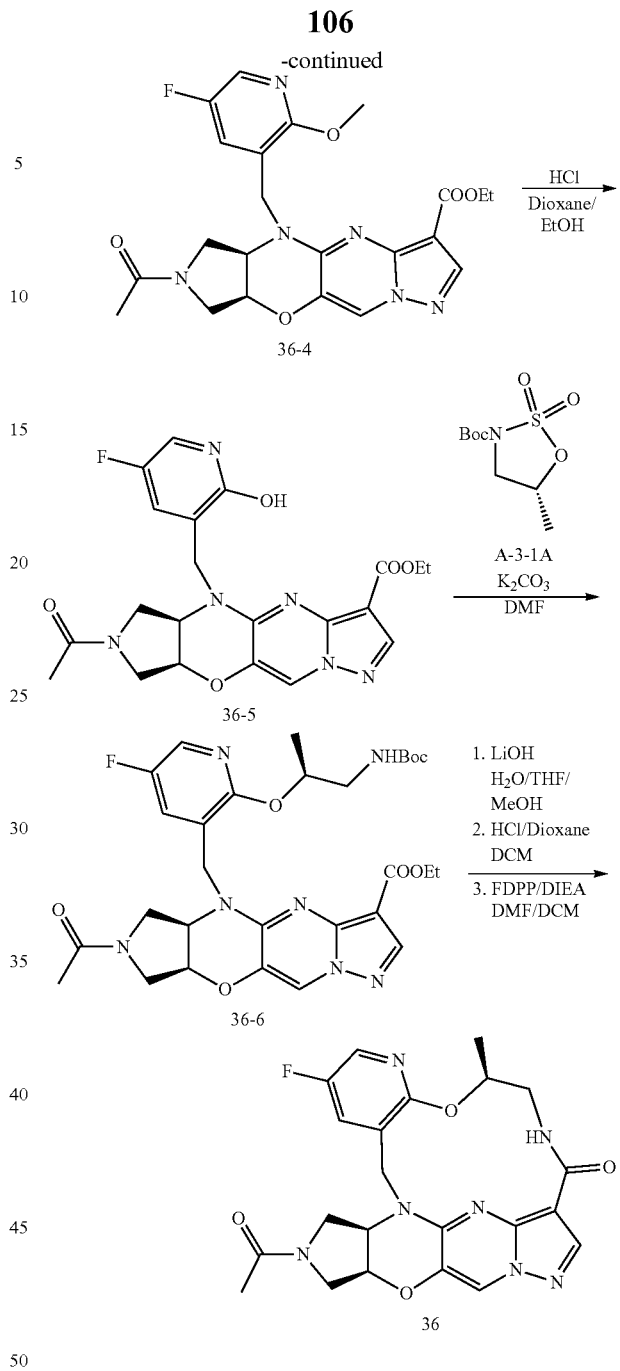

Step 1. To a solution of A-6 (255.4 mg, 748.15 umol, racemic mix) dissolved in anhydrous isopropanol (3.74 mL) at room temperature. DIEA (290.08 mg, 2.24 mmol, 390.94 uL) was added followed by C-1-5 (200.49 mg, 822.96 umol). The mixture stirred at 80° C. for 18 hr and then concentrated under reduced pressure. The crude was purified by flash column chromatography (ISCO, silica, 12 g, ethyl acetate in hexanes) to afford 36-1 (142.1 mg, 259.05 umol, 34.63% yield).

Step 2. To a solution of 36-1 (142.1 mg, 259.05 umol) in DMSO (1.30 mL) at room temperature, $Cs_2CO_3$ (168.81 mg, 518.10 umol) was added and the mixture was stirred at room temperature for 72 hr. Diluted with water (15 mL) and extracted with DCM (5 mL×5). The organic layer was back washed with water (10 mL) and brine (10 mL), then dried over sodium sulfate. The mixture was filtered and the filtrate was concentrated under reduced pressure. The crude was purified by flash column chromatography (ISCO, silica, 12 g, ethyl acetate in hexanes) to afford 36-2 (78.1 mg, 147.77 umol, 57.04% yield).

To a solution of 36-2 (20.5 mg, 38.79 umol) in anhydrous DCM (2 mL) was added HCl in dioxane (4 M, 1 mL). The mixture was stirred at ambient temperature for 1 hr, concentrated under reduced pressure, and dried under high vacuum to afford 36-3. Used directly in subsequent step without further purification.

To crude 36-3 (14.5 mg, 33.85 umol) in DCM (338.46 uL) was added acetic acid (3.05 mg, 50.77 umol, 2.90 uL) and Hunig's base (21.87 mg, 169.23 umol, 29.48 uL) followed by FDPP (16.91 mg, 44.00 umol) in one portion. Let stir for 72 hr then quenched with 2 M Na$_2$CO$_3$ solution (5 mL). Mixture was stirred for 5 min then extracted with DCM (3×10 mL). Combined organic extracts were dried with Na$_2$SO$_4$ and concentrated under reduced pressure. Flash chromatography (ISCO system, silica 12 g, methanol in dichloromethane) provide 36-4 (9.9 mg, 21.04 umol, 62.18% yield)

To a solution of 36-4 (9.9 mg, 21.04 umol) dissolved in anhydrous ethanol (1 mL) was added HCl in dioxane (4 M, 1 mL). The mixture was stirred at 70° C. for 2 hr, then concentrated under reduced pressure and dried under high vacuum to afford 36-5. Used directly in subsequent step without further purification.

36-5 was converted to compounds 36 and 37 as a racemic mixture (cis) following the procedure used in General Method E. The mixture was separated by flash column chromatography (ISCO, silica, 12 g, methanol in DCM) to provide 36 (1.23 mg, 2.63 umol, 26.89% yield) and 37 (1.38 mg, 2.95 umol, 30.17% yield).

Compound 38, 39, 40, and 41 were prepared according to General Method K.

Compound 42 was prepared according to General Method K using rac trans-tert-butyl-3-hydroxycyclopentyl)carbamate and separating from 41 after final step by flash column chromatography (ISCO, silica, 12 g, ethyl acetate in hexanes)

Compound 43 was prepared according to General Method M. Final product was purified by flash column chromatography (ISCO, silica, 12 g, ethyl acetate in hexanes)

General Method P.

Preparation of ethyl (5aS,8aR)-5,5a,6,7,8,8a-hexahydrocyclopenta[b]pyrazolo[1',5':1,2]pyrimido[4,5-e][1,4]oxazine-3-carboxylate (C-5)

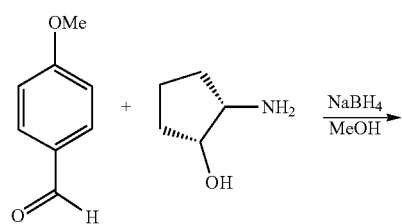

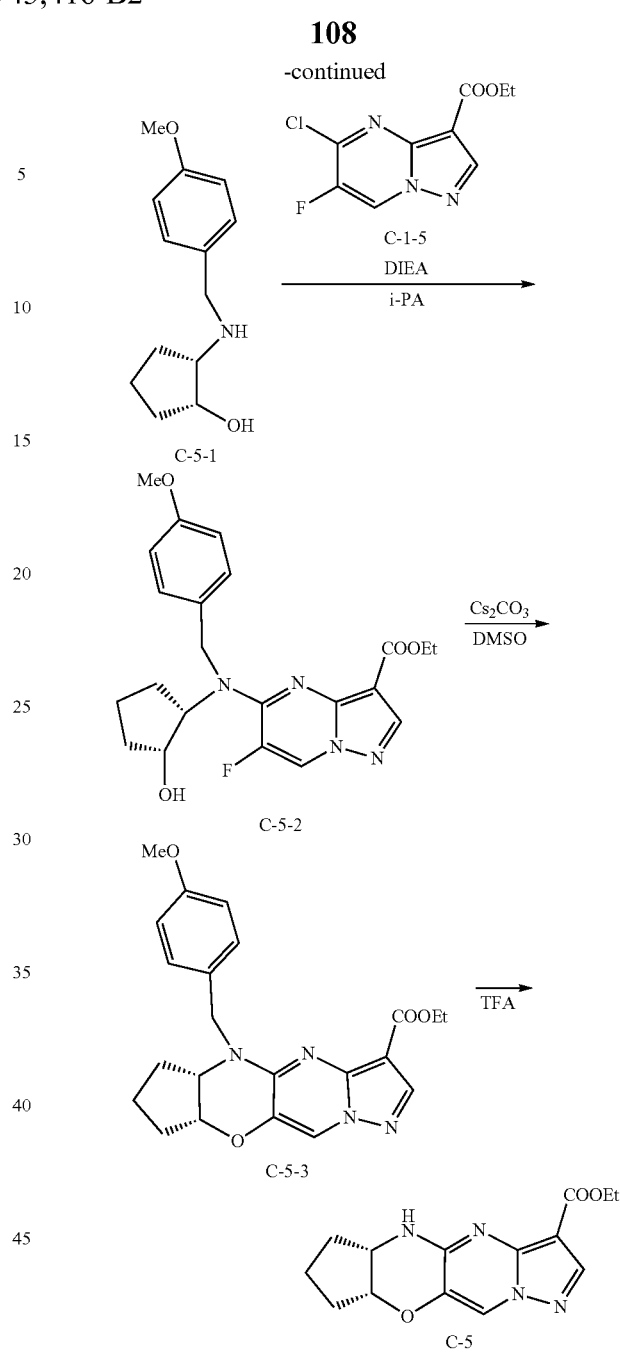

Step 1: (1R,2S)-2-aminocyclopentanol, HCl (3.6 g, 26.16 mmol) was dissolved in anhydrous MeOH (96.89 mL) and treated with strongly basic ion exchange resin (Amberlite IRN-78). 4-methoxybenzaldehyde (3.56 g, 26.16 mmol) was added and the solution was stirred and heated to 65° C. for 3 hr. The mixture was cooled to room temperature and NaBH$_4$ (989.68 mg, 26.16 mmol) was added. The reaction was stirred for 30 minutes, then quenched with water (50 mL) and stirred for another 30 minutes. MeOH was removed under reduced pressure and the aqueous phase was extracted with DCM (3×50 mL). The organic phase was combined and dried over Na$_2$SO$_4$. The crude was purified by flash chromatography (ISCO system, 80 g, 0-10% MeOH/DCM) to give C-5-1 (4.92 g, 22.23 mmol, 84.98% yield)

Step 2: C-5-1 (2.6 g, 11.75 mmol), C-1-5 (2.5 g, 10.26 mmol) and DIEA (4.56 g, 35.25 mmol, 6.14 mL) were dissolved in i-PA (58.75 mL). The mixture was stirred at 80° C. for 16 hr after which volatiles were removed under reduced pressure. The resulting crude was purified by flash column chromatography (ISCO, silica, 80 g, 0-60% EtOAc in hexanes) to afford C-5-2 (2.1 g, 4.90 mmol, 41.72% yield).

Step 3: C-5-2 (2.1 g, 4.90 mmol) and Cs$_2$CO$_3$ (6.39 g, 19.61 mmol) were dissolved in DMSO (49.01 mL) and stirred at room temperature for 3 hr. Diluted with water (500 mL) and extracted with EtOAc (3×100 mL). The combined organic layer was washed with 20% brine solution (3×100 mL) and dried over Na$_2$SO$_4$. The crude was purified by flash chromatography (ISCO, 80, 0-60% EtOAc in hexanes) to afford C-5-3 (1.69 g, 4.14 mmol, 84.42% yield).

C-5-3 (1.69 g, 4.14 mmol) was dissolved in TFA (41.38 mL) and stirred at 75° C. for 16 hr, the reaction was cooled to room temperature and TFA was removed under reduced pressure. The residue was treated with Sat. NaHCO$_3$ and EtOAc (100 mL each) and separated. The aqueous layer was extracted again with EtOAc (2×50 mL) and the combined organic layer was dried over Na$_2$SO$_4$. The crude was purified by flash column chromatography (ISCO, silica, 80 g, 0-80% EtOAc in Hexanes) to afford C-5 (1.12 g, 3.87 mmol, 93.47% yield)

Compounds C-6 and C-7 were prepared according to General Method P using (1R,2R)-2-aminocyclopentanol, HCl and (1S, 2S)-2-aminocyclopentanol, HCl respectively in step 1, and in high dilution (30 mM in DMSO) in step 3.

| Compd# | Structure | MS [M + H] m/z |
|---|---|---|
| C-5 | 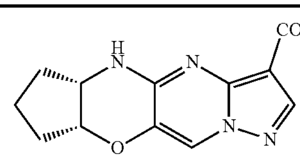 | 289.1 |
| C-6 | 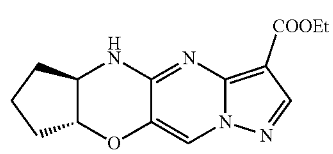 [SMILES: CCOC(=O)c1cnn2cc3c(nc12)N[C@@H]1CCC[C@H]1O3] | 289.1 |
| C-7 | 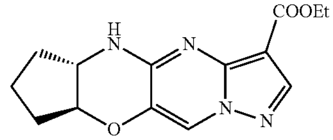 [SMILES: CCOC(=O)c1cnn2cc3c(nc12)N[C@H]1CCC[C@@H]1O3] | 289.1 |

Compound 44 was prepared according to General Method I using starting materials C-5 and D-2.

Compounds 45, 46, 47, and 48 was prepared according to General Method K.

General Method Q

Preparation of (3aR,11S,20aS)-7-fluoro-11-(hydroxymethyl)-2,3,3a,12,13,20a-hexahydro-1H,5H-17,19-(metheno)cyclopenta[5,6][1,4]oxazino[3,4-i]pyrazolo[4,3-f]pyrido[3,2-l][1,4,8,10]oxatriazacyclotridecin-14(11H)-one (49)

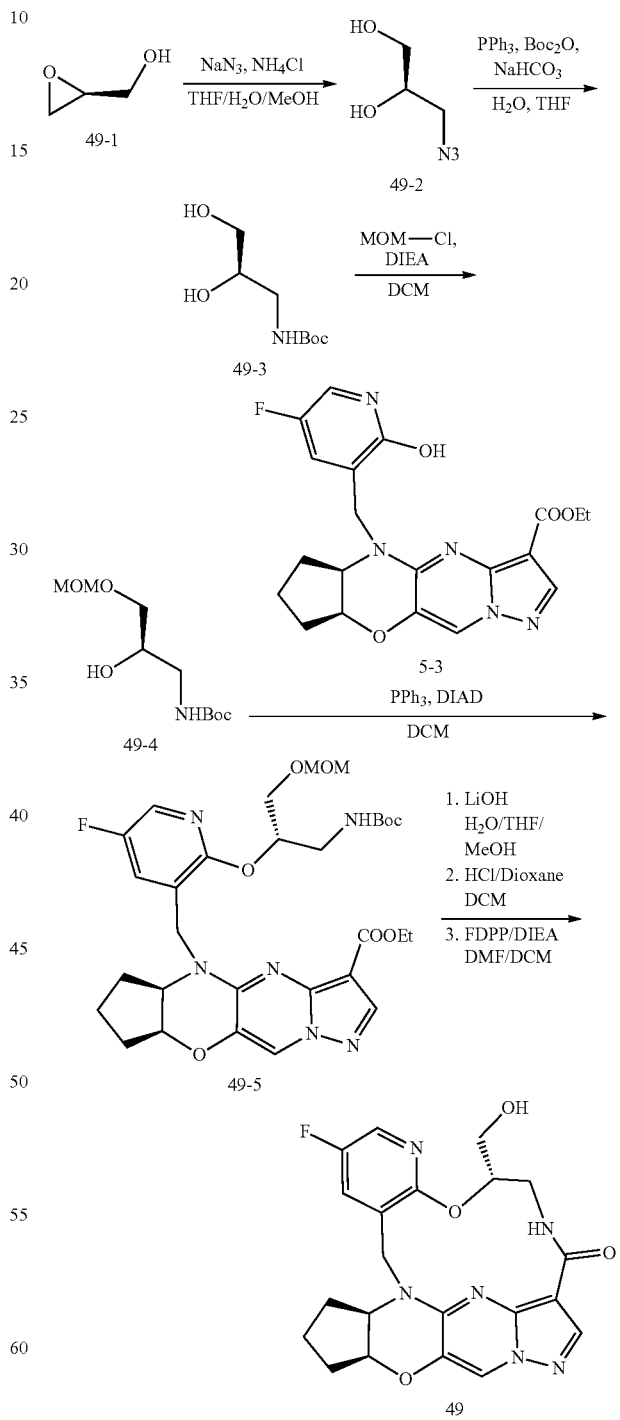

Step 1.49-1 (1.00 g, 13.50 mmol) was dissolved in THF (2.70 mL), water (2.70 mL) and methanol (21.60 mL). Ammonium chloride (1.66 g, 31.05 mmol) was added followed by sodium azide (4.39 g, 67.50 mmol). The mixture was stirred at 75° C. for 3 hr and then cooled to ambient temperature. Volume was carefully reduced under reduced pressure to a third and then diluted with DCM (50 mL) and water (50 mL). The layers were partitioned and the aqueous layer was extracted 2× with DCM (2×20 mL). The combined organic layer was washed with brine and dried over sodium sulfate. Flash column chromatography (ISCO, 24 g, silica, ethyl acetate in hexanes) gave 49-2 (450.00 mg, 3.84 mmol, 28.46% yield)

Step 2.49-2 (450.00 mg, 3.84 mmol) was dissolved in THF (19.20 mL) and PPh$_3$ (2.32 g, 8.83 mmol) was added. Stirred for 4 hr and water (1.59 g, 88.32 mmol, 1.59 mL) was added and continued to stir for 16 hr when boc anhydride (1.09 g, 4.99 mmol) was added followed by sodium bicarbonate (32.26 mg, 384.00 umol). The mixture was stirred at RT for 4 hr and ethyl acetate and water were added (30 mL each). The layers were partitioned and the aqueous layer was extracted 2× with ethyl acetate (2×20 mL). The combined organic layer was washed with brine and then dried over sodium sulfate. Purified by flash column chromatography (ISCO, 24 g, silica, EtOAc in Hexanes) to provide 49-3 (525.30 mg, 2.75 mmol, 71.54% yield).

Step 3.49-3 (525.86 mg, 2.75 mmol) was dissolved in DCM (4.58 mL) and MOM-Cl (332.10 mg, 4.13 mmol, 313.30 uL) was added followed by DIEA (710.82 mg, 5.50 mmol, 960.57 uL) at 0° C. Stirred for 18 hr slowly warming to RT. Water (5 mL) was added and the layers were partitioned. The aqueous layer was extracted 2× with DCM (5 mL). The combined organic layer was washed with brine and dried over sodium sulfate. Salts were filtered and volatiles were carefully removed via rotary evaporation at temperatures <30° C. to afford 49-4 (132.2 mg, 0.561 mmol, 20% yield). Used directly without further purification.

Compound 49 was prepared according to General Method K using 49-4 and 5-3.

| Cpd | Structure | MS [M + H] m/z | $^1$ H NMR(DMSO-d$_6$) δ ppm |
|---|---|---|---|
| 1 | 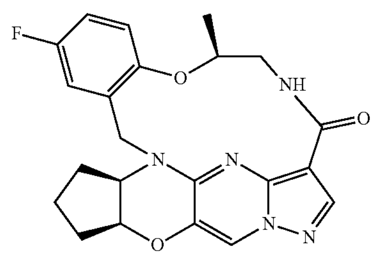 [SMILES: C[C@H]1CNC(=O)c2cnn3cc4c(nc23)N(Cc2cc(F)ccc2O1)[C@@H]1CCC[C@@H]1O4] | 424.2 | (500 MHz) 9.46 (dd, J = 5.73, 4.01 Hz, 1 H) 8.55 (s, 1 H) 7.98 (s, 1 H) 7.36 (dd, J = 9.45, 3.15 Hz, 1 H) 7.07-7.13 (m, 1 H) 6.96-7.07 (m, 1 H) 5.30-5.40 (m, 1 H) 4.63-4.74 (m, 1 H) 4.58 (ddd, J = 10.45, 7.30, 2.86 Hz, 1 H) 4.53 (t, J = 4.01 Hz, 1 H) 4.21 (d, J = 14.89 Hz, 1 H) 3.82 (ddd, J = 13.46, 6.01, 4.58 Hz, 1 H) 3.18-3.24 (m, 1 H) 2.32-2.39 (m, 1 H) 2.10-2.20 (m, 1 H) 1.89-1.97 (m, 2 H) 1.69-1.79 (m, 1 H) 1.50-1.60 (m, 1 H) 1.44 (d, J = 6.30 Hz, 3 H) |
| 2 | 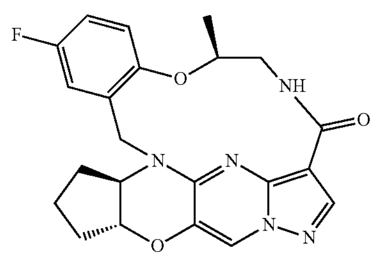 [SMILES: C[C@H]1CNC(=O)c2cnn3cc4c(nc23)N(Cc2cc(F)ccc2O1)[C@@H]1CCC[C@H]1O4] | 424.3 | (300 MHz) 9.52 (br d, J = 5.78 Hz, 1 H) 8.63 (s, 1 H) 8.02 (s, 1 H) 7.21 (dd, J = 8.99, 2.29 Hz, 1 H) 6.97-7.13 (m, 2 H) 5.46 (d, J = 15.04 Hz, 1 H) 4.45-4.59 (m, 1 H) 4.07-4.27 (m, 3 H) 3.86-3.99 (m, 1 H) 3.06-3.19 (m, 1 H) 1.63-2.22 (m, 5 H) 1.44 (d, J = 6.05 Hz, 3 H) |
| 3 | 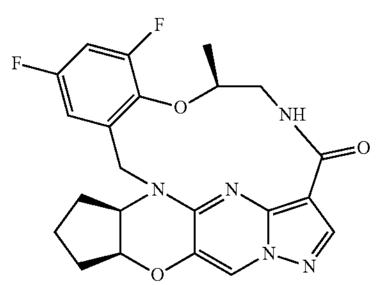 [SMILES: C[C@H]1CNC(=O)c2cnn3cc4c(nc23)N(Cc2cc(F)cc(F)c2O1)[C@@H]1CCC[C@@H]1O4] | 442.2 | (500 MHz) 9.43 (t, J = 5.2 Hz, 1 H), 8.58 (s, 1H), 7.99 (s, 1H), 7.25-7.11 (m, 2H), 5.30 (d, J = 14.8 Hz, 1H), 5.04-5.00 (m, 1H), 4.64 (t, J = 3.8 Hz, 1H), 4.48 (ddd, J = 2.9, 7.3, 10.6 Hz, 1H), 4.26 (d, J = 15.1 Hz, 1H), 3.53-3.47 (m, 2H), 2.34-2.29 (m, 1H), 2.18-2.10 (m, 1H), 1.98-1.91 (m, 2H), 1.73 (br dd, J = 8.8, 17.8 Hz, 1H), 1.60-1.54 (m, 1H), 1.46 (d, J = 6.0 Hz, 3H) |
| 4 | 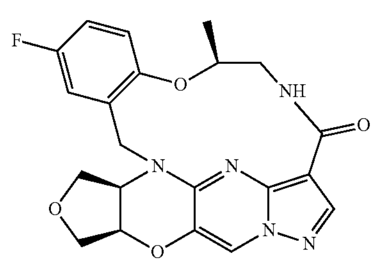 [SMILES: C[C@H]1CNC(=O)c2cnn3cc4c(nc23)N(Cc2cc(F)ccc2O1)[C@@H]1COC[C@@H]1O4] | 426.2 | (500 MHz) 9.40 (br t, J = 4.58 Hz, 1 H) 8.66 (s, 1 H) 8.02 (s, 1 H) 7.43 (dd, J = 9.45, 2.58 Hz, 1 H) 7.06-7.15 (m, 1 H) 6.98-7.06 (m, 1 H) 5.36 (d, J = 14.89 Hz, 1 H) 4.96-5.07 (m, 1 H) 4.85 (br s, 1 H) 4.62-4.75 (m, 1 H) 4.33 (t, J = 7.45 Hz, 1 H) 4.16-4.29 (m, 2 H) 4.03 (d, J = 10.88 Hz, 1 H) 3.77-3.86 (m, 1 H) 3.57 (t, J = 8.88 Hz, 1 H) 3.19-3.24 (m, 1 H) 1.44 (d, J = 5.73 Hz, 3 H) |

| Cpd | Structure | MS [M + H] m/z | ¹H NMR(DMSO-d₆) δ ppm |
|---|---|---|---|
| 5 | 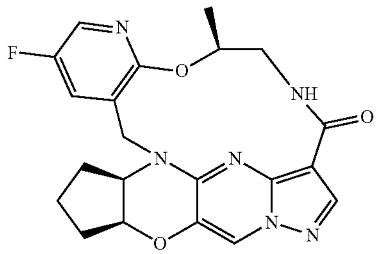 [SMILES: C[C@H]1CNC(=O)c2cnn3cc4c(nc23)N(Cc2cc(F)cnc2O1)[C@@H]1CCC[C@@H]1O4] | 425.3 | (300 MHz) 9.36-9.45 (m, 1 H) 8.55 (s, 1 H) 8.07 (d, J = 2.93 Hz, 1 H) 7.93-8.02 (m, 2 H) 5.10-5.27 (m, 2 H) 4.60 (ddd, J = 10.45, 7.34, 3.30 Hz, 1 H) 4.48-4.54 (m, 1 H) 4.33 (d, J = 14.95 Hz, 1 H) 3.93 (ddd, J = 12.95, 8.05, 4.49 Hz, 1 H) 3.09-3.21 (m, 1 H) 2.29-2.40 (m, 1 H) 2.06-2.17 (m, 1 H) 1.86-2.00 (m, 2 H) 1.66-1.80 (m, 1 H) 1.49-1.63 (m, 1 H) 1.45 (d, J = 6.14 Hz, 3 H) |
| 6 | 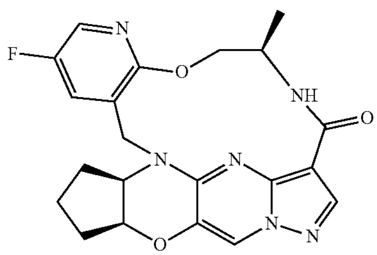 [SMILES: C[C@@H]1COc2ncc(F)cc2CN2c3nc4c(cnn4cc3O[C@H]3CCC[C@H]32)C(=O)N1] | 425.1 | (500 MHz) 9.53 (d, J = 8.02 Hz, 1 H) 8.55 (s, 1 H) 8.09 (d, J = 2.86 Hz, 1 H) 8.03 (dd, J = 8.59, 2.86 Hz, 1 H) 7.99 (s, 1 H) 5.32 (d, J = 14.89 Hz, 1 H) 4.70 (dd, J = 10.88, 4.01 Hz, 1 H) 4.61 (ddd, J = 10.45, 7.30, 3.44 Hz, 1 H) 4.48 (t, J = 4.01 Hz, 1 H) 4.35 (d, J = 14.89 Hz, 1H) 4.26 (br dd, J = 11.17, 6.59 Hz, 1 H) 4.14 (d, J = 10.60, 1.43 Hz, 1 H) 2.33-2.43 (m, 1 H) 2.07-2.19 (m, 1 H) 1.88-1.98 (m, 2 H) 1.69-1.82 (m, 1 H) 1.50-1.62 (m, 1 H) 1.36 (d, J = 6.87 Hz, 3 H) |
| 7 | 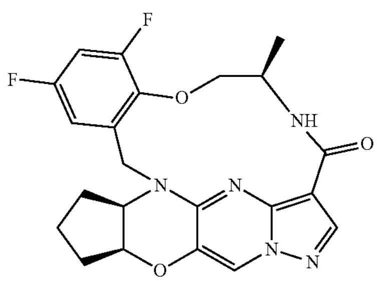 [SMILES: C[C@@H]1COc2c(F)cc(F)cc2CN2c3nc4c(cnn4cc3O[C@H]3CCC[C@H]32)C(=O)N1] | 442.1 | (500 MHz) 9.89 (br d, J = 8.59 Hz, 1 H) 8.58 (s, 1 H) 8.01 (s, 1 H) 7.19-7.30 (m, 2 H) 5.46 (br d, J = 14.89 Hz, 1 H) 4.74 (br dd, J =.45, 6.01 Hz, 1 H) 4.53-4.64 (m, 2 H) 4.25 (br d, J = 15.47 Hz, 1 H) 4.20 (br t, J = 7.16 Hz, 1 H) 3.93-4.05 (m, 1 H) 2.31-2.40 (m, 1 H) 2.09-2.20 (m, 1 H) 1.87-1.97 (m, 2 H) 1.68-1.79 (m, 1 H) 1.48-1.59 (m, 1 H) 1.33 (d, J = 6.87 Hz, 3 H) |
| 8 | 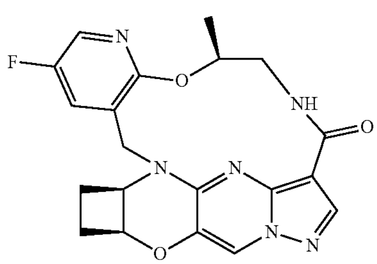 [SMILES: C[C@H]1CNC(=O)c2cnn3cc4c(nc23)N(Cc2cc(F)cnc2O1)[C@@H]1CC[C@@H]1O4] | 411.1 | 9.37 (br d, J = 6.30 Hz, 1 H) 8.62 (s, 1 H) 8.06 (d, J = 2.86 Hz, 1 H) 8.01 (s, 1 H) 7.90 (dd, J = 8.88, 2.58 Hz, 1H) 5.26 (d, J = 15.47 Hz, 1 H) 5.11-5.20 (m, 1 H) 5.05 (q, J = 6.87 Hz, 1 H) 4.91 (br d, J = 2.86 Hz, 1 H) 4.14 (d, J = 14.89 Hz, 1 H) 3.93-4.02 (m, 1 H) 3.07-3.19 (m, 1 H) 2.28-2.35 (m, 1 H) 2.11-2.22 (m, 1 H) 2.02-2.09 (m, 1 H) 1.94-2.02 (m, 1 H) 1.46 (d, J = 6.30 Hz, 3 H) |
| 9 | 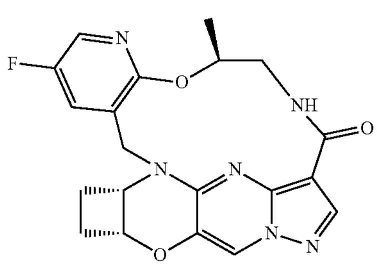 [SMILES: C[C@H]1CNC(=O)c2cnn3cc4c(nc23)N(Cc2cc(F)cnc2O1)[C@H]1CC[C@H]1O4] | 411.0 | 9.38 (br d, J = 5.73 Hz, 1 H) 8.68 (s, 1 H) 8.08 (d, J = 2.86 Hz, 1 H) 8.03 (s, 1 H) 7.42 (dd, J = 8.59, 2.86 Hz, 1 H) 5.34 (br d, J = 14.89 Hz, 1 H) 5.10-5.21 (m, 1 H) 4.74 (br d, J = 2.29 Hz, 1 H) 4.37-4.48 (m, 1 H) 4.24 (d, J = 14.89 Hz, 1 H) 3.96 (ddd, J = 13.03, 8.16, 4.58 Hz, 1 H) 3.11-3.20 (m, 1 H) 2.60-2.72 (m, 1 H) 2.41-2.48 (m, 1 H) 2.19-2.31 (m, 1 H) 2.00-2.08 (m, 1 H) 1.46 (d, J = 6.30 Hz, 3 H) |

-continued

| Cpd | Structure | MS [M + H] m/z | $^1$H NMR(DMSO-$d_6$) δ ppm |
|---|---|---|---|
| 10 | 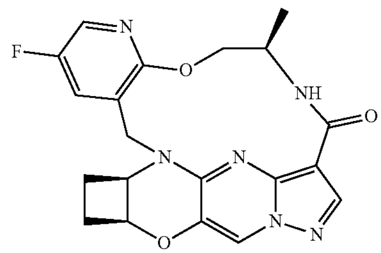 [SMILES: C[C@@H]1COc2ncc(F)cc2CN2c3nc4c(cnn4cc3O[C@H]3CC[C@H]32)C(=O)N1] | 411.0 | (500 MHz) 9.43 (d, J = 8.02 Hz, 1 H) 8.62 (s, 1 H) 8.07 (d, J = 2.86 Hz, 1 H) 8.01 (s, 1 H) 7.93 (dd, J = 8.59, 2.86 Hz, 1 H) 5.34 (dd, J = 14.89, 1.15 Hz, 1 H) 5.03 (q, J = 6.68 Hz, 1 H) 4.90 (dt, J = 5.73, 2.86 Hz, 1 H) 4.75 (dd, J = 10.60, 4.30 Hz, 1 H) 4.25-4.34 (m, 1 H) 4.16 (d, J = 10.88 Hz, 1 H) 4.13 (dd, J = 9.17, 1.72 Hz, 1 H) 2.27-2.35 (m, 1 H) 2.13-2.22 (m, 1 H) 2.05-2.13 (m, 1 H) 1.98-2.05 (m, 1 H) 1.38 (d, J = 6.87 Hz, 3 H) |
| 11 | 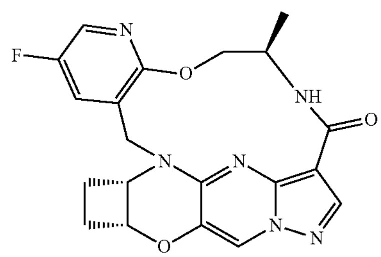 [SMILES: C[C@@H]1COc2ncc(F)cc2CN2c3nc4c(cnn4cc3O[C@@H]3CC[C@@H]32)C(=O)N1] | 411.0 | (500 MHz) 9.47 (d, J = 8.02 Hz, 1 H) 8.68 (s, 1 H) 8.10 (d, J = 3.44 Hz, 1 H) 8.03 (s, 1 H) 7.49 (dd, J = 8.59, 2.86 Hz, 1 H) 5.45 (d, J = 16.04 Hz, 1 H) 4.73 (br d, J = 4.01 Hz, 1 H) 4.70 (dd, J = 10.88, 4.01 Hz, 1 H) 4.42-4.48 (m, 1 H) 4.24-4.31 (m, 2 H) 4.15 (dd, J = 10.60, 2.00 Hz, 1 H) 2.65-2.73 (m, 1 H) 2.42 (dt, J = 18.62, 9.59 Hz, 1 H) 2.19-2.28 (m, 1 H) 1.98-2.04 (m, 1 H) 1.37 (d, J = 6.30 Hz, 3 H) |
| 12 | 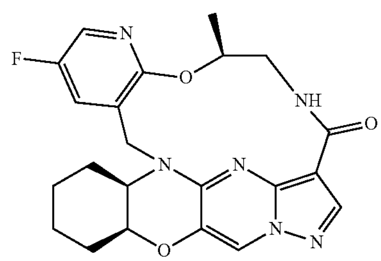 [SMILES: C[C@H]1CNC(=O)c2cnn3cc4c(nc23)N(Cc2cc(F)cnc2O1)[C@@H]1CCCC[C@@H]1O4] | 439.1 | (500 MHz) 9.41 (br d, J=7.45 Hz, 1 H) 8.55 (s, 1 H) 8.06 (br s, 1 H) 7.97 (d, J = 1.72 Hz, 1 H) 7.95 (br d, J = 9.17 Hz, 1 H) 5.07-5.20 (m, 2 H) 4.50 (br s, 1 H) 4.33 (br d, J = 14.89 Hz, 1 H) 4.26 (br s, 1 H) 3.87-3.99 (m, 1 H) 3.09-3.19 (m, 1 H) 2.06-2.17 (m, 2 H) 1.87 (br t, J = 12.32 Hz, 1 H) 1.78 (br d, J = 1.15 Hz, 1 H) 1.47-1.60 (m, 2 H) 1.45 (br d, J = 5.73 Hz, 3 H) 1.41 (br d, J = 8.59 Hz, 2 H) |
| 13 | 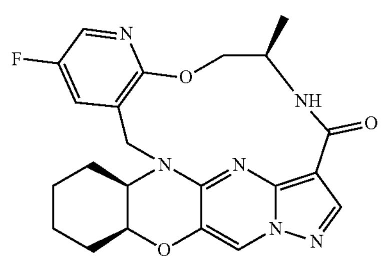 [SMILES: C[C@@H]1COc2ncc(F)cc2CN2c3nc4c(cnn4cc3O[C@H]3CCCC[C@H]32)C(=O)N1] | 439.1 | (500 MHz) 9.51 (d, J = 8.59 Hz, 1 H) 8.54 (s, 1 H) 8.08 (d, J = 3.44 Hz, 1 H) 8.00 (dd, J = 9.16, 2.86 Hz, 1 H) 7.97 (s, 1 H) 5.21 (dd, J = 14.89, 1.15 Hz, 1 H) 4.70 (dd, J = 10.60, 4.30 Hz, 1 H) 4.47 (br s, 1 H) 4.35 (d, J = 14.89 Hz, 1 H) 4.21-4.31 (m, 2 H) 4.14 (dd, J = 10.31, 1.72 Hz, 1 H) 2.07-2.19 (m, 2 H) 1.83-1.92 (m, 1 H) 1.78 (brs, 1 H) 1.38-1.59 (m, 4 H) 1.36 (d, J = 6.30 Hz, 3 H) |
| 14 | 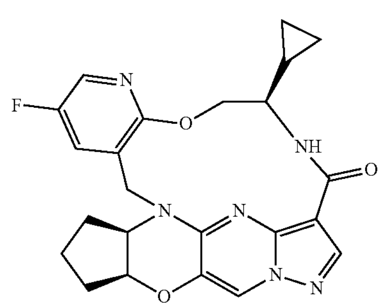 [SMILES: O=C1N[C@H](C2CC2)COc2ncc(F)cc2CN2c3nc4c1cnn4cc3O[C@H]1CCC[C@H]12] | 451.1 | (500 MHz) 9.73 (d, J = 9.16 Hz, 1 H) 8.55 (s, 1 H) 8.10 (d, J = 2.86 Hz, 1 H) 8.05 (dd, J = 8.59, 2.86 Hz, 1 H) 7.99 (s, 1 H) 5.30-5.38 (m, 1 H) 4.64-4.69 (m, 1 H) 4.58-4.64 (m, 1 H) 4.47 (t, J = 3.72 Hz, 1 H) 4.37 (d, J = 8.02 Hz, 1 H) 4.34 (d, J = 4.01 Hz, 1 H) 3.75 (td, J = 8.59, 4.01 Hz, 1 H) 2.33-2.44 (m, 1 H) 2.07-2.19 (m, 1 H) 1.86-1.99 (m, 2 H) 1.67-1.81 (m, 1 H) 1.51-1.63 (m, 1 H) 1.20-1.33 (m, 1 H) 0.42-0.55 (m, 3 H) 0.27-0.37 (m, 1 H) |

| Cpd | Structure | MS [M + H] m/z | ¹H NMR(DMSO-$d_6$) δ ppm |
|---|---|---|---|
| 15 | 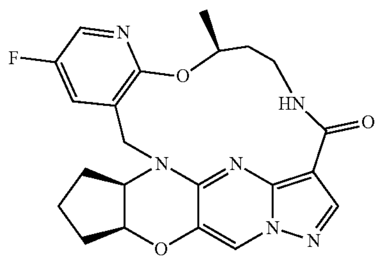 [SMILES: C[C@H]1CCNC(=O)c2cnn3cc4c(nc23)N(Cc2cc(F)cnc2O1)[C@@H]1CCC[C@@H]1O4] | 439.1 | (500 MHz) 8.52 (s, 1 H) 8.11 (t, J = 4.30 Hz, 1 H) 8.04 (d, J = 2.86 Hz, 1 H) 7.99 (s, 1 H) 7.86 (dd, J = 8.59, 2.86 Hz, 1 H) 5.55 (br t, J = 6.59 Hz, 1 H) 5.28 (dd, J = 14.89, 1.15 Hz, 1 H) 4.54-4.58 (m, 1 H) 4.50-4.54 (m, 1 H) 4.29 (d, J = 14.89 Hz, 1 H) 3.61-3.68 (m, 1 H) 3.34-3.37 (m, 1 H) 2.32-2.38 (m, 1 H) 2.09-2.16 (m, 2 H) 1.88-1.97 (m, 3 H) 1.69-1.76 (m, 1 H) 1.51-1.59 (m, 1 H) 1.30 (d, J = 6.30 Hz, 3 H) |
| 16 | 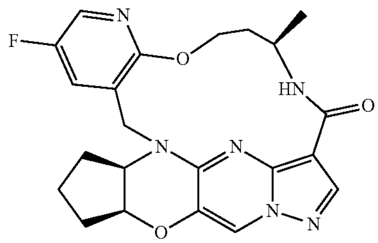 [SMILES: C[C@@H]1CCOc2ncc(F)cc2CN2c3nc4c(cnn4cc3O[C@H]3CCC[C@H]32)C(=O)N1] | 439.1 | (500 MHz) 8.55 (s, 1 H) 8.48 (s, 1 H) 8.14 (d, J = 6.87 Hz, 1 H) 8.05-8.09 (m, 2 H) 7.92 (dd, J = 8.59, 2.86 Hz, 1 H) 7.44 (dd, J = 8.59, 2.86 Hz, 1 H) 5.54 (t, J = 12.03 Hz, 1 H) 5.30-5.42 (m, 2 H) 4.76-4.83 (m, 1 H) 4.47-4.56 (m, 2 H) 4.17-4.38 (m, 5 H) 4.05 (ddd, J = 10.60, 6.87, 3.72 Hz, 1 H) 3.91-3.97 (m, 1 H) 2.50-2.56 (m, 1 H) 2.06-2.38 (m, 5 H) 1.82-2.00 (m, 6H) 1.62-1.75 (m, 2 H) 1.18 (d, J = 6.30 Hz, 3 H) |
| 17 | 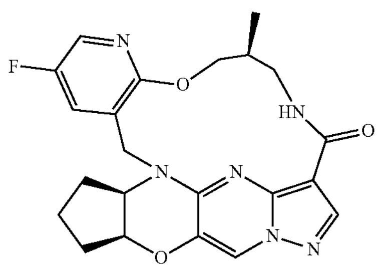 [SMILES: C[C@H]1CNC(=O)c2cnn3cc4c(nc23)N(Cc2cc(F)cnc2OC1)[C@@H]1CCC[C@@H]1O4] | 439.1 | (500 MHz) 8.60 (s, 1 H) 8.53 (s, 1 H) 8.17-8.22 (m, 1 H) 8.06 (d, J = 2.86 Hz, 1 H) 8.02 (s, 1 H) 7.99 (s, 1 H) 7.87 (dd, J = 8.88, 2.58 Hz, 1 H) 7.56 (dd, J = 8.59, 3.44 Hz, 1 H) 5.27 (dd, J = 14.89, 1.15 Hz, 1 H) 4.92-4.96 (m, 1 H) 4.51-4.57 (m, 2 H) 4.31 (d, J = 15.47 Hz, 1 H) 3.95 (dd, J =11.17, 8.88 Hz, 1 H) 3.88 (br dd, J = 13.17, 8.02 Hz, 1 H) 3.06 (ddd, J = 13.75, 8.59, 2.86 Hz, 1 H) 2.30-2.38 (m, 2 H) 2.09-2.16 (m, 1 H) 1.90-1.98 (m, 2 H) 1.69-1.77 (m, 1 H) 1.52-1.60 (m, 1 H) 1.03 (d, J = 6.87 Hz, 3 H) |
| 18 | 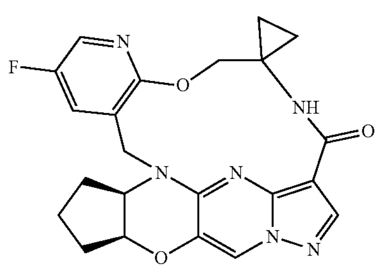 [SMILES: O=C1NC2(CC2)COc2ncc(F)cc2CN2c3nc4c1cnn4cc3O[C@H]1CCC[C@H]12] | 437.1 | (500 MHz) 9.02-9.15 (m, 1 H) 8.47-8.63 (m, 1 H) 8.07 (d, J = 2.86 Hz, 1 H) 8.02 (dd, J = 8.88, 2.58 Hz, 1 H) 7.90-7.96 (m, 1 H) 5.34-5.56 (m, 1 H) 4.79-4.91 (m, 1 H) 4.60 (ddd, J = 10.74, 7.30, 3.15 Hz, 1 H) 4.46 (t, J = 3.72 Hz, 1 H) 4.26-4.36 (m, 1 H) 3.71-3.85 (m, 1 H) 2.32-2.41 (m, 1 H) 2.06-2.20 (m, 1 H) 1.87-2.03 (m, 3 H) 1.67-1.82 (m, 1 H) 1.51-1.63 (m, 1 H) 0.99-1.11 (m, 1 H) 0.90-0.98 (m, 1 H) 0.73-0.87 (m, 1 H) |
| 19 | 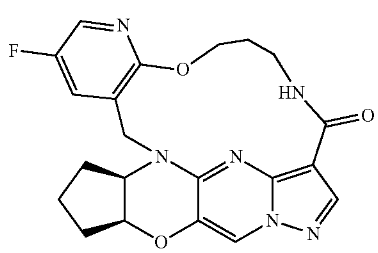 [SMILES: O=C1NCCCOc2ncc(F)cc2CN2c3nc4c1cnn4cc3O[C@H]1CCC[C@H]12] | 425.1 | (500 MHz) 8.60 (s, 1 H) 8.53 (s, 1 H) 8.09-8.14 (m, 1 H) 8.06 (d, J = 2.86 Hz, 1 H) 8.00 (s, 1 H) 7.89 (dd, J = 9.17, 2.86 Hz, 1 H) 7.50 (dd, J = 8.59, 2.29 Hz, 1 H) 5.32 (dd, J = 14.89, 1.15 Hz, 1 H) 4.95-5.05 (m, 1 H) 4.51-4.59 (m, 2 H) 4.27-4.33 (m, 1 H) 4.17-4.24 (m, 1 H) 3.67-3.74 (m, 1 H) 3.35-3.41 (m, 1 H) 2.30-2.40 (m, 1 H) 2.10-2.18 (m, 2 H) 1.86-2.04 (m, 5 H) 1.65-1.79 (m, 1 H) 1.48-1.61 (m, 1 H) |

-continued

| Cpd | Structure | MS [M + H] m/z | $^1$H NMR(DMSO-$d_6$) δ ppm |
|---|---|---|---|
| 20 | 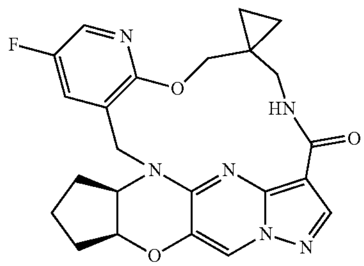 [SMILES: O=C1NCC2(CC2)COc2ncc(F)cc2CN2c3nc4c1cnn4cc3O[C@H]1CCC[C@H]12] | 451.1 | (500 MHz) 8.87 (t, J = 5.16 Hz, 1 H) 8.63 (s, 1 H) 8.05 (d, J = 2.86 Hz, 1 H) 8.01 (s, 1 H) 7.61 (dd, J = 8.88, 2.58 Hz, 1 H) 5.30-5.38 (m, 1 H) 4.93 (dd, J = 15.18, 1.43 Hz, 1 H) 4.53 (d, J = 15.47 Hz, 1 H) 4.20-4.33 (m, 2 H) 3.81 (dt, J = 13.17, 4.87 Hz, 1 H) 3.22-3.31 (m, 1 H) 1.61 (s, 3 H) 1.45 (d, J = 6.30 Hz, 3 H) 1.36 (s, 3 H) |
| 21 | 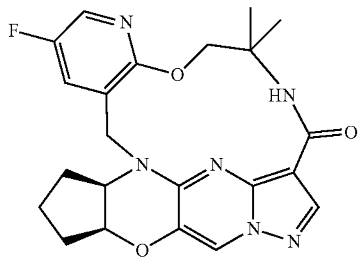 [SMILES: CC1(C)COc2ncc(F)cc2CN2c3nc4c(cnn4cc3O[C@H]3CCC[C@H]32)C(=O)N1] | 439.1 | (500 MHz) 9.09 (s, 1 H) 8.51-8.63 (m, 1 H) 8.06-8.14 (m, 2 H) 7.94-7.99 (m, 1 H) 5.31-5.59 (m, 1 H) 4.56-4.71 (m, 2 H) 4.47 (t, J = 3.81 Hz, 1 H) 4.32 (br d, J = 14.67 Hz, 1 H) 3.90-3.98 (m, 1 H) 2.36-2.44 (m, 1 H) 2.08-2.18 (m, 1 H) 1.89-1.98 (m, 2 H) 1.70-1.82 (m, 1 H) 1.62 (s, 3 H) 1.53-1.59 (m, 1 H) 1.49 (s, 3 H) |
| 22 | 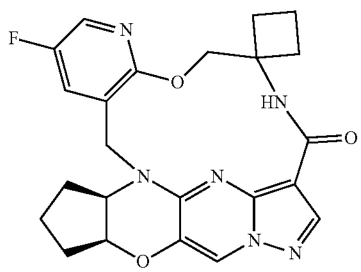 [SMILES: O=C1NC2(CCC2)COc2ncc(F)cc2CN2c3nc4c1cnn4cc3O[C@H]1CCC[C@H]12] | 451.2 | (500 MHz) 8.94-9.12 (m, 1 H) 8.49-8.65 (m, 1 H) 8.11 (d, J = 2.86 Hz, 1 H) 8.06 (dd, J = 8.59, 2.29 Hz, 1 H) 7.94-8.02 (m, 1 H) 5.21-5.48 (m, 1 H) 4.74-4.95 (m, 1 H) 4.54-4.64 (m, 1 H) 4.46 (t, J = 3.44 Hz, 1 H) 4.32-4.40 (m, 1 H) 4.23-4.32 (m, 1 H) 3.38-3.60 (m, 1 H) 2.65-2.84 (m, 1 H) 2.34-2.44 (m, 1 H) 2.16-2.26 (m, 1 H) 2.02-2.16 (m, 2 H) 1.77-1.99 (m, 4 H) 1.66-1.77 (m, 1 H) 1.48-1.62 (m, 1 H) |
| 23 | 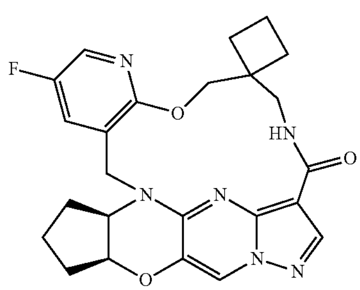 [SMILES: O=C1NCC2(CCC2)COc2ncc(F)cc2CN2c3nc4c1cnn4cc3O[C@H]1CCC[C@H]12] | 465.2 | (500 MHz) 8.47-8.64 (m, 1 H) 8.04-8.13 (m, 2 H) 7.99-8.04 (m, 1 H) 7.51-7.97 (m, 1 H) 5.26-5.46 (m, 1 H) 5.06-5.25 (m, 1 H) 4.53-4.60 (m, 1 H) 4.51 (t, J = 3.72 Hz, 1 H) 4.23-4.34 (m, 1 H) 4.04-4.14 (m, 1 H) 3.68-3.79 (m, 1 H) 2.31-2.41 (m, 1 H) 2.10-2.22 (m, 2 H) 1.87-2.04 (m, 7 H) 1.77-1.85 (m, 1 H) 1.66-1.75 (m, 1 H) 1.49-1.61 (m, 1 H) |
| 24 | 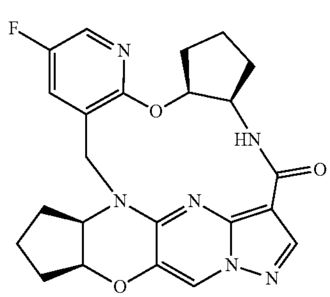 [SMILES: O=C1N[C@@H]2CCC[C@@H]2Oc2ncc(F)cc2CN2c3nc4c1cnn4cc3O[C@H]1CCC[C@H]12] | 451.2 | (500 MHz) 9.31 (d, J = 6.87 Hz, 1 H) 8.54 (s, 1 H) 8.04 (d, J = 2.86 Hz, 1 H) 7.97 (s, 1 H) 7.95 (dd, J = 8.88, 2.58 Hz, 1 H) 5.73 (td, J = 6.30, 3.44 Hz, 1 H) 5.22 (d, J = 14.89 Hz, 1 H) 4.57 (ddd, J = 10.45, 7.30, 3.44 Hz, 1 H) 4.51 (t, J = 4.01 Hz, 1 H) 4.34 (d, J = 14.89 Hz, 1 H) 4.25 (quin, J = 7.02 Hz, 1 H) 2.31-2.40 (m, 1 H) 2.03-2.21 (m, 3 H) 1.89-1.98 (m, 2 H) 1.78-1.89 (m, 2 H) 1.67-1.78 (m, 2 H) 1.51-1.65 (m, 2H) |

-continued

| Cpd | Structure | MS [M + H] m/z | 1 H NMR(DMSO-d6) δ ppm |
|---|---|---|---|
| 25 | 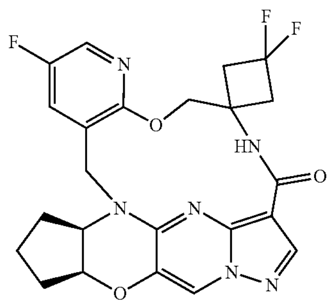 [SMILES: O=C1NC2(COc3ncc(F)cc3CN3c4nc5c1cnn5cc4O[C@H]1CCC[C@H]13)CC(F)(F)C2] | 487.1 | (500 MHz) 8.94-9.15 (m, 1 H) 8.52-8.67 (m, 1 H) 8.12 (d, J = 2.29 Hz, 1 H) 8.02-8.09 (m, 1 H) 7.93-8.02 (m, 1 H) 5.20-5.43 (m, 1 H) 4.99-5.12 (m, 1 H) 4.59 (ddd, J = 10.45, 7.59, 3.15 Hz, 1 H) 4.47 (t, J = 3.72 Hz, 1 H) 4.25-4.36 (m, 2 H) 3.89-4.19 (m, 1 H) 3.57-3.85 (m, 1 H) 2.99-3.21 (m, 1 H) 2.74-2.87 (m, 1 H) 2.34-2.44 (m, 1 H) 2.06-2.21 (m, 1 H) 1.88-1.99 (m, 2 H) 1.69-1.82 (m, 1 H) 1.48-1.61 (m, 1 H) |
| 26 | 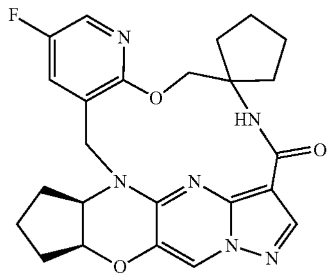 [SMILES: O=C1NC2(CCCC2)COc2ncc(F)cc2CN2c3nc4c1cnn4cc3O[C@H]1CCC[C@H]12] | 465.2 | (500 MHz) 9.19 (s, 1 H) 8.47-8.64 (m, 1 H) 8.04-8.18 (m, 2 H) 7.92 - 8.01 (m, 1 H) 5.26-5.59 (m, 1 H) 4.52-4.71 (m, 2 H) 4.46 (t, J = 4.01 Hz, 1 H) 4.23-4.36 (m, 1 H) 3.95-4.07 (m, 1 H) 2.87 (ddd, J = 13.32, 9.02, 4.01 Hz, 1 H) 2.31-2.45 (m, 1 H) 2.06-2.17 (m, 1 H) 1.85-2.06 (m, 5 H) 1.63-1.85 (m, 3 H) 1.50-1.63 (m, 2 H) 1.39-1.50 (m, 1 H) |
| 27 | 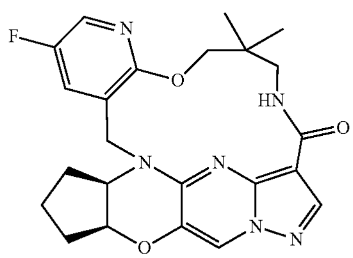 [SMILES: CC1(C)CNC(=O)c2cnn3cc4c(nc23)N(Cc2cc(F)cnc2OC1)[C@@H]1CCC[C@@H]1O4] | 419.2 | (500 MHz) 8.49-8.62 (m, 1 H) 8.12-8.26 (m, 1 H) 7.92-8.09 (m, 3 H) 5.31-5.51 (m, 1 H) 5.00-5.18 (m, 1 H) 4.57 (ddd, J = 10.60, 7.45, 3.15 Hz, 1 H) 4.50-4.53 (m, 1 H) 4.29-4.34 (m, 1 H) 3.65-3.72 (m, 1 H) 3.42-3.49 (m, 1 H) 3.13 (dd, J = 13.75, 2.29 Hz, 1H) 2.32-2.40 (m, 1 H) 2.08-2.19 (m, 1 H) 1.88-1.99 (m, 2 H) 1.68-1.78 (m, 1 H) 1.51-1.63 (m, 1 H) 1.21 (s, 3 H) 1.02 (s, 3 H) |
| 28 | 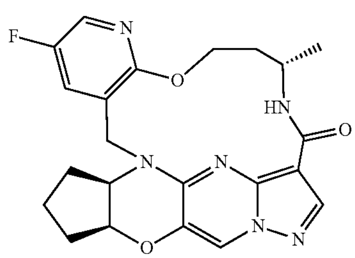 [SMILES: C[C@H]1CCOc2ncc(F)cc2CN2c3nc4c(cnn4cc3O[C@H]3CCC[C@H]32)C(=O)N1] | 439.1 | (500 MHz) 8.49-8.61 (m, 1 H) 7.98-8.19 (m, 3 H) 7.45-7.97 (m, 1 H) 4.75-5.66 (m, 2 H) 4.49-4.61 (m, 1 H) 4.18-4.43 (m, 3 H) 3.92-4.14 (m, 1 H) 2.53-2.66 (m, 1 H) 2.09-2.40 (m, 2 H) 1.46-2.01 (m, 5 H) 1.23 (dd, J = 18.33, 6.87 Hz, 3 H) |
| 29 | 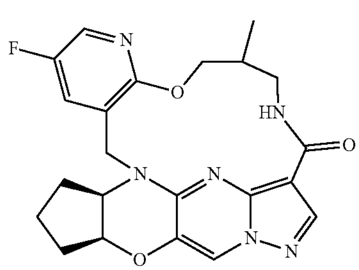 [SMILES: CC1CNC(=O)c2cnn3cc4c(nc23)N(Cc2cc(F)cnc2OC1)[C@@H]1CCC[C@@H]1O4] | 414.3 | (500 MHz) 8.50-8.64 (m, 1 H) 8.18-8.28 (m, 1 H) 7.99-8.09 (m, 2 H) 7.83-7.98 (m, 1 H) 5.23-5.42 (m, 1 H) 4.78-4.99 (m, 1 H) 4.49-4.61 (m, 2 H) 4.26-4.34 (m, 1 H) 3.92-4.00 (m, 1 H) 3.57-3.91 (m, 1 H) 2.97-3.12 (m, 1 H) 2.29-2.39 (m, 2 H) 2.07-2.18 (m, 1 H) 1.87-2.00 (m, 2 H) 1.66-1.79 (m, 1 H) 1.49-1.61 (m, 1 H) 1.03 (dd, J = 6.87, 2.86 Hz, 3 H) |

-continued

| Cpd | Structure | MS [M + H] m/z | ¹H NMR(DMSO-d₆) δ ppm |
|---|---|---|---|
| 30 | 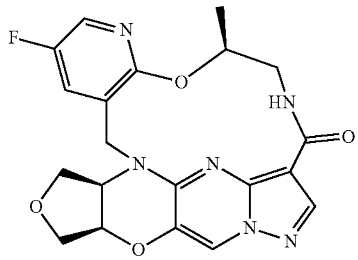 [SMILES: C[C@H]1CNC(=O)c2cnn3cc4c(nc23)N(Cc2cc(F)cnc2O1)[C@@H]1COC[C@@H]1O4] | 427.1 | (500 MHz) 9.33-9.37 (m, 1 H) 8.67 (s, 1 H) 8.08 (d, J = 2.86 Hz, 1 H) 8.02-8.06 (m, 2 H) 5.23 (d, J = 15.47 Hz, 1 H) 5.14-5.20 (m, 1 H) 5.01-5.07 (m, 1 H) 4.82 (t, J = 3.44 Hz, 1 H) 4.30-4.40 (m, 2 H) 4.19 (dd, J = 10.31, 3.44 Hz, 1 H) 4.03 (d, J = 10.88 Hz, 1 H) 3.90-3.97 (m, 1 H) 3.53-3.59 (m, 1 H) 3.15 (ddd, J = 13.60, 8.74, 2.86 Hz, 1 H) 1.45 (d, J = 5.73 Hz, 3 H) |
| 31 | 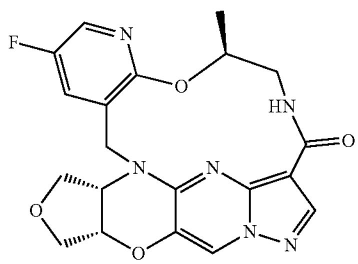 [SMILES: C[C@H]1CNC(=O)c2cnn3cc4c(nc23)N(Cc2cc(F)cnc2O1)[C@H]1COC[C@H]1O4] | 427.1 | (500 MHz) 9.24 (dd, J = 6.59, 3.15 Hz, 1 H) 8.75 (s, 1 H) 8.04-8.09 (m, 2 H) 7.39 (dd, J = 8.59, 2.86 Hz, 1 H) 5.37 (d, J = 14.89 Hz, 1 H) 5.21-5.28 (m, 1 H) 4.65 (t, J = 3.72 Hz, 1 H) 4.61 (t, J = 7.16 Hz, 1 H) 4.46-4.51 (m, 1 H) 4.35 (d, J = 14.89 Hz, 1 H) 4.29 (dd, J = 10.88, 4.58 Hz, 1 H) 4.03 (d, J = 10.31 Hz, 1 H) 3.88-3.95 (m, 1 H) 3.80-3.85 (m, 1 H) 3.17-3.24 (m, 1 H) 1.46 (d, J = 6.30 Hz, 3 H) |
| 32 | 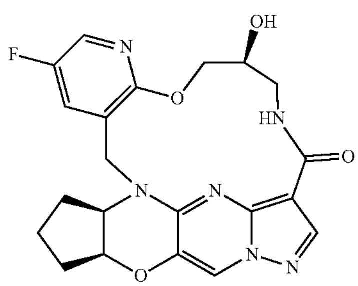 [SMILES: O=C1NC[C@H](O)COc2ncc(F)cc2CN2c3nc4c1cnn4cc3O[C@H]1CCC[C@H]12] | 441.0 | (500 MHz) 8.53 (s, 1 H) 8.13 (dd, J = 8.59, 1.72 Hz, 1 H) 8.05 (d, J = 2.86 Hz, 1 H) 7.99 (s, 1 H) 7.85 (dd, J = 8.59, 2.86 Hz, 1 H) 5.37 (d, J = 4.58 Hz, 1 H) 5.28 (dd, J = 15.18, 1.43 Hz, 1 H) 5.01 (br d, J = 9.74 Hz, 1 H) 4.49-4.58 (m, 2 H) 4.30 (d, J = 15.47 Hz, 1 H) 4.00-4.10 (m, 2 H) 3.91-3.98 (m, 1 H) 3.12 (ddd, J = 13.17, 8.59, 2.29 Hz, 1 H) 2.29-2.38 (m, 1 H) 2.07-2.19 (m, 1 H) 1.86-1.98 (m, 2 H) 1.66-1.76 (m, 1 H) 1.48-1.59 (m, 1 H) |
| 33 | 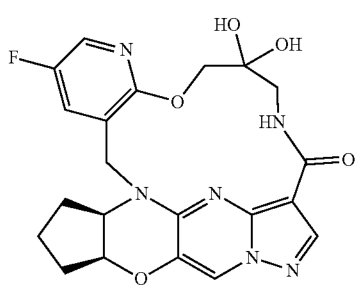 [SMILES: O=C1NCC(O)(O)COc2ncc(F)cc2CN2c3nc4c1cnn4cc3O[C@H]1CCC[C@H]12] | 457.0 | |
| 34 | 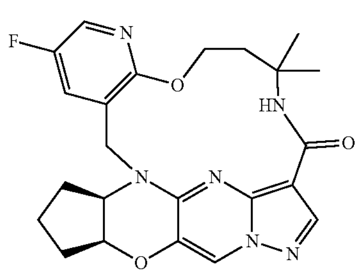 [SMILES: CC1(C)CCOc2ncc(F)cc2CN2c3nc4c(cnn4cc3O[C@H]3CCC[C@H]32)C(=O)N1] | 453.2 | (500 MHz) 8.45-8.58 (m, 1 H) 8.08 (d, J = 2.86 Hz, 1 H) 7.96-8.02 (m, 2 H) 7.81-7.89 (m, 1H) 5.39-5.57 (m, 1 H) 4.89-5.15 (m, 1 H) 4.54-4.60 (m, 1 H) 4.44 (t, J = 3.72 Hz, 1 H) 4.24 (d, J = 15.47 Hz, 1 H) 4.06 (br dd, J = 11.17, 5.44 Hz, 1 H) 1.66-2.44 (m, 8 H), 1.54-1.58 (m, 3 H) 1.50-1.53 (m, 3 H) |

-continued

| Cpd | Structure | MS [M + H] m/z | ¹H NMR(DMSO-d₆) δ ppm |
|---|---|---|---|
| 35 | 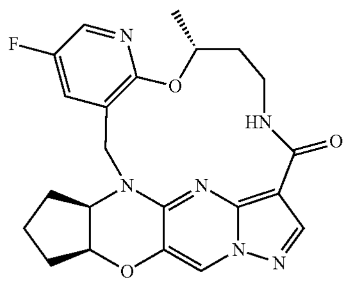 [SMILES: C[C@@H]1CCNC(=O)c2cnn3cc4c(nc23)N(Cc2cc(F)cnc2O1)[C@@H]1CCC[C@@H]1O4] | 439.2 | (500 MHz) 8.59 (s, 1 H) 8.52 (s, 1 H) 8.09 (br t, J = 4.58 Hz, 1 H) 8.03 (d, J = 2.86 Hz, 1 H) 8.00 (s, 1 H) 7.44 (dd, J=8.59, 2.86 Hz, 1 H) 5.62 (br t, J = 6.30 Hz, 1 H) 5.40 (dd, J = 15.18, 1.43 Hz, 1 H) 4.23-4.31 (m, 2 H) 4.06 (ddd, J = 10.60, 6.87, 3.72 Hz, 1 H) 3.56-3.65 (m, 1 H) 2.52-2.57 (m, 1 H) 2.14-2.27 (m, 2 H) 1.86-2.01 (m, 5 H) 1.66-1.74 (m, 1 H) 1.29-1.33 (m, 4 H) |
| 36 | 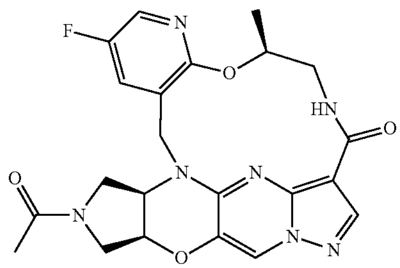 [SMILES: CC(=O)N1C[C@@H]2Oc3cn4ncc5c4nc3N(Cc3cc(F)cnc3O[C@@H](C)CNC5=O)[C@@H]2C1] | 468.2 | (500 MHz) 9.38 (br d, J = 4.01 Hz, 1 H) 8.68 (d, J = 9.74 Hz, 1 H) 8.09 (t, J = 2.58 Hz, 1 H) 7.97-8.05 (m, 2 H) 4.98-5.27 (m, 3 H) 4.78-4.88 (m, 1 H) 4.22-4.44 (m, 2 H) 3.80-3.99 (m, 2 H) 3.67-3.69 (m, 1 H) 3.03-3.19 (m, 2 H) 2.00 (d, J = 7.45 Hz, 3 H) 1.46 (d, J = 6.30 Hz, 3 H) |
| 37 | 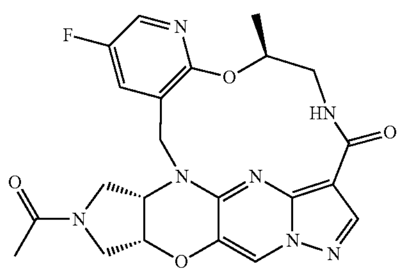 [SMILES: CC(=O)N1C[C@H]2Oc3cn4ncc5c4nc3N(Cc3cc(F)cnc3O[C@@H](C)CNC5=O)[C@H]2C1] | 468.2 | (500 MHz) 9.17-9.24 (m, 1 H) 8.75 (d, J = 13.75 Hz, 1 H) 8.10 (t, J = 3.15 Hz, 1 H) 8.05-8.08 (m, 1 H) 7.39-7.57 (m, 1H) 5.35-5.44 (m, 1 H) 5.21-5.30 (m, 1 H) 4.28-4.73 (m, 4 H) 3.62-4.02 (m, 4 H) 3.19-3.24 (m, 1 H) 2.01-2.10 (m, 3 H) 1.46 (d, J = 6.30 Hz, 3 H) |
| 38 | 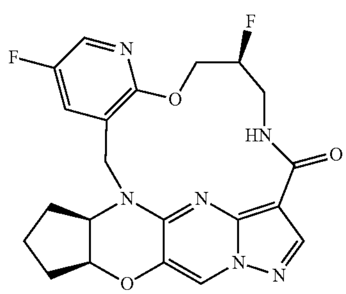 [SMILES: O=C1NC[C@H](F)COc2ncc(F)cc2CN2c3nc4c1cnn4cc3O[C@H]1CCC[C@H]12] | 443.2 | (500 MHz) 8.54 (s, 1 H) 8.19 (t, J = 4.87 Hz, 1 H) 8.09 (d, J = 2.86 Hz, 1 H) 8.01 (s, 1 H) 7.94 (dd, J = 8.88, 2.58 Hz, 1 H) 5.30-5.41 (m, 1 H) 5.27 (dd, J = 14.89, 1.15 Hz, 1 H) 5.07-5.21 (m, 1 H) 4.50-4.58 (m, 2 H) 4.30-4.39 (m, 2 H) 3.93-4.02 (m, 1 H) 3.56-3.69 (m, 1 H) 2.30-2.39 (m, 1 H) 2.09-2.18 (m, 1 H) 1.89-1.99 (m, 2 H) 1.65-1.79 (m, 1 H) 1.50-1.65 (m, 1 H) |
| 39 | 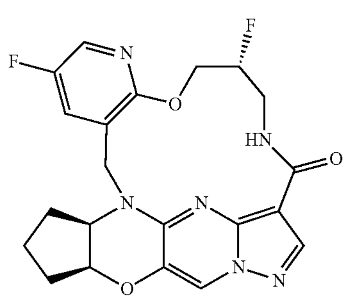 [SMILES: O=C1NC[C@@H](F)COc2ncc(F)cc2CN2c3nc4c1cnn4cc3O[C@H]1CCC[C@H]12] | 443.2 | (500 MHz) 8.53 - 8.62 (m, 1 H) 8.10-8.27 (m, 1 H) 8.08 (t, J=2.58 Hz, 1 H) 8.02 (d, J = 2.29 Hz, 1 H) 7.49-7.97 (m, 1H) 5.44-5.53 (m, 1 H) 5.33-5.43 (m, 1 H) 5.00-5.21 (m, 1 H) 4.52-4.60 (m, 1 H) 4.22-4.41 (m, 3 H) 3.95-4.14 (m, 1 H) 3.52-3.67 (m, 1 H) 2.32-2.40 (m, 1 H) 2.09-2.27 (m, 1 H) 1.87-2.00 (m, 2 H) 1.66-1.78 (m, 1 H) 1.46-1.58 (m, 1 H) |

| Cpd | Structure | MS [M + H] m/z | ¹H NMR(DMSO-d$_6$) δ ppm |
|---|---|---|---|
| 40 | 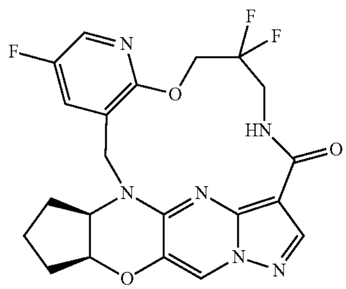 [SMILES: O=C1NCC(F)(F)COc2ncc(F)cc2CN2c3nc4c1cnn4cc3O[C@H]1CCC[C@H]12] | 461.1 | (500 MHz) 8.53-8.62 (m, 1 H) 8.10-8.27 (m, 1 H) 8.08 (t, J = 2.58 Hz, 1 H) 8.02 (d, J = 2.29 Hz, 1 H) 7.49-7.97 (m, 1H) 5.44-5.53 (m, 1 H) 5.33-5.43 (m, 1 H) 5.00-5.21 (m, 1 H) 4.52-4.60 (m, 1 H) 4.22-4.41 (m, 3 H) 3.95-4.14 (m, 1 H) 3.52-3.67 (m, 1 H) 2.32-2.40 (m, 1 H) 2.09-2.27 (m, 1 H) 1.87-2.00 (m, 2 H) 1.66-1.78 (m, 1 H) 1.46-1.58 (m, 1 H) |
| 41 | 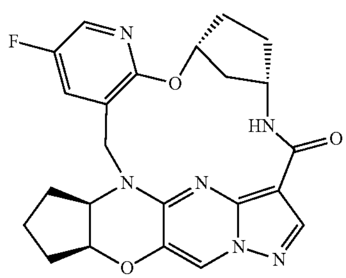 [SMILES: O=C1N[C@H]2CC[C@H](C2)Oc2ncc(F)cc2CN2c3nc4c1cnn4cc3O[C@H]1CCC[C@H]12] | 10-840 | (300 MHz) 8.34-8.67 (m, 2 H) 7.94-8.19 (m, 2 H) 7.48 (dd, J = 8.67, 2.61 Hz, 1 H) 5.38-5.62 (m, 1 H) 5.18-5.38 (m, 1 H) 4.50-4.85 (m, 1 H) 4.17-4.49 (m, 2 H) 3.97-4.14 (m, 1 H) 1.60-2.43 (m, 12 H) |
| 42 | 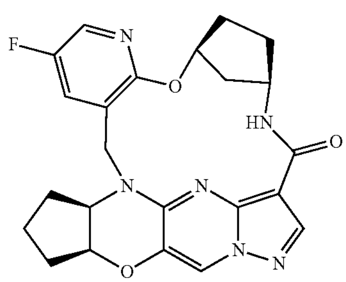 [SMILES: O=C1N[C@@H]2CC[C@@H](C2)Oc2ncc(F)cc2CN2c3nc4c1cnn4cc3O[C@H]1CCC[C@H]12] | 451.2 | (300 MHz) 8.53 (s, 1 H) 8.41 (d, J = 10.55 Hz, 1 H) 8.07 (d, J = 2.93 Hz, 1 H) 7.98 (s, 1 H) 7.86 (dd, J = 8.89, 2.66 Hz, 1 H) 5.37 (br s, 1 H) 5.23-5.32 (m, 1 H) 4.69-4.84 (m, 1 H) 4.49-4.61 (m, 2 H) 4.31 (br d, J = 15.31 Hz, 1 H) 2.23-2.39 (m, 2 H) 2.01-2.19 (m, 4 H) 1.67-1.96 (m, 5 H) 1.50-1.64 (m, 1 H) |
| 43 | 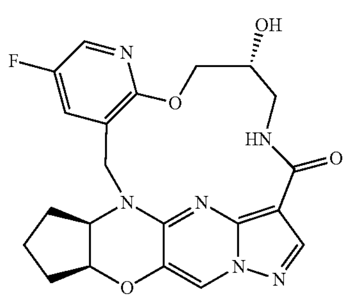 [SMILES: O=C1NC[C@@H](O)COc2ncc(F)cc2CN2c3nc4c1cnn4cc3O[C@H]1CCC[C@H]12] | 441.2 | (300 MHz) 8.50-8.67 (m, 1 H) 7.36 - 8.20 (m, 4 H) 5.21-5.52 (m, 2 H) 4.85-5.11 (m, 1 H) 3.70-4.67 (m, 6 H) 2.97-3.19 (m, 1 H) 2.03-2.42 (m, 2 H) 1.87-2.02 (m, 2 H) 1.66-1.83 (m, 1 H) 1.56 (br d, J = 10.73 Hz, 1 H) |
| 44 | 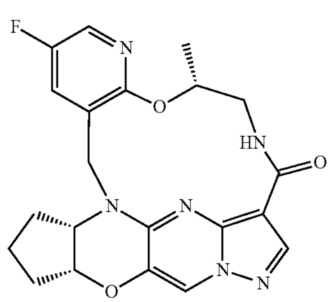 [SMILES: C[C@@H]1CNC(=O)c2cnn3cc4c(nc23)N(Cc2cc(F)cnc2O1)[C@H]1CCC[C@H]1O4] | 425.1 | (300 MHz) 9.40 (dd, J = 7.61, 2.11 Hz, 1 H) 8.55 (s, 1 H) 8.07 (d, J = 2.93 Hz, 1 H) 7.94-8.02 (m, 2 H) 5.11-5.27 (m, 2 H) 4.60 (ddd, J = 10.41, 7.34, 3.16 Hz, 1 H) 4.51 (t, J = 3.76 Hz, 1 H) 4.33 (d, J = 14.95 Hz, 1 H) 3.86-4.01 (m, 1 H) 3.15 (ddd, J = 13.25, 8.76, 2.57 Hz, 1 H) 2.28-2.42 (m, 1 H) 2.03-2.22 (m, 1 H) 1.85-2.00 (m, 2 H) 1.66-1.82 (m, 1 H) 1.49-1.64 (m, 1 H) 1.45 (d, J = 6.24 Hz, 3 H) |

| Cpd | Structure | MS [M + H] m/z | $^1$H NMR(DMSO-$d_6$) δ ppm |
|---|---|---|---|
| 45 | 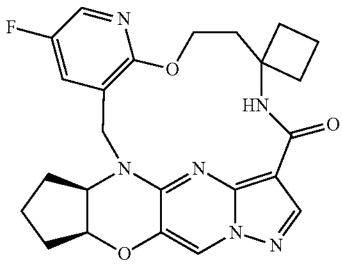 [SMILES: O=C1NC2(CCC2)CCOc2ncc(F)cc2CN2c3nc4c1cnn4cc3O[C@H]1CCC[C@H]12] | 465.2 | (300 MHz) 8.43-8.62 (m, 1 H) 7.86-8.13 (m, 4 H) 5.35-5.56 (m, 1 H) 4.65-4.93 (m, 1 H) 4.49-4.62 (m, 1 H) 4.40-4.48 (m, 1 H) 4.25 (br d, J = 14.40 Hz, 1 H) 4.06-4.17 (m, 1 H) 3.15-3.27 (m, 2 H) 2.09-2.35 (m, 4 H) 1.84-2.00 (m, 4 H) 1.67-1.77 (m, 3 H) 1.46-1.58 (m, 1 H) |
| 46 | 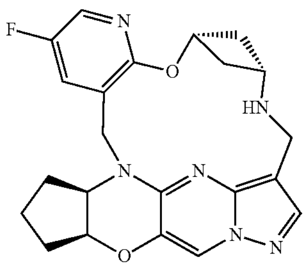 [SMILES: Fc1cnc2c(c1)CN1c3nc4c(cnn4cc3O[C@H]3CCC[C@H]31)CN[C@H]1C[C@H](C1)O2] | 437.1 | (300 MHz) 8.97-9.10 (m, 1 H) 8.53-8.68 (m, 1 H) 7.96-8.11 (m, 3 H) 5.44-5.59 (m, 1 H) 5.12 (q, J = 4.49 Hz, 1 H) 4.50-4.71 (m, 3 H) 4.24-4.42 (m, 1 H) 2.79-3.10 (m, 2 H) 2.30-2.42 (m, 1 H) 2.03-2.22 (m, 2 H) 1.87-2.01 (m, 2 H) 1.49-1.82 (m, 3 H) |
| 47 | 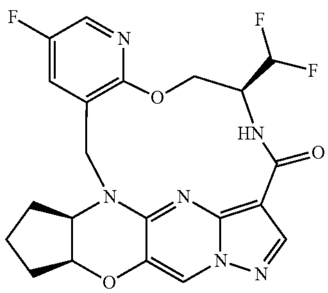 [SMILES: O=C1N[C@H](C(F)F)COc2ncc(F)cc2CN2c3nc4c1cnn4cc3O[C@H]1CCC[C@H]12] | 461.1 | (300 MHz) 9.83 (d, J = 9.08 Hz, 1 H) 8.59 (s, 1 H) 8.11 (d, J = 2.84 Hz, 1 H) 8.00-8.08 (m, 2 H) 6.10-6.56 (m, 1 H) 5.32 (dd, J = 14.76, 1.38 Hz, 1 H) 4.87 (br dd, J = 11.60, 4.81 Hz, 1 H) 4.52-4.67 (m, 2 H) 4.30-4.48 (m, 3 H) 2.35-2.45 (m, 1 H) 2.08-2.20 (m, 1 H) 1.89-1.99 (m, 2 H) 1.69-1.81 (m, 1 H) 1.49-1.63 (m, 1 H) |
| 48 | 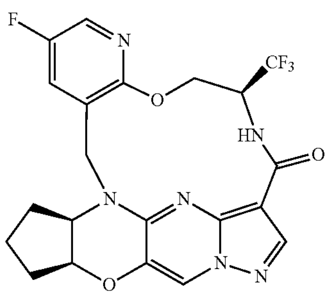 [SMILES: O=C1N[C@H](C(F)(F)F)COc2ncc(F)cc2CN2c3nc4c1cnn4cc3O[C@H]1CCC[C@H]12] | 479.1 | (300 MHz) 10.07 (d, J = 8.71 Hz, 1 H) 8.60 (s, 1 H) 8.13 (d, J = 2.93 Hz, 1 H) 8.04-8.11 (m, 2 H) 5.18-5.28 (m, 1 H) 4.95-5.08 (m, 2 H) 4.63 (ddd, J = 10.34, 7.36, 3.12 Hz, 1 H) 4.36-4.51 (m, 3 H) 2.39 (br d, J = 10.64 Hz, 1 H) 2.11-2.20 (m, 1 H) 1.91-2.00 (m, 2 H) 1.75 (br d, J = 8.07 Hz, 1 H) 1.55-1.64 (m, 1 H) |
| 49 | 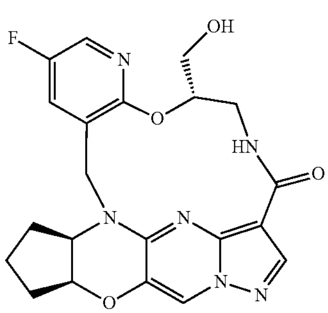 [SMILES: O=C1NC[C@@H](CO)Oc2ncc(F)cc2CN2c3nc4c1cnn4cc3O[C@H]1CCC[C@H]12] | 441.1 | (300 MHz) 9.12 (t, J = 5.00 Hz, 1 H) 8.62 (s, 1 H) 8.06 (d, J = 2.93 Hz, 1 H) 8.00 (s, 1 H) 7.55 (dd, J = 8.67, 2.80 Hz, 1 H) 5.35 (dd, J = 14.81, 1.51 Hz, 1 H) 5.18 (t, J = 5.73 Hz, 1 H) 5.08 (t, J = 5.87 Hz, 1 H) 4.26-4.38 (m, 2 H) 4.10-4.17 (m, 1 H) 3.76-3.91 (m, 2 H) 3.63-3.72 (m, 1 H) 3.41 (ddd, J = 13.25, 6.14, 4.17 Hz, 1 H) 2.56-2.65 (m, 1 H) 2.14-2.28 (m, 1 H) 1.91-2.01 (m, 2 H) 1.63-1.86 (m, 2 H) |

Biologic Assays
In-Vitro Assays
Materials and Methods
Biochemical Kinase Assay Method The biochemical kinase assay was performed at Reaction Biology Corporation (www.reactionbiology.com, Malvern, Pa.) following the procedures described in the reference (Anastassiadis T, et al *Nat Biotechnol.* 2011, 29, 1039).

Specific kinase/substrate pairs along with required cofactors were prepared in reaction buffer; 20 mM Hepes pH 7.5, 10 mM MgCl$_2$, 1 mM EGTA, 0.02% Brij35, 0.02 mg/ml BSA, 0.1 mM Na$_3$VO$_4$, 2 mM DTIT, 1% DMSO. Compounds were delivered into the reaction, followed ~20 minutes later by addition of a mixture of ATP (Sigma, St. Louis Mo.) and $^{33}$P ATP (Perkin Elmer, Waltham Mass.) to a final concentration of 10 μM. Reactions were carried out at room temperature for 120 min, followed by spotting of the reactions onto P81 ion exchange filter paper (Whatman Inc., Piscataway, N.J.). Unbound phosphate was removed by extensive washing of filters in 0.75% phosphoric acid. After subtraction of background derived from control reactions containing inactive enzyme, kinase activity data was expressed as the percent remaining kinase activity in test samples compared to vehicle (dimethyl sulfoxide) reactions. IC$_{50}$ values and curve fits were obtained using Prism (GraphPad Software).

Cell Lines and Cell Culture:

Human medulla thyroid carcinoma cell line TT (containing RET M918T mutation) and acute myelogenous cell line KG-1 were purchased from ATCC. Human colon cancer cell line KM12 (containing TPM3-TRKA) was obtained from NCI.

Cloning and Ba/F3 Stable Cell Line Creation

The EML4-ALK gene (variant 1) was synthesized at GenScript and cloned into pCDH-CMV-MCS-EF1-Puro plasmid (System Biosciences, Inc). Ba/F3-EML4-ALK wild type were generated by transducing Ba/F3 cells with lentivirus containing EML4-ALK wide type. Stable cell lines were selected by puromycin treatment, followed by IL-3 withdrawal. Briefly, 5×10$^6$ Ba/F3 cells were transduced with lentivirus supernatant in the presence of 8 μg/mL protamine sulfate. The transduced cells were subsequently selected with 1 μg/mL puromycin in the presence of IL3-containing medium RPMI1640, plus 10% FBS. After 10-12 days of selection, the surviving cells were further selected for IL3 independent growth.

The KIF5B-RET gene was synthesized at GenScript and cloned into pCDH-CMV-MCS-EF1-Puro plasmid (System Biosciences, Inc). KIF5B-RET point mutation V804M was generated at GenScript by PCR and confirmed by sequencing. Ba/F3-KIF5B-RET wild type and mutant were generated by transducing Ba/F3 cells with lentivirus containing KIF5B-RET wide type or mutant. Stable cell lines were selected by puromycin treatment, followed by IL-3 withdrawal. Briefly, 5×10$^6$ Ba/F3 cells were transduced with lentivirus supernatant in the presence of 8 μg/mL protamine sulfate. The transduced cells were subsequently selected with 1 pg/mL puromycin in the presence of IL3-containing medium RPMI1640, plus 10% FBS. After 10-12 days of selection, the surviving cells were further selected for IL3 independent growth.

Cell Proliferation Assays:

Two thousand cells per well were seeded in 384 well white plate for 24 hrs, and then treated with compounds for 72 hours (37° C., 5% CO$_2$). Cell proliferation was measured using CellTiter-Glo luciferase-based ATP detection assay (Promega) following the manufactures's protocol. IC$_{50}$ determinations were performed using GraphPad Prism software (GraphPad, Inc., San Diego, Calif.).

Immunoblotting for Cellular Kinase Phosphorylation Assays

Half a million cells per well were seeded in 24 well plate for 24 hrs, and then treated with compounds for 4 hours. Cells were collected after treatment and lysed in RIPA buffer (50 mM Tris, pH 7.4, 150 mM NaCl, 1% NP-40, 0.5% Deoxycholate, 0.1% SDS) supplemented with 10 mM EDTA, 1× Halt protease and phosphatase inhibitors (Thermo Scientific). Protein lysates (approximately 20 pg) was resolved on 4-12% Bolt Bis-Tris precasted gels with MES running buffer (Life Technologies), transferred to nitrocellulose membranes using Trans-Blot Turbo Transfer System (Bio-Rad) and detected with antibodies targeting phosphorylated RET (Y905) (Cell Signaling Technology), total RET (Cell Signaling Technology), actin (Cell Signaling Technology). Antibodies were typically incubated overnight at 4° C. with gentle shake, followed by washes and incubation with the appropriate HRP-conjugated secondary antibodies. Membranes were incubated with chemiluminescent substrate for 5 min at room temperature (SuperSignal West Femto, Thermo Scientific). The chemiluminescent images were acquired with a C-DiGit Imaging System (LI-COR Biosciences). The relative density of the chemiluminescent bands were quantified via Image Studio Digits from LICOR. The half inhibitory concentration (IC$_{50}$) value is calculated using non-linear regression analysis through GraphPad Prism software (GraphPad, Inc., San Diego, Calif.).

Data and Results:

Enzymatic kinase activities of Compound 1 and 5.

| Enzyme | IC$_{50}$ (nM) at 10 μM ATP Compound 1 | IC$_{50}$ (nM) at 10 μM ATP Compound 5 |
|---|---|---|
| RET | 0.0994 | 1.01 |
| RET (A883F) | 0.520 | 3.08 |
| RET (E762Q) | 2.07 | 0.58 |
| RET (G691S) | 3.01 | 0.941 |
| RET (L790F) | 0.120 | 1.31 |
| RET (M918T) | 0.114 | 1.42 |
| RET (R749T) | 0.271 | 0.32 |
| RET (R813Q) | 0.341 | 2.46 |
| RET (S891A) | 0.664 | 0.303 |
| RET (S904A) | 0.159 | 1.22 |
| RET (S904F) | 0.0621 | 0.364 |
| RET (V778I) | <0.0508 | 0.233 |
| RET (V804L) | 10.0 | 2350 |
| RET (V804M) | 7.86 | 18.8 |
| RET (Y791F) | <0.0508 | 7.95 |
| RET (Y806H) | 0.385 | 0.261 |
| RET-CCDC6 (PTC1) | 0.0893 | 1.97 |
| RET-NCOA4 (PTC3) | 0.0635 | 0.691 |
| RET-PRKAR1A (PTC2) | 0.129 | 0.29 |
| Src | 0.875 | 1.46 |
| FYN | 1.81 | 1.94 |
| YES | 1.72 | 2.64 |
| HCK | 1.95 | 2.71 |
| LYN | 1.97 | 2.03 |

Anti-Cell Proliferation Activity

| Cpd | BaF3 EML4-ALK IC$_{50}$ (nM) | KG-1 IC$_{50}$ (nM) | TT cell (RET C634W) IC$_{50}$ (nM) | BaF3 KIF5B-RET IC$_{50}$ (nM) | BaF3 KIF5B-RET_V804M IC$_{50}$ (nM) | BaF3 KIF5B-RET_G810R IC$_{50}$ (nM) | KM12 cell (TPM3-TRKA) IC$_{50}$ (nM) |
|---|---|---|---|---|---|---|---|
| 1 | 211.4 | 131.2 | <0.5 | 0.25 | 1002 | 30 | 3.0 |
| 2 | >10000 | 5000 | 1784 | 1452 | >10000 | | 254.9 |
| 3 | 1500 | 505 | 7.9 | <0.2 | 1704 | | 4.2 |
| 4 | 3287 | 5000 | 461.9 | 184.4 | 5000 | | 22 |
| 5 | 515.6 | 26.8 | 0.9 | 2.4 | 598 | 22 | 6.9 |
| 6 | 145.5 | 1 | | 0.2 | 573.1 | 3 | 0.2 |
| 7 | 674.8 | 343.8 | | 0.2 | 1845 | 99.2 | 37 |
| 8 | 4000 | 188.9 | | 341.8 | 1928 | | 0.3 |
| 9 | 8000 | 1000 | | 2364 | >10000 | | 3.3 |
| 10 | 4000 | 78.3 | | 274.4 | 1213 | | 0.2 |
| 11 | 10000 | 307.3 | | 838.9 | 3000 | | 0.4 |
| 12 | 2709 | 159.9 | | 100.5 | 4619 | 1014 | 13.8 |
| 13 | 5000 | 452 | | 341.5 | >10000 | 1121 | 28.4 |
| 14 | 907.8 | 273 | | 120.3 | 10000 | 530 | 26.6 |
| 15 | 364.4 | 5.2 | | 1.1 | 1245 | 8.7 | 5.1 |
| 16 | 340.5 | 47.4 | | 16.6 | 5000 | 41.2 | 45.5 |
| 17 | 615.6 | 5 | | 1.8 | 2731 | 10.7 | 4 |
| 18 | 77.2 | 16.9 | | 7.1 | 1533 | 24.4 | 11.3 |
| 19 | 895.1 | 73.1 | | 5.2 | 3073 | 78 | 7.8 |
| 20 | 1400 | 2.4 | | 1.1 | 1855 | 7.8 | 0.5 |
| 21 | 461.7 | 86.9 | — | <0.2 | 3459 | 82 | 13.8 |
| 22 | 157.5 | 155.8 | — | <0.2 | 1763 | 127.6 | 49.3 |
| 23 | 1682 | 228.2 | — | 98.9 | 3000 | 422.2 | 52.9 |
| 24 | 468.9 | 8.7 | — | 1.8 | 1222 | 73.6 | 2.8 |
| 25 | 3000 | 677.3 | — | 193.3 | 3000 | 559.1 | 277.3 |
| 26 | 1412 | 737.1 | — | 160 | 5000 | 323.2 | 210.1 |
| 27 | 1000 | 0.3 | — | <0.2 | 2000 | 63 | 0.3 |
| 28 | 803.5 | 22.8 | — | 1.5 | 2000 | 72 | 11.8 |
| 29 | 901 | 7.9 | — | 0.3 | 1377 | 133.7 | 1.7 |
| 30 | 2000 | 853.2 | — | 161.9 | 337.2 | 1857 | 13.5 |
| 31 | 10000 | 10000 | — | 4000 | >10000 | >10000 | 365 |
| 32 | 1056 | 223 | — | 89 | 5718 | 500.8 | 20.2 |
| 33 | 2000 | 356.2 | — | 197.9 | 4000 | 1196 | 124.5 |
| 34 | 1000 | 407.5 | — | 62.2 | 10000 | 651.1 | 50 |
| 35 | 1105 | 55.7 | — | 8.8 | — | — | <0.2 |
| 36 | >10000 | 10000 | — | 8000 | — | — | 1000 |
| 37 | >10000 | 3000 | — | 8000 | — | — | 1201 |
| 38 | 82.1 | <0.2 | — | <0.2 | 349.3 | 0.3 | <0.2 |
| 39 | 151.5 | 59.2 | — | 10.2 | 3000 | 57.3 | 7.4 |
| 40 | 1951 | 19.1 | — | <0.2 | 5000 | 1.8 | <0.2 |
| 41 | 1448 | 389.2 | — | 5.1 | — | 155.6 | 431.2 |
| 42 | 338.5 | 41 | — | 0.5 | — | 17.4 | 9.8 |
| 43 | 2991 | 359.4 | — | 68.9 | — | 395.9 | 108.6 |
| 44 | >10000 | >10000 | — | >10000 | >10000 | >10000 | 668.5 |
| 45 | 3109 | 1134 | — | 525.7 | 5000 | 1712 | 202.4 |
| 46 | 55.5 | 5.9 | — | <0.2 | 71.5 | 2.9 | 2.8 |
| 47 | 139.2 | 3.5 | — | <0.2 | 469.3 | 3.6 | <0.2 |
| 48 | 455.9 | 117 | — | 0.2 | 1067 | 90.9 | 5.9 |
| 49 | >10000 | 5238 | — | 396.6 | 5000 | 1643 | 1457 |

Compound 5 Inhibited the Phosphorylation of RET

Figure 2:
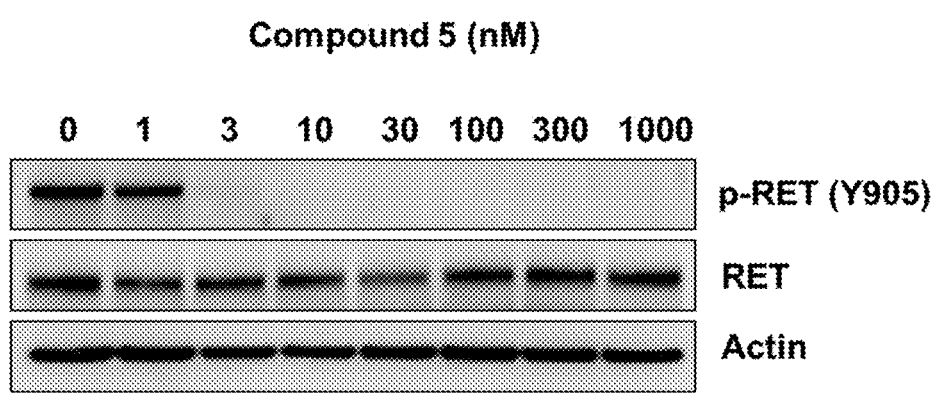
FIG. 2 shows the pharmacodynamic inhibiting activity of Compound 5 on RET in RET-driven cells, specifically that Compound 5 caused the suppression of RET autophosphorylation at IC50s of around 1-3 nM in Ba/F3 KIF5B-RET WT.
Figure 3:
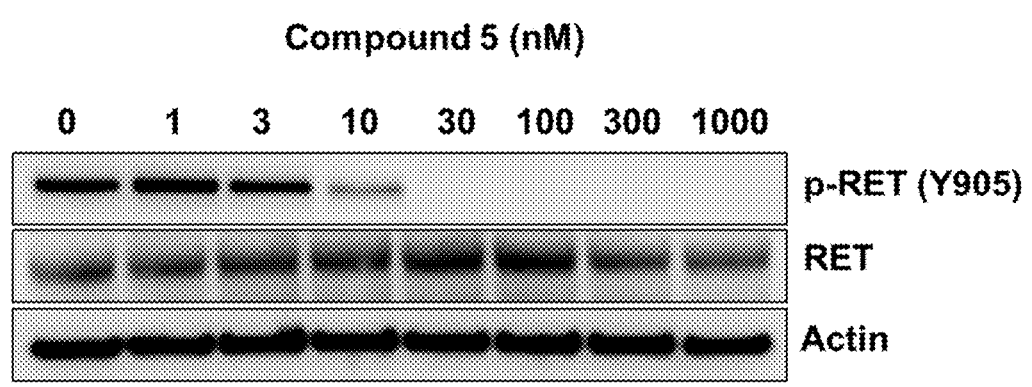
FIG. 3 shows the pharmacodynamic inhibiting activity of Compound 5 on RET in RET-driven cells, specifically that Compound 5 caused the suppression of RET autophosphorylation at IC50s of around 3-10 nM in Ba/F3 KIF5B-RET G810R.

The pharmacodynamic inhibiting activity of Compound 5 on RET in RET-driven cells was evaluated, and the results were shown in FIGS. 1, 2 and 3. Compound 5 caused the suppression of RET autophosphorylation at IC50s of around 0.3, 1-3 and 3-10 nM in T, Ba/F3 KIF5B-RET WT and Ba/F3 KIF5B-RET G810R respectively (FIGS. 1,2 &3).

In Vivo Methods

Cell Lines

BaF3 KIF5B-RET WT and BaF3 KIF5B-RET G810R cells were cultured using standard techniques in RPMI-1640 medium (Corning, Inc) with 10% fetal bovine serum (Thermo Fisher Scientific, Inc) at 37° C. in a humidified atmosphere with 5% $CO_2$. TI cells were cultured using standard techniques in F-12K medium (Corning, Inc) with 10% fetal bovine serum (Thermo Fisher Scientific, Inc) at 37° C. in a humidified atmosphere with 5% $CO_2$. For implantation, cells were harvested and pelleted by centrifugation at 250 g for 2 minutes. Cells were washed once and resuspended in serum-free medium supplemented with 50% matrigel (v/v).

Subcutaneous Xenograft Models in Immune Compromised Mice

For cell derived xenograft models, female SCID/Beige mice (5-8 weeks of age) were obtained from Charles River Laboratory and were housed in Innovive IVC disposable cages on HEPA filtered ventilated racks with ad libitum access to rodent chow and water. Five million cells in 100 µL serum-free medium supplemented with 50% matrigel (Corning, Inc) were implanted subcutaneously in the right flank region of the mouse. Tumor size and body weight were measured on designated days. Tumor size was measured with an electronic caliper and tumor volume was calculated as the product of length*width$^2$*0.5. Mice were randomized by tumor size into treatment groups when tumor volume reached about 200 mm$^3$ and Compound 5 was administered orally (BID) at determined doses.

For PDX models, primary human tumor xenograft model LU2503 tumors were grown in stock mice. Tumor fragments (2-3 mm in diameter) were harvested from stock mice an dinoculated into the right front back of each female BALB/c nude mice for tumor development. Tumor size and body weight were measured on designated days. Tumor size was measured with an electronic caliper and tumor volume was calculated as the product of length*width2*0.5. Mice were randomized by tumor size into treatment groups when tumor volume reached about 200 mm3 and Compound 5 was administered orally (BID) at determined doses.

Antitumor Efficacy of Compound 5 in Xenograft Tumor Models

The antitumor efficacy of Compound 5 was evaluated in several tumor xenograft models representing cancer populations in which dysregulation of RET is implicated.

TT Thyroid Medullary Carcinoma Model

Figure 4A:
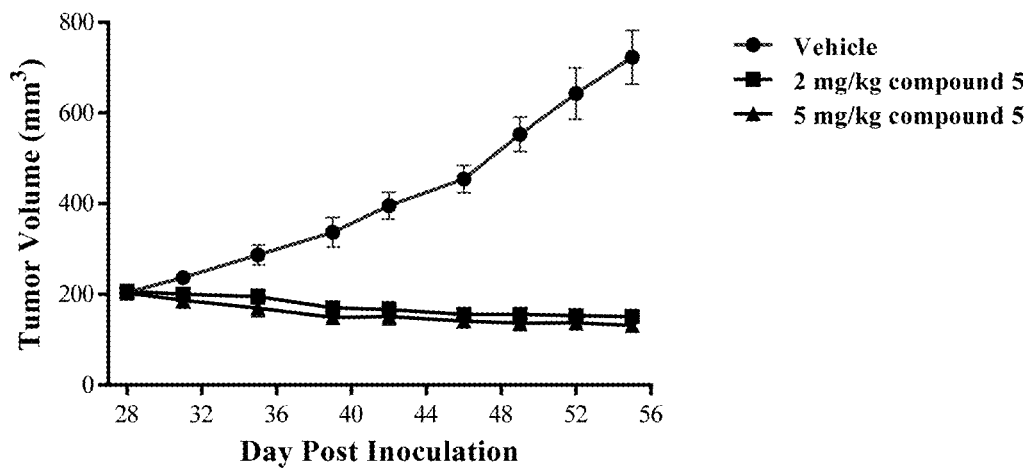
FIG. 4A is a chart that shows that Compound 5 dosed at 2 mg/kg BID and 5 mg/kg BID for 27 days decreased tumor size in test mice compared to untreated control. Untreated control (●), 2 mg/kg (■), 5 mg/kg (▲).
Figure 4B:
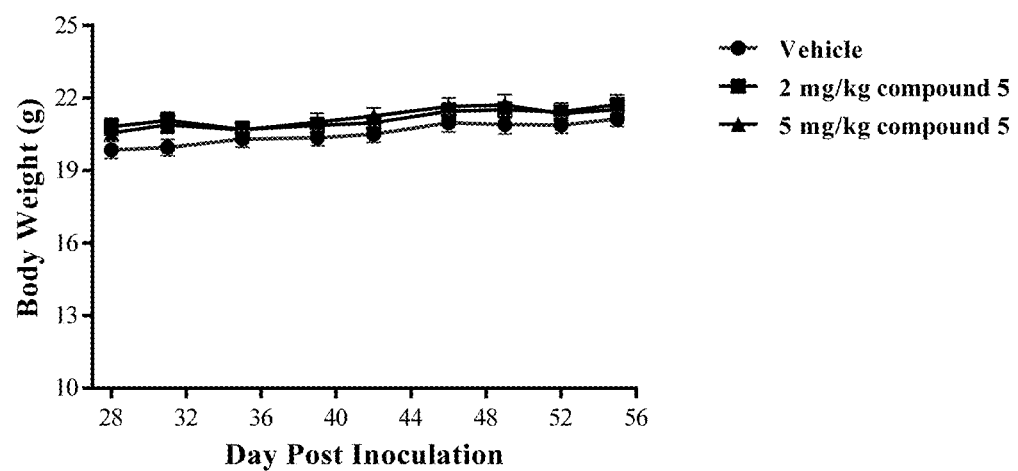
FIG. 4B is a cart at shows % weight change for test mice dosed at 2 mg/kg BID and 5 mg/kg BID for 27 days compared to untreated control. Untreated control (●), 2 mg/kg (■), 5 mg/kg (▲).

The C634W mutation of RET in T cells underlies the molecular mechanism for tumor growth. SCID/Beige mice bearing TT tumors (at the average tumor size of around 200 mm$^3$) were dosed with Compound 5 orally BID for 27 days (FIG. 4A). The control group of mice were given vehicle only. Tumor volume (TMV) was measured by caliper on the indicated days and is shown at mean±sem in FIG. 4A. The mean TMVs are significantly lower in the treated groups compared to that of the control group (p<0.0001) as determined by two-way repeated ANOVA followed by post hoc analysis. Tumor growth inhibition (TGI) was calculated as $100\% * \{1-[(TMV_{Treated\ Last\ Day\ of\ Treatment} - TMV_{Treated\ First\ Day\ of\ Treatment})/(TMV_{Control\ on\ Last\ Day\ of\ Treatment} - TMV_{Control\ on\ First\ Day\ of\ Treatment})]\}$ when $TMV_{Treated\ Last\ Day\ of\ Treatment} \geq TMV_{Treated\ First\ Day\ of\ Treatment}$. In the case of $TMV_{Treated\ Last\ Day\ of\ Treatment} < TMV_{Treated\ First\ Day\ of\ Treatment}$, tumor regression (REG) was calculated as $100\% * (1 - TMV_{Treated\ Last\ Day\ of\ Treatment}/TMV_{Treated\ First\ Day\ of\ Treatment})$. In this study, Compound 5 demonstrated the ability to induce tumor regression of 27% and 35% at the dose of 2 mg/kg BID and 5 mg/kg BID, respectively. Tumor size was reduced in 10 out 10 mice treated with Compound 5 at both dose levels. Body weight of the mice were measured on the designated days of the mice as shown in FIG. 4B. No body weight loss or overt abnormality was observed at either dose levels.

Inhibition of the Growth of BaF3 KIF5B-RET WT Tumors and BaF3 KIF5B-RET G810R Tumors Following Oral Administration of Compound 5

Figure 5A:
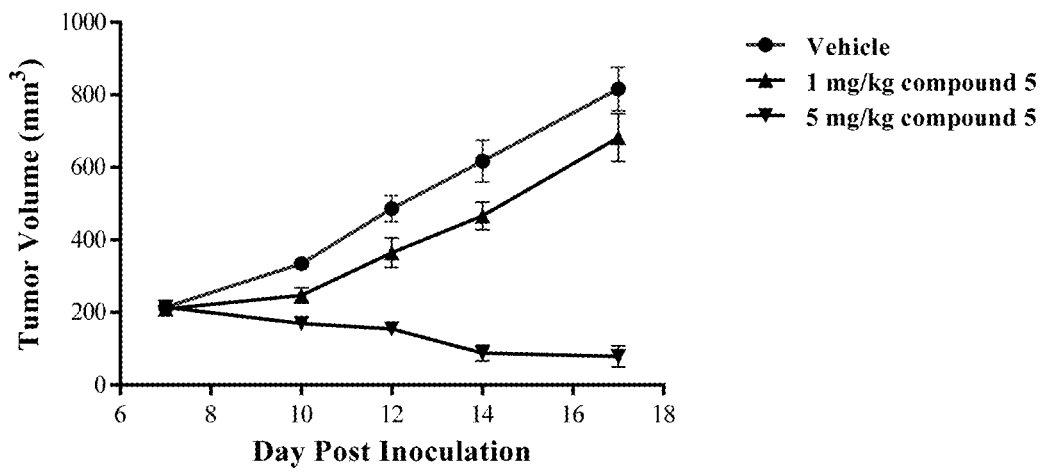
FIG. 5A is a chart that shows the effect of Compound 5 dosed at 1 mg/kg BID and 5 mg/kg BID for 10 days on tumor size in test mice compared to untreated control. Untreated control (●), 1 mg/kg (▲), 5 mg/kg (▼).
Figure 5B:
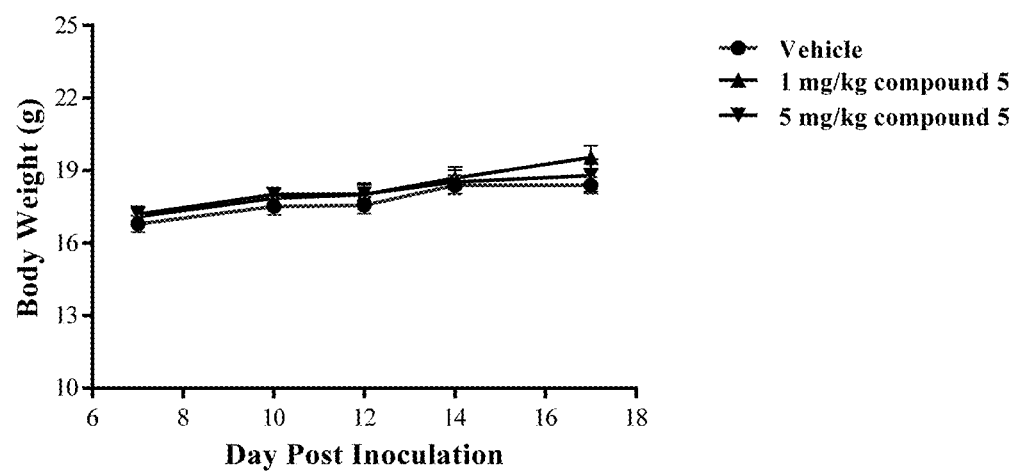
FIG. 5B is a chart that shows % weight change for test mice dosed at 1 mg/kg BID and 5 mg/kg BID for 10 days compared to untreated control. Untreated control (●), 1 mg/kg (▲), 5 mg/kg (▼).
Figure 6A:
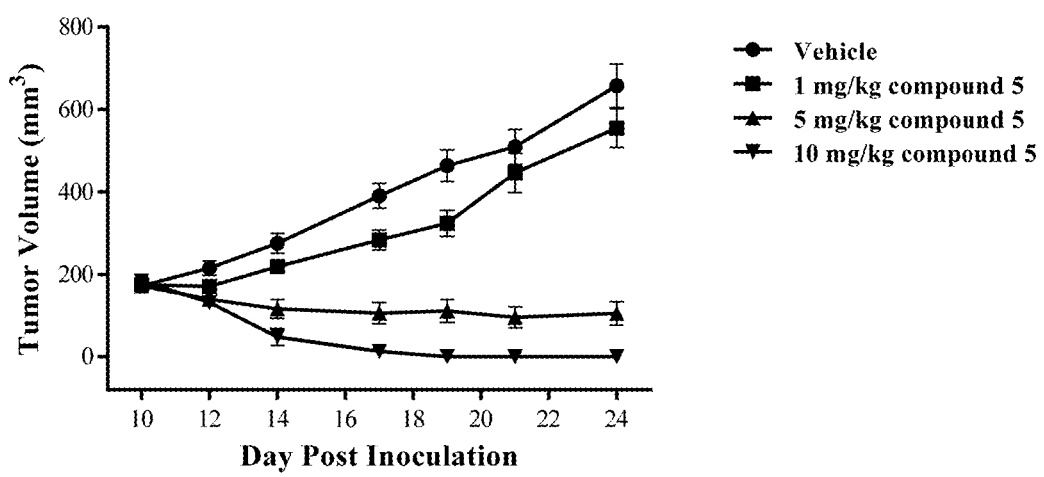
FIG. 6A is a chart that shows the effect of Compound 5 dosed at 1 mg/kg BID, 5 mg/kg BID, and 10 mg/kg BID for 14 days on tumor size in test mice compared to untreated control. Untreated control (●), 1 mg/kg (■), 5 mg/kg (▲), 10 mg/kg (▼).
Figure 6B:
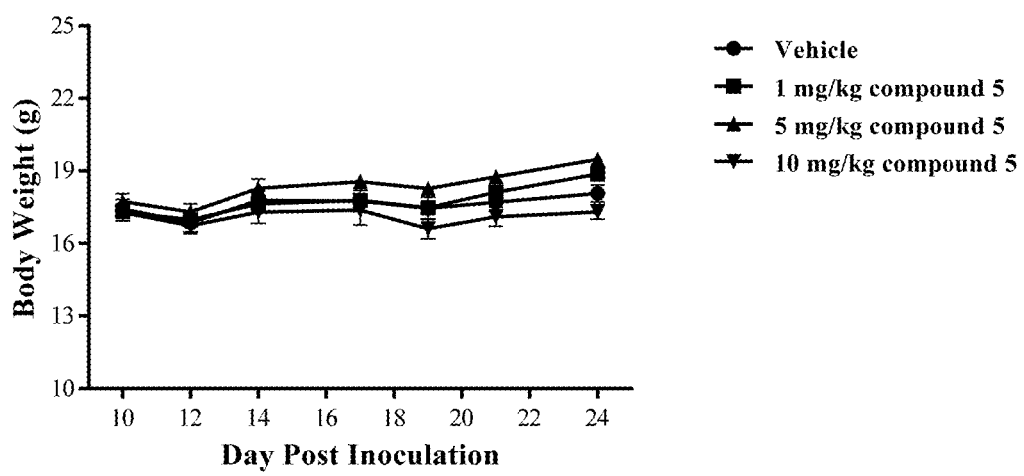
FIG. 6B is a chart that shows % weight change for test mice dosed at 1 mg/kg BID, 5 mg/kg BID, and 10 mg/kg BID for 14 days compared to untreated control. Untreated control (●), 1 mg/kg (■), 5 mg/kg (▲), 10 mg/kg (▼).

In the BaF3 KIF5B-RET WT and BaF3 KIF5B-RET G810R xenograft tumor models, the growth of tumor is presumably dependent on the extopic RET activity. SCID/Beige mice bearing BaF3 KIF5B-RET WT tumors (with average tumor size of ~210 mm$^3$) were dosed with Compound 5 orally BID for 10 days (FIG. 5A). The control group of mice were given vehicle only. Tumor volume (TMV) was measured by caliper on the indicated days and is shown at mean±sem in FIG. 5A. The mean TMVs are lower in the groups treated with compound 5 at 1 mg/kg BID (p>0.05) and 5 mg/kg BID (p<0.0001) compared to that of the control group as determined by two-way repeated ANOVA followed by post hoc analysis. Compound 5 demonstrated the ability to inhibit tumor growth at 21% at the dose of 1 mg/kg BID. Compound 5 treatment at 5 mg/kg BID resulted in a tumor regression of 63%, with tumor size reduction in 9 out 10 mice. Body weight of the mice were measured on the designated days of the mice as shown in FIG. 5B. No body weight loss or overt abnormality was observed in compound 5 treatment groups. SCID/Beige mice bearing BaF3 KIF5B-RET G810R tumors (with average tumor size of ~170 mm$^3$) were dosed with Compound 5 orally BID for 14 days (FIG. 6A). The control group of mice were given vehicle only. Tumor volume (TMV) was measured by caliper on the indicated days and is shown at mean±sem in FIG. 6A. The mean TMVs are lower in the groups treated with compound 5 at 1 mg/kg BID (p>0.05), 5 mg/kg BID (p<0.0001) and 10 mg/kg BID (p<0.0001) compared to that of the control group as determined by two-way ANOVA followed by post hoc analysis. Compound 5 treatment at 1 mg/mg BID inhibited tumor growth with a TGI of 22%. Compound 5 treatment at 5 mg/kg BID resulted in a tumor regression of 39%, with tumor size reduction in 9 out 10 mice. Compound 5 treatment at 10 mg/kg BID resulted in complete tumor regression in 9 out 9 mice. Body weight of the mice were measured on the designated days of the mice as shown in FIG. 6B. No body weight loss or overt abnormality was observed in compound 5 treatment groups during the treatment period.

CR1520 Patient Derived Xenograft (PDX) Colorectal Cancer Model

Figure 7A:
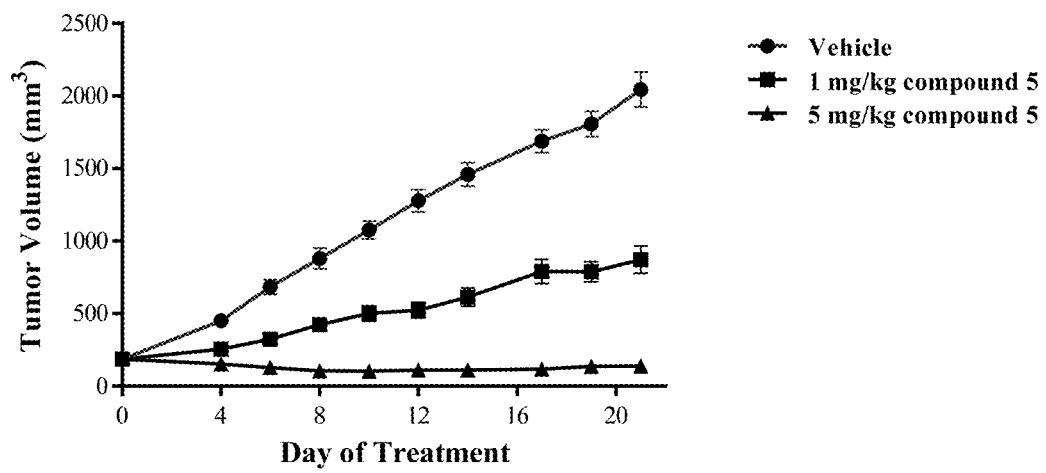
FIG. 7A is a chart that shows the effect of Compound 5 dosed at 1 mg/kg BID and 5 mg/kg BID for 21 days on tumor size in test mice compared to untreated control. Untreated control (●), 1 mg/kg (■), 5 mg/kg (▲).
Figure 7B:
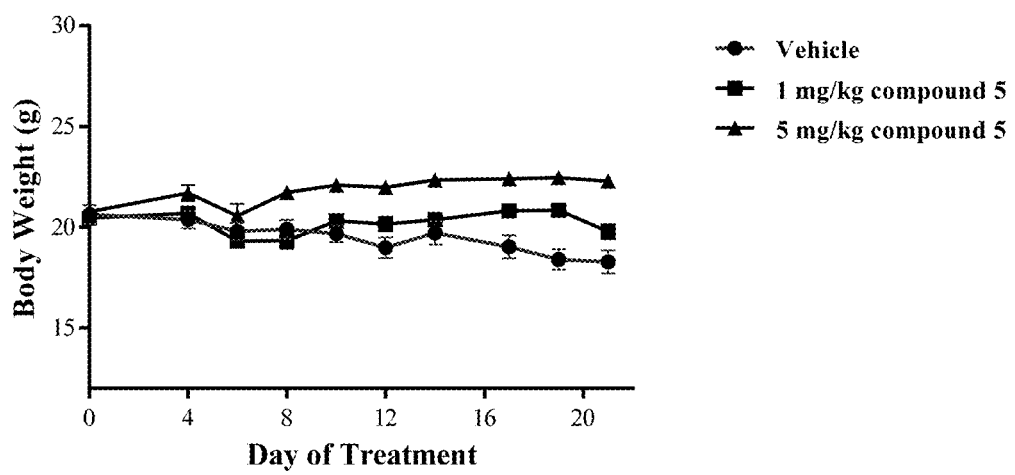
FIG. 7B is a chart that shows % weight change for test mice dosed at 1 mg/kg BID and 5 mg/kg BID for 21 days compared to untreated control. Untreated control (●), 1 mg/kg (■), 5 mg/kg (▲).

The CR1520 is a PDX model derived from a colorectal cancer patient harboring the NCOA4-RET fusion gene. Treating mice bearing CR1520 tumors with Compound 5 at 1 mg/kg BID for 21 days resulted inhibited tumor growth with a TGI of 63%, with tumors grew from 187 mm$^3$ to 872 mm$^3$. For comparison, the tumors grew from 187 mm$^3$ to 2044 mm$^3$ in the vehicle treated group (FIG. 7A). Treating mice bearing CR1520 tumors with Compound 5 at 5 mg/kg BID for 21 days resulted a tumor regression from 187 mm$^3$ to 138 mm$^3$, corresponding to a 26% tumor regression (FIG. 7A). No body weight loss was observed after 21 days of BID treatment with Compound 5 at 1 mg/kg BID or 5 mg/kg BID (FIG. 7B).

CTG-0838 Patient Derived Xenograft (PDX) NSCLC Model

Figure 8A:
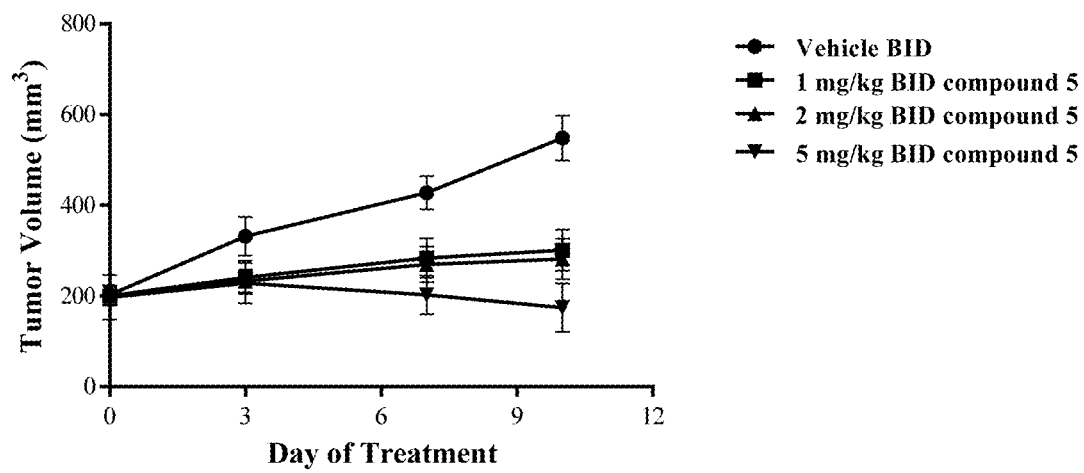
FIG. 8A is a chart that shows the effect of Compound 5 dosed at 1 mg/kg BID, 2 mg/kg BID, and 5 mg/kg BID for 10 days on tumor size in test mice compared to untreated control. Untreated control (●), 1 mg/kg (■), 2 mg/kg (▲), 5 mg/kg (▼).
Figure 8B:
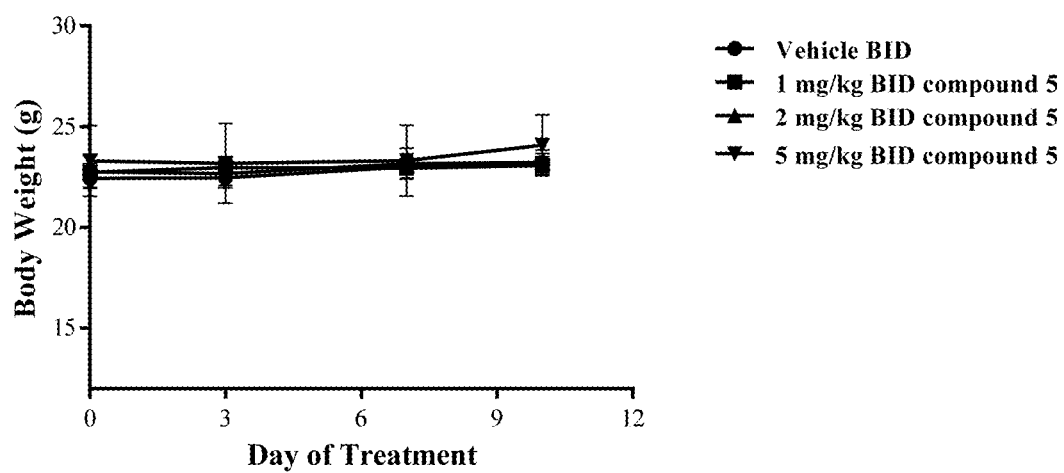
FIG. 8B is a chart that shows % weight change for test mice dosed at 1 mg/kg BID, 2 mg/kg BID, and 5 mg/kg BID for 10 days compared to untreated control. Untreated control (●), 1 mg/kg (■), 2 mg/kg (▲), 5 mg/kg (▼).

The CTG-0838 is a PDX model derived from a non-small cell lung cancer patient harboring the KIF5B-RET fusion gene. Treating mice bearing CTG-0838 tumors with Compound 5 at 1 mg/kg BID and 2 mg/kg BID for 10 days resulted inhibited tumor growth with a TGI of 71% and 76%, respectively (FIG. 8A). Treating mice bearing CTG-0838 tumors with Compound 5 at 5 mg/kg BID for 10 days resulted a tumor regression from 197 mm$^3$ to 174 mm$^3$, corresponding to a 12% tumor regression (FIG. 8A). No body weight loss was observed after 10 days of BID treatment with Compound 5 at the 1, 2 or 5 mg/kg BID (FIG. 8B).

What is claimed is:
1. A compound of the formula I

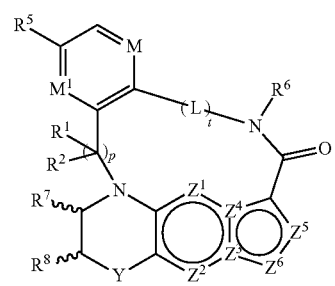

I wherein
each L is independently —C($R^1$)($R^2$)— or X; with the proviso that, when t is 1, then L is —C($R^1$)($R^2$)—;
X is O, S, S(O) or S(O)$_2$;
each $R^1$ and $R^2$ is independently H, deuterium, halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, mono- or bi-cyclic heteroaryl, —OR$^a$, —OC(O)R$^a$, —OC(O)R$^a$, —OC(O)NR$^a$R$^b$, —OS(O)R$^a$, —OS(O)$_2$R$^a$, —SR$^a$, —S(O)R$^a$, —S(O)$_2$R$^a$, —S(O)NR$^a$R$^b$, —S(O)$_2$NR$^a$R$^b$, —OS(O)NR$^a$R$^b$, —OS(O)$_2$NR$^a$R$^b$, —NR$^a$R$^b$, —NR$^a$C(O)R$^b$, —NR$^a$C(O)OR$^b$, —NR$^a$C(O)NR$^a$R$^b$, —NR$^a$S(O)R$^b$, —NR$^a$S(O)$_2$R$^b$, —NR$^a$S(O)NR$^a$R$^b$, —NR$^a$S(O)$_2$ NR$^a$R$^b$, —C(O)R$^a$, —C(O)OR$^a$, —C(O)NR$^a$R$^b$, —PR$^a$R$^b$, —P(O)R$^a$R$^b$, —P(O)$_2$R$^a$R$^b$, —P(O)NR$^a$R$^b$, —P(O)$_2$NR$^a$R$^b$, —P(O)OR$^a$, —P(O)$_2$ OR$^a$, —CN, or —NO$_2$, or $R^1$ and $R^2$ taken together with the carbon to which they are attached form a $C_3$-$C_6$ cycloalkyl or a 4- to 6-membered heterocycloalkyl, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, mono- or bi-cyclic heteroaryl, or 4- to 6-membered heterocycloalkyl is independently optionally substituted by deuterium, halogen, $C_1$-$C_6$ alkyl, $C_1$-$C_6$ haloalkyl, $C_3$-$C_6$ cycloalkyl, 3- to 7-membered heterocycloalkyl, —OR$^e$, —OC(O)R$^e$, —OC(O)NR$^e$R$^f$, —OC(=N)NR$^e$R$^f$, —OS(O)R$^e$, —OS(O)$_2$R$^e$, —OS(O)NR$^e$R$^f$, —OS(O)$_2$NR$^e$R$^f$, —SR$^e$, —S(O)R$^e$, —S(O)$_2$R$^e$, —S(O)NR$^e$R$^f$, —S(O)$_2$NR$^e$R$^f$, —NR$^e$R$^f$, —NR$^e$C(O)R$^f$, —NR$^e$C(O)OR$^f$, —NR$^e$C(O)NR$^e$R$^f$, —NR$^e$S(O)R$^f$, —NR$^e$S(O)$_2$R$^f$, —NR$^e$S(O)NR$^e$R$^f$, —NR$^e$S(O)$_2$NR$^e$R$^f$, —C(O)R$^e$, —C(O)OR$^e$, —C(O)NR$^e$R$^f$, —PR$^e$R$^f$, —P(O)R$^e$R$^f$, —P(O)$_2$R$^e$R$^f$, —P(O)NR$^e$R$^f$, —P(O)$_2$NR$^e$R$^f$, —P(O)OR$^e$, —P(O)$_2$OR$^e$, —CN, or —NO$_2$;
M is CR$^3$ or N;
$M^1$ is CR$^4$;
each $R^3$, $R^4$, and $R^5$ is independently hydrogen, deuterium, halogen, —OR$^c$, —OC(O)R$^c$, —OC(O)NR$^c$R$^d$, —OC(=N)NR$^c$R$^d$, —OS(O)R$^c$, —OS(O)$_2$R$^c$, —OS(O)NR$^c$R$^d$, —OS(O)$_2$NR$^c$R$^d$, —SR$^c$, —S(O)R$^c$, —S(O)$_2$R$^c$, —S(O)NR$^c$R$^d$, —S(O)$_2$NR$^c$R$^d$, —NR$^c$R$^d$, —NR$^c$C(O)R$^d$, —NR$^c$C(O)OR$^d$, —NR$^c$C(O)NR$^c$R$^d$, —NR$^c$C(=N)NR$^c$R$^d$, —NR$^c$S(O)R$^d$, —NR$^c$S(O)$_2$R$^d$, —NR$^c$S(O)NR$^c$R$^d$, —NR$^c$S(O)$_2$NR$^c$R$^d$, —C(O)R$^c$, —C(O)OR$^c$, —C(O)NR$^c$R$^d$, —C(=N)NR$^c$R$^d$, —PR$^c$R$^d$, —P(O)R$^c$R$^d$, —P(O)$_2$R$^c$R$^d$, —P(O)NR$^c$R$^d$, —P(O)$_2$NR$^c$R$^d$, —P(O)OR$^c$, —P(O)$_2$OR$^c$, —CN, —NO$_2$, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bi-cyclic heteroaryl, or $R^4$ and $R^5$ taken together with the ring to which they are attached form a $C_5$-$C_8$ cycloalkyl, or a 5- to 8-membered heterocycloalkyl, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, mono- or bi-cyclic heteroaryl, $C_5$-$C_8$ cycloalkyl, or 5- to 8-membered heterocycloalkyl is independently optionally substituted by deuterium, halogen, $C_1$-$C_6$ alkyl, $C_1$-$C_6$ haloalkyl, —OR$^e$, —OC(O)R$^e$, —OC(O)NR$^e$R$^f$, —OC(=N)NR$^e$R$^f$, —OS(O)R$^e$, —OS(O)$_2$R$^e$, —OS(O)NR$^e$R$^f$, —OS(O)$_2$NR$^e$R$^f$, —SR$^e$, —S(O)R$^e$, —S(O)$_2$R$^e$, —S(O)NR$^e$R$^f$, —S(O)$_2$NR$^e$R$^f$, —NR$^e$R$^f$, —NR$^e$C(O)R$^f$, —NR$^e$C(O)OR$^f$, —NR$^e$C(O)NR$^e$R$^f$, —NR$^e$S(O)R$^f$, —NR$^e$S(O)$_2$R$^f$, —NR$^e$S(O)NR$^e$R$^f$, —NR$^e$S(O)$_2$NR$^e$R$^f$, —C(O)R$^e$, —C(O)OR$^e$, —C(O)NR$^e$R$^f$, —PR$^e$R$^f$, —P(O)R$^e$R$^f$, —P(O)$_2$R$^e$R$^f$, —P(O)NR$^e$R$^f$, —P(O)$_2$NR$^e$R$^f$, —P(O)OR$^e$, —P(O)$_2$OR$^e$, —CN, or —NO$_2$;
$R^6$ is H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bi-cyclic heteroaryl, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bi-cyclic heteroaryl is independently optionally substituted by deuterium, halogen, $C_3$-$C_6$ cycloalkyl, or 5- to 7-membered heterocycloalkyl, —OR$^e$, —OC(O)R$^e$, —OC(O)NR$^e$R$^f$, —OC(=N)NR$^e$R$^f$, —OS(O)R$^e$, —OS(O)$_2$R$^e$, —OS(O)NR$^e$R$^f$, —OS(O)$_2$NR$^e$R$^f$, —SR$^e$, —S(O)R$^e$, —S(O)$_2$R$^e$, —S(O)NR$^e$R$^f$, —S(O)$_2$NR$^e$R$^f$, —NR$^e$R$^f$, —NR$^e$C(O)R$^f$, —NR$^e$C(O)OR$^f$, —NR$^e$C(O)NR$^e$R$^f$, —NR$^e$S(O)R$^f$, —NR$^e$S(O)$_2$R$^f$, —NR$^e$S(O)NR$^e$R$^f$, —NR$^e$S(O)$_2$NR$^e$R$^f$, —C(O)R$^e$, —C(O)OR$^e$, —C(O)NR$^e$R$^f$, —PR$^e$R$^f$, —P(O)R$^e$R$^f$, —P(O)$_2$R$^e$R$^f$, —P(O)NR$^e$R$^f$, —P(O)$_2$NR$^e$R$^f$, —P(O)OR$^e$, —P(O)$_2$OR$^e$, —CN, or —NO$_2$;
$R^7$ and $R^8$ combine to form a $C_3$-$C_7$ cycloalkyl, 5- to 8-membered heterocycloalkyl, $C_6$-$C_{10}$ aryl, or 5- to 7-membered heteroaryl; wherein each hydrogen atom in $C_3$-$C_7$ cycloalkyl, 5- to 8-membered heterocycloalkyl, $C_6$-$C_{10}$ aryl, or 5- to 7-membered heteroaryl is independently optionally substituted by deuterium, halogen, —OR$^e$, —OC(O)R$^e$, —OC(O)NR$^e$R$^f$, —OC(=N)NR$^e$R$^f$, —OS(O)R$^e$, —OS(O)$_2$R$^e$, —OS(O)NR$^e$R$^f$, —OS(O)$_2$NR$^e$R$^f$, —SR$^e$, —S(O)R$^e$, —S(O)$_2$R$^e$, —S(O)NR$^e$R$^f$, —S(O)$_2$NR$^e$R$^f$, —NR$^e$R$^f$, —NR$^e$C(O)R$^f$, —NR$^e$C(O)OR$^f$, —NR$^e$C(O)NR$^e$R$^f$, —NR$^e$S(O)R$^f$, —NR$^e$S(O)$_2$R$^f$, —NR$^e$S(O)NR$^e$R$^f$, —NR$^e$S(O)$_2$NR$^e$R$^f$, —C(O)R$^e$, —C(O)OR$^e$, —C(O)NR$^e$R$^f$, —PR$^e$R$^f$, —P(O)R$^e$R$^f$, —P(O)$_2$R$^e$R$^f$, —P(O)NR$^e$R$^f$, —P(O)$_2$NR$^e$R$^f$, —P(O)OR$^e$, —P(O)$_2$OR$^e$, —CN, or —NO$_2$;
Y is O, S, NR$^9$, or CR$^9$R$^{10}$;
$R^9$ and $R^{10}$ are each independently H, deuterium, halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bi-cyclic heteroaryl, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bi-cyclic heteroaryl is optionally substituted by a halogen, —OR$^e$, —OC(O)R$^e$, —OC(O)NR$^e$R$^f$, —OC(=N)NR$^e$R$^f$, —OS(O)R$^e$, —OS(O)$_2$R$^e$, —OS(O)NR$^e$R$^f$, —OS(O)$_2$NR$^e$R$^f$, —SR$^e$, —S(O)R$^e$, —S(O)$_2$R$^e$, —S(O)NR$^e$R$^f$, —S(O)$_2$NR$^e$R$^f$, —NR$^e$R$^f$, —NR$^e$C(O)R$^f$, —NR$^e$C(O)OR$^f$, —NR$^e$C(O)NR$^e$R$^f$, —NR$^e$S(O)R$^f$, —NR$^e$S(O)$_2$R$^f$, —NR$^e$S(O)NR$^e$R$^f$, —NR$^e$S(O)$_2$NR$^e$R$^f$, —C(O)R$^e$, —C(O)OR$^e$, —C(O)NR$^e$R$^f$, —PR$^e$R$^f$, —P(O)R$^e$R$^f$, —P(O)$_2$R$^e$R$^f$, —P(O)NR$^e$R$^f$, —P(O)$_2$NR$^e$R$^f$, —P(O)OR$^e$, or —P(O)$_2$OR$^e$;
each R$^a$, R$^b$, R$^c$, R$^d$, R$^e$, and R$^f$ is independently selected from the group consisting of H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or 5- to 7-membered heteroaryl;
each of $Z^1$, $Z^2$, $Z^3$, $Z^4$, $Z^5$, and $Z^6$ is independently N, NH, C or CH;

p is 1, 2, 3, or 4; and t is 1, 2, 3, 4, or 5;

or a pharmaceutically acceptable salt thereof.

2. The compound of claim 1, or a pharmaceutically acceptable salt thereof, wherein p is 1.

3. The compound of claim 2, or a pharmaceutically acceptable salt thereof, wherein t is 3 or 4.

4. The compound of claim 1, having the formula III

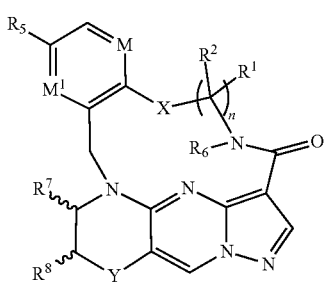

III wherein n is 2 or 3;

or a pharmaceutically acceptable salt thereof.

5. The compound of claim 4, or a pharmaceutically acceptable salt thereof, wherein n is 2.

6. The compound of claim 1, having the formula IV or V

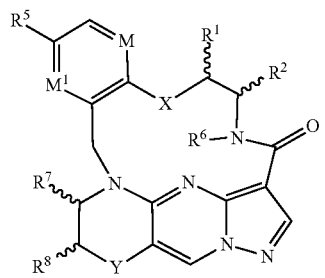

IV

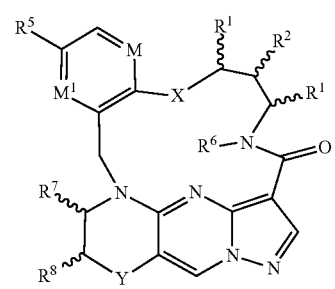

V or a pharmaceutically acceptable salt thereof.

7. The compound of claim 5, or a pharmaceutically acceptable salt thereof, wherein Y is O.

8. The compound of claim 7, or a pharmaceutically acceptable salt thereof, wherein M is N.

9. The compound of claim 8, or a pharmaceutically acceptable salt thereof, wherein $R^4$, when present, is H, deuterium, $C_1$-$C_6$ alkyl or halogen.

10. The compound of claim 9, or a pharmaceutically acceptable salt thereof, wherein $R^5$ is F.

11. The compound of claim 10, or a pharmaceutically acceptable salt thereof, wherein each $R^1$ is independently H or $C_1$-$C_6$ alkyl, and each $R^2$ is independently H, $C_1$-$C_6$ alkyl, or $C_3$-$C_7$ cycloalkyl.

12. The compound of claim 11, or a pharmaceutically acceptable salt thereof, wherein $R^7$ and $R^8$ combine to form a 4-, 5- or 6-membered cycloalkyl, wherein each hydrogen atom in the 4-, 5- or 6-membered cycloalkyl is independently optionally substituted by deuterium, halogen, —OH, —CN, —O$C_1$-$C_6$ alkyl, —O$C_1$-$C_6$ alkyl($C_6$-$C_{10}$ aryl), —NH$_2$, —OC(O)$C_1$-$C_6$ alkyl, —OC(O)N($C_1$-$C_6$ alkyl)$_2$, —OC(O)NH($C_1$-$C_6$ alkyl), —OC(O)NH$_2$, —OC(=N)N($C_1$-$C_6$ alkyl)$_2$, —OC(=N)NH($C_1$-$C_6$ alkyl), —OC(=N)NH$_2$, —OS(O)$C_1$-$C_6$ alkyl, —OS(O)$_2$$C_1$-$C_6$ alkyl, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH($C_1$-$C_6$ alkyl), —N($C_1$-$C_6$ alkyl)C(O)NH$_2$, —N($C_1$-$C_6$ alkyl)C(O)NH($C_1$-$C_6$ alkyl), —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHC(O)OH, —N($C_1$-$C_6$ alkyl)C(O)OH, —NHS(O)$C_1$-$C_6$ alkyl, —NHS(O)$_2$$C_1$-$C_6$ alkyl, —N($C_1$-$C_6$ alkyl)S(O)$C_1$-$C_6$ alkyl, —N($C_1$-$C_6$ alkyl)S(O)$_2$$C_1$-$C_6$ alkyl, —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —C(O)$C_1$-$C_6$ alkyl, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —S(O)NH$_2$, —S(O)$_2$NH$_2$, —OS(O)N($C_1$-$C_6$ alkyl)$_2$, —OS(O)$_2$N($C_1$-$C_6$ alkyl)$_2$, —OS(O)NH($C_1$-$C_6$ alkyl), —OS(O)$_2$NH($C_1$-$C_6$ alkyl), —OS(O)NH$_2$, —OS(O)$_2$NH$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl.

13. The compound of claim 11, or a pharmaceutically acceptable salt thereof, wherein $R^7$ and $R^8$ combine to form a 5- or 6-membered heterocycloalkyl, wherein each hydrogen atom in the 5- or 6-membered heterocycloalkyl is independently optionally substituted by deuterium, halogen, —OH, —CN, —O$C_1$-$C_6$ alkyl, —O$C_1$-$C_6$ alkyl($C_6$-$C_{10}$ aryl), —NH$_2$, —OC(O)$C_1$-$C_6$ alkyl, —OC(O)N($C_1$-$C_6$ alkyl)$_2$, —OC(O)NH($C_1$-$C_6$ alkyl), —OC(O)NH$_2$, —OC(=N)N($C_1$-$C_6$ alkyl)$_2$, —OC(=N)NH($C_1$-$C_6$ alkyl), —OC(=N)NH$_2$, —OS(O)$C_1$-$C_6$ alkyl, —OS(O)$_2$$C_1$-$C_6$ alkyl, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH($C_1$-$C_6$ alkyl), —N($C_1$-$C_6$ alkyl)C(O)NH$_2$, —N($C_1$-$C_6$ alkyl)C(O)NH($C_1$-$C_6$ alkyl), —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHC(O)OH, —N($C_1$-$C_6$ alkyl)C(O)OH, —NHS(O)$C_1$-$C_6$ alkyl, —NHS(O)$_2$$C_1$-$C_6$ alkyl, —N($C_1$-$C_6$ alkyl)S(O)$C_1$-$C_6$ alkyl, —N($C_1$-$C_6$ alkyl)S(O)$_2$$C_1$-$C_6$ alkyl, —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —C(O)$C_1$-$C_6$ alkyl, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —S(O)NH$_2$, —S(O)$_2$NH$_2$, —OS(O)N($C_1$-$C_6$ alkyl)$_2$, —OS(O)$_2$N($C_1$-$C_6$ alkyl)$_2$, —OS(O)NH($C_1$-$C_6$ alkyl), —OS(O)$_2$NH($C_1$-$C_6$ alkyl), —OS(O)NH$_2$, —OS(O)$_2$NH$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl.

14. The compound of claim 11, or a pharmaceutically acceptable salt thereof, wherein $R^7$ and $R^8$ combine to form a tetrahydrofuran ring, a cyclobutane ring, cyclopentane ring, or cyclohexane ring.

15. The compound of claim 1, selected form the group consisting of

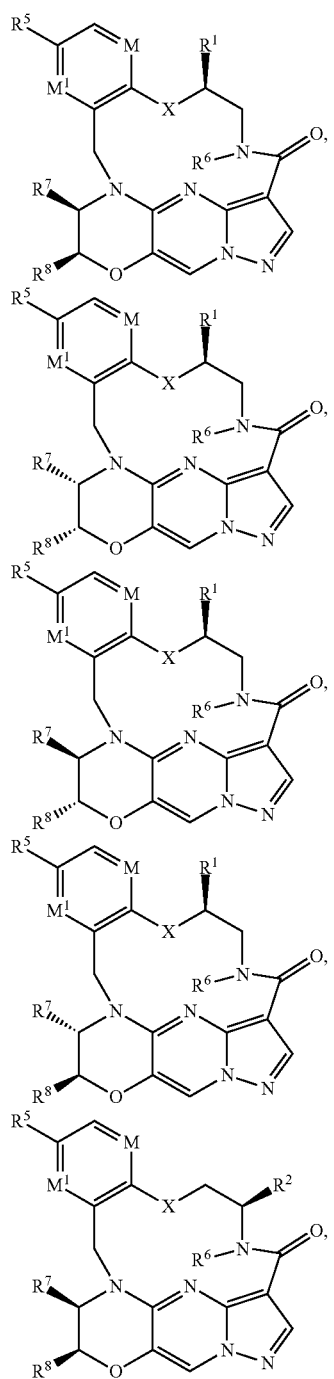

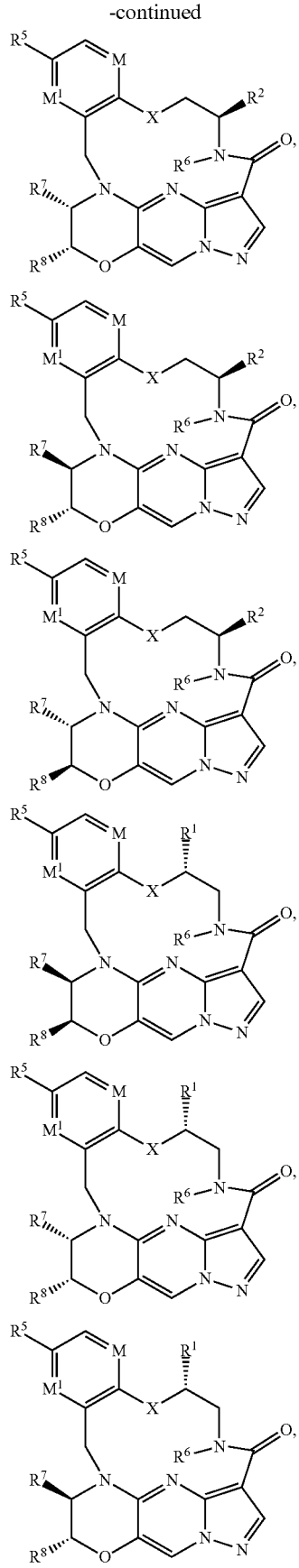

143
-continued
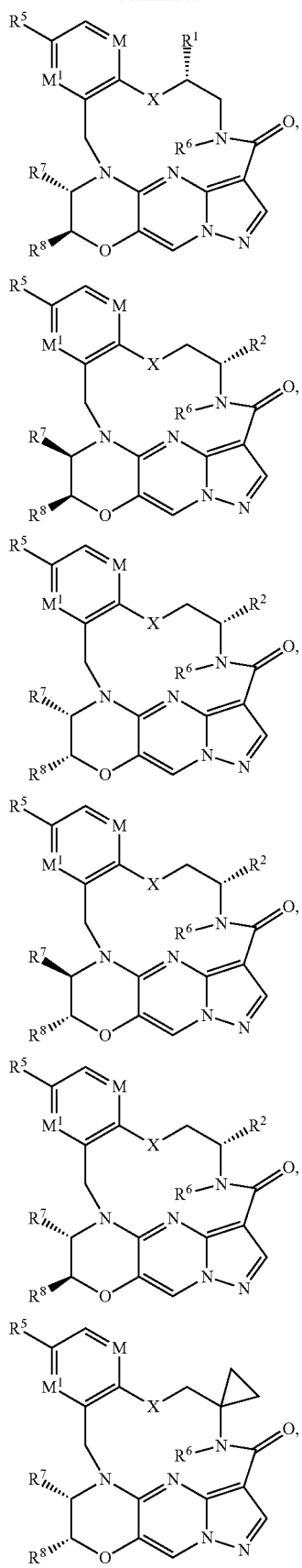
144
-continued
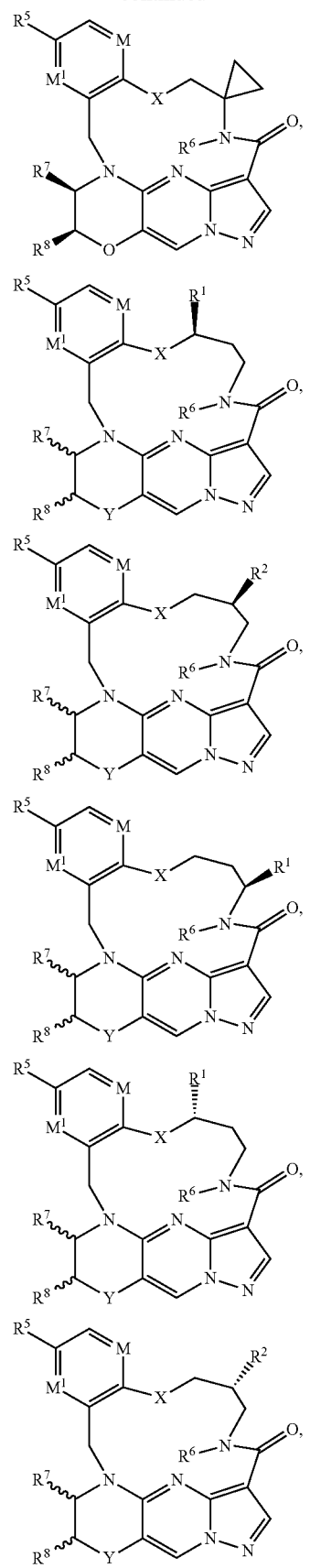

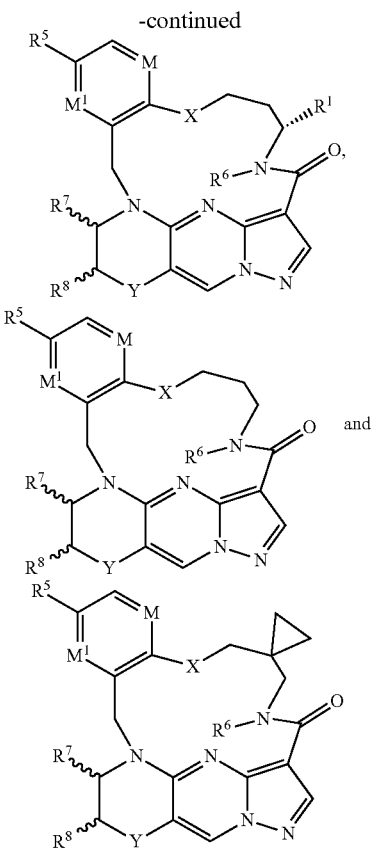

wherein

M is CR³ or N;

M¹ is CR⁴;

X is O, S, S(O), or S(O)₂;

R¹ and R² are each independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —OR$^a$, —SR$^a$, —NR$^a$R$^b$, —C(O)OR$^a$, or —C(O)NR$^a$R$^b$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —O$C_1$-$C_6$ alkyl($C_6$-$C_{10}$ aryl), —NH₂, —OC(O)$C_1$-$C_6$ alkyl, —OC(O)N($C_1$-$C_6$ alkyl)₂, —OC(O)NH($C_1$-$C_6$ alkyl), —OC(O)NH₂, —OC(=N)N($C_1$-$C_6$ alkyl)₂, —OC(=N)NH($C_1$-$C_6$ alkyl), —OC(=N)NH₂, —OS(O)$C_1$-$C_6$ alkyl, —OS(O)₂$C_1$-$C_6$ alkyl, —NH($C_1$-$C_6$ alkyl), —N($C_1$-$C_6$ alkyl)₂, —NHC(O)$C_1$-$C_6$ alkyl, —N($C_1$-$C_6$ alkyl)C(O)$C_1$-$C_6$ alkyl, —NHC(O)NH₂, —NHC(O)NH($C_1$-$C_6$ alkyl), —N($C_1$-$C_6$ alkyl)C(O)NH₂, —N($C_1$-$C_6$ alkyl)C(O)NH($C_1$-$C_6$ alkyl), —NHC(O)N($C_1$-$C_6$ alkyl)₂, —N($C_1$-$C_6$ alkyl)C(O)N($C_1$-$C_6$ alkyl)₂, —NHC(O)O$C_1$-$C_6$ alkyl, —N($C_1$-$C_6$ alkyl)C(O)O$C_1$-$C_6$ alkyl, —NHC(O)OH, —N($C_1$-$C_6$ alkyl)C(O)OH, —NHS(O)$C_1$-$C_6$ alkyl, —NHS(O)₂$C_1$-$C_6$ alkyl, —N($C_1$-$C_6$ alkyl)S(O)$C_1$-$C_6$ alkyl, —N($C_1$-$C_6$ alkyl)S(O)₂$C_1$-$C_6$ alkyl, —NHS(O)NH₂, —NHS(O)₂NH₂, —N($C_1$-$C_6$ alkyl)S(O)NH₂, —N($C_1$-$C_6$ alkyl)S(O)₂NH₂, —NHS(O)NH($C_1$-$C_6$ alkyl), —NHS(O)₂NH($C_1$-$C_6$ alkyl), —NHS(O)N($C_1$-$C_6$ alkyl)₂, —NHS(O)₂N($C_1$-$C_6$ alkyl)₂, —N($C_1$-$C_6$ alkyl)S(O)NH($C_1$-$C_6$ alkyl), —N($C_1$-$C_6$ alkyl)S(O)₂NH($C_1$-$C_6$ alkyl), —N($C_1$-$C_6$ alkyl)S(O) N($C_1$-$C_6$ alkyl)₂, —N($C_1$-$C_6$ alkyl)S(O)₂N($C_1$-$C_6$ alkyl)₂, —C(O)$C_1$-$C_6$ alkyl, —CO₂H, —C(O)O$C_1$-$C_6$ alkyl, —C(O)NH₂, —C(O)NH($C_1$-$C_6$ alkyl), —C(O)N($C_1$-$C_6$ alkyl)₂, —S$C_1$-$C_6$ alkyl, —S(O)$C_1$-$C_6$ alkyl, —S(O)₂$C_1$-$C_6$ alkyl, —S(O)NH($C_1$-$C_6$ alkyl), —S(O)₂NH($C_1$-$C_6$ alkyl), —S(O)N($C_1$-$C_6$ alkyl)₂, —S(O)₂N($C_1$-$C_6$ alkyl)₂, —S(O)NH₂, —S(O)₂NH₂, —OS(O)N($C_1$-$C_6$ alkyl)₂, —OS(O)₂N($C_1$-$C_6$ alkyl)₂, —OS(O)NH($C_1$-$C_6$ alkyl), —OS(O)₂NH($C_1$-$C_6$ alkyl), —OS(O)NH₂, —OS(O)₂NH₂, —P($C_1$-$C_6$ alkyl)₂, —P(O)($C_1$-$C_6$ alkyl)₂, $C_3$-$C_6$ cycloalkyl, or 3- to 7-membered heterocycloalkyl;

R³, R⁴, and R⁵ are each independently H, fluoro, chloro, bromo, $C_1$-$C_6$ alkyl, —OH, —CN, —O$C_1$-$C_6$ alkyl, —NH$C_1$-$C_6$ alkyl, —N($C_1$-$C_6$ alkyl)₂ or —CF₃;

R⁶ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —O$C_1$-$C_6$ alkyl, —NH₂, —NH($C_1$-$C_6$ alkyl), —N($C_1$-$C_6$ alkyl)₂, —CO₂H, —C(O)O$C_1$-$C_6$ alkyl, —C(O)NH₂, —C(O)NH($C_1$-$C_6$ alkyl), —C(O)N ($C_1$-$C_6$ alkyl)₂, $C_3$-$C_6$ cycloalkyl, or monocyclic 5- to 7-membered heterocycloalkyl;

R⁷ and R⁸ combine to form a $C_3$-$C_7$ cycloalkyl, a 5- to 8-membered heterocycloalkyl, $C_6$-$C_{10}$ aryl, or 5- to 7-membered heteroaryl; wherein each hydrogen atom in $C_3$-$C_7$ cycloalkyl, a 5- to 8-membered heterocycloalkyl, $C_6$-$C_{10}$ aryl, or 5- to 7-membered heteroaryl is independently optionally substituted by deuterium, halogen, —OH, —O$C_1$-$C_6$ alkyl, —OC(O)$C_1$-$C_6$ alkyl, —OC(O)NH₂, —OC(O)NH($C_1$-$C_6$ alkyl), —OC(O)N($C_1$-$C_6$ alkyl)₂, —OC(=N)NH₂, —OC(=N)NH($C_1$-$C_6$ alkyl), —OC(=N)N($C_1$-$C_6$ alkyl)₂, —OS(O)$C_1$-$C_6$ alkyl, —OS(O)₂$C_1$-$C_6$ alkyl, —OS(O)NH₂, —OS(O)NH($C_1$-$C_6$ alkyl), —OS(O) N($C_1$-$C_6$ alkyl)₂, —OS(O)₂NH₂, —OS(O)₂NH($C_1$-$C_6$ alkyl), —OS(O)₂N($C_1$-$C_6$ alkyl)₂, —SH, —S$C_1$-$C_6$ alkyl, —S(O)$C_1$-$C_6$ alkyl, —S(O)₂$C_1$-$C_6$ alkyl, —S(O)NH₂, —S(O)NH($C_1$-$C_6$ alkyl), —S(O)($C_1$-$C_6$ alkyl)₂, —S(O)₂NH₂, —S(O)₂NH($C_1$-$C_6$ alkyl), —S(O)₂N($C_1$-$C_6$ alkyl)₂, —NH₂, —NH($C_1$-$C_6$ alkyl), —N($C_1$-$C_6$ alkyl)₂, —NHC(O)$C_1$-$C_6$ alkyl, —N($C_1$-$C_6$ alkyl)C(O)$C_1$-$C_6$ alkyl, —NHC(O)OH, —NHC(O)O$C_1$-$C_6$ alkyl, —N($C_1$-$C_6$ alkyl)C(O)OH, —N($C_1$-$C_6$ alkyl)C(O)O$C_1$-$C_6$ alkyl, —NHC(O)NH₂, —NHC(O)NH($C_1$-$C_6$ alkyl), —NHC(O)N($C_1$-$C_6$ alkyl)₂, —N($C_1$-$C_6$ alkyl)C(O)NH₂, —N($C_1$-$C_6$ alkyl)C(O)NH($C_1$-$C_6$ alkyl), —N($C_1$-$C_6$ alkyl)C (O)N($C_1$-$C_6$ alkyl)₂, —NHS(O)$C_1$-$C_6$ alkyl, —N($C_1$-$C_6$ alkyl)S(O)$C_1$-$C_6$ alkyl, —NHS(O)₂$C_1$-$C_6$ alkyl, —N($C_1$-$C_6$ alkyl)S(O)₂$C_1$-$C_6$ alkyl, —NHS(O)NH₂, —NHS(O)NH($C_1$-$C_6$ alkyl), —NHS(O)N($C_1$-$C_6$ alkyl)₂, —N($C_1$-$C_6$ alkyl)S(O) NH₂, —N($C_1$-$C_6$ alkyl)S(O)NH($C_1$-$C_6$ alkyl), —N($C_1$-$C_6$ alkyl)S(O)N($C_1$-$C_6$ alkyl)₂, —NHS(O)₂ NH₂, —NHS(O)₂NH($C_1$-$C_6$ alkyl), —NHS(O)₂N ($C_1$-$C_6$ alkyl)₂, —N($C_1$-$C_6$ alkyl)S(O)₂NH₂, —N($C_1$-$C_6$ alkyl)S(O)₂NH($C_1$-$C_6$ alkyl), —N($C_1$-$C_6$ alkyl)S(O)₂N($C_1$-$C_6$ alkyl)₂, —C(O)$C_1$-$C_6$ alkyl, —C(O)O$C_1$-$C_6$ alkyl, —C(O)NH₂, —C(O)NH($C_1$-$C_6$ alkyl), —C(O)N($C_1$-$C_6$ alkyl)₂, —P($C_1$-$C_6$ alkyl)₂, —P(O)($C_1$-$C_6$ alkyl)₂, —P(O)₂($C_1$-$C_6$ alkyl)₂, —P(O)NH₂, —P(O)NH($C_1$-$C_6$ alkyl), —P(O)N($C_1$-$C_6$ alkyl)₂, —P(O)₂NH₂, —P(O)₂NH ($C_1$-$C_6$ alkyl), —P(O)$_2$N($C_1$-$C_6$ alkyl)$_2$, —P(O)OH, —P(O)O$C_1$-$C_6$ alkyl, —P(O)$_2$OH, —P(O)$_2$O$C_1$-$C_6$ alkyl, —CN, or —NO$_2$;

Y is O, S, NR$^9$, or CR$^9$R$^{10}$; and

R$^9$ and R$^{10}$ are each independently H, deuterium, halogen, or $C_1$-$C_6$ alkyl, wherein each hydrogen atom in $C_1$-$C_6$ alkyl is optionally substituted by a halogen, —OH, —O$C_1$-$C_6$ alkyl, —OC(O)$C_1$-$C_6$ alkyl, —OC(O)N($C_1$-$C_6$ alkyl)$_2$, —OC(O)NH($C_1$-$C_6$ alkyl), —OC(O)NH$_2$, —OC(=N)N($C_1$-$C_6$ alkyl)$_2$, —OC(=N)NH($C_1$-$C_6$ alkyl), —OC(=N)NH$_2$, —OS(O)$C_1$-$C_6$ alkyl, —OS(O)$_2$$C_1$-$C_6$ alkyl, —OS(O)N($C_1$-$C_6$ alkyl)$_2$, —OS(O)NH($C_1$-$C_6$ alkyl), —OS(O)NH$_2$, —OS(O)$_2$N($C_1$-$C_6$ alkyl)$_2$, —OS(O)$_2$NH($C_1$-$C_6$ alkyl), —OS(O)$_2$NH$_2$, —SH, —S$C_1$-$C_6$ alkyl, —S(O)$C_1$-$C_6$ alkyl, —S(O)$_2$$C_1$-$C_6$ alkyl, —S(O)N($C_1$-$C_6$ alkyl)$_2$, —S(O)NH($C_1$-$C_6$ alkyl), —S(O)NH$_2$, —S(O)$_2$N($C_1$-$C_6$ alkyl)$_2$, —S(O)$_2$NH($C_1$-$C_6$ alkyl), —S(O)$_2$NH$_2$, —N($C_1$-$C_6$ alkyl)$_2$, —NH($C_1$-$C_6$ alkyl), —NH$_2$, —N($C_1$-$C_6$ alkyl)C(O)$C_1$-$C_6$ alkyl, —NHC(O)$C_1$-$C_6$ alkyl, —N($C_1$-$C_6$ alkyl)C(O)O$C_1$-$C_6$ alkyl, —N($C_1$-$C_6$ alkyl)C(O)OH, —NHC(O)O$C_1$-$C_6$ alkyl, —NHC(O)OH, —N($C_1$-$C_6$ alkyl)C(O)N($C_1$-$C_6$ alkyl)$_2$, —N($C_1$-$C_6$ alkyl)C(O)NH($C_1$-$C_6$ alkyl), —N($C_1$-$C_6$ alkyl)C(O)NH$_2$, —NHC(O)N($C_1$$C_6$ alkyl)$_2$, —NHC(O)NH($C_1$$C_6$ alkyl), —NHC(O)NH$_2$, —N($C_1$-$C_6$ alkyl)S(O)$C_1$-$C_6$ alkyl, —NHS(O)$C_1$-$C_6$ alkyl, —N($C_1$-$C_6$ alkyl)S(O)$_2$ $C_1$-$C_6$ alkyl, —NHS(O)$_2$$C_1$-$C_6$ alkyl, —N($C_1$-$C_6$ alkyl)S(O)N($C_1$-$C_6$ alkyl)$_2$, —N($C_1$-$C_6$ alkyl)S(O)NH($C_1$-$C_6$ alkyl), —N($C_1$-$C_6$ alkyl)S(O)NH$_2$, —NHS(O)N($C_1$-$C_6$ alkyl)$_2$, —NHS(O)NH($C_1$-$C_6$ alkyl), —NHS(O)NH$_2$, —N($C_1$-$C_6$ alkyl)S(O)$_2$N($C_1$-$C_6$ alkyl)$_2$, —N($C_1$-$C_6$ alkyl)S(O)$_2$NH($C_1$-$C_6$ alkyl), —N($C_1$-$C_6$ alkyl)S(O)$_2$NH$_2$, —NHS(O)$_2$N($C_1$-$C_6$ alkyl)$_2$, —NHS(O)$_2$NH($C_1$-$C_6$ alkyl), —NHS(O)$_2$NH$_2$, —C(O)$C_1$-$C_6$ alkyl, —C(O)O$C_1$-$C_6$ alkyl, —C(O)N($C_1$-$C_6$ alkyl)$_2$, —C(O)NH($C_1$-$C_6$ alkyl), —C(O)NH$_2$, —P($C_1$-$C_6$ alkyl)$_2$, —P(OX)($C_1$-$C_6$ alkyl)$_2$, —P(O)$_2$($C_1$-$C_6$ alkyl)$_2$, —P(O)N($C_1$-$C_6$ alkyl)$_2$, —P(O)$_2$N($C_1$-$C_6$ alkyl)$_2$, —P(O)O$C_1$-$C_6$ alkyl, or —P(O)$_2$O$C_1$-$C_6$ alkyl.

16. The compound of claim 15, or a pharmaceutically acceptable salt thereof, wherein M is N.

17. The compound of claim 16, or a pharmaceutically acceptable salt thereof, wherein R$^4$ is H, deuterium, $C_1$-$C_6$ alkyl or halogen.

18. The compound of claim 17, or a pharmaceutically acceptable salt thereof, wherein R$^5$ is F.

19. The compound of claim 18, or a pharmaceutically acceptable salt thereof, wherein R$^7$ and R$^8$ combine to form a 4-, 5- or 6-membered cycloalkyl, wherein each hydrogen atom in the 4-, 5- or 6-membered cycloalkyl is independently optionally substituted by deuterium, halogen, —OH, —CN, —O$C_1$-$C_6$ alkyl, —O$C_1$-$C_6$ alkyl($C_6$-$C_{10}$ aryl), —NH$_2$, —OC(O)$C_1$-$C_6$ alkyl, —OC(O)N($C_1$-$C_6$ alkyl)$_2$, —OC(O)NH($C_1$-$C_6$ alkyl), —OC(O)NH$_2$, —OC(=N)N($C_1$-$C_6$ alkyl)$_2$, —OC(=N)NH($C_1$-$C_6$ alkyl), —OC(=N)NH$_2$, —OS(O)$C_1$-$C_6$ alkyl, —OS(O)$_2$$C_1$-$C_6$ alkyl, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH($C_1$-$C_6$ alkyl), —N($C_1$-$C_6$ alkyl)C(O)NH$_2$, —N($C_1$-$C_6$ alkyl)C(O)NH($C_1$-$C_6$ alkyl), —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHC(O)OH, —N($C_1$-$C_6$ alkyl)C(O)OH, —NHS(O)$C_1$-$C_6$ alkyl, —NHS(O)$_2$$C_1$-$C_6$ alkyl, —N($C_1$-$C_6$ alkyl)S(O)$C_1$-$C_6$ alkyl, —N($C_1$-$C_6$ alkyl)S(O)$_2$$C_1$-$C_6$ alkyl, —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —C(O)$C_1$-$C_6$ alkyl, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —S(O)NH$_2$, —S(O)$_2$NH$_2$, —OS(O)N($C_1$-$C_6$ alkyl)$_2$, —OS(O)$_2$N($C_1$-$C_6$ alkyl)$_2$, —OS(O)NH($C_1$-$C_6$ alkyl), —OS(O)$_2$NH($C_1$-$C_6$ alkyl), —OS(O)NH$_2$, —OS(O)$_2$NH$_2$, —P($C_1$-$C_6$ alkyl)$_2$, —P(OX)($C_1$-$C_6$ alkyl)$_2$, $C_3$-$C_6$ cycloalkyl, or 3- to 7-membered heterocycloalkyl.

20. The compound of claim 18, or a pharmaceutically acceptable salt thereof, wherein R$^7$ and R$^8$ combine to form a 5- or 6-membered heterocycloalkyl, wherein each hydrogen atom in the 5- or 6-membered heterocycloalkyl is independently optionally substituted by deuterium, halogen, —OH, —CN, —O$C_1$-$C_6$ alkyl, —O$C_1$-$C_6$ alkyl($C_6$-$C_{10}$ aryl), —NH$_2$, —OC(O)$C_1$-$C_6$ alkyl, —OC(O)N($C_1$-$C_6$ alkyl)$_2$, —OC(O)NH($C_1$-$C_6$ alkyl), —OC(O)NH$_2$, —OC(=N)N($C_1$-$C_6$ alkyl)$_2$, —OC(=N)NH($C_1$-$C_6$ alkyl), —OC(=N)NH$_2$, —OS(O)$C_1$-$C_6$ alkyl, —OS(O)$_2$$C_1$-$C_6$ alkyl, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH($C_1$-$C_6$ alkyl), —N($C_1$-$C_6$ alkyl)C(O)NH$_2$, —N($C_1$-$C_6$ alkyl)C(O)NH($C_1$-$C_6$ alkyl), —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHC(O)OH, —N($C_1$-$C_6$ alkyl)C(O)OH, —NHS(O)$C_1$-$C_6$ alkyl, —NHS(O)$_2$$C_1$-$C_6$ alkyl, —N($C_1$-$C_6$ alkyl)S(O)$C_1$-$C_6$ alkyl, —N($C_1$-$C_6$ alkyl)S(O)$_2$$C_1$-$C_6$ alkyl, —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —C(O)$C_1$-$C_6$ alkyl, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —S(O)NH$_2$, —S(O)$_2$NH$_2$, —OS(O)N($C_1$-$C_6$ alkyl)$_2$, —OS(O)$_2$N($C_1$-$C_6$ alkyl)$_2$, —OS(O)NH($C_1$-$C_6$ alkyl), —OS(O)$_2$NH($C_1$-$C_6$ alkyl), —OS(O)NH$_2$, —OS(O)$_2$NH$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl.

21. The compound of claim 18, or a pharmaceutically acceptable salt thereof, wherein R$^7$ and R$^8$ combine to form a tetrahydrofuran ring, a cyclobutane ring, cyclopentane ring, or cyclohexane ring.

22. The compound of claim 19, or a pharmaceutically acceptable salt thereof, wherein X is O.

23. A compound selected from the group consisting of
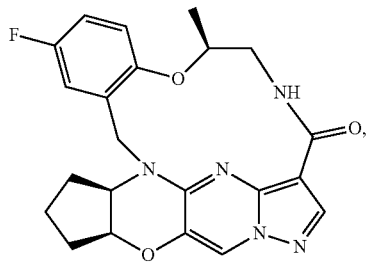
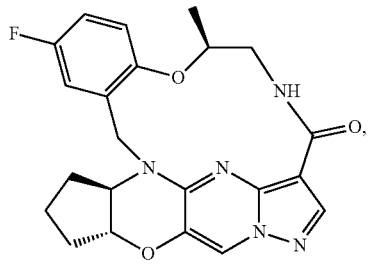
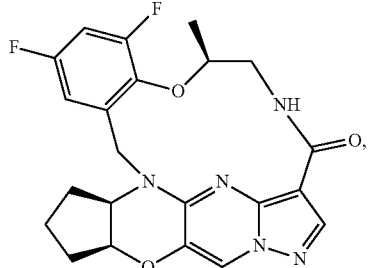
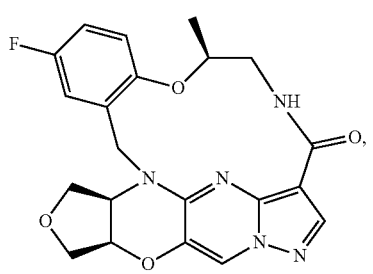
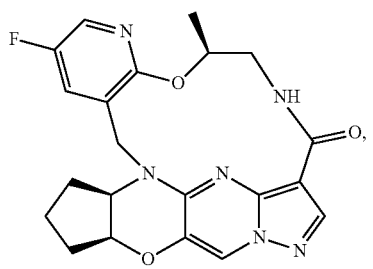
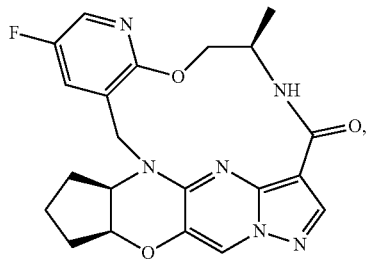
-continued
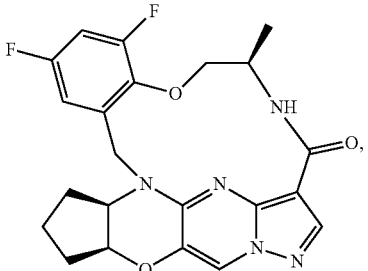
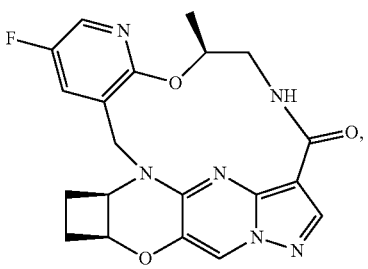
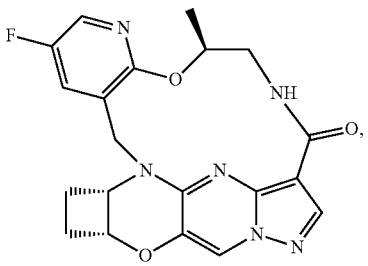
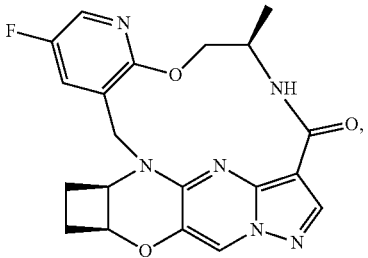
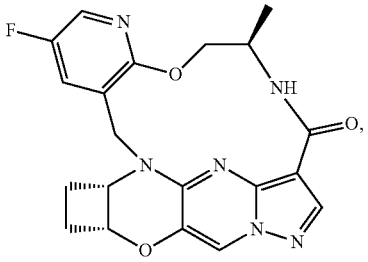
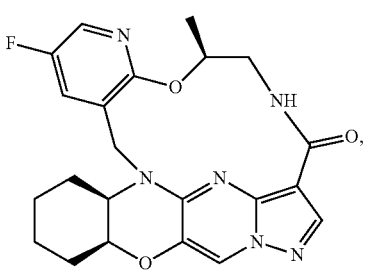

-continued

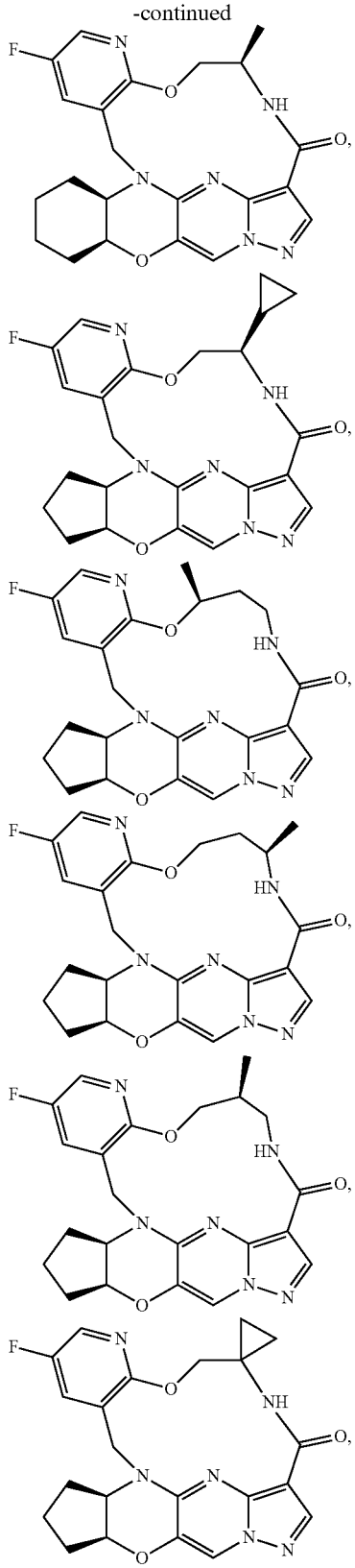

-continued

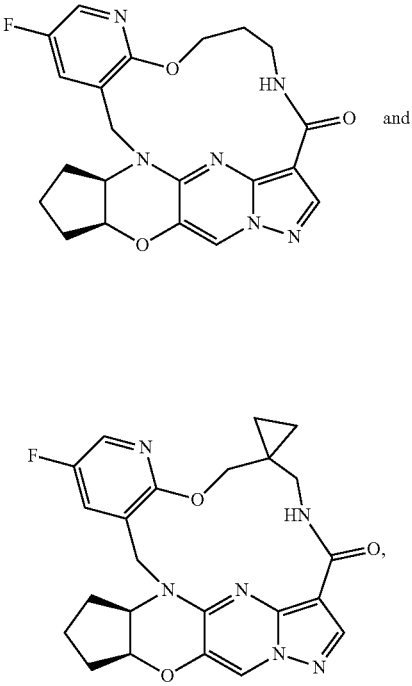

or a pharmaceutically acceptable salt thereof.

24. A pharmaceutical composition comprising a compound of claim 1, or a pharmaceutically acceptable salt thereof, and optionally at least one diluent, carrier or excipient.

25. A method of ameliorating the worsening of cancer comprising administering to a subject an effective amount of a compound of claim 1, or a pharmaceutically acceptable salt thereof, wherein the cancer is thyroid medullary carcinoma, non-small cell lung cancer, or colorectal cancer.

26. A method of inhibiting RET or SRC kinase, comprising contacting a cell comprising one or more of RET or SRC kinase with an effective amount of a compound of claim 1, or a pharmaceutically acceptable salt thereof, wherein the contacting is in vitro, ex vivo, or in vivo.

27. A pharmaceutical composition comprising a compound of claim 23, or a pharmaceutically acceptable salt thereof, and optionally at least one diluent, carrier or excipient.

28. A method of ameliorating the worsening of cancer comprising administering to a subject an effective amount of a compound of claim 23, or a pharmaceutically acceptable salt thereof, wherein the cancer is thyroid medullary carcinoma, non-small cell lung cancer, or colorectal cancer.

29. A method of inhibiting RET or SRC kinase, comprising contacting a cell comprising one or more of RET or SRC kinase with an effective amount of a compound of claim 23, or a pharmaceutically acceptable salt thereof, wherein the contacting is in vitro, ex vivo, or in vivo.

\* \* \* \* \*